US007368275B2

(12) United States Patent
Schultz et al.

(10) Patent No.: US 7,368,275 B2
(45) **Date of Patent: *May 6, 2008**

(54) IN VIVO INCORPORATION OF UNNATURAL AMINO ACIDS

(75) Inventors: Peter Schultz, La Jolla, CA (US); Lei Wang, San Diego, CA (US); John Christopher Anderson, San Diego, CA (US); Jason W. Chin, Cambridge (GB); David R. Liu, Lexington, MA (US); Thomas J. Magliery, North Haven, CT (US); Eric Meggers, Philadelphia, PA (US); Ryan Aaron Mehl, Lancaster, PA (US); Miro Pastrnak, San Diego, CA (US); Steven William Santoro, Cambridge, MA (US); Zhiwen Zhang, San Diego, CA (US)

(73) Assignees: The Scripps Research Institute, La Jolla, CA (US); The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/254,161

(22) Filed: Oct. 18, 2005

(65) Prior Publication Data

US 2006/0233744 A1 Oct. 19, 2006

Related U.S. Application Data

(63) Continuation of application No. 10/126,927, filed on Apr. 19, 2002, now Pat. No. 7,045,337.

(60) Provisional application No. 60/355,514, filed on Feb. 6, 2002, provisional application No. 60/285,030, filed on Apr. 19, 2001.

(51) Int. Cl.
*C12N 9/10* (2006.01)
*C12N 15/12* (2006.01)
*C12N 15/54* (2006.01)
*C12P 21/00* (2006.01)

(52) U.S. Cl. .................. 435/252.3; 435/193; 435/91.4; 435/252.33; 435/320; 435/15; 435/69.1; 536/23.2

(58) Field of Classification Search ................ 435/325, 435/193, 91.4, 69.1, 252.3, 252.33, 320; 536/23.2
See application file for complete search history.

(56) References Cited

U.S. PATENT DOCUMENTS

| | | | |
|---|---|---|---|
| 5,370,995 | A | 12/1994 | Hennecke et al. |
| 7,045,337 | B2 | 5/2006 | Schultz et al. |
| 7,083,970 | B2 | 8/2006 | Schultz et al. |

OTHER PUBLICATIONS

Kowal et al Twenty-first amino-acyl tRNA synthetase suppressor tRNA pairs for possible use in site specific incorporation of amino acid analogues into proteins in eukaryotes and eubacteria. PNASFeb. 27, 2001, vol. 98, No. 5, pp. 2268-2273.*

Anderson et al., Exploring the Limits of Codon and Anticodon Size, *Chemistry and Biology*, vol. 9, 237-244 (2002).

Azoulay et al., Glutamine analogues as Potential Antimalarials, *Eur. J. Med. Chem*. 26, 201-5 (1991).

Bain et al., Biosynthetic site-specific Incorporation of a non-natural amino acid into a polypeptide, *J. Am. Chem. Soc.*, 111:8013-8014 (1989).

Barton et al., Synthesis of Novel a-Amino-Acids and Derivatives Using Radical Chemistry: Synthesis of L- and D-a-Amino-Adipic Acids, L-a,-aminopimelic Acid and Appropriate Unsaturated Derivatives. *Tetrahedron Lett*. 43, 4297-4308 (1987).

Boles et al., *Nat. Struct. Biol.*, 1:283 (1994).

Bradley et al., tRNA2GIn Su+2 mutants that increase amber suppression, *J. Bacteriol*. 145:704-712 (1981).

Brick et al., *J. Mol. Biol.*, 208:83-98 (1988).

Brunner, New Photolabeling and crosslinking methods, *Annu. Rev. Biochem.*, 62:483-514 (1993).

Budisa et al., *Eur. J. Biochem.*, 230:788 (1995).

Budisa et al., *Faseb J.* 13:41-51 (1999).

Budisa et al., *J. Mol. Biol.*, 270:616 (1997).

Budisa et al., *Proc. Natl. Acad. Sci.* U S A, 95:455 (1998).

Christie & Rapoport, Synthesis of Optically Pure Pipecolates from L-Asparagine. Application to the Total Synthesis of (+)-Apovincamine through Amino Acid Decarbonylation and Iminium Ion Cyclization. *J. Org. Chem*. 50:1239-1246 (1985).

Cornish et al., *Angew. Chem. Int. Ed. Engl.*, 34:621 (1995).

Cornish et al., *J. Am. Chem. Soc.*, 118:8150-8151 (1996).

Craig et al., Absolute Configuration of the Enantiomers of 7-Chloro-4 [[4-(diethylamino)-1-methylbutyl]amino]quinoline (Chloroquine). *J. Org. Chem*. 53, 1167-1170 (1988).

Database NCBI, GenBank Accession No. E64348, Bult et al. 'Complete genome sequence of the methanogenic archaeon, Methanococcus jannaschii,' Gene Sequence, Jun. 3, 1996.

Doctor & Mudd, *J. Biol. Chem.*, 238:3677 (1963).

Doring et al., *Science*, 292:501 (2001).

Dougherty, *Curr. Opin. Chem. Biol.*, 4:645 (2000).

Duewel et al., *Biochemistry*, 36:3404 (1997).

Dunten & Mowbray, Crystal structure of the dipeptide binding protein from *Escherichia coli* involved in active transport and chemotaxis. *Protein Science* 4, 2327-34 (1995).

Ellman et al., Biosynthetic method for introducing unnatural amino acids site-specifically into proteins, *Methods in Enz.*, 202:301-336 (1992).

Ellman et al., Site-specific incorporation of novel backbone structures into proteins, *Science*, 255:197-200 (1992).

England et al., *Cell*, 96:89 (1999).

Fechter et al., Major tyrosine identity determinants in *Methanococcus jannaschii* and *Saccharomyces cerevisiae* tRNA Tyr are conserved but expressed differently, *Eur. J. Biochem*. 268:761-767 (2001).

(Continued)

*Primary Examiner*—Rebecca E. Prouty
*Assistant Examiner*—Kagnew Gebreyesus
(74) *Attorney, Agent, or Firm*—Quine Intellectual Property Law Group, P.C.

(57) ABSTRACT

The invention provides methods and compositions for in vivo incorporation of unnatural amino acids. Also provided are compositions including proteins with unnatural amino acids.

4 Claims, 37 Drawing Sheets

OTHER PUBLICATIONS

Francisco et al., Production and fluorescence-activated cell sorting of *Escherichia coli* expressing a functional antibody fragment on the external surface. *Proc Natl Acad Sci* U S A. 90:10444-8 (1993).
Francklyn et al. (2002) "Aminoacyl-tRNA synthetases: Versatile players in the changing theater of translation." *RNA*, 8:1363-1372.
Friedman & Chatterrji, Synthesis of Derivatives of Glutamine as Model Substrates for Anti-Tumor Agents. *J. Am. Chem. Soc*. 81, 3750-3752 (1959).
Furter, *Protein Sci*., 7:419 (1998).
Gabriel & McClain, A set of plasmids constitutively producing different RNA levels in *Escherichia coli*, *J. Mol. Biol*. 290 (1999) 385-389.
Gallivan et al., *Chem. Biol*., 4:739 (1997).
GenBank Accession No. Q57834, publicly available Nov. 1, 1997.
Giegé et al., *Biochimie*, 78:605 (1996).
Giegé et al., Universal rules and idiosyncratic features in tRNA identity, *Nucleic Acids Res*. 26:5017-5035 (1998).
Gay et al., *FEBS Lett*. 318:167 (1993).
Gucklan et al., *Angew. Chem. Int. Ed. Engl*., 36, 2825 (1997).
Hamano-Takaku et al., *J. Biol. Chem*., 275:40324 (2000).
Hartley et al., Expression of its cloned inhibitor permits expression of a cloned ribonuclease, *J. Mol. Biol*. 202:913-915 (1988).
He, et al., *Microbiology*, 147:2817-2829 (2001).
Hendrickson et al., *Embo J*., 9:1665 (1990).
Hirao, et al., An unnatural base pair for incorporating amino acid analogues into protein, *Nature Biotechnology*, 20:177-182 (2002).
Hohsaka et al., *J. Am. Chem. Soc*., 121:34 (1999).
Ibba & Hennecke, *FEBS Lett*., 362:272 (1995).
Ibba et al., *Biochemistry*, 33:7107 (1994).
Ibba et al., "Strategies for in vitro and in vivo incorporation translation with non-natural amino acids" *Biotechnol. Genet. Eng. Rev*. 13:197-216.
Jakubowski & Goldman, *Microbiol. Rev*., 56:412 (1992).
Jeruzalmi & Steitz, *Embo J*., 17, 4101-4113 (1998).
Jacovic & Hartley, Protein-protein interaction: a genetic selection for compensating mutations at the barnase-barstar interface. *Proceedings of the National Academy of Sciences of the* United States of America, 93: 2343-2347 (1996).
Kiga et al. (2002) "An engineered *Escherichia coli* tyrosyl-tRNA synthetase for site-specific incorporation of an unnatural amino acid into proteins in eukaryotic translation and its application in a wheat germ cell-free system." *PNAS*, vol. 99, No. 15, pp. 9715-9723.
Klick & Tirrell, *Tetrahedron*, 56:9487 (2000).
*Escherichia coli*, *J. Mol. Biol*. 290 (1999) 385-389.
Ibba (1996) "Strategies for in vitro and in vivo incorporation translation with non-natural amino acids" *Biotechnol. Genet. Eng. Rev*. 13:197-216.
King et al., A New Synthesis of Glutamine and of γ-Dipeptides of Glutamic Acid from Phthylated Intermediates. *J. Chem. Soc*., 4:3315-3319 (1949).
Kleeman et al., *J. Biol. Chem*., 272:14420 (1997).
Kleina et al., Construction of *Escherichia coli* amber suppressor tRNA genes. II. Synthesis of additional tRNA genes and improvement of suppressor efficiency, *J. Mol. Biol*. 213:705-717 (1990).
Kool, *Curr. Opin. Chem. Biol*., 4:602 (2000).
Koskinen & Rapoport, Synthesis of 4-Substituted Prolines as Conformationally Constrained Amino Acid Analogues. *J. Org. Chem*. 54, 1859-1866. (1989).
Kowal & Oliver, *Nucl. Acid. Res*., 25:4685 (1997).
Kowal et al., *Proc. Natl. Acad. Sci*. U S A, 98:2268 (2001).
Krieg et al., Photocrosslinking of the signal sequence of nascent preprolactin of the 54-kilodalton polypeptide of the signal recognition particle, *Proc. Natl. Acad. Sci*, 83(22):8604-8608 (1986).
Kwok & Wong, *Can. J. Biochem*., 58:213 (1980).
Lee et al., *Biotechnology Letters*, 20:479-482, (1998).
Liu & Schultz, Progress toward the evolution of an organism with an expanded genetic code, *Proc. Natl. Acad. Sci*. USA 96:4780-4785 (1999).
Liu et al., *Chem. Biol*., 4:685 (1997).
Liu et al., Engineering a tRNA and aminoacyl-tRNA synthetase for the site-specific incorporation of unnatural amino acids into proteins in vivo, *Proc. Natl. Acad. Sci*. USA 94:10091-10097 (1997).
Lorincz et al., *Cytometry*, 24, 321-329 (1996).
Lu et al., *Nat. Neurosci*., 4:239 (2001).
Ma et al., *Biochemistry*, 32:7939 (1993).
Magliery, Expanding the Genetic Code: Selection of Efficient Suppressors of Four-base Codons and Identification of "Shifty" Four-base Codons with a Library Approach in *Escherichia coli*, *J. Mol. Biol*. 307: 755-769 (2001).
Matsoukas et al., *J. Med. Chem*., 38: 4660-4669 (1995).
McMinn et al., *J. Am. Chem. Soc*., 121:11586 (1999).
Meggers et al., *J. Am. Chem. Soc*., 122:10714 (2000).
Mendel et al., SIte-Directed Mutagenesis with an Expanded Genetic Code, *Annu. Rev. Biophys. Biomol. Struct*. 24, 435-62 (1995).
Miller et al., *Neuron*, 20:619 (1998).
Minks et al., *Anal. Biochem*., 284:29 (2000).
Moore et al., *J. Mol. Biol*., 298:195 (2000).
Nagagawa et al. (2000) "Mutational Analysis of Invariant Valine B12 in Insulin: Implications for Receptor Binding." *Biochemistry*, 39:15826-15835.
Nichitenko et al., A structure of DppA, a periplasmic depeptide transport/chemosensory receptor. *Biochemistry* 34, 16585-16595 (1995).
Nilsson, et al. *Protein Eng*. 1:107-113 (1987).
Noren et al., A general method for site-specific incorporation of unnatural amino acids into proteins, *Science* 244 182-188 (1989).
Nowak et al., *Science*, 268:439-42 (1995).
Ogawa et al., *J. Am. Chem. Soc*., 122:3274 (2000).
Ogawa et al., *J. Am. Chem. Soc*., 122:8803 (2000).
Ohno et al. (1998) "Co-expression of yeast amber suppressor tRNATyr and tyrosyl-tRNA synthetase in *Escherichia coli*: possibility to expand the genetic code." *J. Biochem* 124(6):23169-23175.
O'Mahony et al., Glycine tRNA mutants with normal anticodon loop size cause 1 frameshifting, *Proc. Natl. Acad. Sci*. USA 86:7979-7983 (1989).
Pastrnak & Schultz, *Bioorg. Med. Chem*., 9:2373 (2001).
Pastrnak et al., A new orthogonal suppressor tRNA/aminoacyl-tRNA synthetase pair for evolving an organism with an expanded genetic code, *Helv. Chim. Acta* 83:2277-2286 (2000).
Piccirilli et al., *Nature*, 1990, 343:33 (1990).
Saks et al. (1996) "An engineered Tetrahymena tRNAGln for in Vivo Incorporation of Unnatural Amino Acids into Proteins by Nonsense Suppression" *J. Biol. Chem* 271(38):23169-23175.
Santoro & Schultz, *Proc. Natl. Acad Sci* USA, Apr. 2; 99(7):4185-90, 2002.
Santoro et al., *Nature Biotech*, 20:1044-1048, Oct. 2002.
Sayers et al., 5', 3' Exonuclease in phosphorothioate-based oligonucleotide-directed mutagenesis, *Nucleic Acids Res*., 16(3):791-802 (1988).
Shao & Tam, *J. Am. Chem. Soc*., 117:3893-3899 (1995).
Sharma et al., *FEBS Lett*., 467:37 (2000).
Sieber et al., *Nature Biotechnology*, 19:456-460 (2001).
Sprinzl et al., Compilation of tRNA sequences and sequences of tRNA genes, *Nucleic Acids Res*. 26:148-153 (1998).
Steer & Schimmel, Major anticodon-binding region missing from an archaebacterial tRNA synthetase, *J. Biol. Chem*. 274:35601-35606 (1999).
Subasinghe et al., Quisqualic acid analogues: synthesis of beta-heterocyclic 2-aminopropanoic acid derivatives and their activity at a novel quisqualate-sensitized site. *J. Med. Chem*. 35 4602-7 (1992).
Sussman et al., Crystal structure of yeast phenylalanine transfer RNA. I. Crystallographic refinement, *J. Mol. Biol*. 123:607-630 (1978).
Switzer et al., *J. Am. Chem. Soc*., 111:8322 (1989).
Tae et al., *J. Am. Chem. Soc*., 123:7439 (2001).
Tang et al., *Angew. Chem. Int. Ed. Engl*., 40:1494 (2001).
Turcatti et al., *J. Biol. Chem*., 271:19991 (1996).
van Hest & Tirrell, *FEBS Lett*., 428:68 (1998).
van Hest et al., *J. Am. Chem. Soc*., 122:1282 (2000).

Wakasugl et al., *Embo J.* 17:297-305 (1998).
Wang & Schultz, *Chem. and Biol.* 8:883-890 (2001).
Wang & Schultz, Expanding the genetic code, *Chem. Commun.*, 1:1-11 (2002).
Wang et al., A new functional suppressor tRNA/aminoacyl-tRNA synthetase pair for the in vivo incorporation of unnatural amino acids into proteins, *J. Am. Chem. Soc.* 122:5010-5011 (2000).
Wang et al., Expanding the genetic code of *Escherichia coli*, *Science*, 292:498-500 (2001).
Wang et al., *J. Am. Chem. Soc.* 124, 1836-1837(2002).
Weiner et al., A binding protein for L-glutamine and its relation to active transport in E. coli. *Archives of Biochemistry and Biophysics*, 142:715-717 (1971).
Whelihan & Schimmel, *Embo J.*, 16:2968 (1997).
Yarus, Translational efficiency of transfer RNA's: Use of an expanded anticodon, *Science* 218:646-652 (1982).
Zlokarnik et al., *Science*, 279, 84-88 (1998).

* cited by examiner

Fig. 2A
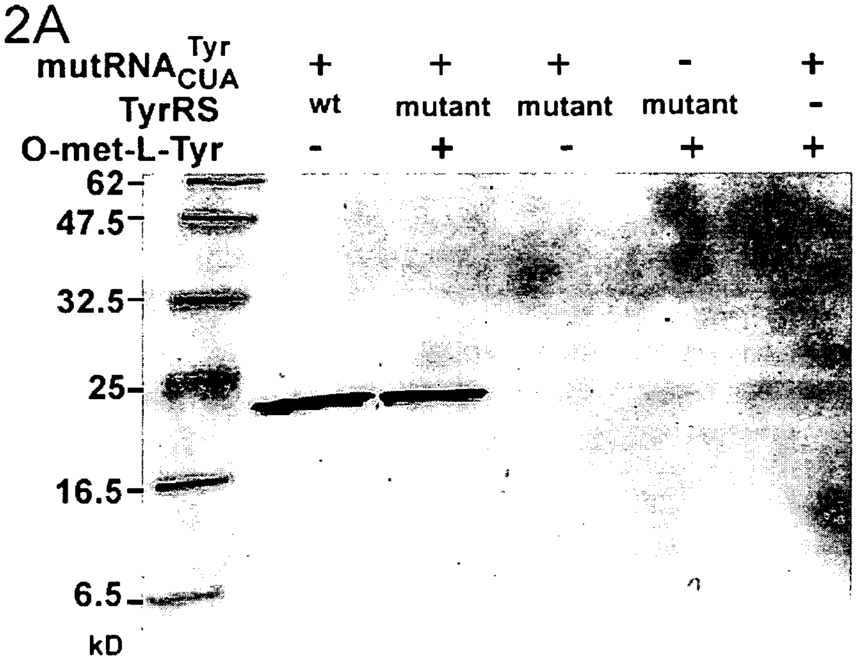
Fig. 2B
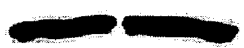
Fig. 2 mutRNA Tyr CUA + + + - +
TyrRS wt SS12 SS12 SS12 -
L-3-(2-naphthyl)-Ala - + - + +
60
50
40
30
25
20
15
kD

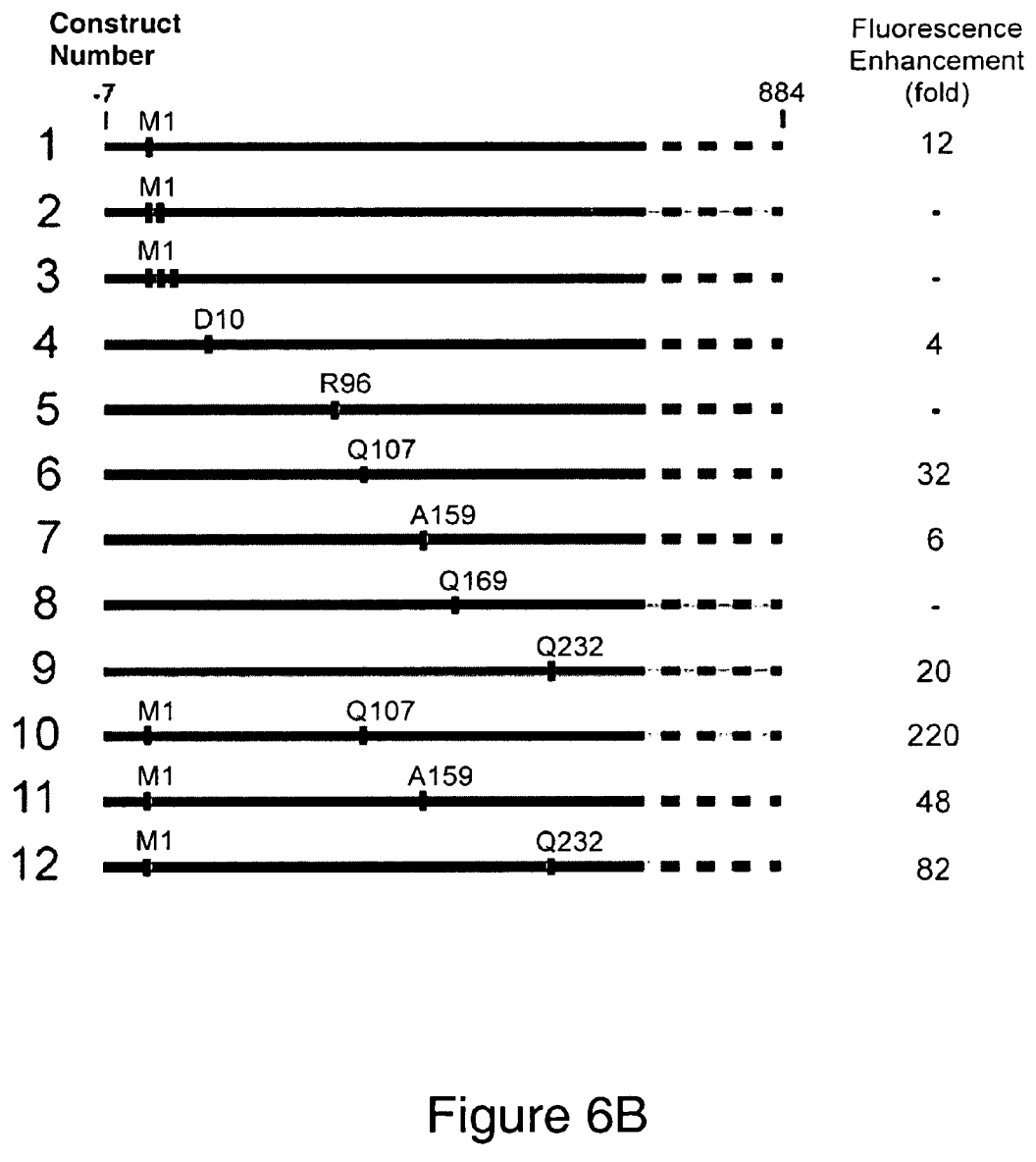

| Construct Number | Construct (-7 to 884) | Fluorescence Enhancement (fold) |
|---|---|---|
| 1 | M1 | 12 |
| 2 | M1 | - |
| 3 | M1 | - |
| 4 | D10 | 4 |
| 5 | R96 | - |
| 6 | Q107 | 32 |
| 7 | A159 | 6 |
| 8 | Q169 | - |
| 9 | Q232 | 20 |
| 10 | M1, Q107 | 220 |
| 11 | M1, A159 | 48 |
| 12 | M1, Q232 | 82 |

Figure 6B

| Cm $IC_{50}$ ($\mu$g/mL) | *p*IF-RS | *p*AF-RS | *O*AY-RS(1) |
|---|---|---|---|
| – Unnatural | < 5 | < 5 | < 5 |
| + Unnatural | 75 | 100 | 120 |

Figure 8C

Enzyme
in vivo

IN VIVO INCORPORATION OF UNNATURAL AMINO ACIDS

CROSS-REFERENCES TO RELATED APPLICATIONS

This application is a continuation of U.S. patent application Ser. No. 10/126,927 filed Apr. 19, 2002, and claims priority to and benefit of U.S. provisional patent application Ser. No. 60/285,030, filed Apr. 19, 2001, and U.S. provisional patent application Ser. No. 60/355,514, filed Feb. 6, 2002, the specifications of which are incorporated herein in their entirety.

STATEMENT REGARDING FEDERALLY SPONSORED RESEARCH AND DEVELOPMENT

The invention was made with United States Government support under Grant No. N0001498F0402 from the Office of Naval Research, Contract No. NIH GM62159 from the National Institutes of Health, and Contract Nos. DE-FG03-00ER45812, DE-AC03-76SF00098 from the Department of Energy. The United States Government has certain rights in the invention.

FIELD OF THE INVENTION

The invention relates to the field of protein biochemistry. In particular, the invention relates to the field of compositions and methods for producing proteins that include unnatural amino acids.

BACKGROUND OF THE INVENTION

Proteins carry out virtually all of the complex processes of life, from photosynthesis to signal transduction and the immune response. To understand and control these intricate activities, a better understanding of the relationship between the structure and function of proteins is needed.

Unlike small organic molecule synthesis wherein almost any structural change can be made to influence functional properties of a compound, the synthesis of proteins is limited to changes encoded by the twenty natural amino acids. The genetic code of every known organism, from bacteria to human, encodes the same twenty common amino acids. These amino acids can be modified by posttranslational modification of proteins, e.g., glycosylation, phosphorylation or oxidation, or in rarer instances, by the enzymatic modification of aminoacylated suppressor tRNAs, e.g., in the case of selenocysteine. Nonetheless, polypeptides, which are synthesized from only these 20 simple building blocks, carry out all of the complex processes of life.

Both site-directed and random mutagenesis, in which specific amino acids in a protein can be replaced with any of the other nineteen common amino acids, have become important tools for understanding the relationship between the structure and function of proteins. These methodologies have made possible the generation of proteins with enhanced properties, including stability, catalytic activity and binding specificity. Nevertheless, changes in proteins are limited to the 20 common amino acids, most of which have simple functional groups. See Knowles, J. R. Tinkering with enzymes: what are we learning? *Science*, 236(4806) 1252-1258 (1987); and, Zoller, M. J., Smith, M. Oligonucleotide-directed mutagenesis of DNA fragments cloned into M13 vectors, *Methods Enzymol*, 154:468-500 (1983). By expanding the genetic code to include additional amino acids with novel biological, chemical or physical properties, the properties of proteins, e.g., the size, acidity, nucleophilicity, hydrogen-bonding, hydrophobic properties, can be modified as compared to a protein composed of only amino acids from the 20 common amino acids, e.g., as in a naturally occurring protein.

Several strategies have been employed to introduce unnatural amino acids into proteins. The first experiments involved the derivatization of amino acids with reactive side-chains such as Lys, Cys and Tyr, for example, the conversion of lysine to $N^2$-acetyl-lysine. Chemical synthesis also provides a straightforward method to incorporate unnatural amino acids, but routine solid-phase peptide synthesis is generally limited to small peptides or proteins with less than 100 residues. With the recent development of enzymatic ligation and native chemical ligation of peptide fragments, it is possible to make larger proteins, but the method is not easily scaled. See, e.g., P. E. Dawson and S. B. H. Kent, *Annu. Rev. Biochem*., 69:923 (2000). A general in vitro biosynthetic method in which a suppressor tRNA chemically acylated with the desired unnatural amino acid is added to an in vitro extract capable of supporting protein biosynthesis, has been used to site-specifically incorporate over 100 unnatural amino acids into a variety of proteins of virtually any size. See, e.g., V. W. Cornish, D. Mendel and P. G. Schultz, *Angew. Chem. Int. Ed. Engl*., 1995, 34:621 (1995); C. J. Noren, S. J. Anthony-Cahill, M. C. Griffith, P. G. Schultz, A general method for site-specific incorporation of unnatural amino acids into proteins, *Science* 244 182-188 (1989); and, J. D. Bain, C. G. Glabe, T. A. Dix, A. R. Chamberlin, E. S. Diala, Biosynthetic site-specific incorporation of a non-natural amino acid into a polypeptide, *J. Am. Chem. Soc*. 111 8013-8014 (1989). A broad range of functional groups has been introduced into proteins for studies of protein stability, protein folding, enzyme mechanism, and signal transduction. Although these studies demonstrate that the protein biosynthetic machinery tolerates a wide variety of amino acid side chains, the method is technically demanding, and yields of mutant proteins are low.

Over 50 years ago, it was found that many analogs of natural amino acids inhibit the growth of bacteria. Analysis of the proteins produced in the presence of these amino acid analogs revealed that they had been substituted for their natural counterparts, to various extents. See, e.g., M. H. Richmond, *Bacteriol. Rev*., 26:398 (1962). This occurs because the aminoacyl-tRNA synthetase, the enzyme responsible for the attachment of the correct amino acid to its cognate tRNA, cannot rigorously distinguish the analog from the corresponding natural amino acid. For instance, norleucine is charged by methionyl-tRNA synthetase, and p-fluorophenylalanine is charged by phenylalanine-tRNA synthetase. See, D. B. Cowie, G. N. Cohen, E. T. Bolton and H. DeRrobinchon-Szulmajst, *Biochim. Biophys. Acta*, 1959, 34:39 (1959); and, R. Munier and G. N. Cohen, *Biochim. Biophys. Acta*, 1959, 31:378 (1959).

An in vivo method, termed selective pressure incorporation, was later developed to exploit the promiscuity of wild-type synthetases. See, e.g., N. Budisa, C. Minks, S. Alefelder, W. Wenger, F. M. Dong, L. Moroder and R. Huber, *FASEB J*., 13:41 (1999). An auxotrophic strain, in which the relevant metabolic pathway supplying the cell with a particular natural amino acid is switched off, is grown in minimal media containing limited concentrations of the natural amino acid, while transcription of the target gene is repressed. At the onset of a stationary growth phase, the natural amino acid is depleted and replaced with the unnatural amino acid analog. Induction of expression of the recombinant protein results in the accumulation of a protein containing the unnatural analog. For example, using this strategy, o, m and p-fluorophenylalanines have been incorporated into proteins, and exhibit two characteristic shoulders in the UV spectrum which can be easily identified, see, e.g., C. Minks, R. Huber, L. Moroder and N. Budisa, *Anal. Biochem*., 284:29 (2000); trifluoromethionine has been used to replace methionine in bacteriophage T4 lysozyme to study its interaction with chitooligosaccharide ligands by $^{19}$F NMR, see, e.g., H. Duewel, E. Daub, V. Robinson and J. F. Honek, *Biochemistry*, 36:3404 (1997); and trifluoroleucine has been inserted in place of leucine, resulting in increased thermal and chemical stability of a leucine-zipper protein. See, e.g., Y. Tang, G. Ghirlanda, W. A. Petka, T. Nakajima, W. F. DeGrado and D. A. Tirrell, Angew. *Chem. Int. Ed. Engl*., 40:1494 (2001). Moreover, selenomethionine and telluromethionine are incorporated into various recombinant proteins to facilitate the solution of phases in X-ray crystallography. See, e.g., W. A. Hendrickson, J. R. Horton and D. M. Lemaster, *EMBO J*., 9:1665 (1990); J. O. Boles, K. Lewinski, M. Kunkle, J. D. Odom, B. Dunlap, L. Lebioda and M. Hatada, *Nat. Struct. Biol*., 1:283 (1994); N. Budisa, B. Steipe, P. Demange, C. Eckerskorn, J. Kellermann and R. Huber, *Eur. J. Biochem*., 230:788 (1995); and, N. Budisa, W. Kambrock, S. Steinbacher, A. Humm, L. Prade, T. Neuefeind, L. Moroder and R. Huber, *J. Mol. Biol*., 270:616 (1997). Methionine analogs with alkene or alkyne functionalities have also been inserted efficiently, allowing for additional modification of proteins by chemical means. See, e.g., J. C. M. vanHest and D. A. Tirrell, *FEBS Lett*., 428:68 (1998); J. C. M. van Hest, K. L. Kiick and D. A. Tirrell, *J. Am. Chem. Soc*., 122:1282 (2000); and, K. L. Kiick and D. A. Tirrell, Tetrahedron, 56:9487 (2000).

The success of this method depends on the recognition of the unnatural amino acid analogs by aminoacyl-tRNA synthetases, which, in general, require high selectivity to insure the fidelity of protein translation. Therefore, the range of chemical functionality accessible via this route is limited. For instance, although thiaproline can be incorporated quantitatively into proteins, oxaproline and selenoproline cannot. See, N. Budisa, C. Minks, F. J. Medrano, J. Lutz, R. Huber and L. Moroder, *Proc. Natl. Acad. Sci. USA*, 95:455 (1998). One way to expand the scope of this method is to relax the substrate specificity of aminoacyl-tRNA synthetases, which has been achieved in a limited number of cases. For example, it was found that replacement of $Ala^{294}$ by Gly in *Escherichia coli* phenylalanyl-tRNA synthetase (PheRS) increases the size of substrate binding pocket, and results in the acylation of tRNAPhe by p-Cl-phenylalanine (p-Cl-Phe). See, M. Ibba, P. Kast and H. Hennecke, *Biochemistry*, 33:7107 (1994). An *Escherichia coli* strain harboring this mutant PheRS allows the incorporation of p-Cl-phenylalanine or p-Br-phenylalanine in place of phenylalanine. See, e.g., M. Ibba and H. Hennecke, *FEBS Lett*., 364:272 (1995); and, N. Sharma, R. Furter, P. Kast and D. A. Tirrell, *FEBS Lett*., 467:37 (2000). Similarly, a point mutation Phe130Ser near the amino acid binding site of *Escherichia coli* tyrosyl-tRNA synthetase was shown to allow azatyrosine to be incorporated more efficiently than tyrosine. See, F. Hamano-Takaku, T. Iwama, S. Saito-Yano, K. Takaku, Y. Monden, M. Kitabatake, D. Soll and S. Nishimura, *J. Biol. Chem*., 275:40324 (2000).

The fidelity of aminoacylation is maintained both at the level of substrate discrimination and proofreading of non-cognate intermediates and products. Therefore, an alternative strategy to incorporate unnatural amino acids into proteins in vivo is to modify synthetases that have proofreading mechanisms. These synthetases cannot discriminate and therefore activate amino acids that are structurally similar to the cognate natural amino acids. This error is corrected at a separate site, which deacylates the mischarged amino acid from the tRNA to maintain the fidelity of protein translation. If the proofreading activity of the synthetase is disabled, structural analogs that are misactivated may escape the editing function and be incorporated. This approach has been demonstrated recently with the valyl-tRNA synthetase (ValRS). See, V. Doring, H. D. Mootz, L. A. Nangle, T. L. Hendrickson, V. de Crecy-Lagard, P. Schimmel and P. Marliere, *Science*, 292:501 (2001). ValRS can misaminoacylate tRNAVal with Cys, Thr, or aminobutyrate (Abu); these noncognate amino acids are subsequently hydrolyzed by the editing domain. After random mutagenesis of the *Escherichia coli* chromosome, a mutant *Escherichia coli* strain was selected that has a mutation in the editing site of ValRS. This edit-defective ValRS incorrectly charges tRNAVal with Cys. Because Abu sterically resembles Cys (—SH group of Cys is replaced with —CH3 in Abu), the mutant ValRS also incorporates Abu into proteins when this mutant *Escherichia coli* strain is grown in the presence of Abu. Mass spectrometric analysis shows that about 24% of valines are replaced by Abu at each valine position in the native protein.

At least one major limitation of the methods described above is that all sites corresponding to a particular natural amino acid throughout the protein are replaced. The extent of incorporation of the natural and unnatural amino acid may also vary—only in rare cases can quantitative substitution be achieved since it is difficult to completely deplete the cognate natural amino acid inside the cell. Another limitation is that these strategies make it difficult to study the mutant protein in living cells, because the multisite incorporation of analogs often results in toxicity. Finally, this method is applicable in general only to close structural analogs of the common amino acids, again because substitutions must be tolerated at all sites in the genome.

Solid-phase synthesis and semisynthetic methods have also allowed for the synthesis of a number of small proteins containing novel amino acids. For example, see the following publications and references cited within, which are as follows: Crick, F. J. C., Barrett, L. Brenner, S. Watts-Tobin, R. General nature of the genetic code for proteins. *Nature*, 1227-1232 (1961); Hofmann, K., Bohn, H. Studies on polypeptides. XXXVI. The effect of pyrazole-imidazole replacements on the S-protein activating potency of an S-peptide fragment, *J. Am Chem*, 5914-5919 (1966); Kaiser, E. T. Synthetic approaches to biologically active peptides and proteins including enyzmes, *Acc Chem Res*, 47-54 (1989); Nakatsuka, T., Sasaki, T., Kaiser, E. T. Peptide segment coupling catalyzed by the semisynthetic enzyme thiosubtilisin, *J Am Chem Soc*, 3808-3810 (1987); Schnolzer, M., Kent, S B H. Constructing proteins by dovetailing unprotected synthetic peptides: backbone-engineered HIV protease, *Science*, 221-225 (1992); Chaiken, I. M. Semisynthetic peptides and proteins, *CRC Crit Rev Biochem*, 255-301 (1981); Offord, R. E. Protein engineering by chemical means? *Protein Eng*., 151-157 (1987); and, Jackson, D. Y., Burnier, J., Quan, C., Stanley, M., Tom, J., Wells, J. A. A Designed Peptide Ligase for Total Synthesis of Ribonuclease A with Unnatural Catalytic Residues, *Science*, 243 (1994).

Chemical modification has been used to introduce a variety of unnatural side chains, including cofactors, spin labels and oligonucleotides into proteins in vitro. See, e.g., Corey, D. R., Schultz, P. G. Generation of a hybrid sequence-specific single-stranded deoxyribonuclease, *Science*, 1401-1403 (1987); Kaiser, E. T., Lawrence D. S., Rokita, S. E. The chemical modification of enzymatic specificity, *Rev Biochem*, 565-595 (1985); Kaiser, E. T., Lawrence, D. S. Chemical mutation of enyzme active sites, *Science*, 505-511 (1984); Neet, K. E., Nanci A, Koshland, D. E. Properties of thiol-subtilisin, *J Biol. Chem*, 6392-6401 (1968); Polgar, L. B., M. L. A new enzyme containing a synthetically formed active site. Thiol-subtilisin. *J. Am Chem Soc*, 3153-3154 (1966); and, Pollack, S. J., Nakayama, G. Schultz, P. G. Introduction of nucleophiles and spectroscopic probes into antibody combining sites, *Science*, 1038-1040 (1988).

Alternatively, biosynthetic methods that employ chemically modified aminoacyl-tRNAs have been used to incorporate several biophysical probes into proteins synthesized in vitro. See the following publications and references cited within: Brunner, J. New Photolabeling and crosslinking methods, *Annu. Rev Biochem*, 483-514 (1993); and, Krieg, U. C., Walter, P., Hohnson, A. E. Photocrosslinking of the signal sequence of nascent preprolactin of the 54-kilodalton polypeptide of the signal recognition particle, *Proc. Natl. Acad. Sci*, 8604-8608 (1986).

Previously, it has been shown that unnatural amino acids can be site-specifically incorporated into proteins in vitro by the addition of chemically aminoacylated suppressor tRNAs to protein synthesis reactions programmed with a gene containing a desired amber nonsense mutation. Using these approaches, one can substitute a number of the common twenty amino acids with close structural homologues, e.g., fluorophenylalanine for phenylalanine, using strains auxotropic for a particular amino acid. See, e.g., Noren, C. J., Anthony-Cahill, Griffith, M. C., Schultz, P. G. A general method for site-specific incorporation of unnatural amino acids into proteins, *Science*, 244: 182-188 (1989); M. W. Nowak, et al., *Science* 268:439-42 (1995); Bain, J. D., Glabe, C. G., Dix, T. A., Chamberlin, A. R., Diala, E. S. Biosynthetic site-specific Incorporation of a non-natural amino acid into a polypeptide, *J. Am Chem Soc*, 111:8013-8014 (1989); N. Budisa et al., *FASEB J.* 13:41-51 (1999); Ellman, J. A., Mendel, D., Anthony-Cahill, S., Noren, C. J., Schultz, P. G. Biosynthetic method for introducing unnatural amino acids site-specifically into proteins, *Methods in Enz*., 301-336 (1992); and, Mendel, D., Cornish, V. W. & Schultz, P. G. Site-Directed Mutagenesis with an Expanded Genetic Code, *Annu Rev Biophys. Biomol Struct*. 24, 435-62 (1995).

For example, a suppressor tRNA was prepared that recognized the stop codon UAG and was chemically aminoacylated with an unnatural amino acid. Conventional site-directed mutagenesis was used to introduce the stop codon TAG, at the site of interest in the protein gene. See, e.g., Sayers, J. R., Schmidt, W. Eckstein, F. 5', 3' Exonuclease in phosphorothioate-based olignoucleotide-directed mutagensis, *Nucleic Acids Res*, 791-802 (1988). When the acylated suppressor tRNA and the mutant gene were combined in an in vitro transcription/translation system, the unnatural amino acid was incorporated in response to the UAG codon which gave a protein containing that amino acid at the specified position. Experiments using [$^3$H]-Phe and experiments with $\alpha$-hydroxy acids demonstrated that only the desired amino acid is incorporated at the position specified by the UAG codon and that this amino acid is not incorporated at any other site in the protein. See, e.g., Noren, et al, supra; and, Ellman, J. A., Mendel, D., Schultz, P. G. Site-specific incorporation of novel backbone structures into proteins, *Science*, 197-200 (1992).

In general, these in vitro approaches are limited by difficulties in achieving site-specific incorporation of the amino acids, by the requirement that the amino acids be simple derivatives of the common twenty amino acids or problems inherent in the synthesis of large proteins or peptide fragments.

Microinjection techniques have also been use incorporate unnatural amino acids into proteins. See, e.g., M. W. Nowak, P. C. Kearney, J. R. Sampson, M. E. Saks, C. G. Labarca, S. K. Silverman, W. G. Zhong, J. Thorson, J. N. Abelson, N. Davidson, P. G. Schultz, D. A. Dougherty and H. A. Lester, *Science*, 268:439 (1995); and, D. A. Dougherty, *Curr. Opin. Chem. Biol*., 4:645 (2000). A *Xenopus oocyte* was coinjected with two RNA species made in vitro: an mRNA encoding the target protein with a UAG stop codon at the amino acid position of interest and an amber suppressor tRNA aminoacylated with the desired unnatural amino acid. The translational machinery of the oocyte then inserts the unnatural amino acid at the position specified by UAG. This method has allowed in vivo structure-function studies of integral membrane proteins, which are generally not amenable to in vitro expression systems. Examples include the incorporation of a fluorescent amino acid into tachykinin neurokinin-2 receptor to measure distances by fluorescence resonance energy transfer, see, e.g., G. Turcatti, K. Nemeth, M. D. Edgerton, U. Meseth, F. Talabot, M. Peitsch, J. Knowles, H. Vogel and A. Chollet, *J. Biol. Chem*., 271:19991 (1996); the incorporation of biotinylated amino acids to identify surface-exposed residues in ion channels, see, e.g., J. P. Gallivan, H. A. Lester and D. A. Dougherty, *Chem. Biol*., 4:739 (1997); the use of caged tyrosine analogs to monitor conformational changes in an ion channel in real time, see, e.g., J. C. Miller, S. K. Silverman, P. M. England, D. A. Dougherty and H. A. Lester, Neuron, 20:619 (1998); and, the use of alpha hydroxy amino acids to change ion channel backbones for probing their gating mechanisms. See, e.g., P. M. England, Y. Zhang, D. A. Dougherty and H. A. Lester, *Cell*, 96:89 (1999); and, T. Lu, A. Y. Ting, J. Mainland, L. Y. Jan, P. G. Schultz and J. Yang, *Nat. Neurosci*., 4:239 (2001).

However, there are limitations microinjection method, e.g., the suppressor tRNA has to be chemically aminoacylated with the unnatural amino acid in vitro, and the acylated tRNA is consumed as a stoichiometric reagent during translation and cannot be regenerated. This limitation results in poor suppression efficiency and low protein yields, necessitating highly sensitive techniques to assay the mutant protein such as electrophysiological measurements. Moreover, this method is only applicable to cells that can be microinjected.

The ability to incorporate unnatural amino acids directly into proteins in vivo offers the advantages of high yields of mutant proteins, technical ease, the potential to study the mutant proteins in cells or possibly in living organisms and the use of these mutant proteins in therapeutic treatments. The ability to include unnatural amino acids with various sizes, acidities, nucleophilicities, hydrophobicities, and other properties into proteins can greatly expand our ability to rationally and systematically manipulate the structures of proteins, both to probe protein function and create new proteins or organisms with novel properties. However, the process is difficult, because the complex nature of tRNA-synthetase interactions that are required to achieve a high degree of fidelity in protein translation.

In one attempt to site-specifically incorporate para-F-Phe, a yeast amber suppressor tRNAPheCUA/phenylalanyl-tRNA synthetase pair was used in a p-F-Phe resistant, Phe auxotrophic *Escherichia coli* strain. See, e.g., R. Furter,

*Protein Sci*., 7:419 (1998). Because yeast PheRS does not have high substrate specificity for p-F-Phe, the mutagenesis site was translated with only 64-75% p-F-Phe and the remainder as Phe and Lys even in the excess of p-F-Phe added to the growth media. In addition, at the Phe codon positions, 7% p-F-Phe was found, indicating that the endogenous *Escherichia coli* PheRS incorporates p-F-Phe in addition to Phe. Besides of its translational infidelity, e.g., the suppressor tRNA and PheRS are not truly orthogonal, this approach is not generally applicable to other unnatural amino acids.

Therefore, improvements to the process are needed to provide more efficient and effective methods to alter the biosynthetic machinery of the cell. The present invention addresses these and other needs, as will be apparent upon review of the following disclosure.

SUMMARY OF THE INVENTION

The present invention provides a variety of methods for making and using translation systems that can incorporate unnatural amino acids into proteins, as well as related compositions. Proteins comprising unnatural amino acids made by the translation system are also a feature of the invention. Both known and new unnatural amino acids can be incorporated into proteins using the translation system of the invention. The invention further provides novel unnatural amino acids; various compositions including the unnatural amino acids, e.g., proteins and cells including unnatural amino acids; chemical and biosynthetic methods for producing unnatural amino acids; and methods for producing and compositions comprising an autonomous twenty-one amino acid cell.

Thus, in one aspect, the present invention provides compositions comprising a translation system. The translation system comprises an orthogonal tRNA (O-tRNA) and an orthogonal aminoacyl tRNA synthetase (O—RS). Typically, the O—RS preferentially aminoacylates the O—tRNA with at least one unnatural amino acid in the translation system and the O—tRNA recognizes at least one selector codon. The translation system thus inserts the unnatural amino acid into a protein produced in the system, in response to an encoded selector codon.

Typical translation systems include cells, such as bacterial cells (e.g., *Escherichia coli*), archeaebacterial cells, eukaryotic cells (e.g., yeast cells, mammalian cells, plant cells, insect cells), or the like. Alternatively, the translation system comprises an in vitro translation system, e.g., a translation extract including a cellular extract.

Example O-tRNAs comprise a nucleic acid comprising a polynucleotide sequence selected from the group consisting of: SEQ ID NO:1-3 and/or a complementary polynucleotide sequence thereof. Similarly, example O—RS include polypeptides selected from the group consisting of: a polypeptide comprising an amino acid sequence selected from the group consisting of SEQ ID NO: 35-66 and a polypeptide encoded by a nucleic acid comprising a polynucleotide sequence selected from the group consisting of: SEQ ID NO: 4-34 and a complementary polynucleotide sequence thereof.

Examples of unnatural amino acids that can be used by the translation system include: an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or any combination thereof; an amino acid with a photoactivatable cross-linker; a spin-labeled amino acid; a fluorescent amino acid; an amino acid with a novel functional group; an amino acid that covalently or noncovalently interacts with another molecule; a metal binding amino acid; a metal-containing amino acid; a radioactive amino acid; a photocaged and/or photoisomerizable amino acid; a biotin or biotin-analogue containing amino acid; a glycosylated or carbohydrate modified amino acid; a keto containing amino acid; amino acids comprising polyethylene glycol or polyether; a heavy atom substituted amino acid; a chemically cleavable or photocleavable amino acid; an amino acid with an elongated side chain; an amino acid containing a toxic group; a sugar substituted amino acid, e.g., a sugar substituted serine or the like; a carbon-linked sugar-containing amino acid; a redox-active amino acid; an $\alpha$-hydroxy containing acid; an amino thio acid containing amino acid; an $\alpha,\alpha$ disubstituted amino acid; a $\beta$-amino acid; and a cyclic amino acid other than proline.

For example, the unnatural amino acid can be an O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAc$\beta$-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, and an isopropyl-L-phenylalanine in one embodiment, the at least one unnatural amino acid is an O-methyl-L-tyrosine. In one specific example embodiment, the at least one unnatural amino acid is an L-3-(2-naphthyl)alanine. In another set of specific examples, the at least one unnatural amino acid is an amino-, isopropyl-, or O-allyl-containing phenylalanine analogue.

Any of a variety of selector codons can be used in the present invention, including nonsense codons, rare codons, four (or more) base codons, or the like. For example, in one embodiment, the at least one selector codon is an amber codon.

A variety of exemplar translation systems are provided herein, including e.g., an *Escherichia coli* cell comprising a $mtRNA_{CUA}^{Tyr}$ and a mutant TyrRS (LWJ16), where the mutant TyrRS (LWJ16) preferentially aminoacylates the $mtRNA_{CUA}^{Tyr}$ with O-methyl-L-tyrosine in the cell and the cell uses the $mtRNA_{CUA}^{Tyr}$ to recognize an amber codon. In another example, an *Escherichia coli* cell comprising a $mtRNA_{CUA}^{Tyr}$ and an SS12-TyrRS is provided, where the SS12-TyrRS preferentially aminoacylates the $mtRNA_{CUA}^{Tyr}$ with L-3-(2-naphthyl)alanine in the cell and the cell uses the $mtRNA_{CUA}^{Tyr}$ to recognize an amber codon.

The translation system herein provides the ability to synthesize proteins that comprise unnatural amino acids in usefully large quantities. For example, proteins comprising at least one unnatural amino acid can be produced at a concentration of at least about 10, 50, 100 or more micrograms per liter, e.g., in a composition comprising a cell extract, a buffer, a pharmaceutically acceptable excipient, and/or the like.

Another aspect of the present invention provides for the production of proteins that are homologous to any available protein, but comprising one or more unnatural amino acid homologue. For example, therapeutic proteins can be made that comprise one or more unnatural amino acid and are homologous to one or more therapeutic protein. For example, in one aspect, the protein is homologous to a therapeutic or other protein such as: a cytokine, a growth factor, a growth factor receptor, an interferon, an interleukin, an inflammatory molecule, an oncogene product, a peptide hormone, a signal transduction molecule, a steroid hormone receptor, a transcriptional activator, a transcriptional suppressor, erythropoietin (EPO), insulin, human growth hormone, epithelial Neutrophil Activating Peptide-78, GROα/MGSA, GROβ, GROγ, MIP-1α, MIP-1β, MCP-1, hepatocyte growth factor, insulin-like growth factor, leukemia inhibitory factor, oncostatin M, PD-ECSF, PDGF, pleiotropin, SCF, c-kit ligand, VEGEF, G-CSF, IL-1, IL-2, IL-8, IGF-I, IGF-II, FGF (fibroblast growth factor), PDGF, TNF, TGF-α, TGF-β, EGF (epidermal growth factor), KGF (keratinocyte growth factor), SCF/c-Kit, CD40L/CD40, VLA-4/VCAM-1, ICAM-1/LFA-1, hyalurin/CD44, Mos, Ras, Raf, Met; p53, Tat, Fos, Myc, Jun, Myb, Rel, estrogen receptor, progesterone receptor, testosterone receptor, aldosterone receptor, LDL receptor, and/or corticosterone. In another set of embodiments, the protein is homologous to a therapeutic or other protein such as: an Alpha-1 antitrypsin, an Angiostatin, an Antihemolytic factor, an antibody, an Apolipoprotein, an Apoprotein, an Atrial natriuretic factor, an Atrial natriuretic polypeptide, an Atrial peptide, a C—X—C chemokine, T39765, NAP-2, ENA-78, a Gro-a, a Gro-b, a Gro-c, an IP-10, a GCP-2, an NAP-4, an SDF-1, a PF4, a MIG, a Calcitonin, a c-kit ligand, a cytokine, a CC chemokine, a Monocyte chemoattractant protein-1, a Monocyte chemoattractant protein-2, a Monocyte chemoattractant protein-3, a Monocyte inflammatory protein-1 alpha, a Monocyte inflammatory protein-1 beta, RANTES, I309, R83915, R91733, HCC1, T58847, D31065, T64262, a CD40, a CD40 ligand, a C-kit Ligand, a Collagen, a Colony stimulating factor (CSF), a Complement factor 5*a*, a Complement inhibitor, a Complement receptor 1, a cytokine, an epithelial Neutrophil Activating Peptide-78, a GROα/MGSA, a GROβ, a GROγ, a MIP-1α, a MIP-1β, a MCP-1, an Epidermal Growth Factor (EGF), an epithelial Neutrophil Activating Peptide, an Erythropoietin (EPO), an Exfoliating toxin, a Factor IX, a Factor VII, a Factor VIII, a Factor X, a Fibroblast Growth Factor (FGF), a Fibrinogen, a Fibronectin, a G-CSF, a GM-CSF, a Glucocerebrosidase, a Gonadotropin, a growth factor, a growth factor receptor, a Hedgehog protein, a Hemoglobin, a Hepatocyte Growth Factor (HGF), a Hirudin, a Human serum albumin, an ICAM-1, an ICAM-1 receptor, an LFA-1, an LFA-1 receptor, an Insulin, an Insulin-like Growth Factor (IGF), an IGF-I, an IGF-II, an interferon, an IFN-α, an IFN-β, an IFN-γ, an interleukin, an IL-1, an IL-2, an IL-3, an IL-4, an IL-5, an IL-6, an IL-7, an IL-8, an IL-9, an IL-10, an IL-11, an IL-12, a Keratinocyte Growth Factor (KGF), a Lactoferrin, a leukemia inhibitory factor, a Luciferase, a Neurturin, a Neutrophil inhibitory factor (NIF), an oncostatin M, an Osteogenic protein, an oncogene product, a Parathyroid hormone, a PD-ECSF, a PDGF, a peptide hormone, a Human Growth Hormone, a Pleiotropin, a Protein A, a Protein G, a Pyrogenic exotoxins A, B, or C, a Relaxin, a Renin, an SCF, a Soluble complement receptor I, a Soluble I-CAM 1, a Soluble interleukin receptors, a Soluble TNF receptor, a Somatomedin, a Somatostatin, a Somatotropin, a Streptokinase, a Superantigens, a *Staphylococcal enterotoxins*, an SEA, an SEB, an SEC1, an SEC2, an SEC3, an SED, an SEE, a steroid hormone receptor, a Superoxide dismutase, a Toxic shock syndrome toxin, a Thymosin alpha 1, a Tissue plasminogen activator, a tumor growth factor (TGF), a TGF-α, a TGF-β, a Tumor Necrosis Factor, a Tumor Necrosis Factor alpha, a Tumor necrosis factor beta, a Tumor necrosis factor receptor (TNFR), a VLA-4 protein, a VCAM-1 protein, a Vascular Endothelial Growth Factor (VEGEF), a Urokinase, a Mos, a Ras, a Raf, a Met; a p53, a Tat, a Fos, a Myc, a Jun, a Myb, a Rel, an estrogen receptor, a progesterone receptor, a testosterone receptor, an aldosterone receptor, an LDL receptor, and/or a corticosterone. In one aspect, the compositions herein comprise a protein comprising an unnatural amino acid and a pharmaceutically acceptable exipient, including, e.g., any of the proteins noted above and a pharmaceutically acceptable exipient.

Homology to the polypeptide can be inferred by performing a sequence alignment, e.g., using BLASTN or BLASTP, e.g., set to default parameters. For example, in one embodiment, the protein is at least about 50%, at least about 75%, at least about 80%, at least about 90% or at least about 95% identical to a known therapeutic protein (e.g., a protein present in Genebank or other available databases). For example, in one preferred embodiment, the therapeutic protein is erythropoeitin (EPO).

The protein of interest can contain 1, 2, 3, 4, 5, 6, 7, 6, 9, 10, 11, 12, 13, 14, 15 or more unnatural amino acids. The unnatural amino acids can be the same or different, e.g., there can be 1, 2, 3, 4, 5, 6, 7, 6, 9, 10, 11, 12, 13, 14, 15 or more different sites in the protein that comprise 1, 2, 3, 4, 5, 6, 7, 6, 9, 10, 11, 12, 13, 14, 15 or more different unnatural amino acids. For example, in one embodiment, the protein is DHFR, and the at least one unnatural amino acid is selected from the group consisting of O-methyl-L-tyrosine and L-3-(2-naphthyl)alanine.

The present invention also provides methods for producing at least one protein in a translation system such that the at least one protein comprises at least one unnatural amino acid. In the methods, the translation system is provided with at least one nucleic acid comprising at least one selector codon, wherein the nucleic acid encodes the at least one protein. The translation system is also provided with an orthogonal tRNA (O-tRNA), that functions in the translation system and recognizes the at least one selector codon and an orthogonal aminoacyl tRNA synthetase (O—RS), that preferentially aminoacylates the O-tRNA with the at least one unnatural amino acid in the translation system. The translation system is also provided with the at least one unnatural amino, thereby producing, in the translation system, the at least one protein comprising the at least one unnatural amino acid.

All of the above structural features of the compositions can be embodied in the methods, e.g., types of translation systems (e.g., cells, cell extracts, etc.), types of proteins produced in the translation systems (e.g., EPO homologues and the other proteins noted herein) specific mutant proteins, specific unnatural amino acids, and the like.

In one aspect, the protein(s) comprising unnatural amino acids that are produced are processed and modified in a cell-dependent manner. This provides for the production of proteins that are stably folded, glycosylated, or otherwise modified by the cell.

The unnatural amino acid is optionally provided exogenously to the translation system. Alternately, e.g., where the translation system is a cell, the unnatural amino acid can be biosynthesized by the translation system.

In one specific example embodiment, the invention provides methods for producing in an *Escherichia coli* cell at least one protein comprising at least one O-methyl-L-tyrosine. The method includes providing the translation system with at least one nucleic acid comprising an amber codon, wherein the nucleic acid encodes the at least one protein; providing the translation system with a $mtRNA_{CUA}^{Tyr}$, wherein the $mtRNA_{CUA}^{Tyr}$ functions in the cell and wherein the $mtRNA_{CUA}^{Tyr}$ recognizes the amber codon; providing the translation system with a mutant TyrRS (LWJ16), wherein the mutant TyrRS (LWJ16) aminoacylates the $mtRNA_{CUA}^{Tyr}$ with the O-methyl-L-tyrosine in the cell; and, providing the cell with the O-methyl-L-tyrosine, thereby producing in the cell at least one protein comprising the O-methyl-L-tyrosine.

In another example embodiment, the invention provides a method for producing in an *Escherichia coli* cell at least one protein comprising at least one L-3-(2-naphthyl)alanine. In this example embodiment, the method includes: providing the translation system with at least one nucleic acid comprising an amber codon, wherein the nucleic acid encodes the at least one protein; providing the cell with a $mtRNA_{CUA}^{Tyr}$, wherein the $mtRNA_{CUA}^{Tyr}$ functions in the cell and wherein the $mtRNA_{CUA}^{Tyr}$ recognizes the amber codon; providing the cell with an SS12-TyrRS, wherein the SS12-TyrRS aminoacylates the $mtRNA_{CUA}^{Tyr}$ with the L-3-(2-naphthyl)alanine in the cell; and, providing the cell with the L-3-(2-naphthyl)alanine, thereby producing in the cell at least one protein comprising the L-3-(2-naphthyl)alanine.

In another aspect, the present invention provides unnatural amino acids, e.g., meta substituted phenylalanine analogues, such as 3-acetyl-phenylalanine and 3-methoxy phenylalanine; tyrosine analogues, such as 4-allyl tyrosine; glycosylated amino acids, and the like.

Various compositions comprising unnatural amino acids, e.g., proteins and cells comprising the unnatural amino acids of the invention, are also provided. For example, compositions comprising an unnatural amino acid and an orthogonal tRNA, e.g., covalently bonded, are provided. Compositions comprising unnatural amino acids and an orthogonal aminoacyl tRNA synthetase, e.g., hydrogen bonded, are also provided.

In another aspect, the present invention provides methods of synthesizing amino acids. For example, 4-allyl-L-tyrosine, is typically synthesized by reacting a protected tyrosine with allyl bromide, e.g., in the presence of sodium hydride and DMF, and deprotecting to yield 4-allyl-L-tyrosine. Typically an NBoc or Fmoc protected tyrosine is used, e.g., with an acidic deprotection, e.g., in the presence of hydrochloric acid and dioxane. The final product is optionally extracted, e.g., with ethanol or dichloromethane.

Meta-substituted phenylalanine analogues are typically synthesized by condensing diethylacetamidomalonate and a meta-substituted benzyl bromide. The product of the condensation is then typically hydrolyzed to yield the meta-substituted phenylalanine analogue, e.g., a keto, acetyl, or methoxy substituted phenylalanine such as 3-methoxy-phenylalanine or 3-acetyl-phenylalanine. The desired meta substituted benzyl bromide is optionally synthesized by reacting N-bromosuccinimide (NBS) with 3-methylacetophenone to produce a brominated product, and crystallizing the brominated product in a hexane solution. The crystallization yields a monobromide product as opposed to a mixture of a monobromide and a dibromide.

In another aspect, the present invention provides biosynthetic methods for producing unnatural amino acids. For example, glycosylated amino acids are optionally synthesized in vivo, e.g., by transforming a cell with a plasmid comprising a gene for an N-acetyl-galactosaminidase, a transglycosylase, or a serine-glycosylhydrolase. The cell then produces the desired glycosylated amino acid, e.g. from cellular resources. In another example, p-aminophenylalanine is synthesized, e.g., in vivo, by enzymatically converting chorismate to 4-amino-4-deoxychorismic acid; which is enzymatically converted to 4-amino-4-deoxyprephenic acid; and enzymatically converting the 4-amino-4-deoxyprephenic acid to p-aminophenyl-pyruvic acid, which is enzymatically converted to p-aminophenylalanine. The enzymatic conversions are typically performed using a 4-amino-4-deoxychorismate synthase, e.g., PapA, a chorismate mutase, e.g., Pap B, and a prephenate dehydrogenase, e.g., PapC, respectively. The final step is typically performed by contacting the p-aminophenyl-pyruvic acid with an aminotransferease, e.g., a non-specific tyrosine aminotransferase, e.g., derived from *E coli*. Aminotransfereases of use in the present invention include, but are not limited to, tyrB, aspS, or ilvE. Typically the above steps are performed in vivo, e.g., by transforming a cell with a plasmid comprising the genes which encode the enzymes used for the synthesis.

In another aspect, the present invention provides a method of producing p-aminophenylalanine in an *Escherichia coli* cell. The method typically comprises transforming the cell with a plasmid comprising papA, papB, and papC, wherein the cell comprises chorismate and an aminotransferase. Expression of papA, papB, and papC results in a synthase, a mutase, and a dehydrogenase, wherein these enzymes together with the aminotransferase produce p-phenylalanine from chorismate.

In another aspect, the present invention provides an autonomous twenty-one (or more) amino acid cell. The cell, e.g., a bacterial cell, typically comprises a biosynthetic pathway system for producing an unnatural amino acid, e.g., p-aminophenylalanine, from one or more carbon sources within the cell, e.g., chorismate, and a translation system comprising an orthogonal tRNA (O-tRNA) and an orthogonal aminoacyl tRNA synthetase (O—RS). The O—RS preferentially aminoacylates the O-tRNA with the unnatural amino acid and the O-tRNA incorporates the unnatural amino acid into a protein in response to a selector codon, e.g., a nonsense codon such as TAG, a four base codon, or an amber codon. The cell can comprise more than one unnatural amino acid, e.g. 1, 2, 3, 4, 5, 6, 7, 8, 9, 10, 11, 12, 13, 14, 15 or more unnatural amino acids, optionally with more than one orthogonal tRNA (e.g., one per unnatural amino acid to provide for site-specific incorporation of each unnatural amino acid in a protein, or more, or less, to tune the specificity of unnatural amino acid incorporation) and/or more than one orthogonal aminoacyl tRNA synthetase (O—RS) (e.g., one per orthogonal tRNA, or more or less to tune the specificity of unnatural amino acid incorporation).

In some embodiments, the biosynthetic pathway systems produce a natural cellular amount of the unnatural amino acid, e.g., the cell produces the unnatural amino acid in an amount sufficient for protein biosynthesis, which amount does not substantially alter the concentration of natural amino acids or substantially exhaust cellular resources in the production of the unnatural amino acids.

In one example class of embodiments, the autonomous cell is engineered to produce p-aminophenylalanine from chorismate as described above. In this embodiment, the cell is engineered to produce the desired enzymes as described above, e.g., a synthase, a dehydrogenase, and a mutase derived from *Streptomyces Venezuelae* or *Streptomyces pristinaespiralis* and a aminotransferase derived from *E. coli*. For example, the cells of the invention are optionally transformed with a plasmid, e.g., low copy pSC101 derived plasmid, comprising papA, papB, and papC, wherein the plasmid further comprises an lpp promoter and a lac promoter. In some embodiments, the plasmid further comprises one or more ribosome binding sites.

Other unnatural amino acids that are optionally produced by the cells of the invention include, but are not limited to, dopa, O-methyl-L-tyrosine, glycosylated amino acids, pegylated amino acids, other unnatural amino acids noted herein, and the like.

In another related aspect, the present invention provides a cell comprising one or more systems for producing at least twenty one amino acids and specifically incorporating one or more of the amino acids into one or more proteins within the cell, wherein at least one of the incorporated amino acids comprises an unnatural amino acid.

In another aspect, the present invention provides a method of identifying an advantage provided by an unnatural amino acid which has been incorporated into one or more proteins of a cell. The method typically comprises providing a library of cells, each of which cells comprises a randomized plasmid, e.g., derived from an *E. coli* genome. One or more of the randomized plasmids typically confers on the cells an ability to incorporate an unnatural amino acid into a protein. The library of cells is then screened to identify cells with enhanced growth, e.g., as compared to a native *E. coli* cell, thereby identifying an advantage provided by the unnatural amino acid. In some embodiments, a second screen is used to further verify that any advantage identified is due to the unnatural amino acid.

Kits are an additional feature of the invention. For example, the kits can include one or more translation system as noted above (e.g., a cell, a 21 or more amino acid cell, etc.), one or more unnatural amino acid, e.g., with appropriate packaging material, containers for holding the components of the kit, instructional materials for practicing the methods herein and/or the like. Similarly, products of the translation systems (e.g., proteins such as EPO analogues comprising unnatural amino acids) can be provided in kit form, e.g., with containers for holding the components of the kit, instructional materials for practicing the methods herein and/or the like.

BRIEF DESCRIPTION OF THE FIGURES

FIGS. 2A-2B illustrates accumulation of *E. coli* DHFR protein, both wild-type (wt) and mutant under different conditions. Expression conditions are notated at the top of each lane. The left lane is molecular weight marker. FIG. 2A is a silver-stained SDS-PAGE gel of purified DHFR. FIG. 2B is a Western blot of the gel in FIG. 2A.

FIG. 4A is a silver-stained SDS-PAGE gel of purified DHFR. FIG. 4B is a Western blot of the gel in FIG. 4A.

FIG. 6, Panels A-D, illustrate features of the amplifiable fluorescence reporter system. FIG. 6B illustrates composition and fluorescence enhancement of T7 RNA polymerase gene constructs within pREP(1-12). The construct number is indicated to the left of each. Fluorescence enhancements, indicated to the right of each construct, are calculated as the cell concentration-corrected ratio of fluorescence, as measured fluorimetrically, of cells containing pREP(1-12) and pQ or pQD. The positions of amber mutations within the gene are indicated above each construct.

FIG. 7, Panels A-C, illustrates components of a multipurpose reporter plasmid system for directing the evolution of *M. jannaschii* TyrRS.

FIG. 8, Panels A-D, illustrates the activity of the dominant synthetase variant from each successful evolution experiment. FIG. 8C is a table that illustrates a Cm $IC_{50}$ analysis of cells containing pREP/YC-JYCUA and the indicated synthetase variant, grown in either the presence or absence of the corresponding unnatural amino acid.

FIG. 15A illustrates a plasmid used for the biosynthesis of p-aminophenylalanine and FIG. 15B illustrates a biosynthetic scheme for the production of p-aminophenylalanine from chorismate, e.g., using the plasmid of FIG. 15A.

DETAILED DESCRIPTION

In General

Figure 1:
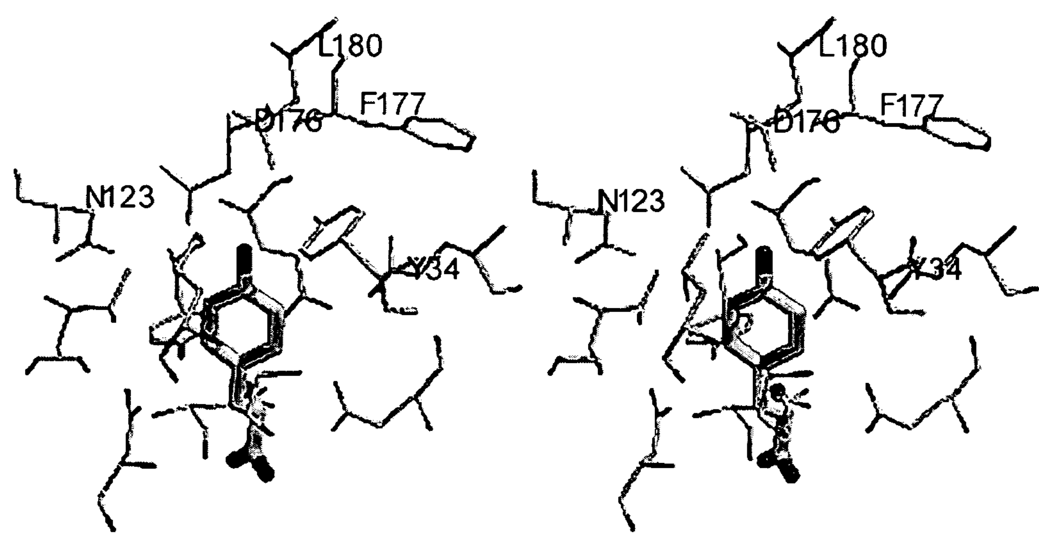
FIG. 1 is a sterioview of the amino acid residues in the active site of TyrRS (modified from P. Brick, T. N. Bhat, D. M. Blow, *J. Mol. Biol.* 208, 83-98 (1988)). Residues from *B. stearothermophilus* TyrRS are shown in the figure.

The present invention provides compositions and methods for augmenting the protein biosynthetic machinery of a cell to accommodate additional genetically encoded amino acids using orthogonal tRNA/aminoacyl tRNA synthetase (O-tRNA/O—RS) pairs. The compositions and methods described here can be used with unnatural amino acids, e.g., providing novel spectroscopic, chemical or structural properties to proteins using any of a wide array of side chains. The invention is applicable to both prokaryotic (e.g., Eubacteria, Archeaebacteria) and eukaryotic (e.g., yeast, mammalian, plant, or insect) cells. These compositions and methods are useful for the site specific incorporation of unnatural amino acids via selector codons, e.g., stop codons, four base codons, and the like. The invention also provides proteins, including unnatural amino acids, produced using the compositions or made by the methods of the invention. The ability to introduce unnatural amino acids into proteins directly in living cells provides new tools for studies of protein and cellular function and can lead to the generation of proteins with enhanced properties useful for, e.g., therapeutics.

Definitions

Homologous: Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. For example, any naturally occurring nucleic acid can be modified by any available mutagenesis method to include one or more selector codon. When expressed, this mutagenized nucleic acid encodes a polypeptide comprising one or more unnatural amino acid. The mutation process can, of course, additionally alter one or more standard codon, thereby changing one or more standard amino acid in the resulting mutant protein as well. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity is routinely used to establish homology. Higher levels of sequence similarity, e.g., 30%, 40%, 50%, 60%, 70%, 80%, 90%, 95% or 99% or more can also be used to establish homology. Methods for determining sequence similarity percentages (e.g., BLASTP and BLASTN using default parameters) are described herein and are generally available.

Orthogonal: As used herein, the term "orthogonal" refers to a molecule (e.g., an orthogonal tRNA (O-tRNA) and/or an orthogonal aminoacyl tRNA synthetase (O—RS)) that is used with reduced efficiency by a system of interest (e.g., a translational system, e.g., a cell). Orthogonal refers to the inability or reduced efficiency, e.g., less than 20% efficient, less than 10% efficient, less than 5% efficient, or e.g., less than 1% efficient, of an orthogonal tRNA and/or orthogonal RS to function in the translation system of interest. For example, an orthogonal tRNA in a translation system of interest is aminoacylated by [aminoacylates] any endogenous RS of a translation system of interest with reduced or even zero efficiency, when compared to aminoacylation of an endogenous tRNA by the endogenous RS. In another example, an orthogonal RS aminoacylates any endogenous tRNA in the translation system of interest with reduced or even zero efficiency, as compared to aminoacylation of the endogenous tRNA by an endogenous RS.

Preferentially aminoacylates: The term "preferentially aminoacylates" refers to an efficiency of, e.g., about 70% efficient, about 75% efficient, about 85% efficient, about 90% efficient, about 95% efficient, or about 99% or more efficient, at which an O—RS aminoacylates an O-tRNA with an unnatural amino acid compared to a naturally occurring tRNA or starting material used to generate the O-tRNA. The unnatural amino acid is then incorporated into a growing polypeptide chain with high fidelity, e.g., at greater than about 75% efficiency for a given selector codon, at greater than about 80% efficiency for a given selector codon, at greater than about 90% efficiency for a given selector codon, at greater than about 95% efficiency for a given selector codon, or at greater than about 99% or more efficiency for a given selector codon.

Selector codon: The term "selector codon" refers to codons recognized by the O-tRNA in the translation process and not recognized by an endogenous tRNA. The O-tRNA anticodon loop recognizes the selector codon on the mRNA and incorporates its amino acid, e.g., an unnatural amino acid, at this site in the polypeptide. Selector codons can include, e.g., nonsense codons, such as, stop codons, e.g., amber, ochre, and opal codons; four or more base codons; codons derived from natural or unnatural base pairs and the like. For a given system, a selector codon can also include one of the natural three base codons, wherein the endogenous system does not use said natural three base codon, e.g., a system that is lacking a tRNA that recognizes the natural three base codon or a system wherein the natural three base codon is a rare codon.

Suppressor tRNA: A suppressor tRNA is a tRNA that alters the reading of a messenger RNA (mRNA) in a given translation system. A suppressor tRNA can read through, e.g., a stop codon, a four base codon, or a rare codon.

Translation system: The term "translation system" refers to the components necessary to incorporate a naturally occurring amino acid into a growing polypeptide chain (protein). Components of a translation system can include, e.g., ribosomes, tRNAs, synthetases, mRNA and the like. The components of the present invention can be added to a translation system, in vivo or in vitro. A translation system can be a cell, either prokaryotic, e.g., an *E. Coli* cell, or eukaryotic, e.g., a yeast, mammalian, plant, or insect cell.

Unnatural amino acid: As used herein, the term "unnatural amino acid" refers to any amino acid, modified amino acid, and/or amino acid analogue that is not one of the 20 naturally occurring amino acids or seleno cysteine.

Unless otherwise defined herein or below in the remainder of the specification, all technical and scientific terms used herein have the same meaning as commonly understood by those of ordinary skill in the art to which the invention belongs.

Discussion

Proteins are at the crossroads of virtually every biological process, from photosynthesis and vision to signal transduction and the immune response. These complex functions result from a polyamide based polymer consisting of twenty relatively simple building blocks arranged in a defined primary sequence.

The present invention includes methods and composition for use in the site-specific incorporation of unnatural amino acids directly into proteins in vivo. Importantly, the unnatural amino acid is added to the genetic repertoire, rather than substituting for one of the common 20 amino acids. The present invention, e.g., (i) allows the site-selective or random insertion of one or more unnatural amino acids at any desired position of any protein, (ii) is applicable to both prokaryotic and eukaryotic cells, (iii) enables in vivo studies of mutant proteins in addition to the generation of large quantities of purified mutant proteins, and (iv) is adaptable to incorporate any of a large variety of non-natural amino acids into proteins in vivo. The invention provides compositions and methods useful for in vivo site specific incorporation of unnatural amino acids. Specifically, the invention provides translation systems, e.g., cells, that include an orthogonal tRNA (O-tRNA), an orthogonal aminoacyl tRNA synthetase (O—RS), and an unnatural amino acid, where the O—RS aminoacylates the O-tRNA with the unnatural amino acid, and the cell uses the components to incorporate the unnatural amino acid into a growing polypeptide chain.

The invention further provides methods for in vivo site-specific incorporation of unnatural amino acids using the translation systems of the invention. The invention also provides proteins produced by the methods of the invention. The claimed proteins include unnatural amino acids.

The compositions and methods of the invention utilize an orthogonal tRNA (O-tRNA) aminoacyl tRNA synthetase (O—RS) pair. A wide range of pairs can be used with the following properties: the O-tRNA is preferentially aminoacylated with an unnatural amino acid by the O—RS. In addition, the orthogonal pair functions in the translation system of interest, e.g., the translation system uses the unnatural amino acid-aminoacylated O-tRNA to incorporate the unnatural amino acid into a polypeptide chain. Incorporation occurs in a site specific manner, e.g., the O-tRNA recognizes a selector codon, e.g., a stop codon, in the mRNA coding for the protein.

In one embodiment, the O-tRNA is derived from a Tyr-tRNA from a *Methanococcus jannaschii* cell. In a preferred embodiment, the O-tRNA is that referred to herein as $mtRNA_{CUA}^{Tyr}$. In another embodiment, the O-tRNA includes a nucleic acid polynucleotide sequence selected from the group that includes SEQ ID NO: 1-3 or a complementary polynucleotide sequence thereof.

In some embodiments of the invention, the O—RS is derived from TyrRS from a *Methanococcus jannaschii* cell. In a preferred embodiment, the O—RS is referred to herein as mutant TyrRS (LWJ16) or SS12-TyrRS. In a further embodiment, the O—RS includes a polypeptide selected from the group consisting of a polypeptide comprising an amino acid sequence selected from the group consisting of SEQ ID NO: 35-66 and a polypeptide encoded by a nucleic acid comprising a polynucleotide sequence selected from the group consisting of: SEQ ID NO: 4-34 or a complementary polynucleotide sequence thereof.

In a preferred embodiment, the invention includes an *Escherichia coli* cell comprising a $mtRNA_{CUA}^{Tyr}$ and a mutant TyrRS (LWJ16), wherein the mutant TyrRS (LWJ16) preferentially aminoacylates the $mtRN_{CUA}^{Tyr}$ with O-methyl-L-tyrosine in the cell and the cell uses the $mtRNA_{CUA}^{Tyr}$ to recognize an amber codon.

In another preferred embodiment, the invention includes an *Escherichia coli* cell comprising a $mtRNA_{CUA}^{Tyr}$ and an SS12-TyrRS, wherein the SS12-TyrRS preferentially aminoacylates the $mtRNA_{CUA}^{Tyr}$ with L-3-(2-naphthyl)alanine in the cell and the cell uses the $mtRNA_{CUA}^{Tyr}$ to recognize an amber codon.

Sequences of exemplary O-tRNA and O—RS molecules are described in the Examples.

Orthogonal tRNA and Orthogonal Aminoacyl-tRNA Synthetase Pairs

An orthogonal pair is composed of an O-tRNA, e.g., a suppressor tRNA, a frameshift tRNA, or the like, and an O—RS. The O-tRNA is not acylated by endogenous synthetases and is capable of decoding a selector codon, as described above. The O—RS recognizes the O-tRNA, e.g., with an extended anticodon loop, and preferentially aminoacylates the O-tRNA with an unnatural amino acid. The development of multiple orthogonal tRNA/synthetase pairs can allow the simultaneous incorporation of multiple unnatural amino acids using different codons.

The O-tRNA and the O—RS can be naturally occurring or can be derived by mutation of a naturally occurring tRNA and/or RS from a variety of organisms, which are described under sources and hosts. In various embodiments, the O-tRNA and O—RS are derived from at least one organism. In another embodiment, the O-tRNA is derived from a naturally occurring or mutated naturally occurring tRNA from a first organism and the O—RS is derived from naturally occurring or mutated naturally occurring RS from a second organism.

Methods (deriving, mutating, screening) for obtaining O-tRNA, O—RS, and pairs to be used in the compositions and methods of the invention are also described U.S. patent application Ser. No. 10/126,931, titled "Methods and Compositions for the production of orthogonal tRNA-tRNA synthetase pairs," filed concurrently with the instant application, the disclosure of which is incorporated in its entirety.

These methods solve the problems discussed in the background section for the other strategies that were attempted to generate orthogonal tRNA/RS pairs. Specifically, these methods include: (a) generating a library of tRNAs derived from at least one tRNA from a first organism; (b) negatively selecting the library for tRNAs that are aminoacylated by an aminoacyl-tRNA synthetase (RS) from a second organism in the absence of a RS from the first organism, thereby providing a pool of tRNAs; (c) selecting the pool of tRNAs for members that are aminoacylated by an introduced orthogonal RS (O—RS), thereby providing at least one recombinant O-tRNA. The at least one recombinant O-tRNA recognizes a selector codon and is not efficiency recognized by the RS from the second organism and is preferentially aminoacylated by the O—RS. The method also includes: (d) generating a library of mutant RSs derived from at least one aminoacyl-tRNA synthetase (RS) from a third organism; (e) selecting the library of RSs for members that preferentially aminoacylate the at least one recombinant O-tRNA in the presence of an unnatural amino acid and a natural amino acid, thereby providing a pool of active RSs; and, (f) negatively selecting the pool for active RSs that preferentially aminoacylate the at least one recombinant O-tRNA in the absence of the unnatural amino acid, thereby providing the at least one specific O-tRNA/O—RS pair, where the at least one specific O-tRNA/O—RS pair comprises at least one recombinant O—RS that is specific for the unnatural amino acid and the at least one recombinant O-tRNA.

One strategy for generating an orthogonal pair involves generating mutant libraries from wihc to screen and/or select an O-tRNA or O—RS.

A second strategy for generating an orthogonal tRNA/synthetase pair involves importing a heterologous tRNA/synthetase pair, e.g., importing a pair from another, e.g., source organism into the host cell. The properties of the heterologous synthetase candidate include, e.g., that it does not charge any host cell tRNA, and the properties of the heterologous tRNA candidate include, e.g., that it is not acylated by any host cell synthetase. In addition, the heterologous tRNA derived from the heterologous tRNA is orthogonal to all host cell synthetases.

Using the methods described herein and in U.S. patent application Ser. No. 10/126,931, titled "Methods and Compositions for the production of orthogonal tRNA-tRNA synthetase pairs," the pairs and components of pairs desired above are evolved to generate orthogonal tRNA/synthetase pairs that possess desired characteristic, e.g., that can preferentially aminoacylate an O-tRNA with an unnatural amino acid.

Although discussed with reference to strategies for incorporating unnatural amino acids into proteins in vivo herein, it will be appreciated that strategies can be developed to incorporate natural amino acids in response to selector codons as well, providing an additional basis of and for mutagenesis. That is, a synthetase can be modified to load a natural amino acid onto an orthogonal tRNA that recognizes a selector codon in a manner similar to the loading of an unnatural amino acid as described throughout.

Production of Orthogonal Aminoacyl tRNA Synthetases (O—RS)

Methods for producing an O—RS are based on generating a pool of mutant synthetases from the framework of a wild-type synthetase, and then selecting for mutated RSs based on their specificity for an unnatural amino acid relative to the common twenty. To isolate such a synthetase, the selection methods of the present invention are: (i) sensitive, as the activity of desired synthetases from the initial rounds can be low and the population small; (ii) "tunable", since it is desirable to vary the selection stringency at different selection rounds; and, (iii) general, so that it can be used for different unnatural amino acids.

Methods to generate an orthogonal aminoacyl tRNA synthetase include mutating the synthetase, e.g., at the active site in the synthetase, at the editing mechanism site in the synthetase, at different sites by combining different domains of synthetases, or the like, and applying a selection process. A strategy is used, which is based on the combination of a positive selection followed by a negative selection. In the positive selection, suppression of the selector codon introduced at a nonessential position(s) of a positive marker allows cells to survive under positive selection pressure. In the presence of both natural and unnatural amino acids, survivors thus encode active synthetases charging the orthogonal suppressor tRNA with either a natural or unnatural amino acid. In the negative selection, suppression of a selector codon introduced at a nonessential position(s) of a negative marker removes synthetases with natural amino acid specificities. Survivors of the negative and positive selection encode synthetases that aminoacylate (charge) the orthogonal suppressor tRNA with unnatural amino acids only. These synthetases can then be subjected to further mutagenesis, e.g., DNA shuffling or other recursive mutagenesis methods.

The library of mutant RSs can be generated using various mutagenesis techniques known in the art. For example, the mutant RSs can be generated by site-specific mutations, random point mutations, homologous recombination, chimeric construction or the like.

The positive selection step can include, e.g., introducing a positive selection marker, e.g., an antibiotic resistance gene, or the like, and the library of mutant RSs into a plurality of cells, wherein the positive selection marker comprises at least one selector codon, e.g., an amber codon; growing the plurality of cells in the presence of a selection agent; selecting cells that survive in the presence of the selection agent by suppressing the at least one selector codon in the positive selection marker, thereby providing a subset of positively selected cells that contains the pool of active mutant RSs. Optionally, the selection agent concentration can be varied.

The negative selection can include, e.g., introducing a negative selection marker with the pool of active mutant RSs from the positive selection into a plurality of cells of a second organism, wherein the negative selection marker is an antibiotic resistance gene, e.g., a chloramphenicol acetyltransferase (CAT) gene, comprising at least one selector codon; and, selecting cells that survive in a 1st media supplemented with the unnatural amino acid and a selection agent, but fail to survive in a 2nd media not supplemented with the unnatural amino acid and the selection agent, thereby providing surviving cells with the at least one recombinant O—RS. Optionally, the concentration of the selection agent is varied.

The positive selection can be based on suppression of a selector codon in a positive selection marker, e.g., a chloramphenicol acetyltransferase (CAT) gene comprising a selector codon, e.g., an amber stop codon, in the CAT gene, so that chloramphenicol can be applied as the positive selection pressure. In addition, the CAT gene can be used as both a positive marker and negative marker as describe herein in the presence and absence of unnatural amino acid. Optionally, the CAT gene comprising a selector codon is used for the positive selection and a negative selection marker, e.g., a toxic marker, such as a barnase gene comprising at least one or more selector codons, is used for the negative selection.

The positive selection can also be based on suppression of a selector codon at a nonessential position in the β-lactamase gene, rendering cells ampicillin resistant; and a negative selection using the ribonuclease barnase as the negative marker is used. In contrast to β-lactamase, which is secreted into the periplasm, CAT localizes in the cytoplasm; moreover, ampicillin is bacteriocidal, while chloramphenicol is bacteriostatic.

The recombinant O—RS can be further mutated and selected. In one embodiment, the methods for producing at least one recombinant orthogonal aminoacyl-tRNA synthetase (O—RS) can further comprise: (d) isolating the at least one recombinant O—RS; (e) generating a second set of mutated O—RS derived from the at least one recombinant O—RS; and, (f) repeating steps (b) and (c) until a mutated O—RS is obtained that comprises an ability to preferentially aminoacylate the O-tRNA. Optionally, steps (d)-(f) are repeated, e.g., at least about two times. In one aspect, the second set of mutated O—RS can be generated by mutagenesis, e.g., random mutagenesis, site-specific mutagenesis, recombination or a combination thereof.

Production of Orthogonal tRNA (O-tRNAs)

Methods for producing a recombinant orthogonal tRNA (O-tRNA) are provided in U.S. patent application Ser. No. 10/126,931, titled "Methods and Compositions for the production of orthogonal tRNA-tRNA synthetase pairs,".

Methods of producing a recombinant O-tRNA include: (a) generating a library of mutant tRNAs derived from at least one tRNA, e.g., a suppressor tRNA, from a first organism; (b) negatively selecting the library for mutant tRNAs that are aminoacylated by an aminoacyl-tRNA synthetase (RS) from a second organism in the absence of a RS from the first organism, thereby providing a pool of mutant tRNAs; and, (c) selecting the pool of mutant tRNAs for members that are aminoacylated by an introduced orthogonal RS (O—RS), thereby providing at least one recombinant O-tRNA; wherein the at least one recombinant O-tRNA recognizes a selector codon and is not efficiency recognized by the RS from the second organism and is preferentially aminoacylated by the O—RS. In one embodiment, the recombinant O-tRNA possesses an improvement of orthogonality.

For example, to improve the orthogonality of a tRNA while preserving its affinity toward a desired RS, the methods include a combination of negative and positive selections with a mutant suppressor tRNA library in the absence and presence of the cognate synthetase, respectively. In the negative selection, a selector codon(s) is introduced in a marker gene, e.g., a toxic gene, such as barnase, at a nonessential position. When a member of the mutated tRNA library, e.g., derived from *Methanococcus jannaschii*, is aminoacylated by endogenous host, e.g., *Escherichia coli* synthetases (i.e., it is not orthogonal to the host, e.g., *Escherichia coli* synthetases), the selector codon, e.g., an amber codon, is suppressed and the toxic gene product produced leads to cell death. Cells harboring orthogonal tRNAs or non-functional tRNAs survive. Survivors are then subjected to a positive selection in which a selector codon, e.g., an amber codon, is placed in a positive marker gene, e.g., a drug resistance gene, such a β-lactamase gene. These cells also contain an expression vector with a cognate RS. These cells are grown in the presence of a selection agent, e.g., ampicillin. tRNAs are then selected for their ability to be aminoacylated by the coexpressed cognate synthetase and to insert an amino acid in response to this selector codon. Cells harboring non-functional tRNAs, or tRNAs that cannot be recognized by the synthetase of interest are sensitive to the antibiotic. Therefore, tRNAs that: (i) are not substrates for endogenous host, e.g., *Escherichia coli*, synthetases; (ii) can be aminoacylated by the synthetase of interest; and (iii) are functional in translation survive both selections.

Libraries of mutated tRNA are constructed. Mutations can be introduced at a specific position(s), e.g., at a nonconservative position(s), or at a conservative position, at a randomized position(s), or a combination of both in a desired loop of a tRNA, e.g., an anticodon loop, (D arm, V loop, TψC arm) or a combination of loops or all loops. Chimeric libraries of tRNA are also included in the present invention. It should be noted that libraries of tRNA synthetases from various organism (e.g., microorganisms such as eubacteria or archaebacteria) such as libraries that comprise natural diversity (see, e.g., U.S. Pat. No. 6,238,884 to Short et al; U.S. Pat. No. 5,756,316 to Schallenberger et al; U.S. Pat. No. 5,783,431 to Petersen et al; U.S. Pat. No. 5,824,485 to Thompson et al; U.S. Pat. No. 5,958,672 to Short et al), are optionally constructed and screened for orthogonal pairs.

For example, negatively selecting the library for mutant tRNAs that are aminoacylated by an aminoacyl-tRNA synthetase can include: introducing a toxic marker gene, wherein the toxic marker gene comprises at least one of the selector codons and the library of mutant tRNAs into a plurality of cells from the second organism; and, selecting surviving cells, wherein the surviving cells contain the pool of mutant tRNAs comprising at least one orthogonal tRNA or nonfunctional tRNA. For example, the toxic marker gene is a ribonuclease barnase gene, wherein the ribonuclease barnase gene comprises at least one amber codon. Optionally, the ribonuclease barnase gene can include two or more amber codons. The surviving cells can be selected, e.g., by using a comparison ratio cell density assay.

In another example, selecting the pool of mutant tRNAs for members that are aminoacylated by an introduced orthogonal RS (O—RS) can include: introducing a positive selection marker gene, wherein the positive selection marker gene comprises a drug resistance gene, e.g., a β-lactamase gene, comprising at least one of the selector codons, e.g., a β-lactamase gene comprising at least one amber stop codon, the O—RS, and the pool of mutant tRNAs into a plurality of cells from the second organism; and, selecting surviving cells grown in the presence of a selection agent, e.g., an antibiotic, thereby providing a pool of cells possessing the at least one recombinant tRNA, wherein the recombinant tRNA is aminoacylated by the O—RS and inserts an amino acid into a translation product encoded by the positive marker gene, in response to the at least one selector codons. In another embodiment, the concentration of the selection agent is varied. Recombinant O-tRNAs produced by the methods are included in the present invention.

The stringency of the selection steps, e.g., the positive selection step, the negative selection step or both the positive and negative selection steps, in the above described-methods, optionally include varying the selection stringency. For example, because barnase is an extremely toxic protein, the stringency of the negative selection can be controlled by introducing different numbers of selector codons into the barnase gene. In one aspect of the present invention, the stringency is varied because the desired activity can be low during early rounds. Thus, less stringent selection criteria are applied in early rounds and more stringent criteria are applied in later rounds of selection.

Other types of selections can be used in the present invention for generating, e.g., O—RS, O-tRNA, and O-tRNA/O—RS pairs. For example, the positive selection step, the negative selection step or both the positive and negative selection steps can include using a reporter, wherein the reporter is detected by fluorescence-activated cell sorting (FACS). For example, a positive selection can be done first with a positive selection marker, e.g., chloramphenicol acetyltransferase (CAT) gene, where the CAT gene comprises a selector codon, e.g., an amber stop codon, in the CAT gene, which followed by a negative selection screen, that is based on the inability to suppress a selector codon(s), e.g., two or more, at positions within a negative marker, e.g., T7 RNA polymerase gene. In one embodiment, the positive selection marker and the negative selection marker can be found on the same vector, e.g., plasmid. Expression of the negative marker drives expression of the reporter, e.g., green fluorescent protein (GFP). The stringency of the selection and screen can be varied, e.g., the intensity of the light need to fluorescence the reporter can be varied. In another embodiment, a positive selection can be done with a reporter as a positive selection marker, which is screened by FACs, followed by a negative selection screen, that is based on the inability to suppress a selector codon(s), e.g., two or more, at positions within a negative marker, e.g., barnase gene.

Optionally, the reporter is displayed on a cell surface, on a phage display or the like. Cell-surface display, e.g., the OmpA-based cell-surface display system, relies on the expression of a particular epitope, e.g., a poliovirus C3 peptide fused to an outer membrane porin OmpA, on the surface of the *Escherichia coli* cell. The epitope is displayed on the cell surface only when a selector codon in the protein message is suppressed during translation. The displayed peptide then contains the amino acid recognized by one of the mutant aminoacyl-tRNA synthetases in the library, and the cell containing the corresponding synthetase gene can be isolated with antibodies raised against peptides containing specific unnatural amino acids. The OmpA-based cell-surface display system was developed and optimized by Georgiou et al. as an alternative to phage display. See, Francisco, J. A., Campbell, R., Iverson, B. L. & Georgoiu, G. Production and fluorescence-activated cell sorting of *Escherichia coli* expressing a functional antibody fragment on the external surface. *Proc Natl Acad Sci USA*. 90:10444-8 (1993).

The selection steps can also be carried out in vitro. The selected component, e.g., synthetase and/or tRNA, can then be introduced into a cell for use in in vivo incorporation of an unnatural amino acid.

Source and Host Organisms

The orthogonal tRNA-RS pair, e.g., derived from at least a first, e.g., source organism or at least two source organisms, which can be the same or different, can be used in a variety of host organisms, e.g., a second organism. The first and the second organisms of the methods of the present invention can be the same or different. In one embodiment, the first organism is a prokaryotic organism, e.g., *Methanococcus jannaschii, Methanobacterium thermoautotrophicum, Halobacterium, Escherichia coli, A. fulgidus, Halobacterium, P. furiosus, P. horikoshii, A. pernix, T. thermophilus*, or the like. Alternatively, the first organism is a eukaryotic organism, e.g., plants (e.g., complex plants such as monocots, or dicots), algae, protists, fungi (e.g., yeast, etc), animals (e.g., mammals, insects, arthropods, etc.), or the like. In another embodiment, the second organism is a prokaryotic organism, *Methanococcus jannaschii, Methanobacterium thermoautotrophicum, Halobacterium, Escherichia coli, A. fulgidus, Halobacterium, P. furiosus, P. horikoshii, A. pernix, T thermophilus*, or the like. Alternatively, the second organism can be a eukaryotic organism, e.g., plants, fungi, animals, or the like.

As described above, the individual components of a pair can be derived from the same organism or different organisms. For example, tRNA can be derived from a prokaryotic organism, e.g., an archaebacterium, such as *Methanococcus jannaschii* and *Halobacterium* NRC-1 or a eubacterium, such as *Escherichia coli*, while the synthetase can be derived from same or another prokaryotic organism, such as, *Methanococcus jannaschii, Archaeoglobus fulgidus, Methanobacterium thermoautotrophicum, P. furiosus, P. horikoshii, A. pernix, T. thermophilus, Halobacterium, Escherichia coli* or the like. Eukaryotic sources can also be used, e.g., plants (e.g., complex plants such as monocots, or dicots), algae, protists, fungi (e.g., yeast, etc.), animals (e.g., mammals, insects, arthropods, etc.), or the like.

Selector Codons

Selector codons of the present invention expand the genetic codon framework of protein biosynthetic machinery. For example, a selector codon includes, e.g., a unique three base codon, a nonsense codon, such as a stop codon, e.g., an amber codon, or an opal codon, an unnatural codon, at least a four base codon or the like. A number of selector codons can be introduced into a desired gene, e.g., one or more, two or more, more than three, etc.

The 64 genetic codons code for 20 amino acids and 3 stop codons. Because only one stop codon is needed for translational termination, the other two can in principle be used to encode nonproteinogenic amino acids. The amber stop codon, UAG, has been successfully used in in vitro biosynthetic system and in *Xenopus oocytes* to direct the incorporation of unnatural amino acids. Among the 3 stop codons, UAG is the least used stop codon in *Escherichia coli*. Some *Escherichia coli* strains contain natural suppressor tRNAs, which recognize UAG and insert a natural amino acid. In addition, these amber suppressor tRNAs have been used in conventional protein mutagenesis.

In one embodiment, the methods involve the use of a selector codon that is a stop codon for the incorporation of unnatural amino acids in vivo. For example, an O-tRNA is generated that recognizes the stop codon, e.g., UAG, and is aminoacylated by an O—RS with a desired unnatural amino acid. This O-tRNA is not recognized by the naturally occurring aminoacyl-tRNA synthetases. Conventional site-directed mutagenesis can be used to introduce the stop codon, e.g., TAG, at the site of interest in the protein gene. See, e.g., Sayers, J. R., Schmidt, W. Eckstein, F. 5',3' Exonuclease in phosphorothioate-based oligonucleotide-directed mutagenesis. *Nucleic Acids Res*, 791-802 (1988). When the O—RS, O-tRNA and the mutant gene are combined in vivo, the unnatural amino acid is incorporated in response to the UAG codon to give a protein containing the unnatural amino acid at the specified position.

The incorporation of unnatural amino acids in vivo can be done without significant perturbation of the host, e.g., *Escherichia coli*. For example, because the suppression efficiency for the UAG codon depends upon the competition between the O-tRNA, e.g., the amber suppressor tRNA, and the release factor 1 (RF 1) (which binds to the UAG codon and initiates release of the growing peptide from the ribosome), the suppression efficiency can be modulated by, e.g., either increasing the expression level of O-tRNA, e.g., the suppressor tRNA, or using an RF1 deficient strain.

Unnatural amino acids can also be encoded with rare codons. For example, when the arginine concentration in an in vitro protein synthesis reaction is reduced, the rare arginine codon, AGG, has proven to be efficient for insertion of Ala by a synthetic tRNA acylated with alanine. See, e.g., C. H. Ma, W. Kudlicki, O. W. Odom, G. Kramer and B. Hardesty, Biochemistry, 32:7939 (1993). In this case, the synthetic tRNA competes with the naturally occurring tRNAArg, which exists as a minor species in *Escherichia coli*. Some organisms do not use all triplet codons. An unassigned codon AGA in Micrococcus luteus has been utilized for insertion of amino acids in an in vitro transcription/translation extract. See, e.g., A. K. Kowal and J. S. Oliver, Nucl. Acid. Res., 25:4685 (1997). Components of the present invention can be generated to use these rare codons in vivo.

Selector codons also comprise four or more base codons, such as, four, five, six or more base codons. Examples of four base codons include, e.g., AGGA, CUAG, UAGA, CCCU and the like. Examples of five base codons include, e.g., AGGAC, CCCCU, CCCUC, CUAGA, CUACU, UAGGC and the like. For example, in the presence of mutated O-tRNAs, e.g., a special frameshift suppressor tRNAs, with anticodon loops, e.g., with at least 8-10 nt anticodon loops, the four or more base codon is read as single amino acid. In other embodiments, the anticodon loops can decode, e.g., at least a four-base codon, at least a five-base codon, or at least a six-base codon or more. Since there are 256 possible four-base codons, multiple unnatural amino acids can be encoded in the same cell using the four or more base codon. See, J. Christopher Anderson et al., Exploring the Limits of Codon and Anticodon Size, *Chemistry and Biology*, Vol. 9, 237-244 (2002); Thomas J. Magliery, Expanding the Genetic Code: Selection of Efficient Suppressors of Four-base Codons and Identification of "Shifty" Four-base Codons with a Library Approach in *Escherichia coli, J. Mol. Biol*. 307: 755-769 (2001).

Methods of the present invention include using extended codons based on frameshift suppression. Four or more base codons can insert, e.g., one or multiple unnatural amino acids into the same protein. For example, four-base codons have been used to incorporate unnatural amino acids into proteins using in vitro biosynthetic methods. See, e.g., C. H. Ma, W. Kudlicki, O. W. Odom, G. Kramer and B. Hardesty, Biochemistry, 1993, 32, 7939 (1993); and, T. Hohsaka, D. Kajihara, Y. Ashizuka, H. Murakami and M. Sisido, J. Am. Chem. Soc., 121:34 (1999). CGGG and AGGU were used to simultaneously incorporate 2-naphthylalanine and an NBD derivative of lysine into streptavidin in vitro with two chemically acylated frameshift suppressor tRNAs. See, e.g., T. Hohsaka, Y. Ashizuka, H. Sasaki, H. Murakami and M. Sisido, J. Am. Chem. Soc., 121:12194 (1999). In an in vivo study, Moore et al. examined the ability of tRNALeu derivatives with NCUA anticodons to suppress UAGN codons (N can be U, A, G, or C), and found that the quadruplet UAGA can be decoded by a tRNALeu with a UCUA anticodon with an efficiency of 13 to 26% with little decoding in the 0 or -1 frame. See, B. Moore, B. C. Persson, C. C. Nelson, R. F. Gesteland and J. F. Atkins, J. Mol. Biol., 298:195 (2000). In one embodiment, extended codons based on rare codons or nonsense codons can be used in present invention, which can reduce missense readthrough and frameshift suppression at other unwanted sites.

A translational bypassing system can also be used to incorporate an unnatural amino acid in a desired polypeptide. In a translational bypassing system, a large sequence is inserted into a gene but is not translated into protein. The sequence contains a structure that serves as a cue to induce the ribosome to hop over the sequence and resume translation downstream of the insertion.

Alternatively, or in combination with others methods described above to incorporate an unnatural amino acid in a polypeptide, a trans-translation system can be used. This system involves a molecule called tmRNA present in *Escherichia coli*. This RNA molecule is structurally related to an alanyl tRNA and is aminoacylated by the alanyl synthetase. The difference between tmRNA and tRNA is that the anticodon loop is replaced with a special large sequence. This sequence allows the ribosome to resume translation on sequences that have stalled using an open reading frame encoded within the tmRNA as template. In the present invention, an orthogonal tmRNA can be generated that is preferentially aminoacylated with an orthogonal synthetase and loaded with an unnatural amino acid. By transcribing a gene using the system, the ribosome stalls at a specific site; the unnatural amino acid is introduced at that site, then translation resumes, using the sequence encoded within the orthogonal tmRNA.

Selector codons optionally include unnatural base pairs. These unnatural base pairs further expand the existing genetic alphabet. One extra base pair increases the number of triplet codons from 64 to 125. Properties of third base pairs include stable and selective base pairing, efficient enzymatic incorporation into DNA with high fidelity by a polymerase, and the efficient continued primer extension after synthesis of the nascent unnatural base pair. Descriptions of unnatural base pairs which can be adapted for methods and compositions include, e.g., Hirao, et al., An unnatural base pair for incorporating amino acid analogues into protein, *Nature Biotechnology*, 20:177-182 (2002). Other relevant publications are listed below.

For in vivo usage, the unnatural nucleoside is membrane permeable and is phosphorylated to form the corresponding triphosphate. In addition, the increased genetic information is stable and not destroyed by cellular enzymes. Previous efforts by Benner and others took advantage of hydrogen bonding patterns that are different from those in canonical Watson-Crick pairs, the most noteworthy example of which is the iso-C:iso-G pair. See, e.g., C. Switzer, S. E. Moroney and S. A. Benner, J. Am. Chem. Soc., 111:8322 (1989); and, J. A. Piccirilli, T. Krauch, S. E. Moroney and S. A. Benner, Nature, 1990, 343:33 (1990); E. T. Kool, Curr. Opin. Chem. Biol., 4:602 (2000). These bases in general mispair to some degree with natural bases and cannot be enzymatically replicated. Kool and co-workers demonstrated that hydrophobic packing interactions between bases can replace hydrogen bonding to drive the formation of base pair. See, E. T. Kool, Curr. Opin. Chem. Biol., 4:602 (2000); and, K. M. Guckian and E. T. Kool, Angew. Chem. Int. Ed. Engl., 36, 2825 (1998). In an effort to develop an unnatural base pair satisfying all the above requirements, Schultz, Romesberg and co-workers have systematically synthesized and studied a series of unnatural hydrophobic bases. A PICS:PICS self-pair is found to be more stable than natural base pairs, and can be efficiently incorporated into DNA by Klenow fragment of *Escherichia coli* DNA polymerase I (KF). See, e.g., D. L. McMinn, A. K. Ogawa, Y. Q. Wu, J. Q. Liu, P. G. Schultz and F. E. Romesberg, J. Am. Chem. Soc., 121:11586 (1999); and, A. K. Ogawa, Y. Q. Wu, D. L. McMinn, J. Q. Liu, P. G. Schultz and F. E. Romesberg, J.

Am. Chem. Soc., 122:3274 (2000). A 3MN:3MN self-pair can be synthesized by KF with efficiency and selectivity sufficient for biological function. See, e.g., A. K. Ogawa, Y. Q. Wu, M. Berger, P. G. Schultz and F. E. Romesberg, J. Am. Chem. Soc., 122:8803 (2000). However, both bases act as a chain terminator for further replication. A mutant DNA polymerase has been recently evolved that can be used to replicate the PICS self pair. In addition, a 7AI self pair can be replicated. See, e.g., E. J. L. Tae, Y. Q. Wu, G. Xia, P. G. Schultz and F. E. Romesberg, *J. Am. Chem. Soc.*, 123:7439 (2001). A novel metallobase pair, Dipic:Py, has also been developed, which forms a stable pair upon binding Cu(II). See, E. Meggers, P. L. Holland, W. B. Tolman, F. E. Romesberg and P. G. Schultz, *J. Am. Chem. Soc.*, 122:10714 (2000). Because extended codons and unnatural codons are intrinsically orthogonal to natural codons, the methods of the present invention can take advantage of this property to generate orthogonal tRNAs for them.

Unnatural Amino Acids

As used herein an unnatural amino acid refers to any amino acid, modified amino acid, or amino acid analogue other than selenocysteine and the following twenty genetically encoded alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine. The generic structure of an alpha-amino acid is illustrated by Formula I:

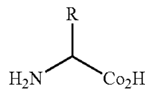

I

An unnatural amino acid is typically any structure having Formula I wherein the R group is any substituent other than one used in the twenty natural amino acids. See, e.g., *Biochemistry* by L. Stryer, 3$^{rd}$ ed. 1988, Freeman and Company, New York, for structures of the twenty natural amino acids. Note that, the unnatural amino acids of the present invention can be naturally occurring compounds other than the twenty alpha-amino acids above.

Because the unnatural amino acids of the invention typically differ from the natural amino acids in side chain only, the unnatural amino acids form amide bonds with other amino acids, e.g., natural or unnatural, in the same manner in which they are formed in naturally occurring proteins. However, the unnatural amino acids have side chain groups that distinguish them from the natural amino acids. For example, R in Formula I optionally comprises an alkyl-, aryl-, acyl-, keto-, azido-, hydroxyl-, hydrazine, cyano-, halo-, hydrazide, alkenyl, alkynl, ether, thiol, seleno-, sulfonyl-, borate, boronate, phospho, phosphono, phosphine, heterocyclic, enone, imine, aldehyde, ester, thioacid, hydroxylamine, amino group, or the like or any combination thereof. Other unnatural amino acids of interest include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, amino acids comprising biotin or a biotin analogue, glycosylated amino acids such as a sugar substituted serine, other carbohydrate modified amino acids, keto containing amino acids, amino acids comprising polyethylene glycol or polyether, heavy atom substituted amino acids, chemically cleavable and/or photocleavable amino acids, amino acids with an elongated side chains as compared to natural amino acids, e.g., polyethers or long chain hydrocarbons, e.g., greater than about 5 or greater than about 10 carbons, carbon-linked sugar-containing amino acids, redox-active amino acids, amino thioacid containing amino acids, and amino acids comprising one or more toxic moiety.

In addition to unnatural amino acids that contain novel side chains, unnatural amino acids also optionally comprise modified backbone structures, e.g., as illustrated by the structures of Formula II and III:

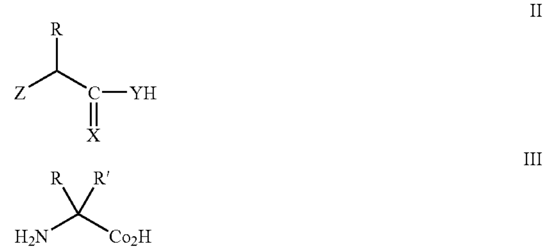

wherein Z typically comprises OH, $NH_2$, SH, NH—R', or S—R'; X and Y, which can be the same or different, typically comprise S or O, and R and R', which are optionally the same or different, are typically selected from the same list of constituents for the R group described above for the unnatural amino acids having Formula I as well as hydrogen. For example, unnatural amino acids of the invention optionally comprise substitutions in the amino or carboxyl group as illustrated by Formulas II and III. Unnatural amino acids of this type include, but are not limited to, α-hydroxy acids, α-thioacids α-aminothiocarboxylates, e.g., with side chains corresponding to the common twenty natural amino acids or unnatural side chains. In addition, substitutions at the α-carbon optionally include L, D, or α-α-disubstituted amino acids such as D-glutamate, D-alanine, D-methyl-O-tyrosine, aminobutyric acid, and the like. Other structural alternatives include cyclic amino acids, such as proline analogues as well as 3,4,6,7,8, and 9 membered ring proline analogues, β and γ amino acids such as substituted β-alanine and γ-amino butyric acid.

For example, many unnatural amino acids are based on natural amino acids, such as tyrosine, glutamine, phenylalanine, and the like. Tyrosine analogs include para-substituted tyrosines, ortho-substituted tyrosines, and meta substituted tyrosines, wherein the substituted tyrosine comprises an acetyl group, a benzoyl group, an amino group, a hydrazine, an hydroxyamine, a thiol group, a carboxy group, an isopropyl group, a methyl group, a $C_6$-$C_{20}$ straight chain or branched hydrocarbon, a saturated or unsaturated hydrocarbon, an O-methyl group, a polyether group, a nitro group, or the like. In addition, multiply substituted aryl rings are also contemplated. Glutamine analogs of the invention include, but are not limited to, α-hydroxy derivatives, γ-substituted derivatives, cyclic derivatives, and amide substituted glutamine derivatives. Example phenylalanine analogs include, but are not limited to, meta-substituted phenylalanines, wherein the substituent comprises a hydroxy group, a methoxy group, a methyl group, an allyl group, an acetyl group, or the like. Specific examples of unnatural amino acids include, but are not limited to, O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcp-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, and an isopropyl-L-phenylalanine, and the like. The structures of a variety of unnatural amino acids are provided in the figures, e.g., FIGS. 17, 18, 19, 26, and 29.

Typically, the unnatural amino acids of the invention are selected or designed to provide additional characteristics unavailable in the twenty natural amino acids. For example, unnatural amino acid are optionally designed or selected to modify the biological properties of a protein, e.g., into which they are incorporated. For example, the following properties are optionally modified by inclusion of an unnatural amino acid into a protein: toxicity, biodistribution, solubility, stability, e.g., thermal, hydrolytic, oxidative, resistance to enzymatic degradation, and the like, facility of purification and processing, structural properties, spectroscopic properties, chemical and/or photochemical properties, catalytic activity, redox potential, half-life, ability to react with other molecules, e.g., covalently or noncovalently, and the like.

Chemical Synthesis of Unnatural Amino Acids

Many of the unnatural amino acids provided above are commercially available, e.g., from Sigma (USA) or Aldrich (Milwaukee, Wis., USA). Those that are not commercially available are optionally synthesized as provided in the examples below or using standard methods known to those of skill in the art. For organic synthesis techniques, see, e.g., *Organic Chemistry* by Fessendon and Fessendon, (1982, Second Edition, Willard Grant Press, Boston Mass.); *Advanced Organic Chemistry* by March (Third Edition, 1985, Wiley and Sons, New York); and *Advanced Organic Chemistry* by Carey and Sundberg (Third Edition, Parts A and B, 1990, Plenum Press, New York).

Figure 14:
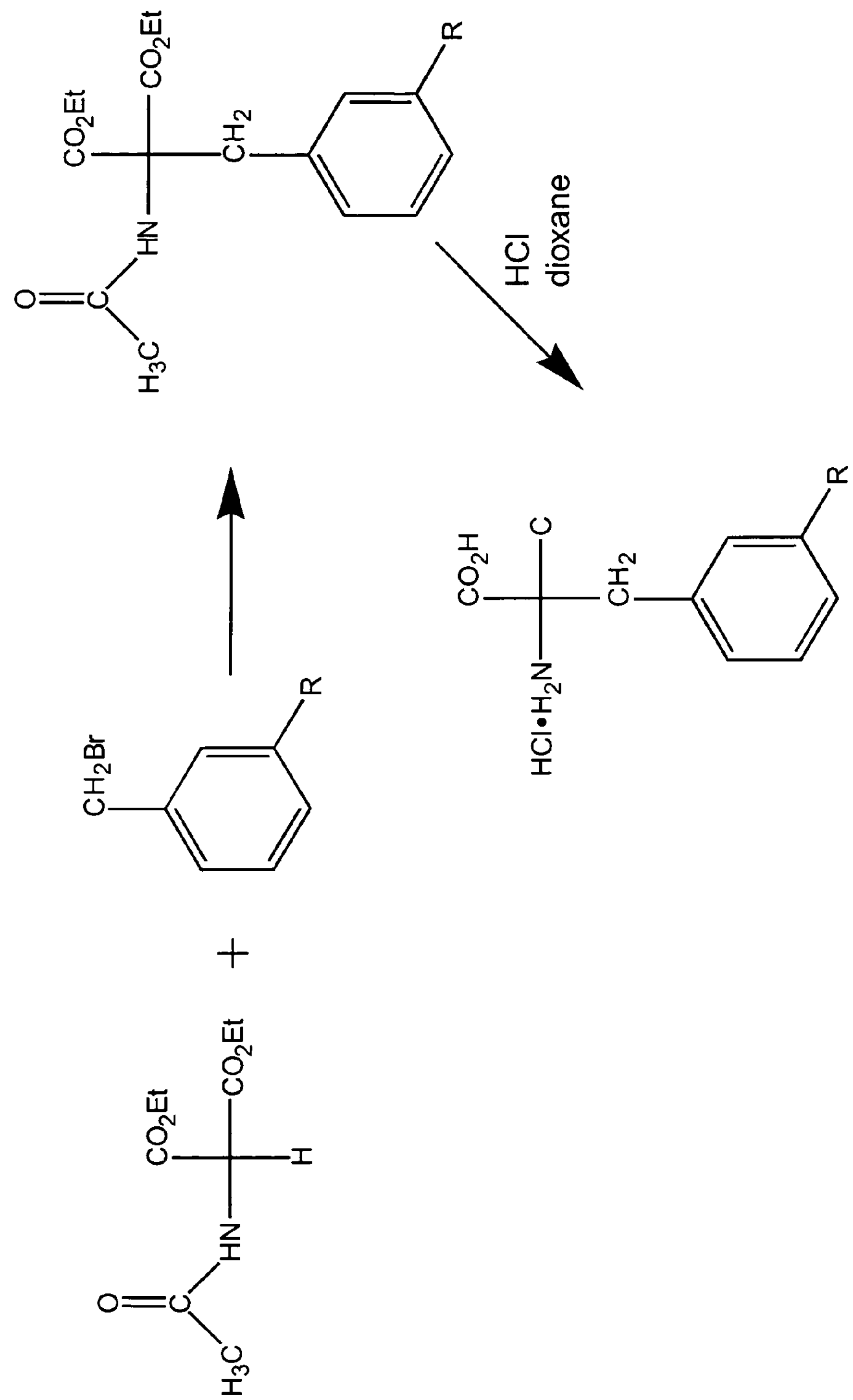
FIG. 14 illustrates a chemical scheme for the synthesis of meta-substituted phenylalanines.

For example, meta-substituted phenylalanines are synthesized in a procedure as outlined in FIG. 14. Typically, NBS (N-bromosuccinimide) is added to a meta-substituted methylbenzene compound to give a meta-substituted benzyl bromide, which is then reacted with a malonate compound to give the meta substituted phenylalanine. Typical substituents used for the meta position include, but are not limited to, ketones, methoxy groups, alkyls, acetyls, and the like. For example, 3-acetyl-phenylalanine is made by reacting NBS with a solution of 3-methylacetophenone. For more details see the examples below. A similar synthesis is used to produce a 3-methoxy phenylalanine. The R group on the meta position of the benzyl bromide in that case is —$OCH_3$. See, e.g., Matsoukas et al., *J. Med. Chem.*, 1995, 38, 4660-4669.

In some embodiments, the design of unnatural amino acids is biased by known information about the active sites of synthetases, e.g., orthogonal tRNA synthetases used to aminoacylate an orthogonal tRNA. For example, three classes of glutamine analogs are provided, including derivatives substituted at the nitrogen of amide (1), a methyl group at the γ-position (2), and a N-$C^{\gamma}$-cyclic derivative (3). Based upon the x-ray crystal structure of *E. coli* GlnRS, in which the key binding site residues are homologous to yeast GlnRS, the analogs were designed to complement an array of side chain mutations of residues within a 10 Å shell of the side chain of glutamine, e.g., a mutation of the active site Phe233 to a small hydrophobic amino acid might be complemented by increased steric bulk at the $C^{\gamma}$ position of Gln.

Figure 23:
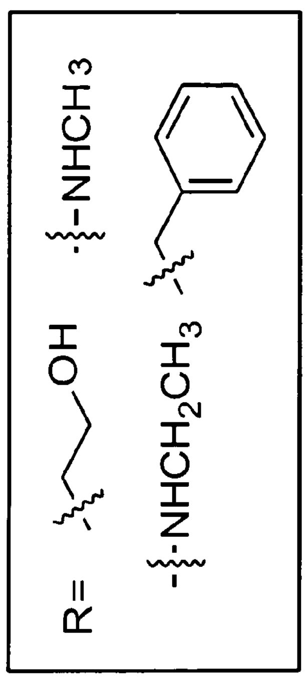
FIG. 23 illustrates the synthesis of various glutamine analogs.
Figure 23:
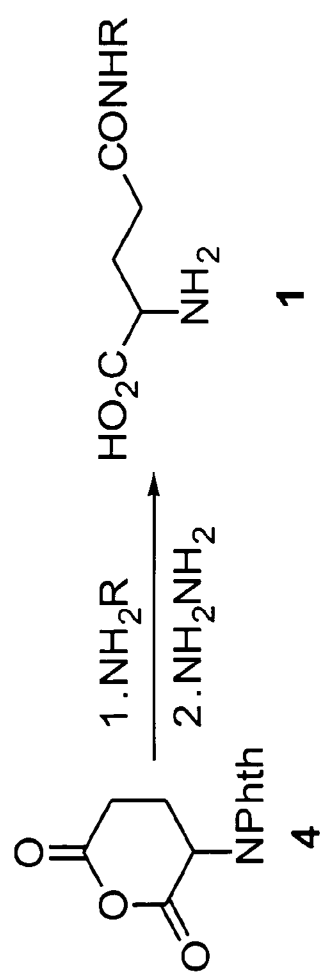

For example, N-phthaloyl-L-glutamic 1,5-anhydride (compound number 4 in FIG. 23) is optionally used to synthesize glutamine analogs with substituents at the nitrogen of the amide. See, e.g., King, F. E. & Kidd, D. A. A. A New Synthesis of Glutamine and of γ-Dipeptides of Glutamic Acid from Phthalate Intermediates. *J. Chem. Soc.*, 3315-3319 (1949); Friedman, O. M. & Chatterrji, R. Synthesis of Derivatives of Glutamine as Model Substrates for Anti-Tumor Agents. *J. Am. Chem. Soc.* 81, 3750-3752 (1959); Craig, J. C. et al. Absolute Configuration of the Enantiomers of 7-Chloro-4 [[4-(diethylamino)-1-methylbutyl]amino]quinoline (Chloroquine). *J. Org. Chem.* 53, 1167-1170 (1988); and Azoulay, M., Vilmont, M. & Frappier, F. Glutamine analogues as Potential Antimalarials,. *Eur. J. Med. Chem.* 26, 201-5 (1991). The anhydride is typically prepared from glutamic acid by first protection of the amine as the phthalimide followed by refluxing in acetic acid. The anhydride is then opened with a number of amines, resulting in a range of substituents at the amide. Deprotection of the phthaloyl group with hydrazine affords a free amino acid as shown in FIG. 23.

Figure 24:
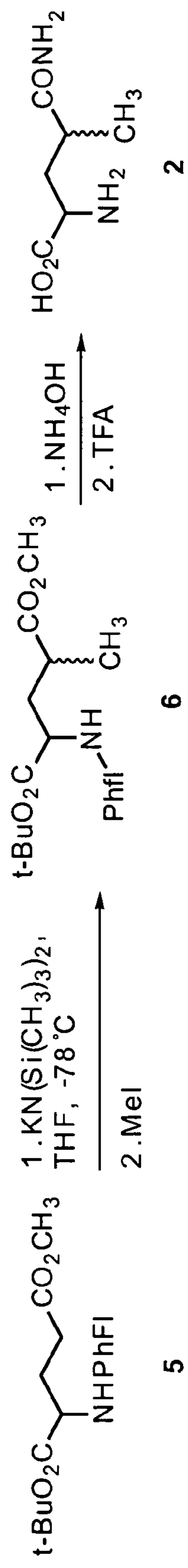
FIG. 24 illustrates the synthesis of a gamma substituted glutamine analog.

Substitution at the γ-position is typically accomplished via alkylation of glutamic acid. See, e.g., Koskinen, A. M. P. & Rapoport, H. Synthesis of 4-Substituted Prolines as Conformationally Constrained Amino Acid Analogues. *J. Org. Chem.* 54, 1859-1866. (1989). A protected amino acid, e.g., as illustrated by compound number 5 in FIG. 24 is optionally prepared by first alkylation of the amino moiety with 9-bromo-9-phenylfluorene (PhflBr) (see, e.g., Christie, B. D. & Rapoport, H. Synthesis of Optically Pure Pipecolates from L-Asparagine. Application to the Total Synthesis of (+)-Apovincamine through Amino Acid Decarbonylation and Iminium Ion Cyclization. *J. Org. Chem.* 1989, 1859-1866 (1985)) and then esterification of the acid moiety using O-tert-butyl-N,N'-diisopropylisourea. Addition of KN(Si$(CH_3)_3)_2$ regioselectively deprotonates at the α-position of the methyl ester to form the enolate, which is then optionally alkylated with a range of alkyl iodides. Hydrolysis of the t-butyl ester and Phfl group gave the desired γ-methyl glutamine analog (Compound number 2 in FIG. 24).

Figure 25:
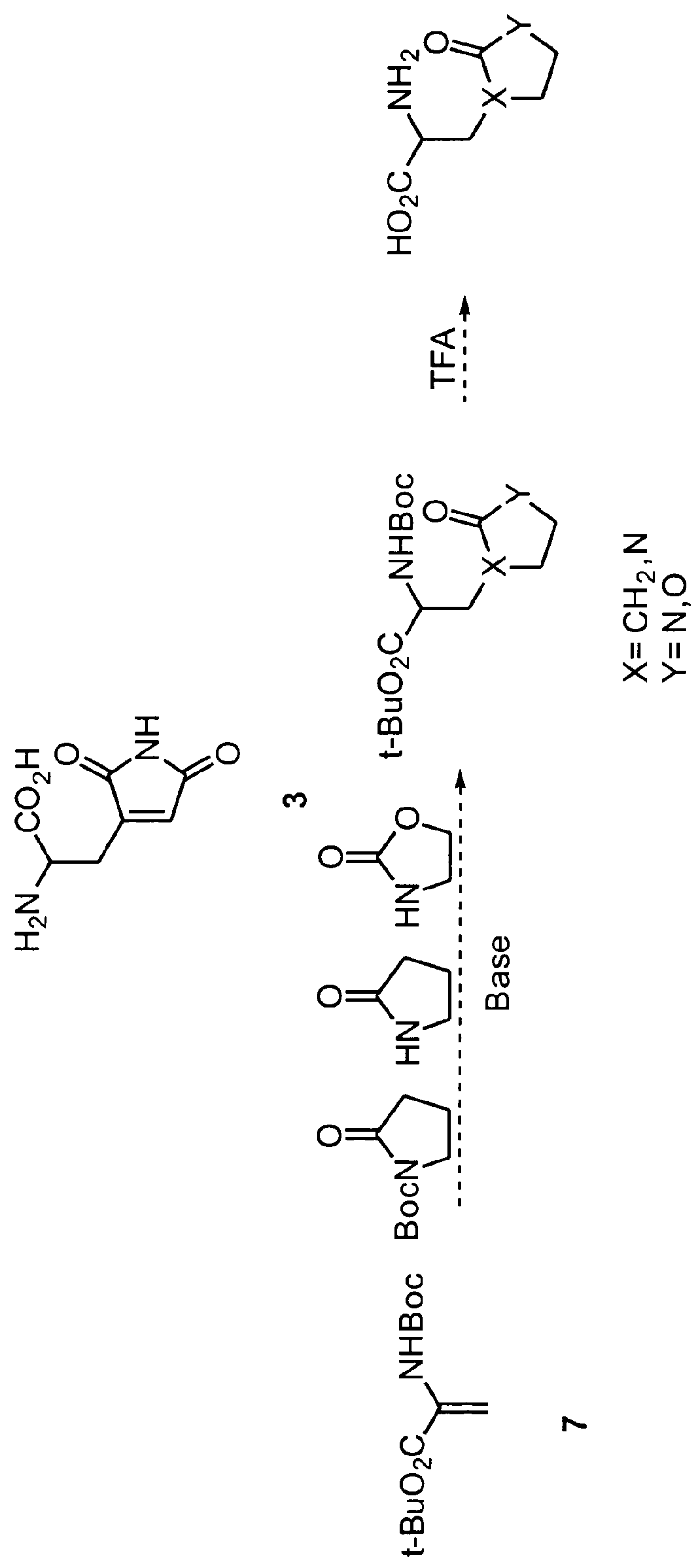
FIG. 25 illustrates the synthesis of a cyclic glutamine derivative.

An N—$C^{\gamma}$ cyclic analog, as illustrated by Compound number 3 in FIG. 25, is optionally prepared in 4 steps from Boc-Asp-Ot-Bu as previously described. See, e.g., Barton, D. H. R., Herve, Y., Potier, P. & Thierry, J. Synthesis of Novel a-Amino-Acids and Derivatives Using Radical Chemistry: Synthesis of L- and D-a-Amino-Adipic Acids, L-a-aminopimelic Acid and Appropriate Unsaturated Derivatives. *Tetrahedron Lett.* 43, 4297-4308 (1987) and, Subasinghe, N., Schulte, M., Roon, R. J., Koerner, J. F. & Johnson, R. L. Quisqualic acid analogues: synthesis of beta-heterocyclic 2-aminopropanoic acid derivatives and their activity at a novel quisqualate-sensitized site. *J. Med. Chem.* 35 4602-7 (1992). Generation of the anion of the N-t-Boc-pyrrolidinone, pyrrolidinone, or oxazolidone followed by the addition of the compound 7, as shown in FIG. 25, results in a Michael addition product. Deprotection with TFA then results in the free amino acids.

Figure 26:
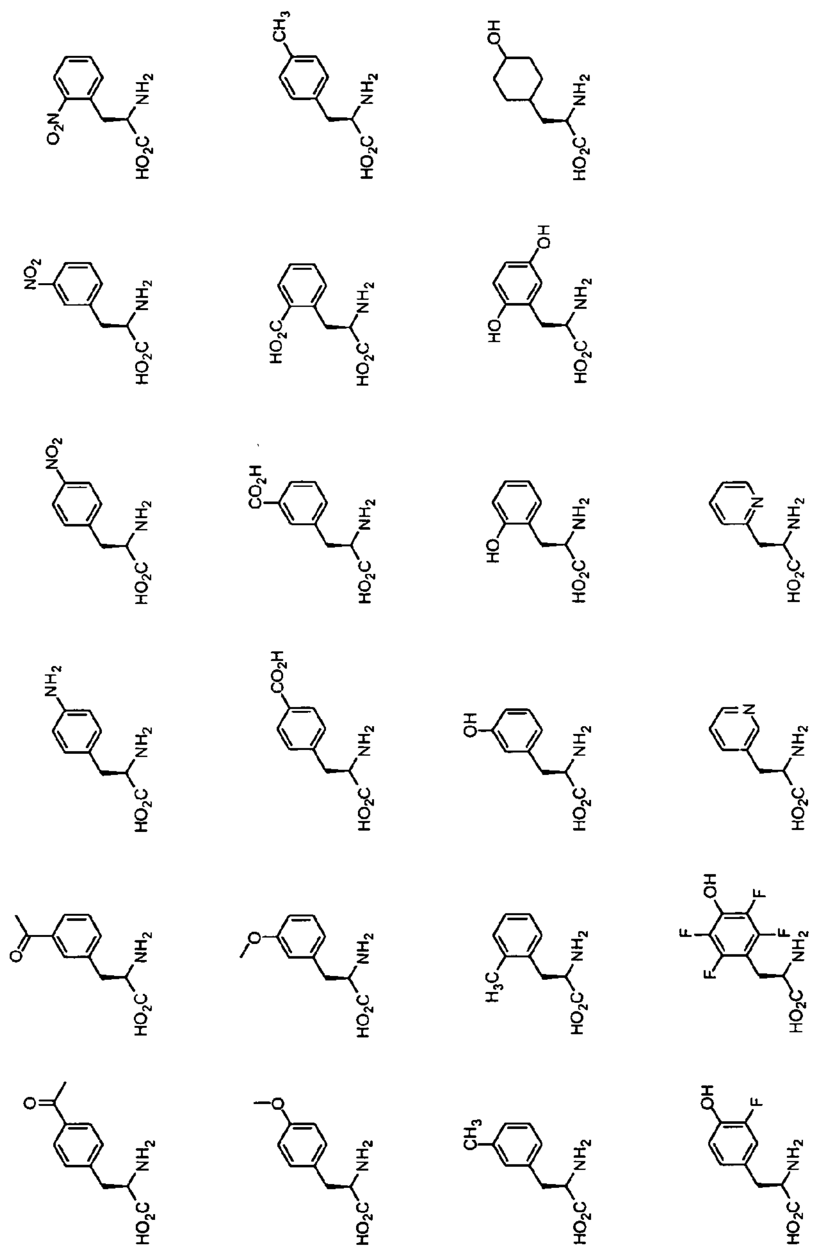
FIG. 26 illustrates a variety of tyrosine analogs.
Figure 27:
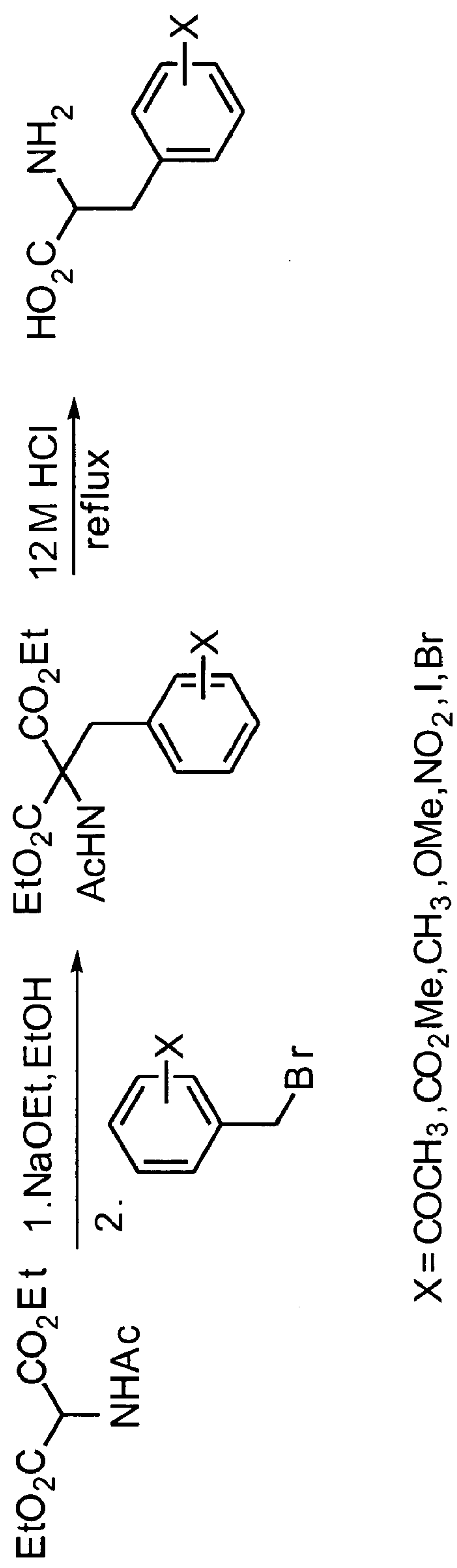
FIG. 27 illustrates a synthetic scheme for the production of tyrosine analogs.

In addition to the above unnatural amino acids, a library of tyrosine analogs has also been designed. Based upon the crystal structure of *B. stearothermophilus* TyrRS, whose active site is highly homologous to that of the *M. jannashii* synthetase, residues within a 10 Å shell of the aromatic side chain of tyrosine were mutated (Y32, G34, L65, Q155, D158, A167, Y32 and D158). The library of tyrosine analogs, as shown in FIG. 26, has been designed to complement an array of substitutions to these active site amino acids. These include a variety of phenyl substitution patterns, which offer different hydrophobic and hydrogen-bonding properties. Tyrosine analogs are optionally prepared using the general strategy illustrated by FIG. 27. For example, an enolate of diethyl acetamidomaionate is optionally generated using sodium ethoxide. A desired tyrosine analog can then be prepared by adding an appropriate benzyl bromide followed by hydrolysis.

Cellular Uptake of Unnatural Amino Acids

Unnatural amino acid uptake is one issue that is typically considered when designing and selecting unnatural amino acids, e.g., for incorporation into a protein. For example, the high charge density of α-amino acids suggests that these compounds are unlikely to be cell permeable. Natural amino acids are taken up into bacteria via a collection of protein-based transport systems displaying varying degrees of amino acid specificity. The present invention therefore provides a rapid screen for assessing which unnatural amino acids, if any, are taken up by cells.

For example, a variety of unnatural amino acids are optionally screened in minimal media for toxicity to cells. Toxicities are typically sorted into five groups: (1) no toxicity, in which no significant change in doubling times occurs; (2) low toxicity, in which doubling times increase by less than about 10%; (3) moderate toxicity, in which doubling times increase by about 10% to about 50%; (4) high toxicity, in which doubling times increase by about 50% to about 100%; and (5) extreme toxicity, in which doubling times increase by more than about 100%. See, e.g., Liu, D. R. & Schultz, P. G. Progress toward the evolution of an organism with an expanded genetic code. *Proceedings of the National Academy of Sciences of the United States of America* 96, 4780-4785 (1999). The toxicity of the amino acids scoring as highly or extremely toxic is typically measured as a function of their concentration to obtain IC50 values. In general, amino acids which are very close analogs of natural amino acids or which display reactive functionality demonstrate the highest toxicities. The former trend suggests that mechanisms of toxicity for these unnatural amino acids can be incorporation into proteins or inhibition of essential enzymes that process natural amino acids.

To identify possible uptake pathways for toxic amino acids, toxicity assays are optionally repeated at IC50 levels, e.g., in media supplemented with an excess of a structurally similar natural amino acid. For toxic amino acids, the presence of excess natural amino acid typically rescues the ability of the cells to grow in the presence of the toxin, presumably because the natural amino acid effectively outcompetes the toxin for either cellular uptake or for binding to essential enzymes. In these cases, the toxic amino acid is optionally assigned a possible uptake pathway and labeled a "lethal allele" whose complementation is required for cell survival. These lethal alleles are extremely useful for assaying the ability of cells to uptake nontoxic unnatural amino acids. Complementation of the toxic allele, evidenced by the restoration of cell growth, suggests that the nontoxic amino acid is taken up by the cell, possibly by the same uptake pathway as that assigned to the lethal allele. A lack of complementation is inconclusive. For example studies and conclusions see the examples provided below.

Results obtained, e.g., as described in the examples below, demonstrate that complementation of lethal unnatural amino acid alleles is an efficient method for qualitatively assessing amino acid uptake. The method typically requires far less effort than radiolabeling large numbers of compounds and is therefore a more advantageous method for analyzing unnatural; amino acids of interest. This general strategy is optionally used to rapidly evaluate the cellular uptake of a wide range of molecules such as nucleic acid base analogs, carbohydrate analogs, or peptide analogs. For example, this strategy is optionally used to evaluate the cellular uptake of the unnatural amino aids presented herein.

The present invention also provides a general method for delivering unnatural amino acids, which is independent of all amino acid uptake pathways. This general method relies on uptake via peptide permeases, which transport dipeptides and tripeptides across the cytoplasmic membrane. Peptide permeases are not very side-chain specific, and the KD values for their substrates are comparable to KD values of amino acid permeases, e.g., about 0.1 mM to about 10 mM). See, e.g., Nickitenko, A., Trakhanov, S. & Quiocho, S. A structure of DppA, a periplasmic depeptide transport/chemosensory receptor. *Biochemistry* 34, 16585-16595 (1995) and Dunten, P., Mowbray, S. L. Crystal structure of the dipeptide binding protein from *Escherichia coli* involved in active transport and chemotaxis. *Protein Science* 4, 2327-34 (1995). The unnatural amino acids are then uptaken as conjugates of natural amino acids, such as lysine, and released into the cytoplasm upon hydrolysis of the dipeptide by one of endogenous *E. coli* peptidases. To test this approach, we synthesized several Unn-Lys and Lys-Unn dipeptides by solid phase synthesis, and tested the growth of an *E. coli* strain deficient in lysine biosynthesis on lysine minimal media in the presence and absence of these dipeptides. The only source of lysine available to these cells is the dipeptide containing the unnatural amino acid. Uptake of phosphonoserine, phosphonotyrosine, pentafluorophenylalanine, and caged serine have been analyzed in this manner. In all four cases, growth was observed on 10 mM and higher dipeptide concentrations. Although uptake is easily analyzed with the method provided herein, an alternative to designing unnatural amino acid that are amenable to cellular uptake pathways, is to provide biosynthetic pathways to create amino acids in vivo.

Biosynthesis of Unnatural Amino Acids

Many biosynthetic pathways already exist in cells for the production of amino acids and other compounds. While a biosynthetic method for a particular unnatural amino acid may not exist in nature, e.g., in *E. coli*, the present invention provide such methods. For example, biosynthetic pathways for unnatural amino acids are optionally generated in *E. coli* by adding new enzymes or modifying existing *E. coli* pathways. Additional new enzymes are optionally naturally occurring enzymes or artificially evolved enzymes. For example, the biosynthesis of p-aminophenylalanine (as presented in an example below) relies on the addition of a combination of known enzymes from other organisms. The genes for these enzymes can be introduced into a cell, e.g., an *E. coli* cell, by transforming the cell with a plasmid comprising the genes. The genes, when expressed in the cell, provide an enzymatic pathway to synthesize the desired compound. Examples of the types of enzymes that are optionally added are provided in the examples below. Additional enzymes sequences are found, e.g., in Genbank. Artificially evolved enzymes are also optionally added into a cell in the same manner. In this manner, the cellular machinery and resources of a cell are manipulated to produce unnatural amino acids.

A variety of methods are available for producing novel enzymes for use in biosynthetic pathways or for evolution of existing pathways. For example, recursive recombination, e.g., as developed by Maxygen, Inc. (on the world wide web at maxygen.com), is optionally used to develop novel enzymes and pathways. See, e.g., Stemmer 1994, "Rapid evolution of a protein in vitro by DNA shuffling," *Nature* Vol. 370 No. 4: Pg. 389-391; and Stemmer, 1994, "DNA shuffling by random fragmentation and reassembly: In vitro recombination for molecular evolution," *Proc. Natl. Acad. Sci. USA*. Vol. 91: Pg. 10747-10751. Similarly DesignPath™, developed by Genencor (on the world wide web at genencor.com) is optionally used for metabolic pathway engineering, e.g., to engineer a pathway to create O-methyl-L-trosine in *E coli*. This technology reconstructs existing pathways in host organisms using a combination of new genes, e.g., identified through functional genomics, and molecular evolution and design. Diversa Corporation (on the world wide web at diversa.com) also provides technology for rapidly screening libraries of genes and gene pathways, e.g., to create new pathways.

Typically, the biosynthesis methods of the present invention, e.g., the pathway to create p-aminophenylalanine (pAF) from chorismate, do not affect the concentration of other amino acids produced in the cell. For example a pathway used to produce pAF from chorismate produces pAF in the cell while the concentrations of other aromatic amino acids typically produced from chorismate are not substantially affected. Typically the unnatural amino acid produced with an engineered biosynthetic pathway of the present invention is produced in a concentration sufficient for efficient protein biosynthesis, e.g., a natural cellular amount, but not to such a degree as to affect the concentration of the other amino acids or exhaust cellular resources. Typical concentrations produced in vivo in this manner are about 10 mM to about 0.05 mM. Once a bacterium is transformed with a plasmid comprising the genes used to produce enzymes desired for a specific pathway and a twenty-first amino acid, e.g., pAF, dopa, O-methyl-L-tyrosine, or the like, is generated, in vivo selections are optionally used to further optimize the production of the unnatural amino acid for both ribosomal protein synthesis and cell growth.

Compositions that Include Proteins with Unnatural Amino Acids

The invention provides compositions of matter, including proteins with at least one unnatural amino acid. The invention also provides compositions of matter that include proteins with at least one unnatural amino acid produced using the compositions and methods of the invention. In one embodiment, the proteins are processed and modified in a cell dependent manner, e.g., phosphorylated, glycosylated, folded, membrane bound, etc.

In one aspect, the composition optionally includes at least about 10 micrograms, e.g., at least about 50 micrograms, at least about 100 micrograms, at least about 500 micrograms, at least about 1 milligram, or even at least about 10 milligrams or more of the protein, e.g., an amount that can be achieved with in vivo protein production methods (details on recombinant protein production and purification are provided herein). For example, the protein is optionally present in the composition at a concentration of at least about 10 micrograms per liter, at least about 50 micrograms per liter, at least about 100 micrograms per liter, at least about 500 micrograms per liter, at least about 1 milligram per liter, or at least about 10 milligrams per liter of the protein, or more micrograms or protein per liter, e.g., in a cell lysate, pharmaceutical buffer, or other liquid suspension (e.g., in a volume of, e.g., anywhere from about 1 nl to about 100L). The production of large quantities (e.g., greater that that typically possible with other methods, e.g., in vitro translation) of a protein including at least one unnatural amino acid is a feature of the invention and is an advantage over the prior art.

The production of large quantities (e.g., greater that that typically possible with other methods, e.g., in vitro translation) of a protein including at least one unnatural amino acid is a feature of the invention and is an advantage over the prior art. For example, the ability to synthesize large quantities of proteins containing, e.g., heavy atoms, facilitates protein structure determination via, e.g., X-ray cystallography.

The incorporation of an unnatural amino acid can be done to, e.g., tailor changes in protein structure and/or function, e.g., to change size, acidity, nucleophilicity, hydrogen bonding, hydrophobicity, accessibility of protease target sites, etc. Proteins that include an unnatural amino acid can have enhanced or even entirely new catalytic or physical properties. For example, the following properties are optionally modified by inclusion of an unnatural amino acid into a protein: toxicity, biodistribution, structural properties, spectroscopic properties, chemical and/or photochemical properties, catalytic ability, half-life (e.g., serum half-life), ability to react with other molecules, e.g., covalently or noncovalently, and the like. The compositions including proteins that include at least one unnatural amino acid are useful for, e.g., novel therapeutics, diagnostics, catalytic enzymes, binding proteins (e.g., antibodies), and e.g., the study of protein structure and function.

In one aspect of the invention, a composition includes at least one protein with at least one, e.g., at least two, at least three, at least four, at least five, at least six, at least seven, at least eight, at least nine, at least ten, or more unnatural amino acids. For a given protein with more than one unnatural amino acids, the unnatural amino acids can be identical or different (e.g., the protein can include two or more different types of unnatural amino acids, or can include two or more different sites having unnatural amino acids, or both).

Essentially any protein that includes an unnatural amino acid (and any corresponding coding nucleic acid, e.g., which includes one or more selector codons) can be produced using the compositions and methods herein. No attempt is made to identify the hundreds of thousands of known proteins, any of which can be modified to include one or more unnatural amino acid, e.g., by tailoring any available mutation methods to include one or more appropriate selector codon in a relevant translation system. Common sequence repositories for known proteins include GenBank EMBL, DDBJ and the NCBI. Other repositories can easily be identified by searching the internet.

One preferred class of proteins that can be made using the compositions and methods for in vivo incorporation of unnatural amino acids described herein includes therapeutic proteins. Examples of therapeutic and other proteins that can be modified to comprise one or more unnatural include, e.g., Alpha-1 antitrypsin, Angiostatin, Antihemolytic factor, antibodies (further details on antibodies are found below), Apolipoprotein, Apoprotein, Atrial natriuretic factor, Atrial natriuretic polypeptide, Atrial peptides, C-X-C chemokines (e.g., T39765, NAP-2, ENA-78, Gro-a, Gro-b, Gro-c, IP-10, GCP-2, NAP-4, SDF-1, PF4, MIG), Calcitonin, CC chemokines (e.g., Monocyte chemoattractant protein-1, Monocyte chemoattractant protein-2, Monocyte chemoattractant protein-3, Monocyte inflammatory protein-1 alpha, Monocyte inflammatory protein-1 beta, RANTES, I309, R83915, R91733, HCC1, T58847, D31065, T64262), CD40 ligand, C-kit Ligand, Collagen, Colony stimulating factor (CSF), Complement factor 5a, Complement inhibitor, Complement receptor 1, cytokines, (e.g., epithelial Neutrophil Activating Peptide-78, GROα/MGSA, GROβ, GROγ, MIP-1α, MIP-1β, MCP-1), Epidermal Growth Factor (EGF), Erythropoietin ("EPO", representing a preferred target for modification by the incorporation of one or more unnatural amino acid), Exfoliating toxins A and B, Factor IX, Factor VII, Factor VIII, Factor X, Fibroblast Growth Factor (FGF), Fibrinogen, Fibronectin, G-CSF, GM-CSF, Glucocerebrosidase, Gonadotropin, growth factors, Hedgehog proteins (e.g., Sonic, Indian, Desert), Hemoglobin, Hepatocyte Growth Factor (HGF), Hirudin, Human serum albumin, Insulin, Insulin-like Growth Factor (IGF), interferons (e.g., IFN-α, IFN-β, IFN-γ), interleukins (e.g., IL-1, IL-2, IL-3, IL-4, IL-5, IL-6, IL-7, IL-8, IL-9, IL-10, IL-11, IL-12, etc.), Keratinocyte Growth Factor (KGF), Lactoferrin, leukemia inhibitory factor, Luciferase, Neurturin, Neutrophil inhibitory factor (NIF), oncostatin M, Osteogenic protein, Parathyroid hormone, PD-ECSF, PDGF, peptide hormones (e.g., Human Growth Hormone), Pleiotropin, Protein A, Protein G, Pyrogenic exotoxins A, B, and C, Relaxin, Renin, SCF, Soluble complement receptor I, Soluble I-CAM 1, Soluble interleukin receptors (IL-1, 2, 3, 4, 5, 6, 7, 9, 10, 11, 12, 13, 14, 15), Soluble TNF receptor, Somatomedin, Somatostatin, Somatotropin, Streptokinase, Superantigens, i.e., *Staphylococcal enterotoxins* (SEA, SEB, SEC1, SEC2, SEC3, SED, SEE), Superoxide dismutase, Toxic shock syndrome toxin (TSST-1), Thymosin alpha 1, Tissue plasminogen activator, Tumor necrosis factor beta (TNF beta), Tumor necrosis factor receptor (TNFR), Tumor necrosis factor-alpha (TNF alpha), Vascular Endothelial Growth Factor (VEGEF), Urokinase and many others.

Many of these proteins are commercially available (See, e.g., the Sigma BioSciences 2002 catalogue and price list), and the corresponding protein sequences and genes and, typically, many variants thereof, are well-known (see, e.g., Genebank). Any of them can be modified by the insertion of one or more unnatural amino acid according to the present invention, e.g., to alter the protein with respect to one or more therapeutic property of interest. Examples of therapeutically relevant properties include serum half-life, shelf half-life, stability, immunogenicity, therapeutic activity, detectability (e.g., by the inclusion of reporter groups (e.g., labels or label binding sites) in the unnatural amino acids), reduction of LD-50 or other side effects, ability to enter the body through the gastric tract (e.g., oral availability), or the like.

One class of proteins that can be made using the compositions and methods for in vivo incorporation of unnatural amino acids described herein includes transcriptional and expression activators. Example transcriptional and expression activators include genes and proteins that modulate cell growth, differentiation, regulation, or the like. Expression and transcriptional activators are found in prokaryotes, viruses, and eukaryotes, including fungi, plants, and animals, including mammals, providing a wide range of therapeutic targets. It will be appreciated that expression and transcriptional activators regulate transcription by many mechanisms, e.g., by binding to receptors, stimulating a signal transduction cascade, regulating expression of transcription factors, binding to promoters and enhancers, binding to proteins that bind to promoters and enhancers, unwinding DNA, splicing pre-mRNA, polyadenylating RNA, and degrading RNA.

One preferred class of proteins of the invention (e.g., proteins with one or more unnatural amino acids) include expression activators such as cytokines, inflammatory molecules, growth factors, their receptors, and oncogene products, e.g., interleukins (e.g., IL-1, IL-2, IL-8, etc.), interferons, FGF, IGF-I, IGF-II, FGF, PDGF, TNF, TGF-α, TGF-β, EGF, KGF, SCF/c-Kit, CD40L/CD40, VLA-4/VCAM-1, ICAM-1/LFA-1, and hyalurin/CD44; signal transduction molecules and corresponding oncogene products, e.g., Mos, Ras, Raf, and Met; and transcriptional activators and suppressors, e.g., p53, Tat, Fos, Myc, Jun, Myb, Rel, and steroid hormone receptors such as those for estrogen, progesterone, testosterone, aldosterone, the LDL receptor ligand and corticosterone.

A variety of other proteins can also be modified to include one or more unnatural amino acid of the invention. For example, the invention can include substituting one or more natural amino acids in one or more vaccine proteins with an unnatural amino acid, e.g., in proteins from infectious fungi, e.g., *Aspergillus, Candida* species; bacteria, particularly *E. coli*, which serves a model for pathogenic bacteria, as well as medically important bacteria such as *Staphylococci* (e.g., *aureus*), or *Streptococci* (e.g., *pneumoniae*); protozoa such as *sporozoa* (e.g., *Plasmodia*), *rhizopods* (e.g., *Entamoeba*) and flagellates (*Trypanosoma, Leishmania, Trichomonas, Giardia*, etc.); viruses such as (+) RNA viruses (examples include Poxviruses e.g., *vaccinia*; Picornaviruses, e.g. *polio*; Togaviruses, e.g., *rubella*; Flaviviruses, e.g., HCV; and Coronaviruses), (−) RNA viruses (e.g., Rhabdoviruses, e.g., VSV; Paramyxovimses, e.g., RSV; Orthomyxovimses, e.g., influenza; Bunyaviruses; and Arenaviruses), dsDNA viruses (Reoviruses, for example), RNA to DNA viruses, i.e., Retroviruses, e.g., HIV and HTLV, and certain DNA to RNA viruses such as Hepatitis B.

A variety of enzymes (e.g., industrial enzymes) can also be modified to include one or more unnatural amino acid according to the methods herein, such as amidases, amino acid racemases, acylases, dehalogenases, dioxygenases, diarylpropane peroxidases, epimerases, epoxide hydrolases, esterases, isomerases, kinases, glucose isomerases, glycosidases, glycosyl transferases, haloperoxidases, monooxygenases (e.g., p450s), lipases, lignin peroxidases, nitrile hydratases, nitrilases, proteases, phosphatases, subtilisins, transaminase, and nucleases.

Agriculturally related proteins such as insect resistance proteins (e.g., the Cry proteins), starch and lipid production enzymes, plant and insect toxins, toxin-resistance proteins, Mycotoxin detoxification proteins, plant growth enzymes (e.g., Ribulose 1,5-Bisphosphate Carboxylase/Oxygenase, "RUBISCO"), lipoxygenase (LOX), and Phosphoenolpyruvate (PEP) carboxylase are also suitable targets for unnatural amino acid modification.

Genes coding for proteins including at least one unnatural amino acid can be mutagenized using methods well-known to one of skill in the art and described herein under "General Molecular Biology Techniques." For example, a nucleic acid for a protein of interest is mutagenized to include one or more selector codon, providing for insertion of the one or more unatural amino acids. The present invention includes any such variant, e.g., mutant, versions of any protein, e.g., including at least one unnatural amino acid.

Similarly, the present invention also includes corresponding nucleic acids, i.e., any nucleic acid with one or more selector codon that encodes one or more unnatural amino acid.

In one example embodiment, the invention provides compositions that include a Asp112TAG mutant of chloramphenicol acetylransferase (CAT) produced by the compositions and methods of the invention, where the CAT protein includes at least one unnatural amino acid, e.g., an O-methyl-L-tyrosine, an L-3-(2-naphthyl)alanine, an amino-, isopropyl-, or allyl-containing tyrosine analogue, etc., and the protein is present in the composition at a concentration of at least about 100 micrograms per liter. In another embodiment, the invention provides compositions that include a Tyr163TAG mutant of mouse dihydrofolate reductase (DHFR) where the DHFR protein includes at least one unnatural amino, e.g., an O-methyl-L-tyrosine, an L-3-(2-naphthyl)alanine, an amino-, isopropyl-, or allyl-containing tyrosine analogue, etc., and the protein is present in the composition at a concentration of at least about 100 micrograms per liter.

Making Antibodies to Proteins Comprising Unnatural Amino Acids

In one aspect, the present invention provides antibodies to unnatural amino acids and to proteins comprising unnatural amino acids. Antibodies to unnatural amino acids and proteins comprising such unnatural amino acids are useful as purification reagents, e.g., for purifying the proteins and unnatural amino acids of the invention. In addition, the antibodies can be used as indicator reagents to indicate the presence of an unnatural amino acid or protein comprising an unnatural amino acid, e.g., to track the presence or location (e.g., in vivo or in situ) of the unnatural amino acid or protein comprising an unnatural amino acid. It is also, of course, the case that the unnatural amino acid can itself comprise one or more unnatural amino acids, thereby providing an antibody with one or more property conferred by the one or more unnatural amino acids.

An antibody of the invention can be a protein comprising one or more polypeptides substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin (e.g., antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain ($V_H$) refer to these light and heavy chains, respectively.

Antibodies exist as intact immunoglobulins or as a number of well characterized fragments produced by digestion with various peptidases. Thus, for example, pepsin digests an antibody below the disulfide linkages in the hinge region to produce $F(ab')_2$, a dimer of Fab which itself is a light chain joined to $V_H$-$C_H1$ by a disulfide bond. The $F(ab')_2$ may be reduced under mild conditions to break the disulfide linkage in the hinge region thereby converting the $F(ab')_2$ dimer into an Fab' monomer. The Fab' monomer is essentially an Fab with part of the hinge region (see, *Fundamental Immunology*, W. E. Paul, ed., Raven Press, N.Y. (1999), for a more detailed description of other antibody fragments). While various antibody fragments are defined in terms of the digestion of an intact antibody, one of skill will appreciate that such Fab' fragments, etc. may be synthesized de novo either chemically or by utilizing recombinant DNA methodology. Thus, the term antibody, as used herein, also optionally includes antibody fragments either produced by the modification of whole antibodies or synthesized de novo using recombinant DNA methodologies. Antibodies include single chain antibodies, including single chain Fv (sFv or scFv) antibodies in which a variable heavy and a variable light chain are joined together (directly or through a peptide linker) to form a continuous polypeptide. Antibodies of the invention can be, e.g., polyclonal, monoclonal, chimeric, humanized, single chain, Fab fragments, fragments produced by an Fab expression library, or the like.

In general, antibodies of the invention are valuable, both as general reagents and as therapeutic reagents in a variety of molecular biological or pharmaceutical processes. Methods of producing polyclonal and monoclonal antibodies are available, and can be applied to making the antibodies of the present invention. A number of basic texts describe standard antibody production processes, including, e.g., Borrebaeck (ed) (1995) *Antibody Engineering*, 2nd Edition Freeman and Company, N.Y. (Borrebaeck); McCafferty et al. (1996) *Antibody Engineering, A Practical Approach* IRL at Oxford Press, Oxford, England (McCafferty), and Paul (1995) *Antibody Engineering Protocols* Humana Press, Towata, N.J. (Paul); Paul (ed.), (1999) *Fundamental Immunology, Fifth edition* Raven Press, N.Y.; Coligan (1991) *Current Protocols in Immunology* Wiley/Greene, N.Y.; Harlow and Lane (1989) *Antibodies: A Laboratory Manual* Cold Spring Harbor Press, N.Y.; Stites et al. (eds.) *Basic and Clinical Immunology* (4th ed.) Lange Medical Publications, Los Altos, Calif., and references cited therein; Goding (1986) *Monoclonal Antibodies: Principles and Practice* (2d ed.) Academic Press, New York, N.Y.; and Kohler and Milstein (1975) *Nature* 256: 495-497.

A variety of recombinant techniques for antibody preparation which do not rely on, e.g., injection of an antigen into an animal have been developed and can be used in the context of the present invention. For example, it is possible to generate and select libraries of recombinant antibodies in phage or similar vectors. See, e.g., Winter et al. (1994) "Making Antibodies by Phage Display Technology" *Annu. Rev. Immunol*. 12:433-55 and the references cited therein for a review. See also, Griffiths and Duncan (1998) "Strategies for selection of antibodies by phage display" *Curr Opin Biotechnol* 9: 102-8; Hoogenboom et al. (1998) "Antibody phage display technology and its applications" *Immunotechnology* 4: 1-20; Gram et al. (1992) "in vitro selection and affinity maturation of antibodies from a naive combinatorial immunoglobulin library" *PNAS* 89:3576-3580; Huse et al. (1989) *Science* 246: 1275-1281; and Ward, et al. (1989) *Nature* 341: 544-546.

In one embodiment, antibody libraries can include repertoires of V genes (e.g., harvested from populations of lymphocytes or assembled in vitro) which are cloned for display of associated heavy and light chain variable domains on the surface of filamentous bacteriophage. Phage are selected by binding to an antigen. Soluble antibodies are expressed from phage infected bacteria and the antibody can be improved, e.g., via mutagenesis. See e.g., Balint and Larrick (1993) "Antibody Engineering by Parsimonious Mutagenesis" *Gene* 137:109-118; Stemmer et al. (1993) "Selection of an Active Single Chain Fv Antibody From a Protein Linker Library Prepared by Enzymatic Inverse PCR" *Biotechniques* 14(2):256-65; Crameri et al. (1996) "Construction and evolution of antibody-phage libraries by DNA shuffling" *Nature Medicine* 2:100-103; and Crameri and Stemmer (1995) "Combinatorial multiple cassette mutagenesis creates all the permutations of mutant and wildtype cassettes" *BioTechniques* 18:194-195.

Kits for cloning and expression of recombinant antibody phage systems are also known and available, e.g., the "recombinant phage antibody system, mouse ScFv module," from Amersham-Pharmacia Biotechnology (Uppsala, Sweden). Bacteriophage antibody libraries have also been produced for making high affinity human antibodies by chain shuffling (See, e.g., Marks et al. (1992) "By-Passing Immunization: Building High Affinity Human Antibodies by Chain Shuffling" *Biotechniques* 10:779-782. Indeed, antibodies can typically be custom ordered from any of a variety of sources, such as PeptidoGenic, HTI Bio-products, inc., BMA Biomedicals Ltd (U.K.), Bio.Synthesis, Inc., Research Genetics (Huntsville, Ala.) and many others.

In certain embodiments, it is useful to "humanize" antibodies of the invention, e.g., where the antibodies are to be administered therapeutically. The use of humanized antibodies tends to reduce the incidence of unwanted immune responses against the therapeutic antibodies (e.g., when the patient is a human). The antibody references above describe humanization strategies. In addition to humanized antibodies, human antibodies are also a feature of the invention. Human antibodies consist of characteristically human immunoglobulin sequences. Human antibodies can be produced in using a wide variety of methods (see, e.g., Larrick et al., U.S. Pat. No. 5,001,065, for a review). A general approach for producing human antibodies by trioma technology is described by Ostberg et al. (1983), *Hybridoma* 2: 361-367, Ostberg, U.S. Pat. No. 4,634,664, and Engelman et al., U.S. Pat. No. 4,634,666.

A variety of methods of using antibodies in the purification and detection of proteins are known and can be applied to detecting and purifying proteins comprising unnatural amino acids as noted herein. In general, antibodies are useful reagents for ELISA, western blotting, immunochemistry, affinity chromatograpy methods, SPR, and many other methods. The references noted above provide details on how to perform ELISA assays, western blots, surface plasmon resonance (SPR) and the like.

In one aspect of the invention, antibodies of the invention themselves include unnatural amino acids, providing the antibodies with properties of interest (e.g., improved half-life, stability, toxicity, or the like. Antibodies account for nearly 50% of all compounds currently in clinical trials (Wittrup, (1999) "Phage on display" *Tibtech* 17: 423-424 and antibodies are used ubiquitously as diagnostic reagents. Accordingly, the ability to modify antibodies with unnatural amino acids provides an important tool for modifying these valuable reagents.

For example, there are many applications of MAbs to the field of diagnostics. Assays range from simple spot tests to more involved methods such as the radio-labeled NR-LU-10 MAb from DuPont Merck Co. used for tumor imaging (Rusch et al. (1993) "NR-LU-10 monoclonal antibody scanning. A helpful new adjunct to computed tomography in evaluating non-small-cell lung cancer." *J Thorac Cardiovasc Surg* 106: 200-4). As noted, MAbs are central reagents for ELISA, western blotting, immunochemistry, affinity chromatograpy methods and the like. Any such diagnostic antibody can be modified to include one or more unnatural amino acid, altering, e.g., the specificity or avidity of the Ab for a target, or altering one or more detectable property, e.g., by including a detectable label (e.g., spectrographic, fluorescent, luminescent, etc.) in the unnatural amino acid.

One class of valuable antibody reagents are therapeutic Abs. For example, antibodies can be tumor-specific MAbs that arrest tumor growth by Targeting tumor cells for destruction by antibody-dependent cell-mediated cytotoxicity (ADCC) or complement-mediated lysis (CML) (these general types of Abs are sometimes referred to as "magic bullets"). One example is Rituxan, an anti-CD20 MAb for the treatment of Non-Hodgkins lymphoma (Scott (1998) "Rituximab: a new therapeutic monoclonal antibody for non-Hodgkin's lymphoma" *Cancer Pract* 6: 195-7). A second example relates to antibodies which interfere with a critical component of tumor growth. Herceptin is an anti-HER-2 monoclonal antibody for treatment of metastatic breast cancer, and provides an example of an antibody with this mechanism of action (Baselga et al. (1998) "Recombinant humanized anti-HER2 antibody (Herceptin) enhances the antitumor activity of paclitaxel and doxorubicin against HER2/neu overexpressing human breast cancer xenografts [published erratum appears in *Cancer Res* (1999) 59(8): 2020], *Cancer Res* 58: 2825-31). A third example relates to antibodies for delivery of cytotoxic compounds (toxins, radionuclides, etc.) directly to a tumor or other site of interest. For example, One application Mab is CYT-356, a 90Y-linked antibody that targets radiation directly to prostate tumor cells (Deb et al. (1996) "Treatment of hormone-refractory prostate cancer with 90Y-CYT-356 monoclonal antibody" *Clin Cancer Res* 2: 1289-97. A fourth application is antibody-directed enzyme prodrug therapy, where an enzyme co-localized to a tumor activates a systemically-administered pro-drug in the tumor vicinity. For example, an anti-Ep-CAM1 antibody linked to carboxypeptidase A is being developed for treatment of colorectal cancer (Wolfe et al. (1999) "Antibody-directed enzyme prodrug therapy with the T268G mutant of human carboxypeptidase A1: in vitro and in vivo studies with prodrugs of methotrexate and the thymidylate synthase inhibitors GW1031 and GW1843" *Bioconjug Chem* 10: 38-48). Other Abs (e.g., antagonists) are designed to specifically inhibit normal cellular functions for therapeutic benefit. An example is Orthoclone OKT3, an anti-CD3 MAb offered by Johnson and Johnson for reducing acute organ transplant rejection (Strate et al. (1990) "Orthoclone OKT3 as first-line therapy in acute renal allograft rejection" *Transplant Proc* 22: 219-20. Another class of antibody products are agonists. These Mabs are designed to specifically enhance normal cellular functions for therapeutic benefit. For example, Mab-based agonists of acetylcholine receptors for neurotherapy are under development (Xie et al. (1997) "Direct demonstration of MuSK involvement in acetylcholine receptor clustering through identification of agonist ScFv" *Nat. Biotechnol.* 15: 768-71. Any of these antibodies can be modified to include one or more unnatural amino acid to enhance one or more therapeutic property (specificity, avidity, serum-half-life, etc.).

Another class of antibody products provide novel functions. The main antibodies in this group are catalytic antibodies such as Ig sequences that have been engineered to mimic the catalytic abilities of enzymes (Wentworth and Janda (1998) "Catalytic antibodies" *Curr Opin Chem Biol* 2: 138-44. For example, an interesting application involves using the catalytic antibody mAb-15A10 to hydrolyze cocaine in vivo for addiction therapy (Mets et al. (1998) "A catalytic antibody against cocaine prevents cocaine's reinforcing and toxic effects in rats" *Proc Natl Acad Sci USA* 95: 10176-81). Catalytic antibodies can also be modified to include one or more unnatural amino acid to improve one or more property of interest.

Purifying Recombinant Proteins Comprising Unnatural Amino Acids

Proteins of the invention, e.g., proteins comprising unnatural amino acids, antibodies to proteins comprising unnatural amino acids, etc., can be purified, either partially or substantially to homogeneity, according to standard procedures known to and used by those of skill in the art. Accordingly, polypeptides of the invention can be recovered and purified by any of a number of methods well known in the art, including, e.g., ammonium sulfate or ethanol precipitation, acid or base extraction, column chromatography, affinity column chromatography, anion or cation exchange chromatography, phosphocellulose chromatography, hydrophobic interaction chromatography, hydroxylapatite chromatography, lectin chromatography, gel electrophoresis and the like. Protein refolding steps can be used, as desired, in making correctly folded mature proteins. High performance liquid chromatography (HPLC), affinity chromatography or other suitable methods can be employed in final purification steps where high purity is desired. In one embodiment, antibodies made against unnatural amino acids (or proteins comprising unnatural amino acids) are used as purification reagents, e.g., for affinity-based purification of proteins comprising one or more unnatural amino acid(s). Once purified, partially or to homogeneity, as desired, the polypeptides are optionally used e.g., as assay components, therapeutic reagents or as immunogens for antibody production.

In addition to other references noted herein, a variety of purification/protein folding methods are well known in the art, including, e.g., those set forth in R. Scopes, *Protein Purification*, Springer-Verlag, N.Y. (1982); Deutscher, *Methods in Enzymology Vol. 182: Guide to Protein Purification*, Academic Press, Inc. N.Y. (1990); Sandana (1997) *Bioseparation of Proteins*, Academic Press, Inc.; Bollag et al. (1996) *Protein Methods*, 2nd Edition Wiley-Liss, NY; Walker (1996) *The Protein Protocols Handbook* Humana Press, N.J., Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification: Principles and Practice* 3rd Edition Springer Verlag, N.Y.; Janson and Ryden (1998) *Protein Purification: Principles, High Resolution Methods and Applications, Second Edition* Wiley-VCH, N.Y.; and Walker (1998) *Protein Protocols on CD-ROM* Humana Press, N.J.; and the references cited therein.

As noted, those of skill in the art will recognize that, after synthesis, expression and/or purification, proteins can possess a conformation different from the desired conformations of the relevant polypeptides. For example, polypeptides produced by prokaryotic systems often are optimized by exposure to chaotropic agents to achieve proper folding. During purification from, e.g., lysates derived from *E. coli*, the expressed protein is optionally denatured and then renatured. This is accomplished, e.g., by solubilizing the proteins in a chaotropic agent such as guanidine HCl.

In general, it is occasionally desirable to denature and reduce expressed polypeptides and then to cause the polypeptides to re-fold into the preferred conformation. For example, guanidine, urea, DTT, DTE, and/or a chaperonin can be added to a translation product of interest. Methods of reducing, denaturing and renaturing proteins are well known to those of skill in the art (see, the references above, and Debinski, et al. (1993) J. Biol. Chem., 268: 14065-14070; Kreitman and Pastan (1993) Bioconjug. Chem.,4: 581-585; and Buchner, et al., (1992) Anal. Biochem., 205: 263-270). Debinski, et al., for example, describe the denaturation and reduction of inclusion body proteins in guanidine-DTE. The proteins can be refolded in a redox buffer containing, e.g., oxidized glutathione and L-arginine. Refolding reagents can be flowed or otherwise moved into contact with the one or more polypeptide or other expression product, or vice-versa.

Nucleic Acid and Polypeptide Sequence Variants

As described above and below, the invention provides for nucleic acid polynucleotide sequences and polypeptide amino acid sequences, e.g., O—tRNAs and O-RSs, and, e.g., compositions and methods comprising said sequences. Examples of said sequences, e.g., O-tRNAs and O—RSs are disclosed herein. However, one of skill in the art will appreciate that the invention is not limited to those sequences disclosed herein, e.g., the Examples. One of skill will appreciate that the present invention also provides many unrelated sequences with the functions described herein, e.g., encoding an O-tRNA or an O—RS.

One of skill will also appreciate that many variants of the disclosed sequences are included in the invention. For example, conservative variations of the disclosed sequences that yield a functionally identical sequence are included in the invention. Variants of the nucleic acid polynucleotide sequences, wherein the variants hybridize to at least one disclosed sequence, are considered to be included in the invention. Unique subsequences of the sequences disclosed herein, as determined by, e.g., standard sequence comparison techniques, are also included in the invention.

Conservative Variations

Owing to the degeneracy of the genetic code, "silent substitutions" (i.e., substitutions in a nucleic acid sequence which do not result in an alteration in an encoded polypeptide) are an implied feature of every nucleic acid sequence which encodes an amino acid. Similarly, "conservative amino acid substitutions," in one or a few amino acids in an amino acid sequence are substituted with different amino acids with highly similar properties, are also readily identified as being highly similar to a disclosed construct. Such conservative variations of each disclosed sequence are a feature of the present invention.

"Conservative variations" of a particular nucleic acid sequence refers to those nucleic acids which encode identical or essentially identical amino acid sequences, or, where the nucleic acid does not encode an amino acid sequence, to essentially identical sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid. Thus, "conservative variations" of a listed polypeptide sequence of the present invention include substitutions of a small percentage, typically less than 5%, more typically less than 2% or 1%, of the amino acids of the polypeptide sequence, with a conservatively selected amino acid of the same conservative substitution group. Finally, the addition of sequences which do not alter the encoded activity of a nucleic acid molecule, such as the addition of a non-functional sequence, is a conservative variation of the basic nucleic acid.

Conservative substitution tables providing functionally similar amino acids are well known in the art. The following sets forth example groups which contain natural amino acids that include "conservative substitutions" for one another.

Conservative Substitution Groups

| | | | | |
|---|---|---|---|---|
| 1 | Alanine (A) | Serine (S) | Threonine (T) | |
| 2 | Aspartic acid (D) | Glutamic acid (E) | | |
| 3 | Asparagine (N) | Glutamine (Q) | | |
| 4 | Arginine (R) | Lysine (K) | | |
| 5 | Isoleucine (I) | Leucine (L) | Methionine (M) | Valine (V) |
| 6 | Phenylalanine (F) | Tyrosine (Y) | Tryptophan (W) | |

Nucleic Acid Hybridization

Comparative hybridization can be used to identify nucleic acids of the invention, including conservative variations of nucleic acids of the invention, and this comparative hybridization method is a preferred method of distinguishing nucleic acids of the invention. In addition, target nucleic acids which hybridize to the nucleic acids represented by SEQ ID NO: 1-34 under high, ultra-high and ultra-ultra high stringency conditions are a feature of the invention. Examples of such nucleic acids include those with one or a few silent or conservative nucleic acid substitutions as compared to a given nucleic acid sequence.

A test nucleic acid is said to specifically hybridize to a probe nucleic acid when it hybridizes at least ½ as well to the probe as to the perfectly matched complementary target, i.e., with a signal to noise ratio at least ½ as high as hybridization of the probe to the target under conditions in which the perfectly matched probe binds to the perfectly matched complementary target with a signal to noise ratio that is at least about 5×-10× as high as that observed for hybridization to any of the unmatched target nucleic acids.

Nucleic acids "hybridize" when they associate, typically in solution. Nucleic acids hybridize due to a variety of well characterized physico-chemical forces, such as hydrogen bonding, solvent exclusion, base stacking and the like. An extensive guide to the hybridization of nucleic acids is found in Tijssen (1993) Laboratory Techniques in Biochemistry and Molecular Biology—Hybridization with Nucleic Acid Probes part I chapter 2, "Overview of principles of hybridization and the strategy of nucleic acid probe assays," (Elsevier, N.Y.), as well as in Ausubel, supra. Hames and Higgins (1995) *Gene Probes* 1 IRL Press at Oxford University Press, Oxford, England, (Hames and Higgins 1) and Hames and Higgins (1995) *Gene Probes* 2 IRL Press at Oxford University Press, Oxford, England (Hames and Higgins 2) provide details on the synthesis, labeling, detection and quantification of DNA and RNA, including oligonucleotides.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of stringent wash conditions is a 0.2× SSC wash at 65° C. for 15 minutes (see, Sambrook, supra for a description of SSC buffer). Often the high stringency wash is preceded by a low stringency wash to remove background probe signal. An example low stringency wash is 2× SSC at 40° C. for 15 minutes. In general, a signal to noise ratio of 5× (or higher) than that observed for an unrelated probe in the particular hybridization assay indicates detection of a specific hybridization.

"Stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993), supra. and in Hames and Higgins, 1 and 2. Stringent hybridization and wash conditions can easily be determined empirically for any test nucleic acid. For example, in determining highly stringent hybridization and wash conditions, the hybridization and wash conditions are gradually increased (e.g., by increasing temperature, decreasing salt concentration, increasing detergent concentration and/or increasing the concentration of organic solvents such as formalin in the hybridization or wash), until a selected set of criteria are met. For example, the hybridization and wash conditions are gradually increased until a probe binds to a perfectly matched complementary target with a signal to noise ratio that is at least 5× as high as that observed for hybridization of the probe to an unmatched target.

"Very stringent" conditions are selected to be equal to the thermal melting point ($T_m$) for a particular probe. The $T_m$ is the temperature (under defined ionic strength and pH) at which 50% of the test sequence hybridizes to a perfectly matched probe. For the purposes of the present invention, generally, "highly stringent" hybridization and wash conditions are selected to be about 5° C. lower than the $T_m$ for the specific sequence at a defined ionic strength and pH.

"Ultra high-stringency" hybridization and wash conditions are those in which the stringency of hybridization and wash conditions are increased until the signal to noise ratio for binding of the probe to the perfectly matched complementary target nucleic acid is at least 10× as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-high stringency conditions.

Similarly, even higher levels of stringency can be determined by gradually increasing the hybridization and/or wash conditions of the relevant hybridization assay. For example, those in which the stringency of hybridization and wash conditions are increased until the signal to noise ratio for binding of the probe to the perfectly matched complementary target nucleic acid is at least 10×, 20×, 50×, 100×, or 500× or more as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-ultra-high stringency conditions.

Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

Unique Subsequences

In one aspect, the invention provides a nucleic acid which comprises a unique subsequence in a nucleic acid selected from the sequences of O-tRNAs and O—RSs disclosed herein. The unique subsequence is unique as compared to a nucleic acid corresponding to any known O-tRNA or O—RS nucleic acid sequence. Alignment can be performed using, e.g., BLAST set to default parameters. Any unique subsequence is useful, e.g., as a probe to identify the nucleic acids of the invention.

Similarly, the invention includes a polypeptide which comprises a unique subsequence in a polypeptide selected from the sequences of O—RSs disclosed herein. Here, the unique subsequence is unique as compared to a polypeptide corresponding to any of known polypeptide sequence.

The invention also provides for target nucleic acids which hybridizes under stringent conditions to a unique coding oligonucleotide which encodes a unique subsequence in a polypeptide selected from the sequences of O—RSs wherein the unique subsequence is unique as compared to a polypeptide corresponding to any of the control polypeptides (e.g., parental sequences from which synthetases of the invention were derived, e.g., by mutation). Unique sequences are determined as noted above.

Sequence Comparison, Identity, and Homology

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill) or by visual inspection.

The phrase "substantially identical," in the context of two nucleic acids or polypeptides (e.g., DNAs encoding an O-tRNA or O—RS, or the amino acid sequence of an O—RS) refers to two or more sequences or subsequences that have at least about 60%, preferably 80%, most preferably 90-95% nucleotide or amino acid residue identity, when compared and aligned for maximum correspondence, as measured using a sequence comparison algorithm or by visual inspection. Such "substantially identical" sequences are typically considered to be "homologous," without reference to actual ancestry. Preferably, the "substantial identity" exists over a region of the sequences that is at least about 50 residues in length, more preferably over a region of at least about 100 residues, and most preferably the sequences are substantially identical over at least about 150 residues, or over the full length of the two sequences to be compared.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math*. 2:482 (1981), by the homology alignment algorithm of Needleman & Wunsch, *J. Mol. Biol*. 48:443 (1970), by the search for similarity method of Pearson & Lipman, *Proc. Natl Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., infra).

One example of an algorithm that is suitable for determining percent sequence identity and sequence similarity is the BLAST algorithm, which is described in Altschul et al., *J. Mol. Biol*. 215:403-410 (1990). Software for performing BLAST analyses is publicly available through the National Center for Biotechnology Information (Bethesda, Md.). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci*. USA 89:10915).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Defining Polypeptides by Immunoreactivity

Because the polypeptides of the invention provide a variety of new polypeptide sequences (e.g., comprising unnatural amino acids in the case of proteins synthesized in the translation systems herein, or, e.g., in the case of the novel synthetases herein, novel sequences of standard amino acids), the polypeptides also provide new structural features which can be recognized, e.g., in immunological assays. The generation of antisera which specifically bind the polypeptides of the invention, as well as the polypeptides which are bound by such antisera, are a feature of the invention.

For example, the invention includes synthetase proteins that specifically bind to or that are specifically immunoreactive with an antibody or antisera generated against an immunogen comprising an amino acid sequence selected from one or more of (SEQ ID NO:35-66. To eliminate cross-reactivity with other homologues, the antibody or antisera is subtracted with available synthetases, such as the wild-type *Methanococcus jannaschii* (*M. jannaschii*) tyrosyl synthetase (TyrRS). Where the the wild-type *Methanococcus jannaschii* (*M. jannaschii*) tyrosyl synthetase (TyrRS) corresponds to a nucleic acid, a polypeptide encoded by the nucleic acid is generated and used for antibody/antisera subtraction purposes.

In one typical format, the immunoassay uses a polyclonal antiserum which was raised against one or more polypeptide comprising one or more of the sequences corresponding to one or more of SEQ ID NO:35-66) or a substantial subsequence thereof (i.e., at least about 30% of the full length sequence provided). The set of potential polypeptide immunogens derived from SEQ ID NO:35-66) are collectively referred to below as "the immunogenic polypeptides." The resulting antisera is optionally selected to have low cross-reactivity against the control synthetase homologues and any such cross-reactivity is removed, e.g., by immunoabsorbtion, with one or more of the control synthetase homologues, prior to use of the polyclonal antiserum in the immunoassay.

In order to produce antisera for use in an immunoassay, one or more of the immunogenic polypeptides is produced and purified as described herein. For example, recombinant protein can be produced in a recombinant cell. An inbred strain of mice (used in this assay because results are more reproducible due to the virtual genetic identity of the mice) is immunized with the immunogenic protein(s) in combination with a standard adjuvant, such as Freund's adjuvant, and a standard mouse immunization protocol (see, e.g., Harlow and Lane (1988) *Antibodies, A Laboratory Manual*, Cold Spring Harbor Publications, New York, for a standard description of antibody generation, immunoassay formats and conditions that can be used to determine specific immunoreactivity. Additional references and discussion of antibodies is also found herein and can be applied here to defining polypeptides by immunoreactivity). Alternatively, one or more synthetic or recombinant polypeptide derived from the sequences disclosed herein is conjugated to a carrier protein and used as an immunogen.

Polyclonal sera are collected and titered against the immunogenic polypeptide in an immunoassay, for example, a solid phase immunoassay with one or more of the immunogenic proteins immobilized on a solid support. Polyclonal antisera with a titer of $10^6$ or greater are selected, pooled and subtracted with the control synthetase polypeptides to produce subtracted pooled titered polyclonal antisera.

The subtracted pooled titered polyclonal antisera are tested for cross reactivity against the control homologues in a comparative immunoassay. In this comparative assay, discriminatory binding conditions are determined for the subtracted titered polyclonal antisera which result in at least about a 5-10 fold higher signal to noise ratio for binding of the titered polyclonal antisera to the immunogenic synthetase as compared to binding to the control synthetase homologues. That is, the stringency of the binding reaction is adjusted by the addition of non-specific competitors such as albumin or non-fat dry milk, and/or by adjusting salt conditions, temperature, and/or the like. These binding conditions are used in subsequent assays for determining whether a test polypeptide (a polypeptide being compared to the immunogenic polypeptides and/or the control polypeptides) is specifically bound by the pooled subtracted polyclonal antisera. In particular, test polypeptides which show at least a 2-5× higher signal to noise ratio than the control synthetase homologues under discriminatory binding conditions, and at least about a ½ signal to noise ratio as compared to the immunogenic polypeptide(s), shares substantial structural similarity with the immunogenic polypeptide as compared to known synthetases, and is, therefore a polypeptide of the invention.

In another example, immunoassays in the competitive binding format are used for detection of a test polypeptide. For example, as noted, cross-reacting antibodies are removed from the pooled antisera mixture by immunoabsorbtion with the control polypeptides. The immunogenic polypeptide(s) are then immobilized to a solid support which is exposed to the subtracted pooled antisera. Test proteins are added to the assay to compete for binding to the pooled subtracted antisera. The ability of the test protein(s) to compete for binding to the pooled subtracted antisera as compared to the immobilized protein(s) is compared to the ability of the immunogenic polypeptide(s) added to the assay to compete for binding (the immunogenic polypeptides compete effectively with the immobilized immunogenic polypeptides for binding to the pooled antisera). The percent cross-reactivity for the test proteins is calculated, using standard calculations.

In a parallel assay, the ability of the control proteins to compete for binding to the pooled subtracted antisera is optionally determined as compared to the ability of the immunogenic polypeptide(s) to compete for binding to the antisera. Again, the percent cross-reactivity for the control polypeptides is calculated, using standard calculations. Where the percent cross-reactivity is at least 5-10× as high for the test polypeptides as compared to the control polypeptides and or where the binding of the test polypeptides is approximately in the range of the binding of the immunogenic polypeptides, the test polypeptides are said to specifically bind the pooled subtracted antisera.

In general, the immunoabsorbed and pooled antisera can be used in a competitive binding immunoassay as described herein to compare any test polypeptide to the immunogenic and/or control polypeptide(s). In order to make this comparison, the immunogenic, test and control polypeptides are each assayed at a wide range of concentrations and the amount of each polypeptide required to inhibit 50% of the binding of the subtracted antisera to, e.g., an immobilized control, test or immunogenic protein is determined using standard techniques. If the amount of the test polypeptide required for binding in the competitive assay is less than twice the amount of the immunogenic polypeptide that is required, then the test polypeptide is said to specifically bind to an antibody generated to the immunogenic protein, provided the amount is at least about 5-10× as high as for the control polypeptide.

As an additional determination of specificity, the pooled antisera is optionally fully immunosorbed with the immunogenic polypeptide(s) (rather than the control polypeptides) until little or no binding of the resulting immunogenic polypeptide subtracted pooled antisera to the immunogenic polypeptide(s) used in the immunosorbtion is detectable. This fully immunosorbed antisera is then tested for reactivity with the test polypeptide. If little or no reactivity is observed (i.e., no more than 2× the signal to noise ratio observed for binding of the fully immunosorbed antisera to the immunogenic polypeptide), then the test polypeptide is specifically bound by the antisera elicited by the immunogenic protein.

General Molecular Biology Techniques

General texts which describe molecular biological techniques include Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (2nd Ed.), Vol. 1-3, Cold Spring Harbor Laboratory, Cold Spring Harbor, N.Y., 1989 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 1999) ("Ausubel")). These texts describe mutagenesis, the use of vectors, promoters and many other relevant topics related to, e.g., the generation of genes that include selector codons for production of proteins that include unnatural amino acids, orthogonal tRNAs, orthogonal synthetases, and pairs thereof.

Various types of mutagenesis are used in the present invention, e.g., to insert selector codons that encode unnatural amino acids in a protein. They include but are not limited to site-directed, random point mutagenesis, homologous recombination (DNA shuffling), mutagenesis using uracil containing templates, oligonucleotide-directed mutagenesis, phosphorothioate-modified DNA mutagenesis, mutagenesis using gapped duplex DNA or the like. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, are also included in the present invention. In one embodiment, mutagenesis can be guided by known information of the naturally occurring molecule or altered or mutated naturally occurring molecule, e.g., sequence, sequence comparisons, physical properties, crystal structure or the like.

The above texts and examples found herein describe these procedures. Additional information is found in the following publications and references cited within: Ling et al., Approaches to DNA mutagenesis: an overview, *Anal Biochem*. 254(2): 157-178 (1997); Dale et al., Oligonucleotide-directed random mutagenesis using the phosphorothioate method, *Methods Mol. Biol*. 57:369-374 (1996); Smith, In vitro mutagenesis, *Ann. Rev. Genet*. 19:423-462(1985); Botstein & Shortle, Strategies and applications of in vitro mutagenesis, *Science* 229:1193-1201(1985); Carter, Site-directed mutagenesis, *Biochem. J*. 237:1-7 (1986); Kunkel, The efficiency of oligonucleotide directed mutagenesis, in *Nucleic Acids & Molecular Biology* (Eckstein, F. and Lilley, D. M. J. eds., Springer Verlag, Berlin)) (1987); Kunkel, Rapid and efficient site-specific mutagenesis without phenotypic selection, *Proc. Natl. Acad. Sci. USA* 82:488-492 (1985); Kunkel et al., Rapid and efficient site-specific mutagenesis without phenotypic selection, *Methods in Enzymol*. 154, 367-382 (1987); Bass et al., Mutant Trp repressors with new DNA-binding specificities, *Science* 242:240-245 (1988); *Methods in Enzymol*. 100: 468-500 (1983); *Methods in Enzymol*. 154: 329-350 (1987); Zoller & Smith, Oligonucleotide-directed mutagenesis using M13-derived vectors: an efficient and general procedure for the production of point mutations in any DNA fragment, *Nucleic Acids Res*. 10:6487-6500 (1982); Zoller & Smith, Oligonucleotide-directed mutagenesis of DNA fragments cloned into M13 vectors, *Methods in Enzymol*. 100:468-500 (1983); Zoller & Smith, Oligonucleotide-directed mutagenesis: a simple method using two oligonucleotide primers and a single-stranded DNA template, *Methods in Enzymol*. 154:329-350 (1987); Taylor et al., The use of phosphorothioate-modified DNA in restriction enzyme reactions to prepare nicked DNA, *Nucl. Acids Res*. 13: 8749-8764 (1985); Taylor et al., The rapid generation of oligonucleotide-directed mutations at high frequency using phosphorothioate-modified DNA, *Nucl. Acids Res*. 13: 8765-8787 (1985); Nakamaye & Eckstein, Inhibition of restriction endonuclease Nci I cleavage by phosphorothioate groups and its application to oligonucleotide-directed mutagenesis, *Nucl. Acids Res*. 14: 9679-9698 (1986); Sayers et al., Y-T Exonucleases in phosphorothioate-based oligonucleotide-directed mutagenesis, *Nucl. Acids Res*. 16:791-802 (1988); Sayers et al., Strand specific cleavage of phosphorothioate-containing DNA by reaction with restriction endonucleases in the presence of ethidium bromide, (1988) *Nucl. Acids Res*. 16: 803-814; Kramer et al., The gapped duplex DNA approach to oligonucleotide-directed mutation construction, *Nucl. Acids Res*. 12: 9441-9456 (1984); Kramer & Fritz Oligonucleotide-directed construction of mutations via gapped duplex DNA, *Methods in Enzymol*. 154:350-367 (1987); Kramer et al., Improved enzymatic in vitro reactions in the gapped duplex DNA approach to oligonucleotide-directed construction of mutations, *Nucl. Acids Res*. 16: 7207 (1988); Fritz et al., Oligonucleotide-directed construction of mutations: a gapped duplex DNA procedure without enzymatic reactions in vitro, *Nucl. Acids Res*. 16: 6987-6999 (1988); Kramer et al., Point Mismatch Repair, *Cell* 38:879-887 (1984); Carter et al., Improved oligonucleotide site-directed mutagenesis using M13 vectors, *Nucl. Acids Res*. 13: 4431-4443 (1985); Carter, Improved oligonucleotide-directed mutagenesis using M13 vectors, *Methods in Enzymol*. 154: 382-403 (1987); Eghtedarzadeh & Henikoff, Use of oligonucleotides to generate large deletions, *Nucl. Acids Res*. 14: 5115 (1986); Wells et al., Importance of hydrogen-bond formation in stabilizing the transition state of subtilisin, *Phil. Trans. R. Soc. Lond*. A 317: 415-423 (1986); Nambiar et al., Total synthesis and cloning of a gene coding for the ribonuclease S protein, *Science* 223: 1299-1301 (1984); Sakamar and Khorana, Total synthesis and expression of a gene for the a-subunit of bovine rod outer segment guanine nucleotide-binding protein (transducin), *Nucl. Acids Res*. 14: 6361-6372 (1988); Wells et al., Cassette mutagenesis: an efficient method for generation of multiple mutations at defined sites, *Gene* 34:315-323 (1985); Grundström et al., Oligonucleotide-directed mutagenesis by microscale 'shot-gun' gene synthesis, *Nucl. Acids Res*. 13: 3305-3316 (1985); Mandecki, Oligonucleotide-directed double-strand break repair in plasmids of *Escherichia coli*: a method for site-specific mutagenesis, *Proc. Natl. Acad. Sci. USA*, 83:7177-7181 (1986); Arnold, Protein engineering for unusual environments, *Current Opinion in Biotechnology* 4:450-455 (1993); Sieber, et al., Nature Biotechnology, 19:456-460 (2001). W. P. C. Stemmer, *Nature* 370, 389-91 (1994); and, I. A. Lorimer, I. Pastan, *Nucleic Acids Res*. 23, 3067-8 (1995). Additional details on many of the above methods can be found in *Methods in Enzymology* Volume 154, which also describes useful controls for trouble-shooting problems with various mutagenesis methods.

The present invention also relates to host cells and organisms for the in vivo incorporation of an unnatural amino acid via orthogonal tRNA/RS pairs. Host cells are genetically engineered (e.g., transformed, transduced or transfected) with the vectors of this invention, which can be, for example, a cloning vector or an expression vector. The vector can be, for example, in the form of a plasmid, a bacterium, a virus, a naked polynucleotide, or a conjugated polynucleotide. The vectors are introduced into cells and/or microorganisms by standard methods including electroporation (From et al., *Proc. Natl. Acad. Sci. USA* 82, 5824 (1985), infection by viral vectors, high velocity ballistic penetration by small particles with the nucleic acid either within the matrix of small beads or particles, or on the surface (Klein et al., *Nature* 327, 70-73 (1987)).

The engineered host cells can be cultured in conventional nutrient media modified as appropriate for such activities as, for example, screening steps, activating promoters or selecting transformants. These cells can optionally be cultured into transgenic organisms.

Several well-known methods of introducing target nucleic acids into bacterial cells are available, any of which can be used in the present invention. These include: fusion of the recipient cells with bacterial protoplasts containing the DNA, electroporation, projectile bombardment, and infection with viral vectors (discussed further, below), etc. Bacterial cells can be used to amplify the number of plasmids containing DNA constructs of this invention. The bacteria are grown to log phase and the plasmids within the bacteria can be isolated by a variety of methods known in the art (see, for instance, Sambrook). In addition, a plethora of kits are commercially available for the purification of plasmids from bacteria, (see, e.g., EasyPrep™, FlexiPrep™, both from Pharmacia Biotech; StrataClean™, from Stratagene; and, QIAprep™ from Qiagen). The isolated and purified plasmids are then further manipulated to produce other plasmids, used to transfect cells or incorporated into related vectors to infect organisms. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or preferably both. See, Giliman & Smith, *Gene* 8:81 (1979); Roberts, et al., *Nature*, 328:731 (1987); Schneider, B., et al., *Protein Expr. Purif.* 6435:10 (1995); Ausubel, Sambrook, Berger (all supra). A catalogue of Bacteria and Bacteriophages useful for cloning is provided, e.g., by the ATCC, e.g., The ATCC Catalogue of Bacteria and Bacteriophage (1992) Ghema et al. (eds) published by the ATCC. Additional basic procedures for sequencing, cloning and other aspects of molecular biology and underlying theoretical considerations are also found in Watson et al. (1992) Recombinant DNA Second Edition Scientific American Books, NY.

Other useful references, e.g. for cell isolation and culture (e.g., for subsequent nucleic acid isolation) include Freshney (1994) *Culture of Animal Cells, a Manual of Basic Technique*, third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York) and Atlas and Parks (eds) *The Handbook of Microbiological Media* (1993) CRC Press, Boca Raton, Fla.

In addition, essentially any nucleic acid (and virtually any labeled nucleic acid, whether standard or non-standard) can be custom or standard ordered from any of a variety of commercial sources, such as The Midland Certified Reagent Company (Midland, Tex.), Operon Technologies Inc. (Alameda, Calif.) and many others.

Pharmaceutical Compositions

The proteins, e.g., polypeptides, peptides, etc., of the invention (e.g., comprising one or more unnatural amino acid) are optionally employed for therapeutic uses, e.g., in combination with a suitable pharmaceutical carrier. Such compositions, e.g., comprise a therapeutically effective amount of the compound, and a pharmaceutically acceptable carrier or excipient. Such a carrier or excipient includes, but is not limited to, saline, buffered saline, dextrose, water, glycerol, ethanol, and/or combinations thereof. The formulation is made to suit the mode of administration. In general, methods of administering proteins are well known in the art and can be applied to administration of the polypeptides of the invention.

Therapeutic compositions comprising one or more polypeptide of the invention are optionally tested in one or more appropriate in vitro and/or in vivo animal models of disease, to confirm efficacy, tissue metabolism, and to estimate dosages, according to methods well known in the art. In particular, dosages can be initially determined by activity, stability or other suitable measures of unnatural herein to natural amino acid homologues (e.g., comparison of an EPO modified to include one or more unnatural amino acids to a natural amino acid EPO), i.e., in a relevant assay.

Administration is by any of the routes normally used for introducing a molecule into ultimate contact with blood or tissue cells. The unnatural amino acid polypeptides of the invention are administered in any suitable manner, optionally with one or more pharmaceutically acceptable carriers. Suitable methods of administering such polypeptides in the context of the present invention to a patient are available, and, although more than one route can be used to administer a particular composition, a particular route can often provide a more immediate and more effective action or reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention.

Polypeptide compositions can be administered by a number of routes including, but not limited to: oral, intravenous, intraperitoneal, intramuscular, transdermal, subcutaneous, topical, sublingual, or rectal means. Unnatural amino acid polypeptide compositions can also be administered via liposomes. Such administration routes and appropriate formulations are generally known to those of skill in the art.

The unnatural amino acid polypeptide, alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations of packaged nucleic acid can be presented in unit-dose or multi-dose sealed containers, such as ampules and vials.

Parenteral administration and intravenous administration are preferred methods of administration. In particular, the routes of administration already in use for natural amino acid homologue therapeutics (e.g., those typically used for EPO, GCSF, GMCSF, IFNs, interleukins, antibodies, and/or any other pharmaceutically delivered protein), along with formulations in current use, provide preferred routes of administration and formulation for the unnatural amino acids of the invention.

The dose administered to a patient, in the context of the present invention, is sufficient to effect a beneficial therapeutic response in the patient over time, or, e.g., to inhibit infection by a pathogen, or other appropriate activity, depending on the application. The dose is determined by the efficacy of the particular vector, or formulation, and the activity, stability or serum half-life of the unnatural amino acid polypeptide employed and the condition of the patient, as well as the body weight or surface area of the patient to be treated. The size of the dose is also determined by the existence, nature, and extent of any adverse side-effects that accompany the administration of a particular vector, formulation, or the like in a particular patient.

In determining the effective amount of the vector or formulation to be administered in the treatment or prophylaxis of disease (e.g., cancers, inherited diseases, diabetes, AIDS, or the like), the physician evaluates circulating plasma levels, formulation toxicities, progression of the disease, and/or where relevant, the production of anti-unnatural amino acid polypeptide antibodies.

The dose administered, e.g., to a 70 kilogram patient are typically in the range equivalent to dosages of currently-used therapeutic proteins, adjusted for the altered activity or serum half-life of the relevant composition. The vectors of this invention can supplement treatment conditions by any known conventional therapy, including antibody administration, vaccine administration, administration of cytotoxic agents, natural amino acid polypeptides, nucleic acids, nucleotide analogues, biologic response modifiers, and the like.

For administration, formulations of the present invention are administered at a rate determined by the LD-50 of the relevant formulation, and/or observation of any side-effects of the unnatural amino acids at various concentrations, e.g., as applied to the mass and overall health of the patient. Administration can be accomplished via single or divided doses.

If a patient undergoing infusion of a formulation develops fevers, chills, or muscle aches, he/she receives the appropriate dose of aspirin, ibuprofen, acetaminophen or other pain/fever controlling drug. Patients who experience reactions to the infusion such as fever, muscle aches, and chills are premedicated 30 minutes prior to the future infusions with either aspirin, acetaminophen, or, e.g., diphenhydramine. Meperidine is used for more severe chills and muscle aches that do not quickly respond to antipyretics and antihistamines. Cell infusion is slowed or discontinued depending upon the severity of the reaction.

EXAMPLES

Example 1

In vivo Incorporation of O-methyl-L-tyrosine

An orthogonal tRNA/synthetase pair in *E. coli* can be generated by importing a pair from a different organism, if cross-species aminoacylation is inefficient (Y. Kwok, J. T. Wong, Can. J. Biochem. 58, 213-8 (1980)), and the anticodon loop is not a key determinant of synthetase recognition. One such candidate pair is the tyrosyl tRNA/synthetase pair of *Methanococcus jannaschii* (*M. jannaschii*), an archaebacterium whose tRNA identity elements differ from those of *E. coli* tRNATyr, and whose tyrosyl synthetase (TyrRS) lacks an anticodon loop binding domain (B. A. Steer, P. Schimmel, J. Biol. Chem. 274, 35601-6 (1999)). In addition, the *M. jannaschii* TyrRS does not have an editing mechanism (H. Jakubowski, E. Goldman, Microbiol. Rev. 56, 412-29 (1992)), and therefore should not proofread an unnatural amino acid ligated to the tRNA.

It has been shown that an amber suppressor tRNA derived from the *M. jannaschii* $tRNA^{Tyr}$ is not efficiently aminoacylated by the *E. coli* synthetases, but functions efficiently in protein translation in *E. coli* (L. Wang, T. J. Magliery, D. R. Liu, P. G. Schultz, J. Am. Chem. Soc. 122, 5010-1 (2000)). Moreover, the *M. jannaschii* TyrRS is orthogonal to *E. coli* tRNAs (B. A. Steer, P. Schimmel, J. Biol. Chem. 274, 35601-6 (1999)), but still efficiently aminoacylates its own suppressor $tRNA_{CUA}^{Tyr}$ (L. Wang, T. J. Magliery, D. R. Liu, P. G. Schultz, J. Am. Chem. Soc. 122, 5010-1 (2000)). Thus, the *M. jannaschii* $tRNA_{CUA}^{Tyr}$/TyrRS functions as an orthogonal pair, and can efficiently incorporate tyrosine in response to the amber codon, UAG, in *E. coli.*

To further reduce recognition of this orthogonal tRNA by *E. coli* synthetases, mutagenesis and selection scheme was performed. For additional details, see U.S. patent application Ser. No. 10/126,931, titled “Methods and Compositions for the production of orthogonal tRNA-tRNA synthetase pairs,” filed concurrently with the instant application, the disclosure of which is incorporated in its entirety.

Briefly, eleven nucleotides of the *M. jannaschii* $tRNA_{CUA}^{Tyr}$ that do not interact directly with the *M. jannaschii* TyrRS were randomly mutated to afford a suppressor tRNA library. This tRNA library was passed through a negative selection that removes tRNAs that are aminoacylated by *E. coli* synthetases, followed by a positive selection for tRNAs that are efficiently aminoacylated by *M. jannaschii* TyrRS. The orthogonality of the resulting suppressor tRNAs was tested by an in vivo complementation assay, based on suppression of an amber stop codon at a nonessential position (Ala184) of the TEM-1 beta-lactamase gene carried on plasmid pBLAM. Aminoacylation of a transformed suppressor tRNA by any endogenous *E. coli* synthetase results in cell growth in the presence of ampicillin. *E. coli* transformed with the *M. jannaschii* $tRNA_{CUA}^{Tyr}$ and pBLAM survive at 55.5 micrograms/mL ampicillin. When the best mutant suppressor tRNA ($mtRNA_{CUA}^{Tyr}$) selected from the library was expressed, cells survived at only 12.4 micrograms/mL ampicillin. The mutant suppressor $mtRNA_{CUA}^{Tyr}$ contained the following nucleotide substitutions: C17A, U17aG, U20C, G37A, and U47G. For comparison, cells with pBLAM only (in the absence of any suppressor tRNA) survive at 9.7 micrograms/mL ampicillin. When the *M. jannaschii* TyrRS is coexpressed with this $mtRNA_{CUA}^{Tyr}$, cells survive at 436 micrograms/mL ampicillin. Thus, the $mtRNA_{CUA}^{Tyr}$ is a poorer substrate for the endogenous synthetases than the *M. jannaschii* $tRNA_{CUA}^{Tyr}$ and is still aminoacylated efficiently by the *M. jannaschii* TyrRS.

To alter the amino acid specificity of the orthogonal *M. jannaschii* TyrRS so that it charges the $mtRNA_{CUA}^{Tyr}$ with a desired unnatural amino acid, a library of TyrRS mutants was generated and screened. Based on the crystal structure of the homologous TyrRS from *Bacillus stearothermophilus* (P. Brick, T. N. Bhat, D. M. Blow, J. Mol. Biol. 208, 83-98 (1988)), five residues (Tyr32, Glu107, Asp158, Ile159 and Leu162) in the active site of *M. jannaschii* TyrRS, which are within 6.5 Å of the para position of the aryl ring of bound tyrosine were mutated. Corresponding residues from a mutant *M. jannaschii* TyrRS (mutTyr RS, for aminoacylation with O-methyl-L-tyrosine) are $Tyr^{32}$ ($Tyr^{34}$), $Glu^{107}$ ($Asn^{123}$), $Asp^{158}$ ($Asp^{176}$), $Iel^{159}$ ($Phe^{177}$), and $Leu^{162}$ ($Leu^{180}$) with *B. stearothermophilus* TyrRS residues in parenthesis.

As described in more detail below, these residues were all initially mutated to alanine to generate an Ala5 TyrRS, which is unable to charge the $mtRNA_{CUA}^{Tyr}$ with tyrosine. This mutant Ala5 TyrRS was used as a template to generate a library of TyrRS mutants in which the five residues were randomly mutated by PCR mutagenesis with doped oligonucleotides.

The *M. jannaschii* TyrRS gene was expressed under the control of *E. coli* GlnRS promoter and terminator in plasmid pBK-JYRS, a pBR322 derived plasmid with kanamycin resistance. Residues Tyr32, Glu107, Asp158, Ile159 and Leu162 were substituted with Ala by site-directed mutagenesis to afford plasmid pBK-JYA5. Oligonucleotides LW157 5'-GGAATTCCATATGGACGAATTTGAAATG-3'(SEQ ID NO:69), LW164 5'-GTATTT TACCACTTGGTTCAAAACCTATMNNAGCAGATTTTTCATCTTTTTTTCATCTTT TTTTAAAAC-3' (SEQ ID NO:70), LW159 5'-TAGGTTTTGAACCAAGTGGTAAAATAC-3' (SEQ ID NO:71), LW165 5'-CATTCAGTGTATAATCCTTATCAAGCTGGAAMNNACTTCCATAA ACATATTTTGCCTTTAAC-3' (SEQ ID NO:72), LW161 5'-TCCAGCTTGATAAGGATTATACA CTGAATG-3' (SEQ ID NO:73), LW167 5'-CATCCCTCCAACTGCAACATCAACGCCMNNATA ATGMNNMNNATTAACCTGCATTATTGGATAGATAAC-3' (SEQ ID NO:74), LW163 5'-GCGT TGATGTTGCAGTTGGAGGGATG-3' (SEQ ID NO:75), and LW105 5'-AAACTGCAGTTATAAT CTCTTTCTAATTGGCTC-3' (SEQ ID NO:76) with NNK (N=A+T+G+C, K=G+T, and M=C+A (Operon, Alameda, Calif.) at the mutation sites were used for PCR amplification of the Ala5 TyrRS mutant (pBK-JYA5) and ligated back into the NdeI-PstI-digested pBK-JYA5 to afford the TyrRS library. The ligated vectors were transformed into *E. coli* DH10B competent cells to yield a library of $1.6\times10^9$ colony forming unit (cfu). The TyrRS genes from 40 randomly picked colonies were sequenced to confirm that there was no base bias at the randomized NNK positions and no other unexpected mutations. The library was amplified by maxiprep, and supercoiled DNA was used to transform the selection strain pYC-J17.

A positive selection was then applied that is based on suppression of an amber stop codon at a nonessential position (Asp 112) in the chloramphenicol acetyltransferase (CAT) gene (M. Pastmak, T. J. Magliery, P. G. Schultz, *Helvetica Chimica Acta*. 83, 2277-86 (2000)). Cells were grown in media containing the unnatural amino acid and selected for their survival in the presence of various concentration of chloramphenicol. If a mutant TyrRS charges the orthogonal $mtRNA_{CUA}^{Tyr}$ with any amino acid, either natural or unnatural, the cell produces CAT and survives.

The surviving cells were then grown in the presence of chloramphenicol and in the absence of the unnatural amino acid. Those cells that did not survive, i.e., which encode mutant TyrRSs that charge the orthogonal $mtRNA_{CUA}^{Tyr}$ with an unnatural amino acid, were isolated from a replica plate supplemented with the unnatural amino acid. The mutant TyrRS genes were isolated from these cells, recombined in vitro by DNA shuffling, and transformed back into *E. coli* for further rounds of selection.

Seven tyrosine analogues with different functional groups at the para position of the aryl ring (acetyl, amino, carboxyl, isopropyl, methyl, O-methyl and nitro) were used individually in the selections that were performed as follows.

The gene encoding $mtRNA_{CUA}^{Tyr}$ under the control of the lpp promoter and rmC terminator was inserted into plasmid pACMD 112TAG (a pACYC 184 plasmid with a TAG stop codon replacing Asp112 in its CAT gene (M. Pastmak, T. J. Magliery, P. G. Schultz, *Helvetica Chimica Acta*. 83, 2277-86 (2000))) to afford plasmid pYC-J17. Supercoiled DNA encoding the TyrRS library was transformed into *E. coli* DH10B competent cells containing pYC-J17 to yield a library of size greater than $3\times10^9$ cfu, ensuring complete coverage of the original library. Cells were then plated on minimal media plates containing 1% glycerol and 0.3 mM leucine (GMML) with 17 micrograms/mL tetracycline(Tet), 25 micrograms/mL kanamycin (Kan), 50 micrograms/mL of chloramphenicol (Cm), and 1 mM unnatural amino acid. After incubation at 37° C. for 44 hours, colonies on plates supplied with O-methyl-L-tyrosine were pooled, plasmids were isolated and retransformed into *E. coli* DH10B competent cells containing pYC-J17, and the transformed cells were positively selected on 50 micrograms/mL of Cm. Colonies (96) were individually picked from the plate, diluted into 100 mL of liquid GMML media, and streaked onto two sets of Kan/Tet GMML plates with various concentration of Cm. No O-methyl-L-tyrosine was added to plate set 1 and the concentration of Cm was varied from 10-25 micrograms/mL; plate set 2 contained 1 mM O-methyl-L-tyrosine and 50 micrograms/mL of Cm. Replicates of colonies that did not grow on 15 micrograms/mL of Cm in plate set 1 were picked from plate set 2. Plasmids containing the TyrRS gene were purified and recombined in vitro by DNA shuffling using Stemmer's protocol (W. P. C. Stemmer, *Nature* 370, 389-91 (1994)) with the exception of 10 mM Mn2+ instead of Mg2+ in the fragmentation reaction (I. A. Lorimer, I. Pastan, *Nucleic Acids Res*. 23, 3067-8 (1995)). The library was then religated into predigested pBK-JYA5 vector to afford a second generation TyrRS library with a typical size of 8×108 to 3×109 cfu. Thirty randomly selected members from the library were sequenced. The mutagenic rate introduced by DNA shuffling was 0.35%. This library was transformed into the selection strain for the next round of selection followed by shuffling. The concentration of Cm in the positive selection and in plate set 2 was raised to 80 micrograms/mL for the second round and 120 micrograms/mL for the third round; the concentration of Cm in plate set 1 was unchanged. After three rounds of DNA shuffling, colonies began to grow on 20-25 micrograms/mL Cm in plate set 1, indicating that the TyrRS mutants were accepting natural amino acids as substrates. Therefore, the best clone selected after two rounds of DNA shuffling was characterized in detail.

Following the two rounds of selection and DNA shuffling, a clone (mutant TyrRS (LWJ16)) was evolved whose survival in chloramphenicol was dependent on the addition of 1 mM O-methyl-L-tyrosine to the growth media. In the absence of O-methyl-L-tyrosine, cells harboring the mutant TyrRS (LWJ16) were not viable on minimal media plates containing 1% glycerol, 0.3 mM leucine (GMML), and 15 micrograms/mL of chloramphenicol. Cells were able to grow on GMML plates with 125 micrograms/mL chloramphenicol in the presence of 1 mM O-methyl-L-tyrosine. Similar results were obtained in liquid GMML. As a control, cells with the mtRNA$_{CUA}^{Tyr}$ and the inactive Ala5 TyrRS did not survive at the lowest concentration of chloramphenicol used, either in the presence or absence of 1 mM O-methyl-L-tyrosine. This indicates that the growth of cells in chloramphenicol relies on the expression of the mutant TyrRS (LWJ16) and is not a simple nutritional effect of O-methyl-L-tyrosine. Addition of 1 mM O-methyl-L-tyrosine itself does not significantly affect the growth rate of *E. coli*.

To further demonstrate that the observed phenotype is due to the site-specific incorporation of O-methyl-L-tyrosine by the orthogonal mtRNA$_{CUA}^{Tyr}$/mutant TyrRS (LWJ16) pair in response to an amber stop codon, an O-methyl-L-tyrosine mutant of dihydrofolate reductase (DHFR) was generated and characterized. The third codon of the *E. coli* DHFR gene (a permissive site) was mutated to TAG and a C-terminal His$_6$ tag was added in order to separate the mutant protein from endogenous *E. coli* DHFR. As a control, the mtRNA$_{CUA}^{Tyr}$ was coexpressed with the wild type *M. jannaschii* TyrRS, resulting in efficient suppression of the nonsense codon in DHFR with tyrosine. See FIG. 2. When the mutant TyrRS (LWJ16) was expressed in the presence of mtRNA$_{CUA}^{Tyr}$ and 1 mM O-methyl-L-tyrosine in liquid GMML growth media, full length DHFR was also produced and could be purified by Ni affinity chromatography with an isolated yield of 2 mg/liter.

The yield of purified protein is approximately 26 fold lower in liquid GMML media compare to 2YT rich media. For example, when the mtRNA$_{CUA}^{Tyr}$ and wild type *M. jannaschii* TyrRS are coexpressed, the yield of DHFR is 67 mg/L in 2YT and 2.6 mg/L in liquid GMML.

In the absence of either O-methyl-L-tyrosine, mtRNA$_{CUA}^{Tyr}$ or mutant TyrRS (LWJ16), no DHFR (<0.1% by densitometry) was observed by analysis with SDS-polyacrylamide gel electrophoresis and silver staining. See FIG. 2. Western analysis further demonstrated that no trace amount of DHFR was produced in the absence of either mtRNA$_{CUA}^{Tyr}$ mutant TyrRS (LWJ16), or O-methyl-L-tyrosine. See FIG. 2.

The identity of the amino acid inserted in response to the TAG codon was confirmed by mass analysis of both the intact protein and tryptic fragments. The average mass of the intact protein was determined by electrospray ionization Fourier Transform Ion Cyclotron Resonance Mass Spectrometry (FT-ICR MS). The observed value for the monoisotopic mass from the cluster next to the internal calibrant was 18096.002 Da, which is within 5 ppm of the theoretical mass of 18095.908 Da and clearly demonstrates the incorporation of O-methyl-L-tyrosine.

For this experiment a DHFR mutant lacking the C-terminal His tag was used and purified by methotrexate affinity chromatography. In the mutant protein, the third codon was changed to TAG, and the fourth codon was changed from CTG to ATG to improve the amber suppression efficiency, resulting in a Leu4Met mutation.

Figure 3:
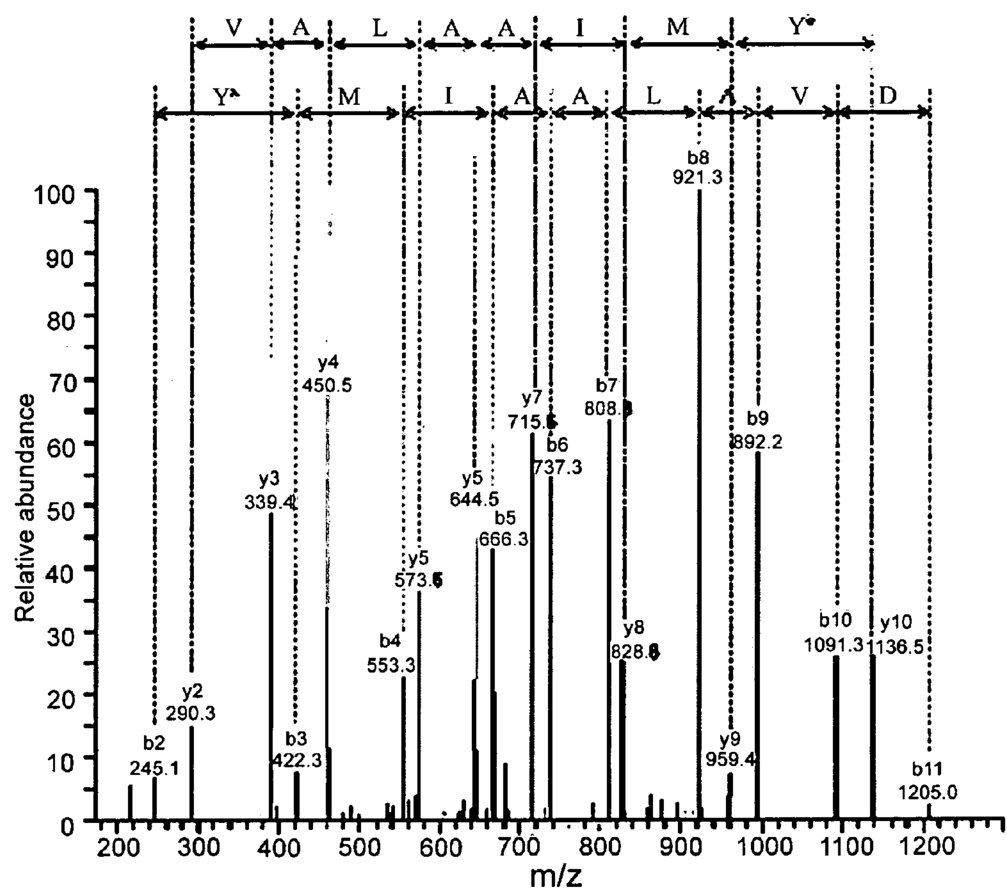
FIG. 3 is a tandem mass spectrum of an NH2 terminal peptide of DHFR, MIY*MIAALAVDR (SEQ ID NO:77). The partial sequence Y*MIAALAVDR (amino acids of 3-12 of SEQ ID NO:77) of the peptide containing the O-methyl-L-tyrosine residue (Y*) can be read from the annotated b or y ion series.

This result also indicates that other endogenous *E. coli* synthetases do not utilize O-methyl-L-tyrosine as a substrate. Liquid chromatography tandem mass spectrometry of tryptic digests was carried out to confirm the sequence of the N-terminal peptide. An example of a tandem MS spectrum is shown in FIG. 3. The doubly charged precursor ion at 691.5 Da, corresponding to the N-terminal tryptic peptide MIY*MIAALAVDR (SEQ ID NO: 77), was selected and fragmented in an ion trap mass spectrometer (ITMS). The fragment ion masses could be unambiguously assigned as shown in FIG. 3, confirming the site-specific incorporation of O-methyl-L-tyrosine. Neither the protein mass spectra nor the tryptic peptide maps gave any indications of the incorporation of tyrosine or other amino acids in place of O-methyl-L-tyrosine—from the signal-to-noise ratio of the protein mass spectra a minimum 95% incorporation purity for O-methyl-L-tyrosine was obtained.

Taken together, the cell growth, protein expression and mass spectrometry experiments demonstrate that the mtRNA$_{CUA}^{Tyr}$/mutant TyrRS (LWJ16) orthogonal pair is capable of selectively inserting O-methyl-L-tyrosine into proteins in response to the amber codon with a fidelity rivaling that of the natural amino acids.

Analysis of the sequence ofthe mutant TyrRS (LWJ16) that charges the mtRNA$_{CUA}^{Tyr}$ with O-methyl-L-tyrosine revealed 12 nucleotide changes, two of which were silent. The ten nonsilent mutations resulted in the following amino acid residue substitutions relative to wild type TyrRS: Tyr32, which hydrogen bonds to the aryl oxygen atom of the native substrate tyrosine, was mutated to Gln; Asp158, which hydrogen bonds to the hydroxyl group of tyrosine, was mutated to Ala; Glu107, which hydrogen bonds to Asp158, was mutated to Thr; and Leu162, which is located at the bottom of the binding pocket, was mutated to Pro. Based on the x-ray crystal structure of the homologous *B. stearothermophilus* TyrRS, it can be speculated that loss of the hydrogen-bonding network between Tyr32, Asp158 and substrate tyrosine should disfavor binding of tyrosine to the mutant TyrRS (LWJ16). Indeed, mutation of Asp176 (which corresponds to Asp158 in *M. jannaschii*) of *B. stearothermophilus* TyrRS yields inactive enzyme (G. D. P. Gray, H. W. Duckworth, A. R. Fersht, FEBS 318, 167-71 (1993)). At the same time, the Asp158Ala and Leu162Pro mutations create a hydrophobic pocket that allows the methyl group of O-methyl-L-tyrosine to extend further into the substrate-binding cavity. Other important catalytic residues in the active site, which bind to the ribose or the phosphate group of the adenylate, were unchanged after two rounds of DNA shuffling. Detailed analysis of these mutations awaits the three-dimensional structure of the mutant TyrRS (LWJ16).

Kinetics of adenylate formation of O-methyl-L-tyrosine and tyrosine with ATP catalyzed by the mutant TyrRS (LWJ16) were analyzed in vitro using a pyrophosphate-exchange assay. The mutant TyrRS (LWJ16) gene with six histidines at its C-terminus was cloned into plasmid pQE-60 (Qiagen, Calif.) to afford plasmid pQE-mJYRS. Protein was purified by immobilized metal affinity chromatography according to manufacture's protocol (Qiagen, Calif.). Pyrophosphate (PPi) exchange was carried out at 37° C. in a reaction mixture containing 100 mM TrisHCl (pH7.5), 10 mM KF, 5 mM MgCl2, 2 mM ATP, 2 mM NaPPi, 0.1 mg/mL bovine serum albumin, approximately 0.01 microCi/mL [32P]NaPPi, and various concentrations of tyrosine or O-methyl-L-tyrosine. Reactions were initiated with the addition of the purified mutant TyrRS (LWJ16), and aliquots were periodically taken and quenched with 0.2 M NaPPi, 7% perchloric acid, and 2% activated charcoal. The charcoal was filtered and washed with 10 mM NaPPi (pH2), then measured by scintillation counting to determine the 32P levels in charcoal-adsorbed ATP. Values of kcat and Km were calculated by direct fitting of the Michaelis-Menten equation using nonlinear regression analysis.

TABLE 1

Kinetic parameters for the mutant TyrRS (LWJ16) toward tyrosine and O-methyl-L-tyrosine measured by pyrophosphate exchange assay.

| Amino acid | Kcat (10−3 s−1) | Km (μM) | kcat/Km (s−1M−1) |
|---|---|---|---|
| O-methyl-L-tyrosine | 14 ± 1 | 443 ± 93 | 32 |
| L-tyrosine | 1.8 ± 0.2 | 5833 ± 902 | 0.31 |

The results of this analysis are shown in Table 1. The Km for tyrosine (5833 μM) is approximately 13 fold higher than that for O-methyl-L-tyrosine, and the kcat for tyrosine (1.8×10-3 s-1) is 8 fold down relative to that for O-methyl-L-tyrosine. Thus the value of kcat/Km of the mutant TyrRS (LWJ16) for O-methyl-L-tyrosine is about 100 fold higher than that of tyrosine. The physiological concentration of tyrosine in *E. coli* is about 80 μM, which is far below Km value (5833 μM) of the mutant TyrRS (LWJ16) for tyrosine. Presumably, the concentration of O-methyl-L-tyrosine in cells is comparable or greater than the Km (443 μM).

Example 2

In vivo incorporation of L-3-(2-naphthyl)alanine

The site-specific incorporation of a second unnatural amino acid, L-3-(2-naphthyl)-alanine into proteins in *E. coli* was accomplished. This result shows that this overall scheme is applicable to a host of amino acids. No synthetase specific for L-3-(2-naphthyl)-alanine were selected from the mutant TyrRS library produced in Example 1, described above.

An amber stop codon and its corresponding orthogonal amber suppressor tRNA, $mtRNA_{CUA}^{Tyr}$ were selected to encode the unnatural amino acid (Wang, L.; Schultz, P. G. *Chem. Biol*. 8, 883-890 (2001)). The *M. jannaschii* tyrosyl-tRNA synthetase (TyrRS) was used as the starting point for the generation of an orthogonal synthetase with unnatural amino acid specificity. This TyrRS does not aminoacylate any endogenous *E. coli* tRNAs (Steer, B. A.; Schimmel, P. *J. Biol. Chem*., 274, 35601-35606 (1999)), but aminoacylates the $mtRNA_{CUA}^{Tyr}$ with tyrosine (Wang, L.; Magliery, T. J.; Liu, D. R.; Schultz, P. G. *J. Am. Chem. Soc*., 122, 5010-5011 (2000)). L-3-(2-naphthyl)-alanine was chosen for this study since it represents a significant structural perturbation from tyrosine and may have novel packing properties.

To change the amino acid specificity of the TyrRS so that it charges the $mtRNA_{CUA}^{Tyr}$ with L-3-(2-naphthyl)-alanine and not any common 20 amino acids, a library of *M. jannaschii* TyrRS mutants was generated and screened. Based on an analysis of the crystal structure of the homologous TyrRS from *Bacillus stearothermophilus* (Brick, P.; Bhat, T. N.; Blow, D. M. *J. Mol. Biol*., 208, 83-98 (1989)) five residues ($Tyr^{32}$, $Asp^{158}$, $Ile^{159}$, $Leu^{162}$, and $Ala^{167}$) in the active site of *M. jannaschii* TyrRS that are within 7 Å of the para position of the aryl ring of tyrosine were mutated. To reduce the wild-type synthetase contamination in the following selection, these residues (except $Ala^{167}$) were first all mutated to alanine. The resulting inactive $Ala_5$ TyrRS gene was used as a template for polymerase chain reaction (PCR) random mutagenesis with oligonucleotides bearing random mutations at the corresponding sites.

The mutant TyrRS library was first passed through a positive selection based on suppression of an amber stop codon at a nonessential position (Asp112) in the chloramphenicol acetyltransferase (CAT) gene. Cells transformed with the mutant TyrRS library and the $mtRNA_{CUA}^{Tyr}$ gene were grown in minimal media containing 1 mM L-3-(2-naphthyl)-alanine and 80 μg/mL chloramphenicol. Cells can survive only if a mutant TyrRS aminoacylates the $mtRNA_{CUA}^{Tyr}$ with either natural amino acids or L-3-(2-naphthyl)-alanine. The surviving cells were then grown in the presence of chloramphenicol and the absence of the unnatural amino acid. Those cells that did not survive must encode a mutant TyrRS that charges the $mtRNA_{CUA}^{Tyr}$ with L-3-(2-naphthyl)-alanine, and were picked from a replica plate supplied with the unnatural amino acid. After three rounds of positive selection followed by a negative screen, four mutant TyrRS's were characterized using an in vivo assay based on the suppression of the Asp112TAG codon in the CAT gene. In the absence of L-3-(2-naphthyl)-alanine, cells expressing the selected TyrRS and the $mtRNA_{CUA}^{Tyr}$ survived in 25 to 35 μg/mL chloramphenicol on minimal media plates containing 1% glycerol and 0.3 mM leucine (GMML plate); in the presence of L-3-(2-naphthyl)-alanine, cells survived in 100 to 120 μg/mL chloramphenicol on GMML plates. Compared to the $IC_{50}$ value in the absence of any TyrRS (4 μg/mL chloramphenicol), these results indicate that the selected TyrRS's accept L-3-(2-naphthyl)-alanine, but also still charge natural amino acids to some degree.

To further reduce the activity of the mutant TyrRS toward natural amino acids, one round of DNA shuffling was carried out using the above four mutant genes as templates. The resulting mutant TyrRS library was passed through two additional rounds of positive selections and negative screens. One mutant TyrRS (SS12-TyrRS) was evolved, whose activity for natural amino acids was greatly reduced ($IC_{50}$=9 μg/mL chloramphenicol) while its activity toward L-3-(2-naphthyl)-alanine was enhanced ($IC_{50}$=150 μg/mL chloramphenicol).

The results of the above described in vivo CAT assays using various mutant Tyr RS are shown in Table 2. A pYC-J17 plasmid was used to express the $mtRNA_{CUA}^{Tyr}$ gene and the chloramphenicol acetyltransferase gene with an amber stop codon at Asp112. A pBK plasmid was used to express TyrRS, and was cotransformed with pYC-J17 into *E. coli* DH10B. Cell survival on GMML plates was titrated in the presence of different concentrations of chloramphenicol.

TABLE 2

In vivo chloramphenicol acetyltransferase assay of mutant TyrRS.

| | $IC_{50}$ (μg/mL of chloramphenicol) | |
|---|---|---|
| | No L-3-(2-naphthyl)-Ala | Add L-3-(2-naphthyl)-Ala |
| Mutant TyrRS | | |
| no TyrRS | 4 | 4 |
| wt TyrRS | 240 | 240 |
| After selection | | |
| S1-TyrRS | 30 | 120 |
| S2-TyrRS | 30 | 120 |
| S3-TyrRS | 25 | 110 |
| S4-TyrRS | 35 | 100 |
| After DNA shuffling | | |
| SS12-TyrRS | 9 | 150 |

Figures 4A, 4B:
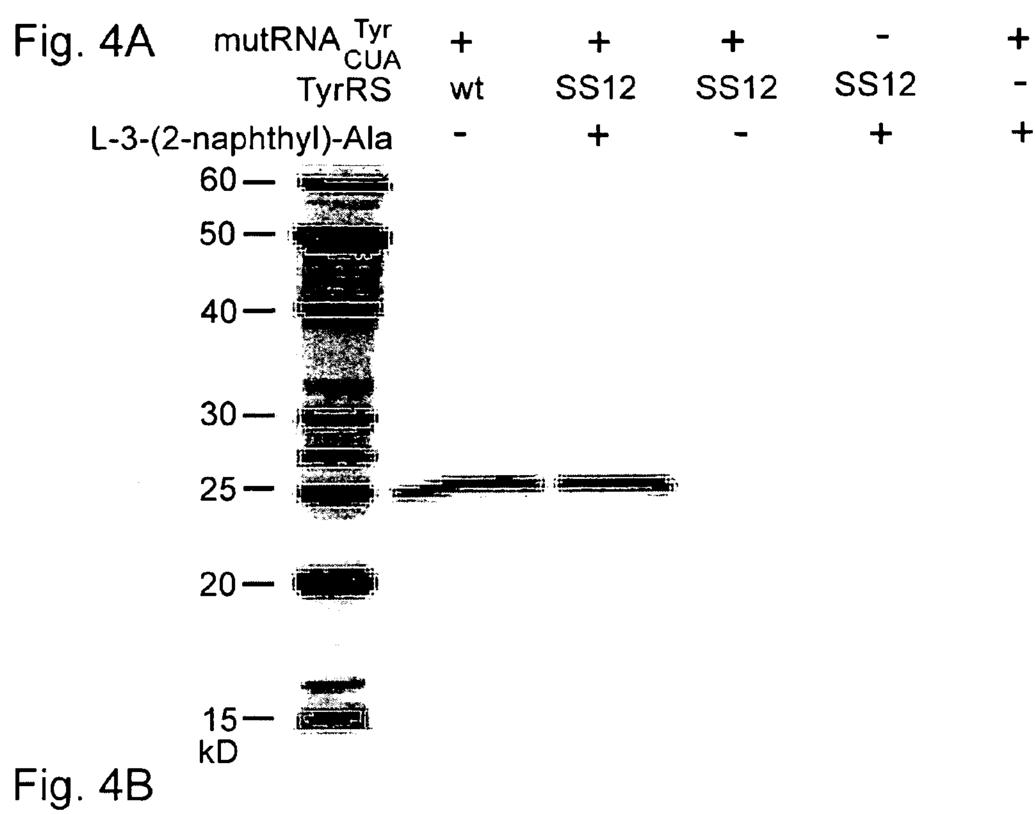
FIGS. 4A-4B illustrates accumulation of mouse DHFR protein, both wild-type (wt) and mutant, under different conditions. Expression conditions are notated at the top of each lane. The left lane is molecular weight marker.

An L-3-(2-naphthyl)-alanine mutant of mouse dihydrofolate reductase (DHFR) was generated and characterized to confirm the ability of the mtRNA$_{CUA}^{Tyr}$/SS12-TyrRS pair to site-specifically incorporate L-3-(2-naphthyl)-alanine in response to an amber stop codon. The Tyr163 codon of the mouse DHFR gene was mutated to TAG, and a His6 tag was added to the COOH-terminus of DHFR to facilitate protein purification using Ni2+ affinity chromatography. As a positive control, wild-type *M. jannaschii* TyrRS was coexpressed with the mtRNA$_{CUA}^{Tyr}$ resulting in efficient suppression of the TAG codon with tyrosine (FIG. 4). When SS12-TyrRS was coexpressed with the mutRNA$_{CUA}^{Tyr}$ in the presence of 1 mM L-3-(2-naphthyl)-alanine, full-length mouse DHFR was also generated (with yield of 2.2 mg/L in liquid GMML minimal medium). In the absence of either L-3-(2-naphthyl)-alanine, mtRNA$_{CUA}^{Tyr}$ or SS 12-TyrRS, no full length DHFR was produced. A penta-His antibody was used to detect the His6 tag at the COOH-terminus of DHFR in a Western blot. No DHFR could be detected in the absence of each of the above three components.

Figure 5:
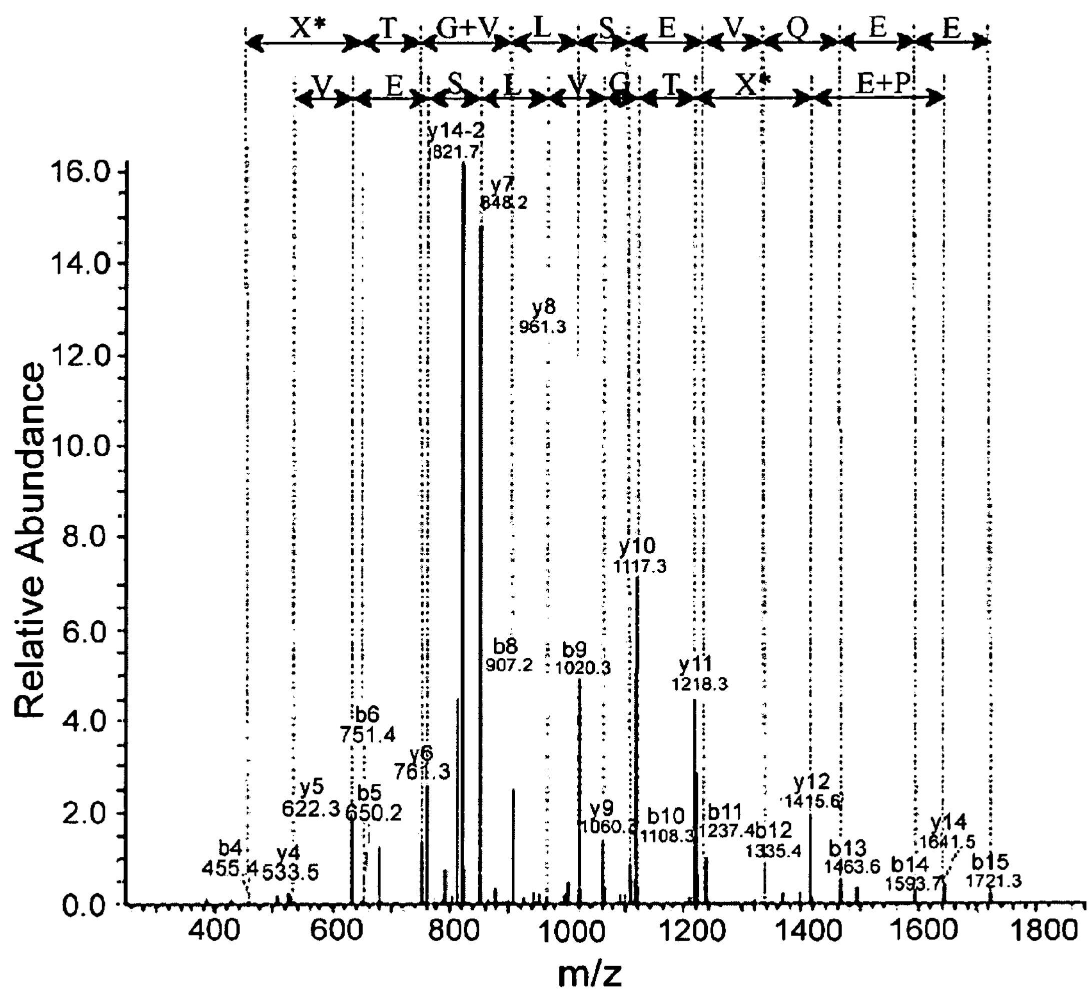
FIG. 5 is a tandem mass spectrum of the tryptic peptide LLPEX*TGVLSEVQEEK (SEQ ID NO;78, X* represents L-3-(2-naphthyl)-alanine). The sequence can be read from the annotated b or y ion series; even so, b7 and y13 are not observed. The base peak 821.7 (100%) assigned to the doubly charged y14 ion is truncated for clarity.

Tryptic digests of the L-3-(2-naphthyl)-alanine mutant of mouse DHFR were analyzed by MALDI FT-ICR and liquid chromatography tandem mass spectrometry to confirm unambiguously the incorporation of L-3-(2-naphthyl)-alanine. The peptide map of the internally calibrated digest shows a major peak at 1867.962, which is within 3.5 ppm of the theoretical mass of the tryptic peptide LLPEX*TGVLSEVQEEK (SEQ ID NO:78) where X* represents the L-3-(2-naphthyl)-alanine residue (Pro164 was mutated to Thr to improve the amber suppression efficiency). Further, the interpreted tandem mass spectrum of precursor ion at m/z 934.5, which corresponds to the doubly charged ion of the peptide of interest is shown in FIG. 5. The sequence information gleaned from the spectrum clearly demonstrates the site-specific incorporation of L-3-(2-naphthyl)-alanine into the protein. Neither peptide maps nor LC MS/MS runs produced any indication of mutants in which the L-3-(2-naphthyl)-alanine residue is substituted by other amino acids. The signal-to-noise ratio of more than 1500 observed in the peptide maps shows a fidelity in the incorporation of L-3-(2-naphthyl)-alanine of better than 99.8%.

The evolved SS12-TyrRS has the following mutations: Tyr32→Leu32, Asp158→Pro158, Ile159→Ala59, Leu162→Gln162, and Ala167→Val167. Corresponding residues from *B. stearothermophilus* are Tyr$^{32}$ (Tyr$^{34}$), Asp$^{158}$ (Asp$^{176}$), Ile$^{159}$ (Phe$^{177}$), Leu$^{162}$ (Leu$^{180}$), and Ala$^{167}$ (Gln$^{189}$) with *B. stearothermophilus* TyrRS residues in parenthesis.

Based on the crystal structure of the homologous *B. stearothermophilus* TyrRS, the mutations of Tyr32→Leu32 and Asp158→Pro158 probably result in the loss of hydrogen bonds between Tyr32, Asp 158, and the native substrate tyrosine, thus disfavoring the binding of tyrosine to SS12-TyrRS. Most residues are mutated to amino acids with hydrophobic side chains, which are expected to favor binding of L-3-(2-naphthyl)-alanine.

In summary, the cell growth, protein expression, and mass spectrometry experiments demonstrate that the mtRNA$_{CUA}^{Tyr}$/SS12-TyrRS pair is capable of selectively inserting L-3-(2-naphthyl)-alanine into proteins in response to the amber codon with fidelity rivaling that of the natural amino acids.

Example 3

In vivo Incorporation of amino-, isopropyl-, or allyl-containing tyrosine Analogues A FACs based screening system was used to rapidly evolve three highly selective synthetase variants that accept amino-, isopropyl-, or allyl-containing tyrosine analogues. The system included a multipurpose reporter plasmid used for application of both positive and negative selection pressure and for the facile and quantitative evaluation of synthetase activity. A chloramphenicol acetyl transferase (CAT) marker allowed positive selection for activity of the *M. jannaschii* tyrosyl-tRNA synthetase (TyrRS). A T7 polymerase/GFP reporter system allowed assessment of synthetase activity within cells grown in both the presence and absence of an unnatural amino acid. Fluorescence activated cell sorting (FACS) was used to screen against synthetase variants that accept natural amino acids, while visual and fluorimetric analyses were to assess synthetase activity qualitatively and quantitatively, respectively.

Design of an amplifiable fluorescence reporter system. Efforts to develop a versatile screening system for the assessment of synthetase activity in living cells initially arose out of a desire for a greater degree of control over the selective pressure applied to populations of synthetase variants, especially negative selective pressure. As the system was to be used to assess the activities of large numbers of synthetase variants, a reporter was sought that would be amenable to high-throughput screening. In addition, a reporter that would allow for facile qualitative and quantitative evaluation of synthetase activity was desired. To meet these requirements, a fluorescence-based screen was designed. The system was based on the synthetase-dependent production of GFPuv, a variant of the green fluorescent protein that has been optimized for expression in *E. coli* (Crameri, A., Whitehom, E. A., Tate, E. & Stemmer, W. P., *Nature Biotechnol*. 1996, 14, 315-319). This fluorophore is amenable to use in FACS and fluorimetry, as well as visual inspection on plates and in liquid culture. The system was designed such that synthetase-dependent suppression of selector, e.g., amber nonsense codons would result in the production of a fluorescence signal. In order to maximize the sensitivity of the reporter, it was made amplifiable by placement of the amber codons within the gene for T7 RNA polymerase, which was designed to drive expression of the GFPuv reporter gene in analogy to other amplifiable intracellular reporter systems (Lorincz, M., Roederer, M., Diwu, Z., Herzenberg, L. A., Nolan, G. P. *Cytometry*, 1996, 24, 321-329; Zlokamik, G., Negulescu, P. A., Knapp, T. E., Mere, L., Burres, N., Feng, L., Whitney, M., Roemer, K. & Tsien, R. Y., *Science*, 1998, 279, 84-88). The T7 RNA polymerase gene was placed under control of the arabinose promoter in order to allow facile optimization of the production of the RNA transcript for amber codon-containing T7 RNA polymerase.

Figure 6A:
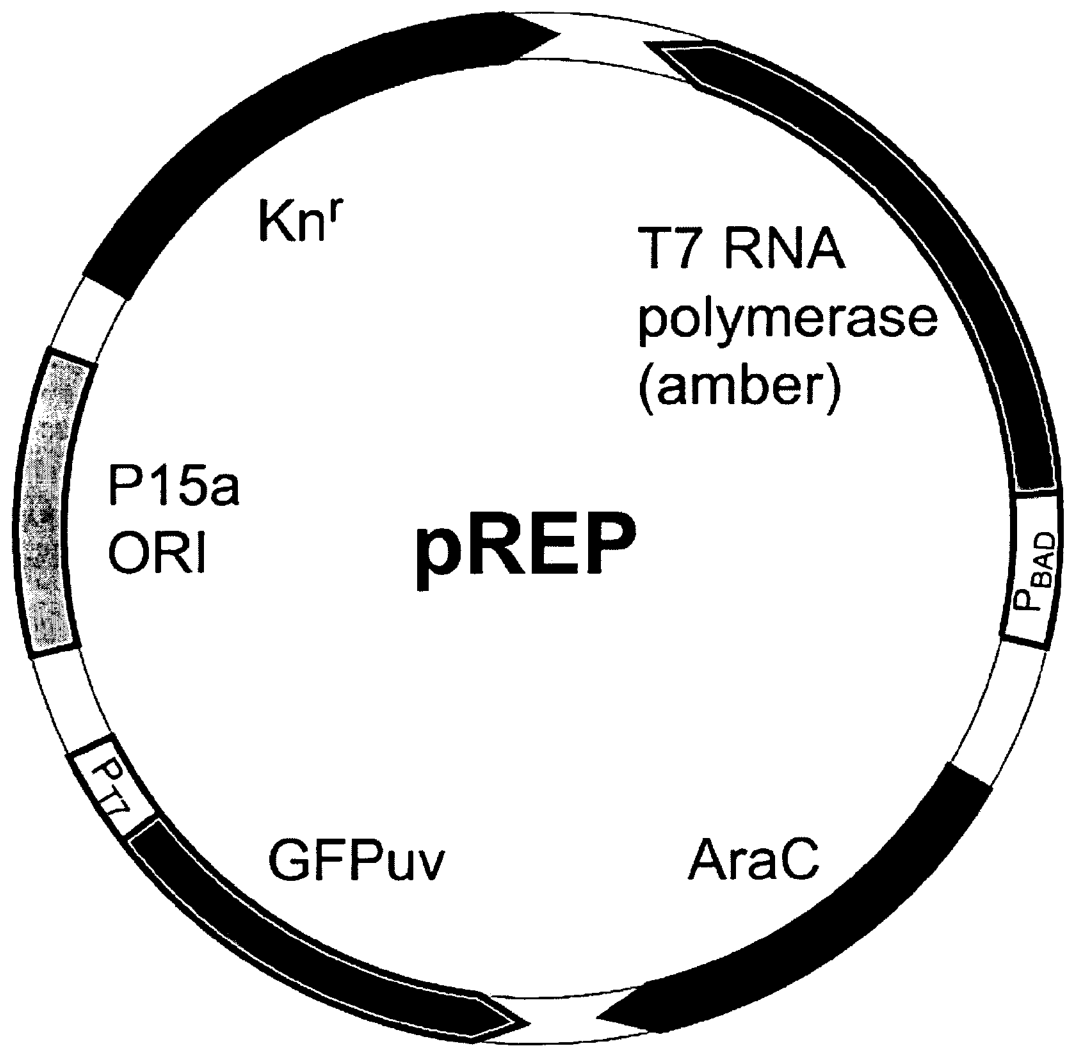
FIG. 6A is plasmid pREP. T7 RNA polymerase transcription is controlled by the ara promoter; protein expression depends on suppression of amber codons at varying locations within the gene. GFPuv expression is controlled by T7 RNA polymerase. Plasmid pREP is compatible for use with a ColE1 plasmid expressing an orthogonal synthetase/tRNA pair.
Figure 6C:
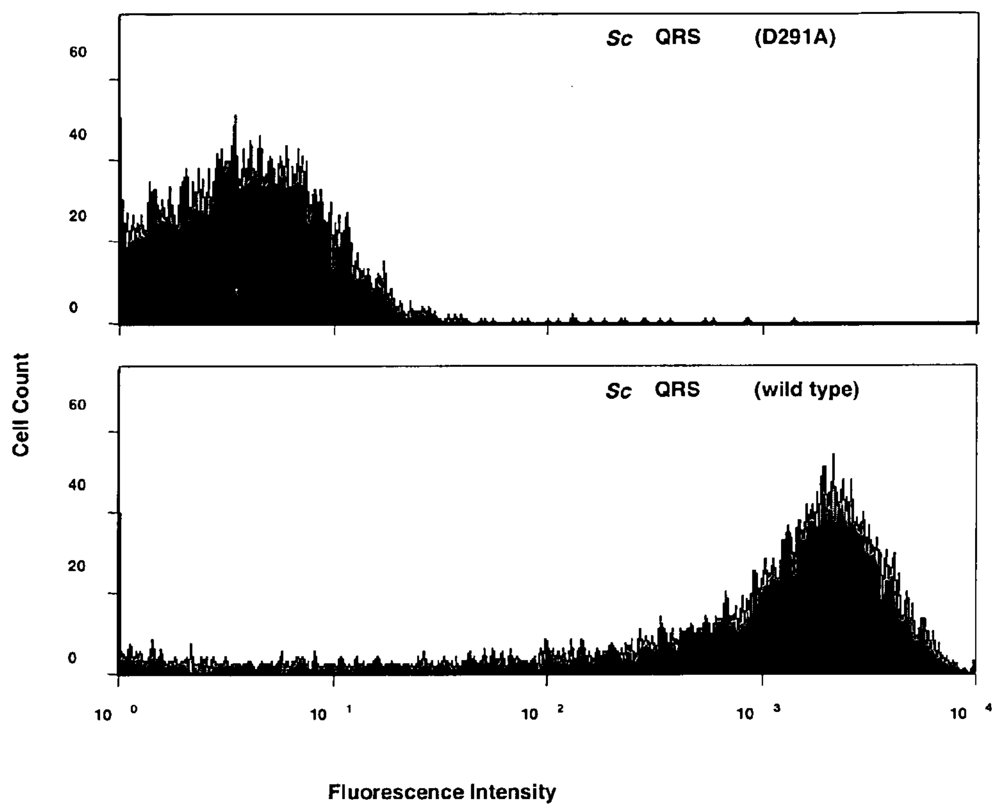
FIG. 6C illustrates cytometric analysis of cells containing PREP(10) and either pQD (top) or pQ (bottom).
Figure 6D:
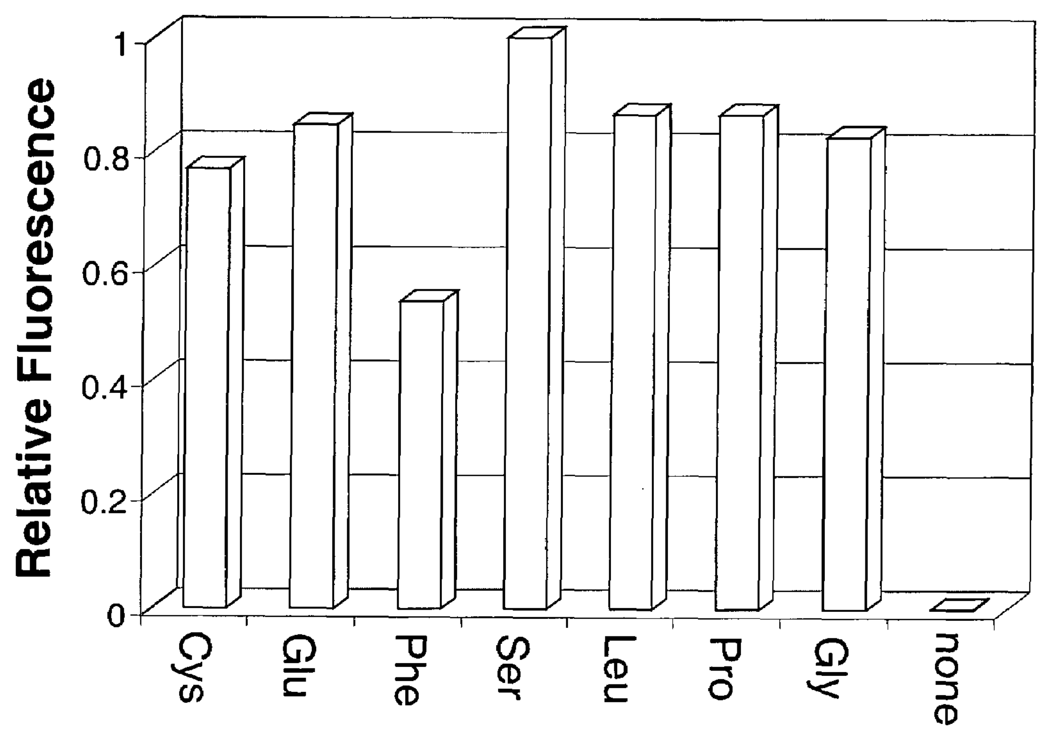
FIG. 6D illustrates fluorimetric analyses of cells containing pREP (10) and expressing various *E. coli* suppressor tRNAs. 'None' indicates that the cells contain no suppressor tRNA.

Optimization of the T7 RNA polymerase/GFPuv reporter system. A medium-copy reporter plasmid, pREP, was designed to express amber-containing T7 RNA polymerase variants under control of the arabinose promoter and the GFPuv gene under control of the T7 promoter (FIG. 6*a*). A series of twelve T7 RNA polymerase variants, designed to optimize synthetase-dependent fluorescence enhancement (FIG. 6*b*), were inserted into pREP to create plasmids pREP(1-12). All variants contained an N-terminal leader sequence of seven amino acids (MTMITVH, SEQ ID NO:79) and 1-3 amber stop codons (TAG). Variants 1-3 contained one, two, and three amber stop codons, respectively, substituted for the original methionine at position one (M1), just downstream of the leader sequence. Variants 4-9 contained an amber codon substituted for D10, R96, Q107, A159, Q169, or Q232, respectively, which were predicted to be located in loop regions of the structure (Jeruzalmi, D. & Steitz, T. A., *EMBO J.*, 1998, 17, 4101-4113). Variants 10-12 contained amber stop codons substituted at postions M1 and either Q107, A159, or Q232, respectively. Plasmid constructs were evaluated by fluorimetry and flow cytometry of live cells for fluorescence enhancement using a compatible plasmid containing the orthogonal glutaminyl-tRNA synthetase and Glutamine $tRNA_{CUA}$ from *S. cerevisiae*. Plasmids pREP(1-12) were found to provide varying levels of synthetase-dependent fluorescence enhancement, with the best construct, pREP(10) exhibiting 220-fold greater fluorescence by fluorimetry (FIG. 6*c*) and ~400-fold greater median fluorescence by cytometry (FIG. 6*d*) in cells containing the wild type synthetase versus an inactive mutant. Substitution of a variety of functional groups at positions corresponding to the amber codons within pREP(10) demonstrate that position 107 within T7 RNA polymerase is highly permissive.

Figure 7A:
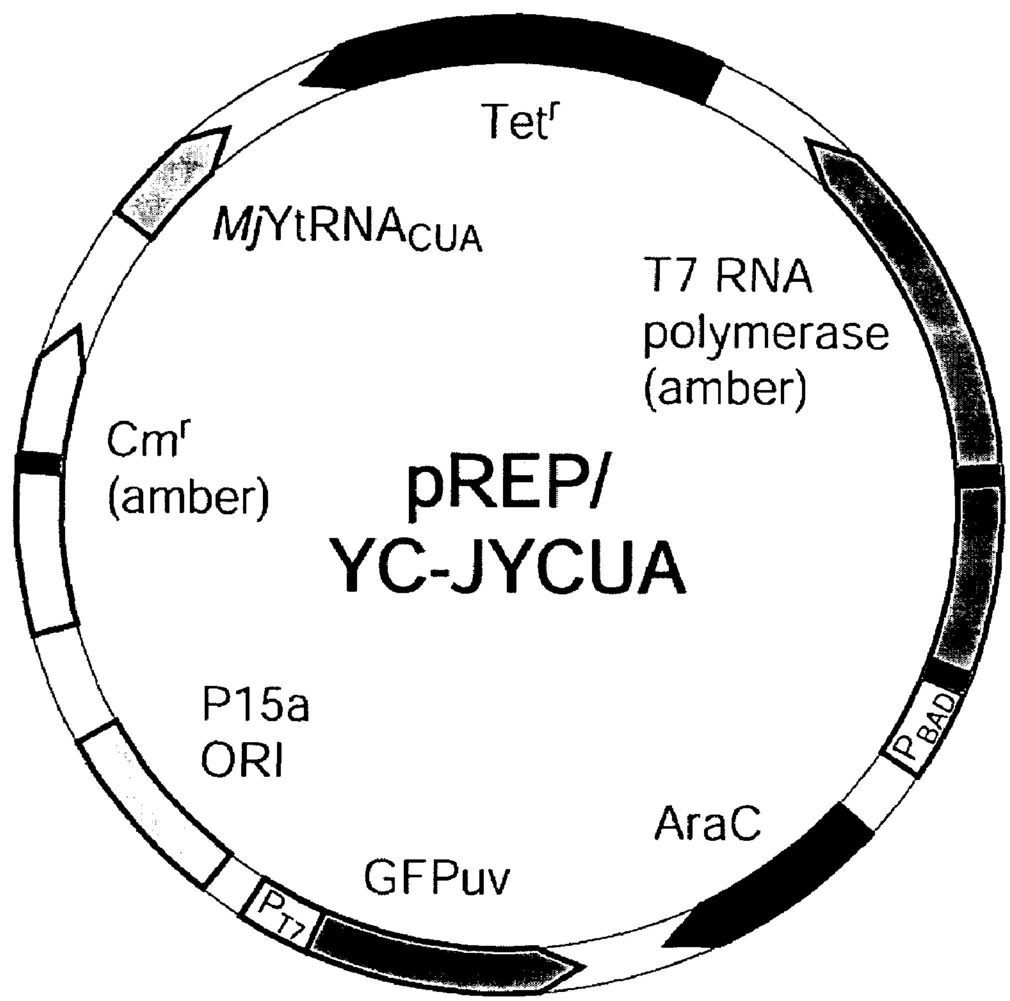
FIG. 7A illustrates plasmid pREP/YC-JYCUA. Plasmid pREP/YC-JYCUA is compatible for use with plasmid pBK and variants.
Figure 7B:
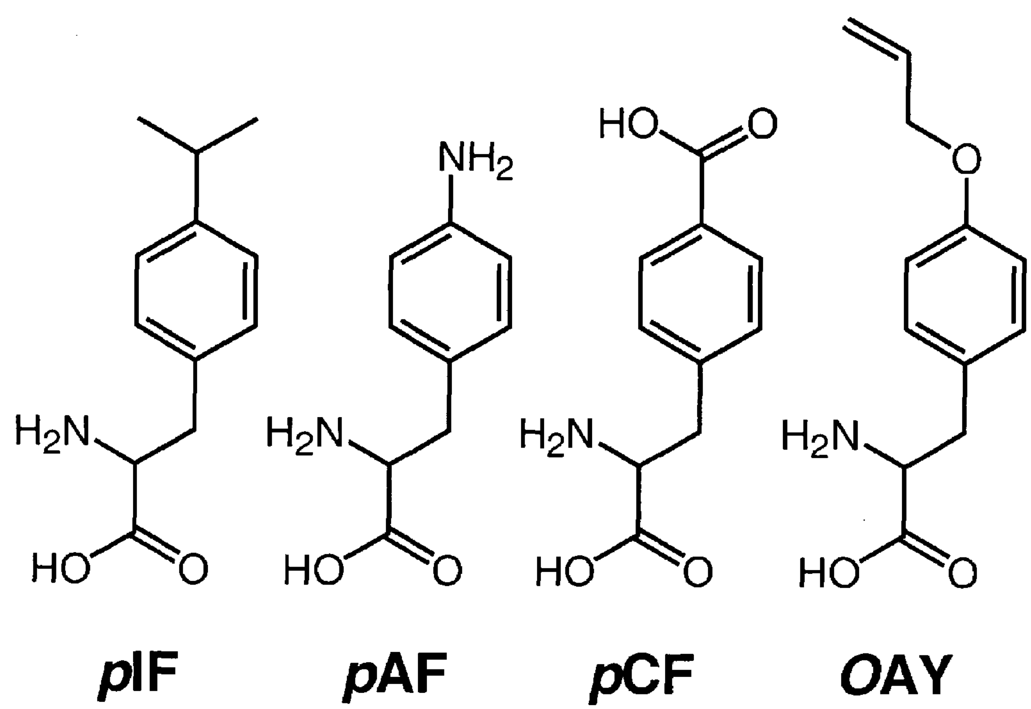
FIG. 7B illustrates structures of unnatural amino acids used as targets for the evolution of *M. jannaschii* TyrRS.

Construction of a multipurpose reporter plasmid. In order to construct a multipurpose plasmid to be used both for selecting and screening variants of a *M. jannaschii* TyrRS, plasmid pREP(10) was combined with plasmid pYC-J17 (Wang, L, Brock, A., Herberich, B. & Schultz, P. G., *Science*, 2001, 292, 498-500) to obtain pREP/YC-JYCUA (FIG. 7*b*). Plasmid pREP/YC-JYCUA was assayed for function with a compatible plasmid expressing a variant of *M. jannaschii* TyrRS (pBK-mJYRS; Wang, L, Brock, A., Herberich, B. & Schultz, P. G., *Science*, 2001, 292, 498-500) selective for incorporating O-Methyl-Tyrosine (OMY). Cells containing pREP/YC-JYCUA and pBK-mJYRS, grown in the presence of OMY, exhibited a chloramphenicol (Cm) $IC_{50}$ value of 120 micrograms/ml, identical to that obtained using plasmid pYC-J17, and a fluorescence enhancement of 330-fold for cells grown in the presence versus the absence of OMY, as measured by fluorimetry.

Figure 7C:
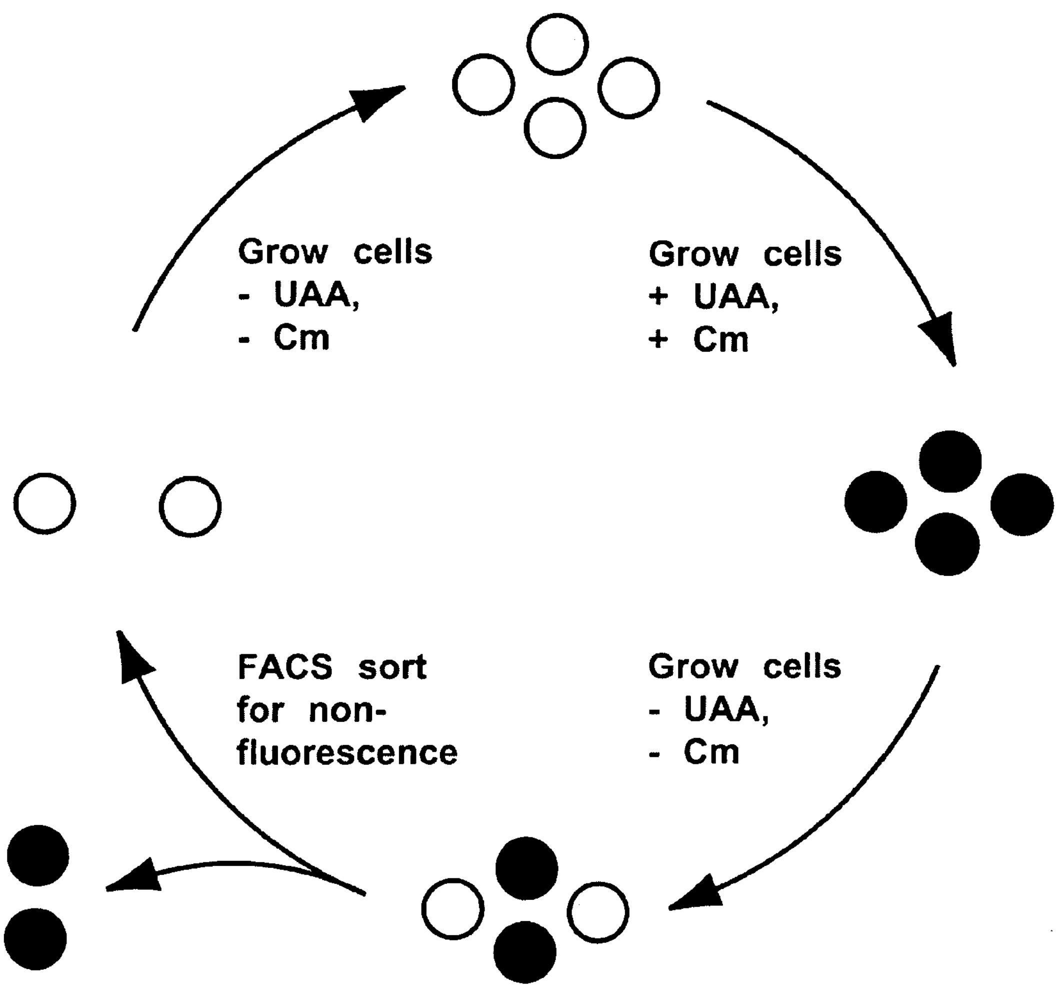
FIG. 7C illustrates a strategy for a evolution of an aminoacyl-tRNA synthetase using plasmid pREP/YC-JYCUA. Fluorescent and non-fluorescent cells are shown in black and grey, respectively.

Evolution of the substrate specificity of the *M. jannaschii* tyrosyl-tRNA synthetase. Results have shown that the amino acid side chain binding pocket of the *M. jannaschii* TyrRS can be evolved to selectively accommodate chemical groups other than the phenol side chain of tyrosine (Wang, L, Brock, A., Herberich, B. & Schultz, P. G., *Science*, 2001, 292, 498-500; Wang, L., Brock, A. & Schultz, P. G. *J. Am. Chem. Soc.* 2002, 124, 1836-1837). We sought to further explore the generality of unnatural amino acid accommodation by *M. jannaschii* TyrRS by challenging the enzyme to accept four new functionalities: p-Isopropyl-Phenylalanine (pIF), p-Amino-Phenylalanine (pAF), p-Carboxyl-Phenylalanine (pCF), or O-Allyl-Tyrosine (OAT) (FIG. 7*b*). A library of *M. jannaschii* TyrRS variants containing randomizations at positions Y32, E107, D158, I159, and L162 (Wang, L, Brock, A., Herberich, B. & Schultz, P. G., *Science*, 2001, 292, 498-500), residues thought to form the binding pocket for the para position of the tyrosyl ring, was introduced into cells containing plasmid pREP/YC-JYCUA. These cells, encompassing a library diversity of $\sim 10^9$, were used to begin four evolution experiments to identify synthetase variants selective for pIF, pAF, pCF, or OAT (FIG. 7*c*). Two cycles of positive selection were carried out by allowing the cell cultures to grow to saturation in the presence of Cm and one of the four unnatural amino acids. Cell aliquots were removed following the second cycle of positive selection and used to inoculate a new culture containing no added amino acid or Cm, and the culture was again allowed to grow to saturation. At this point, cells that fluoresce are likely to contain synthetase variants that can accept one of the 20 natural amino acids. Approximately $10^8$ cells from each line were subjected to negative screening using FACS in order to eliminate natural amino acid-accepting synthetase variants. The non-fluorescent cells were collected and amplified through growth to saturation. These amplified cells were used to inoculate a new culture for a final cycle of positive selection in liquid culture containing unnatural amino acid and Cm. Following growth to saturation, each population of cells was plated on media containing 0, 30, 60, or 100 micrograms/mL Cm and either 0 or 1 mM of the appropriate unnatural amino acid.

Figure 8A:
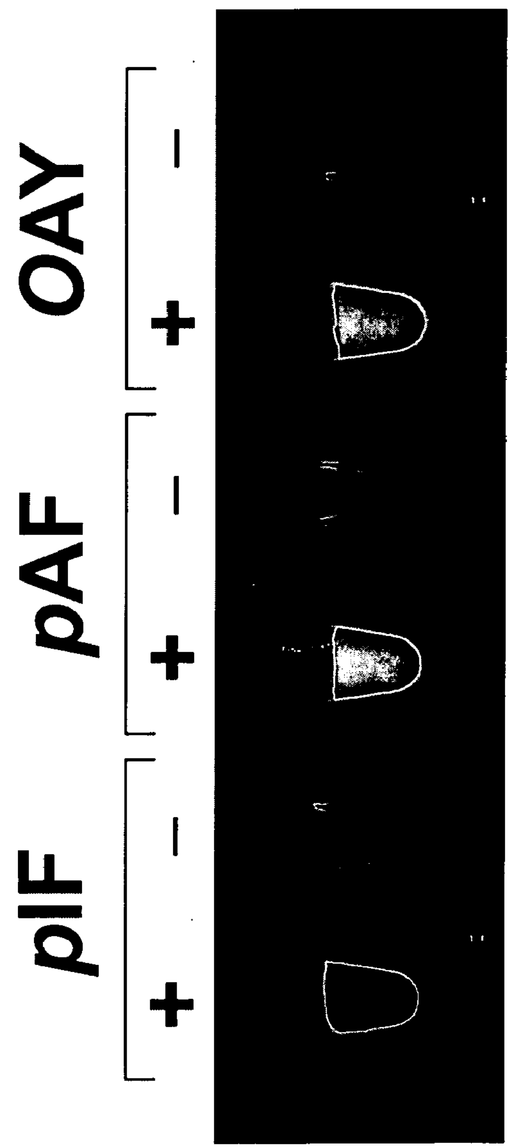
FIG. 8A is a photograph illustrating long-wavelength ultraviolet illumination of cells containing pREP/YC-JYCUA and the indicated synthetase variant, grown in either the presence (+) or absence (−) of the corresponding unnatural amino acid.

Identification and characterization of evolved synthetase variants. Cm plates supplemented with pIF, pAF, and OAT produced 10-100-fold greater numbers of fluorescent colonies than plates containing no added amino acid. In contrast, plates for the pCF population produced the same number of fluorescent colonies with or without addition of pCF. The ten largest fluorescent colonies were picked for each of the pIF, pAF, and OAT populations from unnatural amino acid-containing plates and grown to saturation in liquid media with or without added unnatural amino acid. A qualitative assessment of fluorescence production was made visually with the use of a hand-held long-wavelength ultraviolet lamp (FIG. 8*a*).

Figure 8B:
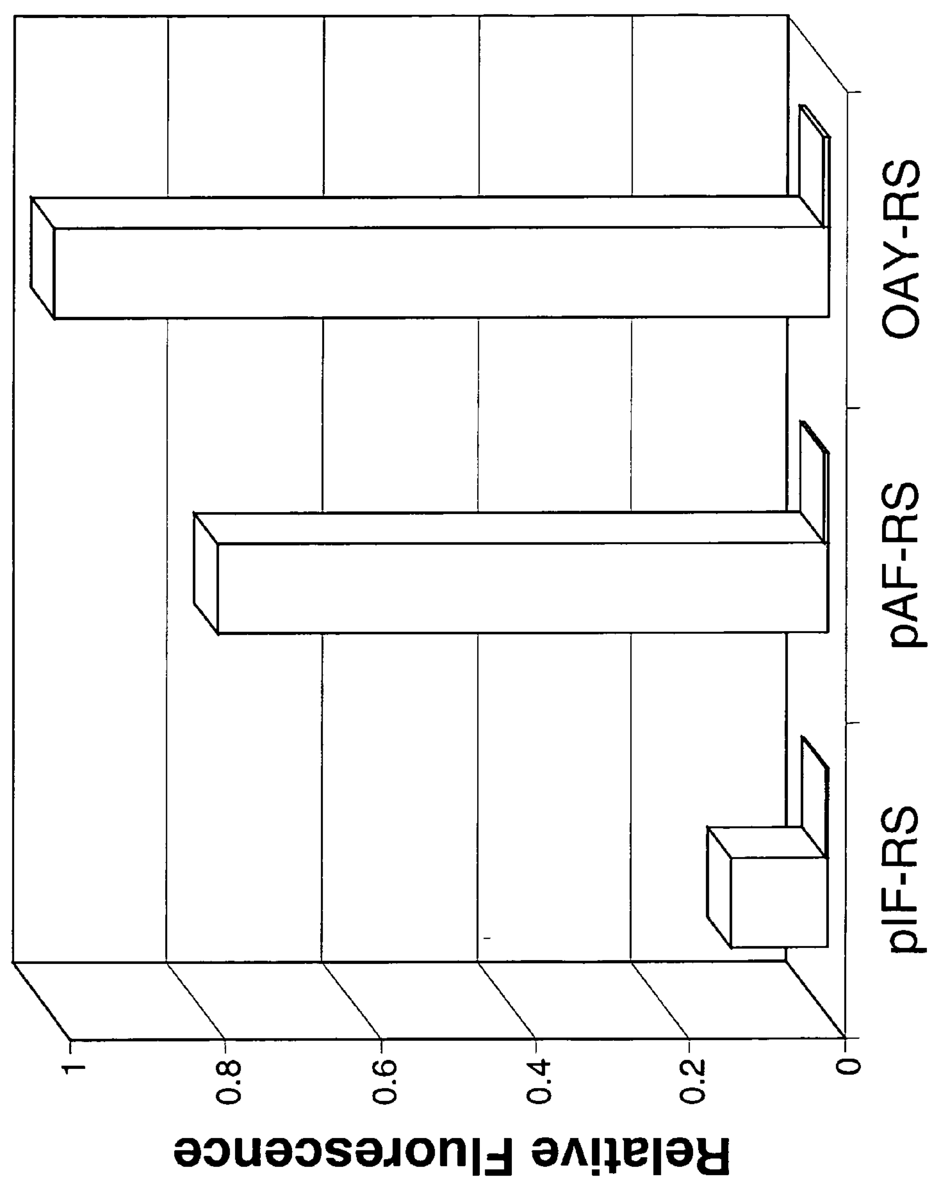
FIG. 8B illustrates a fluorimetric analysis of cells containing pREP/YC-JYCUA and the indicated synthetase variant, grown in either the presence (left) or absence (right) of the corresponding unnatural amino acid.

Synthetase variants corresponding to clones producing significant differences in fluorescence were sequenced. All ten clones from the pIF and pAF populations had identical sequences, while three different clones were identified from the OAT population. Amino acid changes occurred within the five randomized sites in all clones, with the exception of two additional substitutions within the pIF-tRNA synthetase (pIF-RS) variant. The activities of the different clones were quantitatively assessed. Fluorescence was measured fluorimetrically for cells grown in liquid culture in the presence or absence of unnatural amino acid (FIG. 8*b*). The Cm $IC_{50}$s were determined by plating the cells on varying concentrations of Cm in the presence or absence of unnatural amino acid (FIG. 8*c*).

Figure 8D:
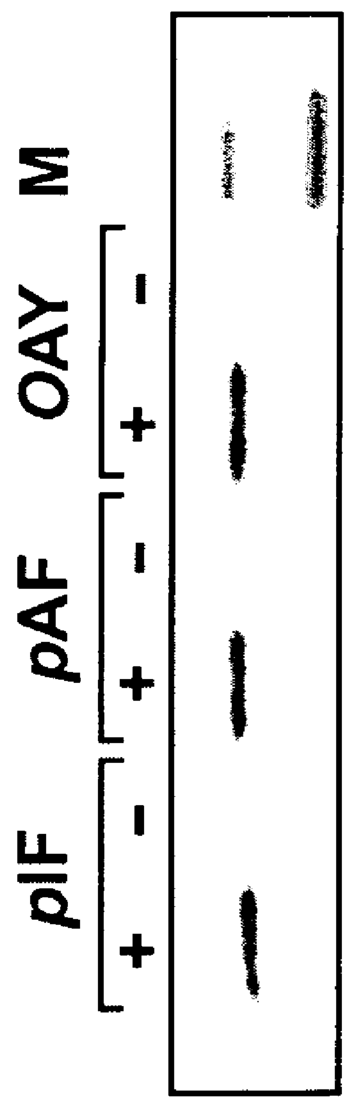
FIG. 8D illustrates a protein expression analysis from cells containing pBAD/JYAMB-4TAG and the indicated synthetase variant, grown in either the presence (+) or absence (−) of the corresponding unnatural amino acid.

A myoglobin gene containing an amber codon in the fourth position was used to assess the production of unnatural amino acid-containing protein. The gene was expressed in cells, using the pIF-RS, pAF-RS, or OMY-RS variant, respectively, in either the presence or absence of pIF, pAF, or OAT (FIG. 8*d*). Protein yields were comparable for all three variants, ranging from 1-2 milligrams of protein per liter of unnatural amino acid-containing cell culture. In contrast, protein production was virtually undetectable in cultures grown in the absence of unnatural amino acid. Proteins were analyzed by electrospray mass spectrometry, giving masses of 18457.40±0.81 (18457.28 expected) for the pIF-containing protein, 18430.30±0.27 (18430.21 expected) for the pAF-containing protein. Activity measurements obtained using the Cm $IC_{50}$, fluorimetry, and protein expression analyses correlated well, however the activity of the pIF-RS appears to be somewhat underestimated by fluorimetry. As compared to other assays, the disproportionately low fluorimetry measurement for the pIF-RS variant, shows that T7 RNA polymerase may be partially destabilized upon incorporation of the pIF analogue, despite the apparent permissivity of the amber positions within the reporter.

Utility of the multipurpose reporter system. The reporter system described here allows the use of a single multipurpose plasmid for both positive selection and negative screening, obviating the need to shuttle plasmids between alternating rounds of positive and negative selection. A total of only three rounds of positive selection and one round of negative screening were required to enable the identification of synthetase variants that selectively accept desired unnatural amino acids. These features allow evolution experiments to be carried out in a matter of days. The screening system can be used to readily identify active synthetase variants using agar plates containing unnatural amino acid and to individually assay the amino acid specificity of the variants.

Figure 9:
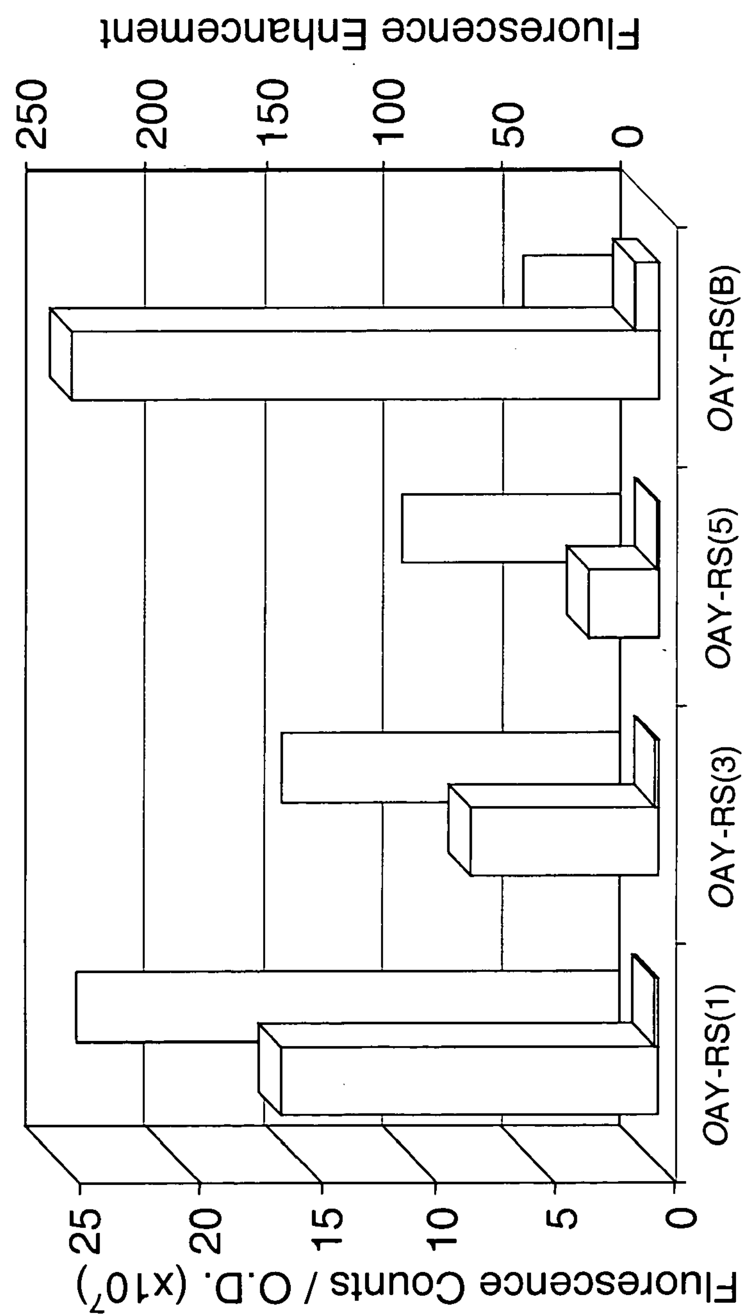
FIG. 9 illustrates activity comparisons of OAY-RS variants derived using a negative FACS-based screen [OAY-RS (1,3,5)] or negative barnase-based selection [OAY-RS(B)]. Cells containing pREP/YC-JYCUA and the indicated synthetase variant were grown in either the presence (solid block, left) or absence (solid block, right) of the corresponding unnatural amino acid and analyzed fluorimetrically. Fluorescence enhancement (bar, back) is calculated as the cell concentration-corrected ratio of fluorescence of cells grown in the presence versus the absence of unnatural amino acid.

As described above, the T7 RNA polymerase/GFP system can be used to quantitatively compare the activities of synthetase variants. The availability of the three OAT-RS clones described here and a different OAT-RS clone derived independently from the same library using a positive/negative selection based on CAT and bamase (Table 2) allows the possibility of comparing the two different evolution systems in terms of the synthetase variants resulting from each (FIG. 9). This analysis reveals that the three clones derived from positive selection and negative screening exhibit slightly lower levels of fluorescence in the presence of OAT, but ~10-fold lower background levels in the absence of the unnatural amino acid. The fluorescence enhancement for cells grown in the presence versus the absence of the unnatural amino acid is thus about 6-fold higher for cells expressing OAT-RS(1) from selection and screening than for cells expressing the OAT-RS clone derived from positive/negative selection using bamase. Although it is not clear whether this example is representative, these data suggest that the T7 RNA polymerase/GFP system may allow more stringency in selecting against synthetase variants that are promiscuous towards natural amino acid substrates. However, the fluorescence enhancement for cells grown in the presence versus the absence of an unnatural amino acid is expected to represent a lower limit for the fidelity of unnatural amino acid incorporation, as competition of unnatural amino acids for being bound by an evolved synthetase variant would reduce binding of natural amino acids. Moreover, although high fidelity is clearly desirable, there is likely to be a trade-off between fidelity and overall synthetase activity, which may depend on the desired application.

Generality of aminoacyl tRNA synthetase evolution. Previous results and those presented here demonstrate that the amino acid side chain binding pocket of the *M. jannaschii* TyrRS is quite malleable. The enzyme can be evolved to accommodate a variety of functionalities in place of the phenol side chain of tyrosine and can do so with high selectivity. In this application it was demonstrated that enzyme can be evolved to accommodate an amine, isopropyl, or allyl ether functionality at the para position of the tyrosine ring, instead of hydroxyl.

Plasmid Construction. Plasmid pREP (FIG. 6*a*) was constructed by insertion of a BamHI/ApaLI overlap PCR fragment containing the T7 RNA polymerase gene upstream of an rrnB transcription termination region, followed by an ApaLI/AhdI overlap PCR fragment containing the araC gene and ara promoter region from the pBAD/Myc-His A plasmid (Invitrogen; for transcriptional control of the T7 RNA polymerase gene) and the GFPuv gene (Clontech; upstream of the T7 terminator region and downstream of the T7 promoter) between the AhdI/BamHI sites of plasmid pACYC177 (New England Biolabs). Plasmids pREP(1-12) were constructed by replacement of an HpaI/ApaLI fragment of T7 RNA polymerase with overlap PCR fragments containing amber mutations at the positions described. Plasmid pREP/YC-JYCUA was constructed by ligation of an AfeI/SacII fragment from pREP(10) and an EarI(blunted)/SacII fragment from pYC-J17 (Wang, L, Brock, A., Herberich, B. & Schultz, P. G., *Science*, 2001, 292, 498-500). The desired construct was identified following transformation into cells containing plasmid pQ screening for fluorescence.

Plasmid pQ was constructed by triple ligation of a AatII/SalI overlap PCR fragment containing the ScQRS downstream of the lac promoter region and upstream of the *E. coli* QRS termination region, a SalI/AvaI overlap PCR fragment containing the *S. cerevisiae* tRNA(CUA)$^{Gln}$ downstream of the lpp promoter region and upstream of an rrnC termination region, and the AvaI/AatII fragment of pBR322 (New England Biolabs). Plasmid pQD was constructed by replacement of pQ fragment between BamHI and BglII with a BamHI/BglII fragment of the ScQRS (D291A) mutant.

Plasmid pBAD/JYAMB-4TAG was constructed by insertion of a PCR fragment of the S4Amber mutant of myoglobin, containing a C-terminal 6His-tag, into the pBAD/YC-JYCUA plasmid, a hybrid of plasmid pYC-J17 (Wang, L, Brock, A., Herberich, B. & Schultz, P. G., *Science*, 2001, 292, 498-500) and pBAD/Myc-His A (Invitrogen) containing the gene for MjYtRNA$_{CUA}$, and the pBAD promoter and cloning regions for heterologous expression of an inserted gene.

Fluorimetric and cytometric analyses. Single colonies containing desired plasmids were used to inoculate 2-mL GMML cultures containing the appropriate antibiotics, 0.002% Arabinose, and an appropriate unnatural amino acid, if desired. Cultures were grown to saturation and cells (200 μL) were pelleted and resuspended in 1 mL phosphate-buffered saline (PBS). Cell concentrations were analyzed by absorbance at 600 nm and fluorescence levels were measured at 505 nm with excitation at 396 nm using a FluoroMax-2 fluorimeter. Cells suspended in PBS were analyzed cytometrically. To evaluate the permissivity of the amber positions within the T7 polymerase gene of pREP(10), the reporter plasmid was transformed into a panel of suppressor strains, which were subsequently analyzed fluorimetrically.

Evolution of aminoacyl-tRNA synthetase variants. *M. jannaschii* TyrRS variants randomized at positions Y32, E107, D158, I159, and L162 (Wang, L, Brock, A., Herberich, B. & Schultz, P. G., *Science,* 2001, 292, 498-500) were transformed into DH10B *E. coli* cells (Life Technologies) containing pREP/YC-JYCUA to generate a library with a diversity of ~10$^9$. Transformants were allowed to recover in SOC medium for 60 min at 37° C., and were grown to saturation in LB medium. To begin an initial positive selection, 2 mL of library culture, pelleted and resuspended in GMML medium, was used to inoculate 500 mL of GMML containing 25 μg/mL Tetracycline (Tet), 35 μg/mL Kanamycin (Kn), and 1 mM pIF, pAF, pCF, or OAY. After incubation for 3 hr at 37° C., Cm was added to a final concentration of 75 μg/mL and cells were grown to saturation (~48 hr). For the second positive selection, a 100-mL GMML culture containing Tet, Kn, 75 μg/mL Cm, and 1 mM pIF, pAF, pCF, or OAY was inoculated with cells from the initial positive selection (500 μL) and grown to saturation at 37° C. (~24-36 hr). In preparation for negative screening, a 25-mL GMML culture containing Tet, Kn, and 0.02% arabinose (Ara) was inoculated with cells from the second positive selection (100 μL, pelleted and resuspended in GMML) and grown to saturation at 37° C. (~24 hr). Ara-induced cells grown in the absence of unnatural amino acids (1 mL) were pelleted and resuspended in 3 mL of phosphate-buffered saline (PBS). Cells were sorted for lack of expression of GFPuv using a BDIS FACVantage TSO cell sorter with a Coherent Enterprise II ion laser with excitation at 351 nm and emissions detected using a 575/25 nm bandpass filter. Collected cells were diluted in at least 10 volumes of LB, containing Tet and Kn, and grown to saturation. To begin the third round of positive selection, 100 μL of cells from the negative screen were pelleted, resuspended in GMML, and used to inoculate 25 mL of GMML containing Tet, Kn, and 1 mMpIF, pAF, pCF, or OAY. After incubation for 3 hr at 37° C., Cm was added to a final concentration of 75 μg/mL and cells were grown to saturation (~24 hr). Following the third positive selection, cells were plated on GMML/agar containing Tet, Kn, 0.002% Ara, 0, 75, or 100 μg/mL Cm, and 0 or 1 mM pIF, pAF, pCF, or OAY, and grown for 48 hr at 37° C.

Expression and characterization of unnatural amino acid-containing proteins. DH10B cells cotransformed with pBAD/JYAMB-4TAG and the appropriate pBK plasmid were used to inoculate a 100-mL GMML starter culture containing Kn and Tet, which was grown to saturation. A 500-mL culture containing Kn, Tet, 0.002% Ara, 5 μM $FeCl_3$, and the desired unnatural amino acid (or none) was inoculated with 50 mL of the starter culture and grown to saturation (~18 hr). Cultures were pelleted, sonicated, and the myoglobin protein isolated according to the protocol of the QiaExpressionist (Qiagen) His-tag purification kit. Proteins were analyzed electrophoretically on a 12-20% gradient SDS polyacrylamide gel and by electrospray mass spectrometry.

Example 4

Creation of an Autonomous 21 Amino Acid Bacterium

As described above, the common twenty amino acids are conserved across all known organisms. However, an expanded genetic code is provided herein, e.g., for added functionality, structure determination and the like. To determine whether the expanded genetic code is advantageous to a cell, e.g., with a particular unnatural amino acid, an autonomous bacterium that produces and incorporates the unnatural amino acid of interest is desirable. The present invention provides such an autonomous twenty-one amino acid organism, and the results can be extended to the production of additional amino acid organisms, e.g., 22 amino acid organisms and the like. To produce an autonomous bacterium, three factors are typically considered: (i) the ability to synthesize a new amino acid from simple carbon sources; (ii) an aminoacyl synthetase that uniquely utilizes this new amino acid and no other; and (iii) a tRNA that is acylated by that synthetase and no other, and which delivers the amino acid into proteins in response to a codon that does not encode any other amino acid.

A great deal of effort has been made toward in vivo incorporation of new amino acids to the genetic code but most of these do not have the incorporation specificity to generate a healthy 21 amino acid bacterium. See, e.g., Hest, J. C. M. v., K. L. Kiick, and D. A. Tirrell, *J. Am. Chem. Soc.*, 2000. 122: p.1282; Hamano-Takaku, F., et al., *J. Biol. Chem.*, 2000. 275: p. 40324; and Budisa, N., et al., *FASEB J.*, 1999. 13: p. 41-51. However, it has recently been shown that that one could add new components to the translational machinery of *E. coli* and site-specifically incorporate a variety of new amino acids into proteins in vivo, e.g., with high fidelity. See, e.g., Wang, L., et al., *Science*, 2001, 292: p. 498-500 and Wang, L. and P. G. Schultz, *Chem. Comm.*, 2002: p.1-10. See, also, co-filed patent application "Methods and Compositions for the Production of Orthogonal tRNA-tRNA Synthetase Pairs," by Schultz et al., U.S. patent application Ser. No. 10/126,931 filed Apr. 19, 2002.

The present invention combines the above technology with a biosynthetic pathway system to produce an autonomous twenty-one amino acid bacterium. In addition, the present invention addresses the question of whether such organisms have or can be evolved to have an evolutionary advantage over organisms that use the twenty natural amino acids.

A completely autonomous bacterium typically comprises a biosynthetic pathway system, e.g., for producing an unnatural amino acid, and a translation system for incorporating the unnatural amino acid into one or more proteins in the bacterium. The translation system typically comprises an aminoacyl synthetase that uniquely utilizes this unnatural amino acid and no other, and a tRNA that is acylated by that synthetase and no other, and which delivers the unnatural amino acid into proteins in response to a codon that does not encode any other amino acid. In one embodiment, the biosynthetic pathway system genes, aminoacyl synthetase genes, and tRNA genes are typically positioned on separate plasmids to maximize control of the modified bacteria.

Figure 15A:
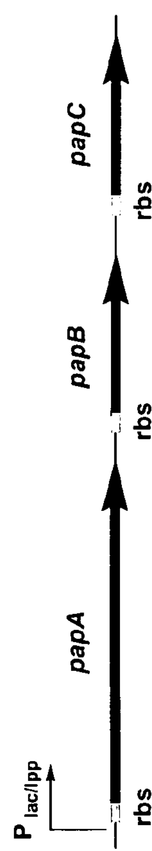
FIGS. 15A-15B illustrates the biosynthesis of p-aminophenylalanine.

In one example, the unnatural amino acid, p-aminophenylalanine (pAF), is biosynthetically produced and incorporated into proteins in vivo. pAF is optionally selected as a unnatural amino acid for an autonomous cell, e.g., based on its interesting physical properties, e.g., π donating effects, hydrogen bonding properties, and weak basicity, its lack of toxicity to *E. coli*, and the fact that it is a known secondary metabolite. Moreover, the genes that lead to the production of pAF as a metabolic intermediate in the production of chloramphenicol and pristinamycin have been identified in *Streptomyces Venezuelae* and *Streptomyces pristinaespiralis*, respectively. See, e.g., Yanai, K. and e. al., *Streptomyces venezuelae* genes papA, papB, papC, in PCT Int. Appl. 2001, Meiji Seika Kaisha Ltd.: Japan. p. 1-83; and Blanc, V., et al., Identification and analysis of genes from Streptomyces pristinaespiralis encoding enzymes involved in the biosynthesis of the 4-dimethylamino-L-phenylalanine precursor of pristinamycin I. Molecular Microbiology, 1997. 23(2): p. 191-202. As discussed above, pAF is optionally synthesized in *E. coli* from chorismate 2 (a biosynthetic intermediate in the synthesis of aromatic amino acids) using the S. Venezuelae enzymes PapA, PapB, and PapC together with an *E. coli* aminotrasferase. A plasmid, e.g., as provided in FIG. 15A is optionally used to transform a cell to provide a cell that synthesizes its own supply of pAF in vivo. An example plasmid for use in the biosynthesis of pAF in vivo is provided by SEQ. ID. NO.:67. SEQ ID NO.:68 provides the sequences for the individual genes papABC that encode the enzymes that are used to carry out the conversion of chorismate to pAF.

Once a cell is modified to produce an unnatural amino acid, e.g., pAF, O-methyl-L-tyrosine, a glycoslyated amino acids, L-dopa or the like, the cell is also typically modified by the addition of a translation system for incorporating the unnatural amino acid into one or more proteins within the cell. The translation system is typically provided to the cell via a separate plasmid than that by which the cell is modified to contain the biosynthetic pathway system as this allows closer control over the functions of the plasmids in the cell, e.g., regarding the number of copies, promoters, etc.

The translation machinery typically comprises an orthogonal tRNA/RS pair, e.g., as provided by co-filed patent application "Methods and Compositions for the Production of Orthogonal tRNA-tRNA Synthetase Pairs," by Schultz et al., U.S. patent application Ser. No. 10/126,931 filed Apr. 19, 2002. For example, an orthogonal tRNA/RS pair for pAF is optionally progenerated using a *Methanococcus jannaschii* tyrosyl-tRNA synthetase (TyrRS) and mutant tyrosine amber suppressor tRNA ($mtRNA_{CUA}^{Tyr}$) pair as a starting point. See, e.g., Wang, L., et al., A new functional suppressor tRNA/aminoacyl-tRNA synthetase pair for the in vivo incorporation of unnatural amino acids into proteins. *J. Am. Chem. Soc*., 2000 122: p. 5010-5011; and Wang, L. and P. G. Schultz, *Chem. and Biol*., 2001, 8:883.

For example, a pAF specific synthetase (pAFRS) is optionally generated by modifying the amino acid specificity of the *M. jannaschii* TyrRS to accept pAF and not any of the common twenty amino acids. See, e.g., Wang, L., et al., Expanding the genetic code of *Escherichia coli. Science*, 2001, 292: p. 498-500; Wang, L. and P. G. Schultz, Expanding the Genetic Code. *Chem. Comm*., 2002: 1: 1-10; and Wang, L., A. Brock, and P. G. Schultz, Adding L-3-(2-naphthyl)alanine to the genetic code of *E. coli. J. Am. Chem. Soc*., 2002. 124: p. 1836. A combination of positive selections and negative screens are optionally used to identify a pAFrs enzyme from a library of TyrRS variants containing random amino acids at five positions, e.g., Tyr32, Glu107, Asp158, Ile159, and Leu162. A single reporter plasmid is optionally used for both selection and screening, e.g., as described in co-filed patent application "Methods and Compositions for the Production of Orthogonal tRNA-tRNA Synthetase Pairs," by Schultz et al., U.S. patent application Ser. No. 10/126,931 filed Apr. 19, 2002. The positive selection is typically based on suppression of a TAG codon at a permissive position within the chloramphenicol acetyltransferase (CAT) gene. (see, e.g., Wang, L., et al., Expanding the genetic code of *Escherichia coli. Science*, 2001, 292: p. 498-500 and Pasternak, M., T. J. Magliery, and P. G. Schultz, A new orthogonal suppressor tRNA/aminoacyl-tRNA synthetase pair for evolving an organism with an expanded genetic code. *Helvetica Chemica Acta*, 2000 83: p. 2277), e.g., by either pAFor an endogenous amino acid. Cells containing the TyrRS library and reporter plasmid grown in liquid culture containing pAF are typically selected for survival, e.g., in the presence of chloramphenicol (Cm). The negative screen based on suppression of two UAG stop codons at permissive positions within the T7 RNA polymerase gene drives the expression of green fluorescent protein (GFP). Positively selected cells grown in the absence of pAF and Cm, are then typically screened, e.g., using fluorescence activated cell sorting (FACS) for the lack of fluorescence.

Evolution of pAFrs: The reporter plasmid, pREP(2)/YC-JYCUA, contains the genes for CAT, T7 RNA polymerase, GFP, and $mtRNA_{CUA}^{Tyr}$, and a selectable marker for Tet resistance (Santoro unpublished results). The CAT gene contains a TAG codon substitution at position D112. The T7 RNA polymerase gene contains a seven-amino acid N-terminal leader peptide and TAG substitutions at M1 and Q107. For the positive selection, cells were grown in GMML minimal media containing 35 μg/ml Kn, 25 μg/ml Tet, 75 μg/ml Cm, and 1 mM pAF (Sigma). For the negative screen, cells were grown in GMML media containing 35 μg/ml Kn, 25 μg/ml Tet, and 0.002% arabinose. FACS was carried out using a BDIS FACVantage TSO cell sorter with a Coherent Enterprise II ion laser. The excitation wavelength was 351 nm and emission was detected using a 575/25 nm bandpass filter. Collected cells were diluted into at least 10 volumes of LB, containing Tet and Kn, and grown to saturation.

Addition of pAF biosynthetic pathway :The papA, papB, and papC genes were PCR amplified from *S. Venezuele* (ATCC 10712) genomic DNA. Genes, papABC were assembled by overlap PCR and inserted into a pSC101 derived plasmid, pLASC, and maintained by ampicillin selection. Ribosome binding sites (rbs) were from the 5' UTR of LacZ, malE, and cro and placed prior to papA, papB, and papC, respectively. The papABC genes were placed under control of lac and lpp promotor to afford two pathway plasmids pLASC-lacPW and pLASC-lppPW.

Testing pAF biosynthesis with pAFRS: *E. coli* DH10B cells harboring three plasmids, the reporter plasmid (pREP (2)/YC-JYCUA), the synthetase (pAFRS), and the pathway plasmid (pLASC-lacPW or pLASC-lppPW) were grown to saturation in GMML minimal media (pLASC was used for background, no pAF, and 1 mM exogenous pAF trials). DH10B was grown with no plasmids to determine the background suppression level of the reporter plasmid. A sample of each cell growth was diluted to an OD of 1.0 (600 nm) with water and 200 μL was pelleted. Cell were suspended in 1 mL 1% PBS and analyzed using a Fluoromax-2 fluorescent detector (excitation wavelength was 351 nm and a peak emission at 505 nm was monitored). DH10B produced 1.0×10 4 fluorescent units, while background fluorescence (no pAF added) from the reporter system produced 2.5×10 4 fluorescent units. The lacPW, lppPW, and 1 mM exogenously added pAF produced 7.9×10 4, 3.0×10 6, and 3.0×10 4 fluorescent units, respectively. Induction of the lacPW with IPTG was not feasible due its inhibitory affect on the arabinose promotor in the reporter plasmid, (pREP (2)/YC-JYCUA).

Aromatic amino acid concentration: *E. coli* DH10B cells harboring the pLASC plasmid and pLASC-lacPW or pLASC-lppPW were grown in GMML minimal media (1% glycerol, 0.3mM leucine) containing 110 μg/ml ampicillin to saturation. Cells grown with exogenously added pAF contained 1 mM amino acid at the start of the growth. Cells were harvested by centrifugation (100 ml), washed, 1 ml of water and 0.2 ml of toluene was added. Cells were shaken at 37° C. 11 for 30 minutes and then separated by centrifugation. The aqueous layer was filtered (microcon YM-10) and analyzed by HPLC-MS (Agilent 1100): 5-15 μL of the aqueous layer separated on Zorbax SB-C18 column (5 μm, 4.6×150 mm) with a gradient of water 1% TFA /acetonitrile 1% TFA (95:5) to (5:95) over 10 minutes. Amino acids were identified by abstracting their MW(+1) from the total ion mass spectrum. The area of the abstracted ion was used to calculate amount of amino acids present in each sample. Cellular concentrations were based on the amount of water in the cell pellet, 70% by mass.

Expression of protein containing pAF: Plasmid pBAD/JYAMB-4TAG with tetracycline resistance was used to express the Tyr CUA mutRNA gene under the control of the lpp promotor and rrnC terminator, and the myoglobin gene (with an amber stop codon at Ser4) under the control of the arabinose promotor and rrnB terminator. A his6-tag was added to the carboxy terminus of myoglobin. The TyrRS and pAFRS genes were expressed under the control of the *E. coli* GlNRS promotor and terminator on a pBR322 derivatived plasmid with kanamycin resistance. The papABC genes were expressed from pLASC-lacPW or pLASC-lppPW (13) under the control of the native terminator. *E. coli* DH10B cells harboring plasmid pBAD/JYAMB-4TAG, pBK-TyrRS or pBK-pAFRS, and a pLASC derived plasmid (PLASC, pLASC-lacPW or pLASC-lppPW as indicated) were grown in 0.5 L of minimal media containing 0.002% arabinose. Expression trials with exogenous pAF contained a final concentration of 1 mM pAF (Sigma). For all trials, cells were grown to saturation (20-30 hrs) in parallel at 37° C., pelleted, and protein was purified by Ni+2 affinity chromatography according to manufacturer's protocol under native conditions (Qiagen, Valencia, Calif.). Fifteen μl of final protein solution (3.5 ml) from each preparation were separated on a 12% SDS polyacrylamide gel and silver-stained.

Example 5

In vivo Incorporation of O-methyl-L-tyrosine in an *E. coli* Cell which has been Genetically Engineered to Biosynthesize the Unnatural Amino Acid As discussed herein, one aspect of the invention is biosynthetic pathways for unnatural amino acids in *E. coli*. This is accomplished by e.g., addition to the cell of genes for new enzymes or modification of existing *E. coli* pathways. In this example, *E. coli* was genetically engineered to produce the unnatural amino acid O-methyl-L-tyrosine.

Plant O-methyltransferases are enzymes involved in secondary metabolism, which converts a hydroxyl group into a methoxyl group. Two enzymes, (iso)eugenol O-methyltransferase (IEMT) and caffeic acid O-methyltransferase (COMT) (Clarkia brewery) were selected for incorporation into *E. Coli*. IEMT methylates eugenol/isoeugenol, and COMT methylates caffeic acid. The substrates of these two enzymes are similar to tyrosine. However, both enzymes have high substrate specificity and methylation regiospecificity.

A combinatorial approach was used to evolve the substrate specificity of both enzymes to tyrosine, thereby converting tyrosine to O-methyl-L-tyrosine. Active sites of the proteins were mutated to produce large mutant libraries and several rounds of selection were completed. Three clones were identified. The clones are characterized and at least one is selected to generate an *E. coli* strain that biosynthesizes O-methyl-L-tyrosine. This strain of *E. coli* is genetically engineered to also express the orthogonal tRNA/RS pair described in Example 1 above, thereby providing a cell for autonomous in vivo incorporation of an unnatural amino acid.

Example 6

In vivo Incorporation of Heavy Atom Amino Acids

Structure-guided drug discovery has historically been a slow, laborious process used in only a modest fraction of drug discovery programs in the industry. One bottleneck is the phase problem encountered when using X-ray crystallography to solve protein structure. Typically, the protein has to be expressed again in the presence of selenomethionine, which doubles the work load and may not necessary result in successful crystallization. An alternative method is to soak the crystal in a heavy-atom-containing solution, which may result in crystal crush. In vivo incorporation of heavy-atom containing unnatural amino acids into proteins is a useful tool to accelerate the solving of protein crystal structures.

The site specific in vivo incorporation of p-iodo-phenylalanine and p-bromo-phenylalanine into proteins was performed. Iodine and bromine are heavy atoms, and the incorporation facilitates solving of phase using MAD. The site-specific introduction of heavy atoms using unnatural amino acids also provides selectivity and flexibility in choosing positions for heavy atoms.

Mutant synthetases with specificities for p-iodo-phenylalanine and p-bromo-phenylalanine, respectively, were generated following the methods and compositions described in Example 1. The protein Z domain (B. Nilsson, et al, *Protein Eng*. 1: 107-113 (1987)) was expressed, in which bromine or iodine was selectively introduced in the form of p-iodo-phenylalanine and p-bromo-phenylalanine using in vivo incorporation of the unnatural amino acids. Protein crystal trays were set up following standard protocols.

The three dimensional structure of the protein is solved using X-ray crystallography; the phase is determined using the heavy atoms present in the protein.

Example 7

In vivo Incorporation of meta-tyrosine Analogues

An orthogonal TyrRS was generated for aminoacylation of the $mtRNA_{CUA}^{Tyr}$ (described in Example 1) with meta-tyrosine analogues.

Preparation of mutant TyrRS library plasmids. A library of plasmids encoding mutant *M. jannaschii* TryRSs directed at meta-substituted tyrosine derivatives was constructed, generally following the methods described in Example 1. Briefly, six residues ($Tyr^{32}$, $Ala^{67}$, $His^{70}$, $Gln^{155}$, $Asp^{158}$, $Ala^{167}$) in the active site of *M. jannaschii* TyrRS that are within 6.9 Å of the meta-position of the aryl ring of bound tyrosine in the crystal structure of *Bacillus stearothermophilus* TyrRS were mutated to all 20 amino acids at DNA level using the NNK codon scheme as described in Example 1 above. The constructed plasmid library pBK-lib contained around $1\times10^9$ independent clones.

Evolution of orthogonal tRNA-synthetase pairs for incorporation of m-acetyl phenylalanine. After 3 rounds of positive selection and 2 rounds of negative selection, five candidate clones (SEQ ID NO: 17-21) emerged whose survival in chloramphenicol was dependent on the addition of the unnatural amino acid. In the absence of m-acetyl phenylalanine, the $IC_{50}$ of chloramphenicol resistance for cells harboring the one of the three mutant TyrRS plasmids is 20 μg/ml. In the presence of m-acetyl phenylalanine, the $IC_{50}$ of resistance to chloramphenicol for the same cells is 100 μg/ml. The large difference between these two numbers reflects the ability of the selected synthetases to specify the incorporation of m-acetyl phenylalanine over the natural amino acids in the cell. The data for m-methoxy phenylalanine were similar; five clones were isolated (SEQ ID NO:22-26).

Figure 10:
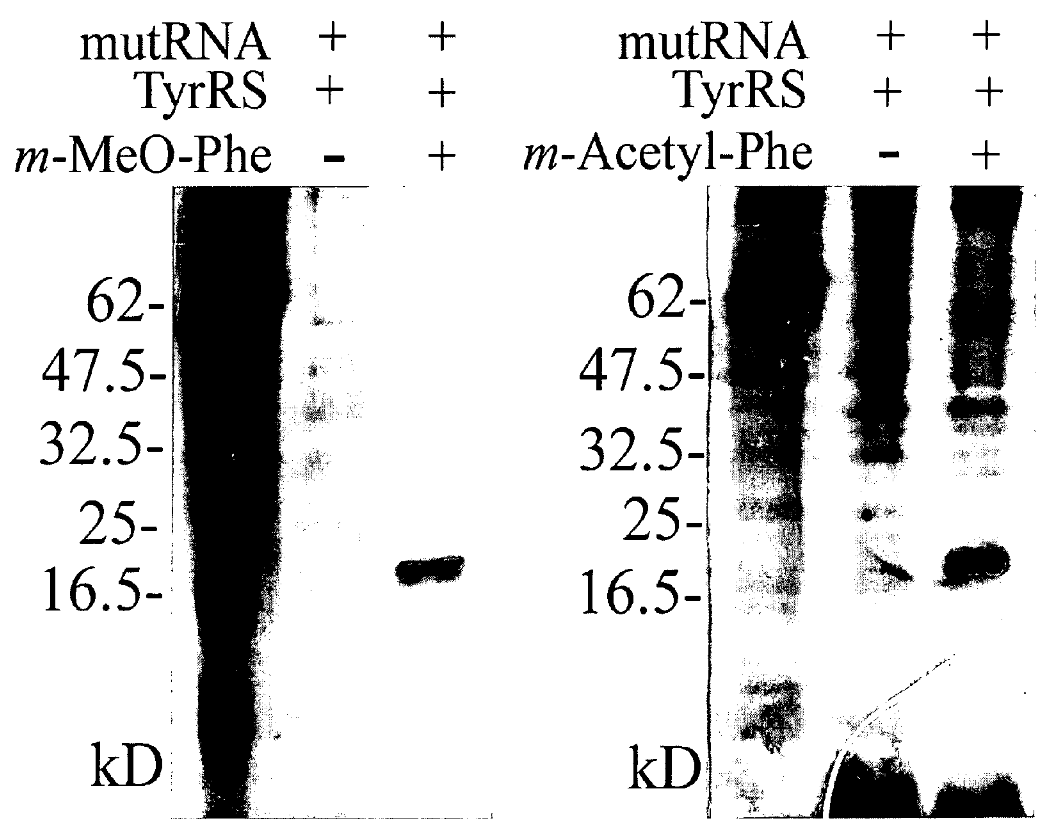
FIG. 10 is an autoradiograph of a western blot demonstrating expression of m-MeO-Phe- and m-Acetyl-Phe-incorporated DHFR.

Protein expression of unnatural amino acid incorporated DHFR. The m-methoxy phenylalanine and m-acetyl phenylalanine synthetases selected above were used to incorporate the relevant unnatural amino acids in response to an amber codon in DHFR as previously described in Example 1 above. As a negative control, cells containing both the orthogonal pair of tRNA-synthetase and amber-mutant vector encoding DHFR were grown in the absence of unnatural amino acids. The results of protein expression are shown in FIG. 10. These results clearly demonstrated the specificity of the orthogonal pair of tRNA-synthetase to incorporate unnatural m-methoxy phenylalanine and m-acetyl phenylalanine. The yields of expressed DHFR protein are approximately 0.5 mg/L of culture in both cases.

Utilizing meta-acetyl phenylalanine as a chemical handle. The m-acetyl phenylalanine incorporated DHFR protein was labeled with hydrazide derivatives, both extra-cellularly and intra-cellularly at a milligram scale. The carbonyl group will react rapidly with hydrazide in aqueous solution to form hydrazone that is stable under physiological conditions (Shao, J.; Tam, J. *J. Am. Chem. Soc*. 117, 3893-3899 (1995)).

This chemistry has been used by Schultz and coworkers to specifically label a ketone containing, purified T4 lysozyme with fluorescein hydrazide (Cornish, V. W.; Hahn, K. M.; Schultz, P. G. *J. Am. Chem. Soc.* 118, 8150-8151 (1996)).

Figure 11:
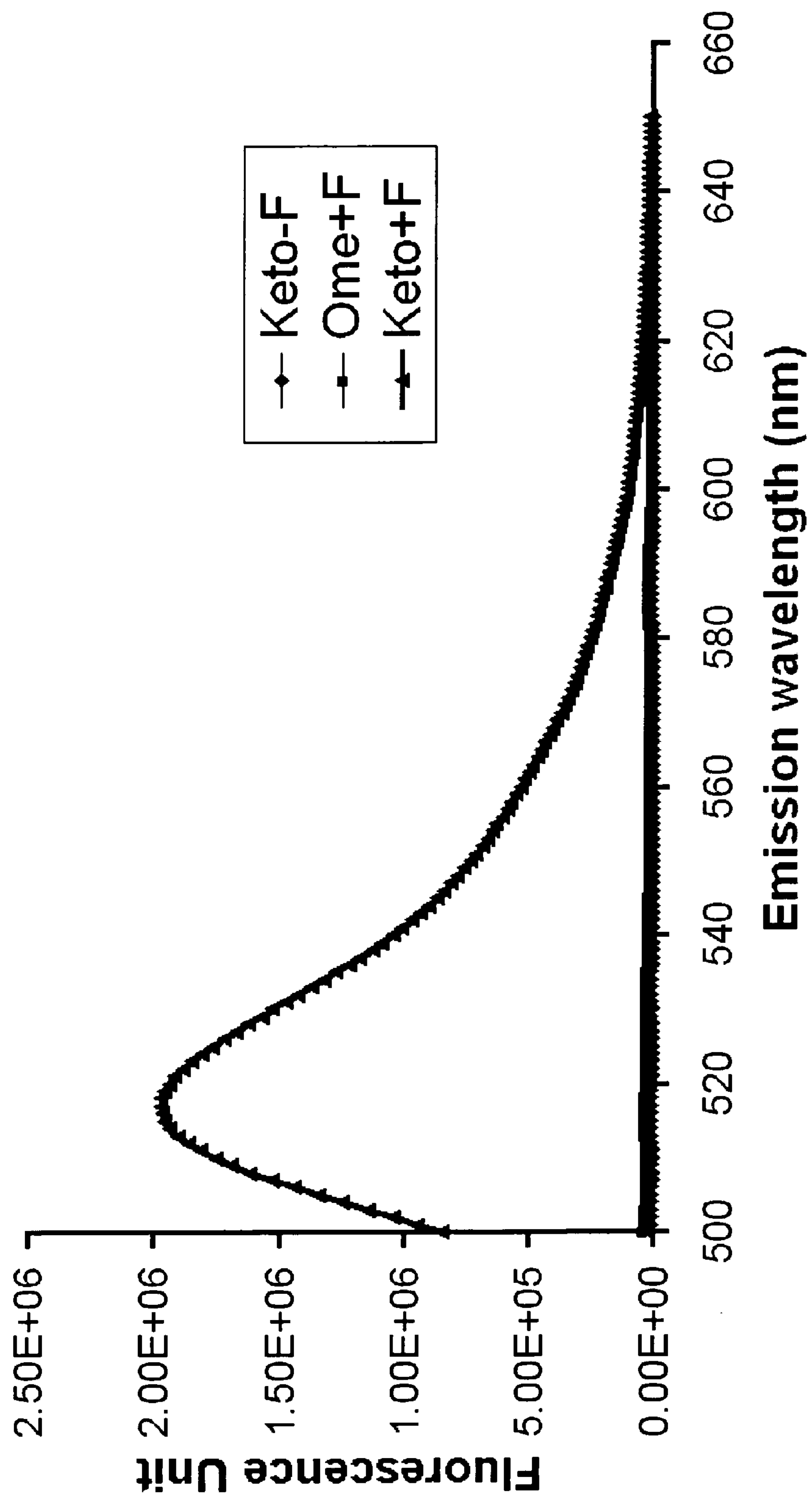
FIG. 11 illustrates the fluorescence emission spectra of fluorescein hydrazide labelled protein.

Purified m-acetyl phenylalanine-incorporated DHFR protein was treated with fluorescein hydrazide in aqueous buffer. As a control in parallel, a purified m-methoxy phenylalanine-incorporated DHFR protein was subjected to the same reaction conditions. After the reaction, both proteins were purified and then excited at 491 nm to obtain fluorescence emission spectra shown in FIG. 11. Under identical conditions, the purified m-acetyl phenylalanine-incorporated DHFR was labeled with fluorescein hydrazide while m-methoxy phenylalanine was not labeled.

The fluorescein hydrazide is cell-permeable and does not lyse cells at 4° C. Thus, it is possible to label the m-acetyl phenylalanine-incorporated DHFR protein intra-cellularly with fluorescein hydrazide. Cells expressing the "ketone handle"-incorporated DHFR were incubated with fluorescein hydrazide solution. After 36 hours at 4° C. and extensive washes to remove excess fluorescein hydrazide, the labeled DHFR protein was purified and subjected to fluorescence emission tests. As a negative control in parallel, m-methoxy phenylalanine-incorporated DHFR was also purified with the same procedures. Similar results to the extracellular experiment (FIG. 15) were obtained when intact cells were labeled with fluorescein hydrazide and the DHFRs were subsequently purified.

These experiments demonstrated one example of the utility of a protein with at least one unnatural amino acid. Other compounds can be used to in vivo label proteins with at least one unnatural amino acid. Examples include, e.g., biotin hydrazide and other hydrazide derivatives.

Example 8

In vivo Incorporation of Photoreactive Amino Acids

Introduction: Experiments were performed in which photocrosslinker amino acids were genetically encoded and site specifically incorporated into a specific protein in vivo. This protein was then crosslinked at will by excitation of the photoreactive group-providing temporal control.

This invention is useful for, e.g., exploring protein interactions. For example, this invention is useful for defining residues in the protein primary sequence that mediate interaction with different cellular components by varying the position of the crosslinker in the protein. Because a covalent bond is formed between the protein and the molecule it interacts with it is possible to detect weak or transient interactions.

Figure 12:
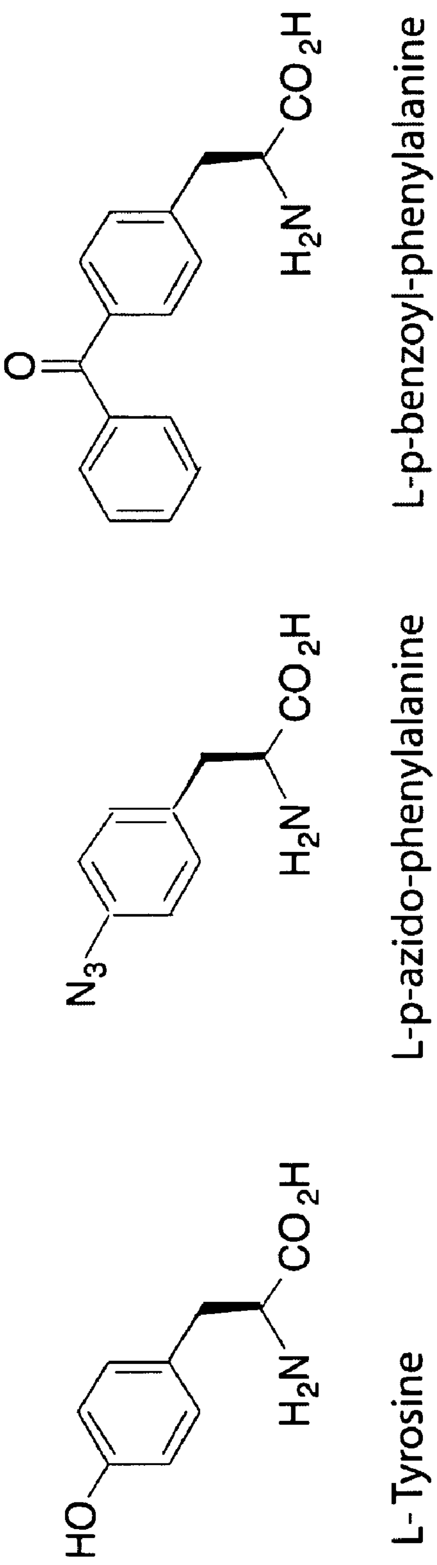
FIG. 12 illustrates the unnatural amino acids para-azido-phelylalanine and para-benzoyl-phenylalanine.

Two chemical functional groups have gained prominence as crosslinkers, aryl-azides and benophenones since they can be activated at wavelengths above 300 nm (below which protein damage via photooxidation may be a problem). These two crosslinking groups were been incorporated into the unnatural amino acids p-azido-phenylalanine and p-benzoyl-phenylalanine respectively (FIG. 12).

Generation of O—RS specific for photocrosslinker amino acids. The orthogonal as the starting point to generate an O—RS specific for the crosslinker-unnatural amino acid p-azido-phenylalanine (pBpa). The methods for mutagenesis, screening and selection were performed following the experimental outline described in Example 1. Briefly, a MjTyrRS library of mutants was generated in which five residues (Tyr 34, Glu 107, Asp 158, Ile 159, Leu 162) were randomized. These residues were chosen on the basis of the crystal structure of *Bacillus Stearothermophilus* TyrRS complexed with tyrosyl adenylate (P. Brick, T. N. Bhat & D. M. Blow *Journal of Molecular Biology* 208, 83 (1989)) in which homologous residues (Tyr34, Asn123, Asp176, Phe177, Leu180) are within 6 Å of the para position of the aryl ring of bound tyrosine. The mutant TyrRS library was passed through a positive selection based on suppression of an amber stop codon at a permissive site (Asp112) in the chloramphenicol acetyl transferase (CAT) gene. Cells transformed with thesynthetase library, and the CAT mutant were challenged to grow in the presence of 1 mM pBpa and chloramphenicol. Surviving cells contained synthetases capable of charging the orthogonal $mtRNA_{CUA}^{Tyr}$ with either a natural or unnatural amino acid. These synthetase genes were transferred into cells containing $mtRNA_{CUA}^{Tyr}$ and a variant of the gene encoding the toxic bamase protein, which contains three amber mutations at permissive sites (Gln2, Asp44, Gly65)(Wang, L., Brock, A., Herberich, B. & Schultz, P. G. *Science* 292, 498-500(2001)). Growth of these cells in the absence of pBpa selected against synthetases capable of utilizing natural amino acids.

After five rounds of positive and negative selection the surviving synthetase plasmids were transformed into a reporter strain in which the production of full length CAT and T7 RNA polymerase (T7 RNAP) are dependent on suppression of amber stop codons in the CAT and T7 RNAP gene, respectively (Santoro S W, Schultz P G. *Proc Natl Acad Sci USA* April 2;99(7):4185-90 (2002)). Because the T7 RNAP drives expression of the green fluorescent protein (GFP) these cells can be fluorometrically screened. Ninety-six clones were screened for pBpa dependent chloramphenicol resistance and GFP fluorescence. Six distinct synthetases conferred Ile chloramphenicol resistance on *E. coli* with $IC_{50}$s of 120 mg/L and 5 mg/L in the presence and absence of 1 mM pBpa respectively; they also showed pBpa dependent GFP fluorescence. The large difference between the chloramphenicol resistance in the presence and absence of pBpa shows a substantial in vivo specificity of the selected synthetase/tRNA pairs for insertion of pBpa over all twenty natural amino acids found in the cell in response to an amber codon.

In vivo incorporation of pBpa into myoglobin. To measure the fidelity and efficiency of pBpa incorporation, the codon for Ser4 in sperm whale myoglobin (containing a C-terminal His6 tag) was converted to an amber codon. In the presence of both Mj p-BpaRS-1, $mtRNA_{CUA}^{Tyr}$ and pBpa, full length myoglobin was produced with a purified yield of 2 mg/L. No myoglobin protein was detectable by silver stain or Western blot against the C-terminal His6 tag on myoglobin if any of the three components responsible for specific amber suppression with pBpa (amino acid, synthetase, or tRNA) were withheld. This data provides further evidence that the selected synthetase is very selective for pBpa.

Electrospray-ionization ion trapmass spectrometry of the mutant myoglobin gave a mass of 18519±0.5 which is identical to the calculated mass of 18519.0 for the pBpa containing protein. This confirms the incorporation of pBpa at a single site in the protein. No masses were observed in the mass spectra corresponding to natural amino acid incorporation providing additional evidence for the high fidelity incorporation of pBp.

Sequence analysis of mutant O—RS. The selected synthetases show interesting sequence convergence. Tyr32 of *M. jannaschii* TyrRS is converted to alanine or glycine in five of the six mutant synthetase clones. Asp158 of the *M.*

*jannaschii* TyrRS is converted to threonine in five of the six selected mutants, while Ile159 is converted to serine in four of the six mutants. Serine or proline substitutions dominate at position 107 of *M. jannaschii* TyrRS; Leu162 is conserved in four of the six mutants. A consensus set of mutations (32: Gly, Ala/107: Ser, Pro/158: Thr/159: Ser/162: Leu) emerges from this analysis.

In vivo incorporation of pBpa into GST. To demonstrate the utility of this methodology for mapping protein-protein interactions, a crosslinking experiment was carried out with glutathione-S-transferase. This protein is a dimer of two identical subunits which have previously been crosslinked non-specifically using gluteraldehyde. The crystal structure of the dimeric *Schistosoma Japonica* glutathione-S-transferase (SjGST) (McTigue, M. A., Williams, D. R. & Tainer, J. A. *Journal of Molecular Biology* 246, 21-27(1995)) was used to identify two sites to substitute with pBp:residue Phe52, which is buried in the dimer interface of the crystal structure, and residue Tyr198 which is solvent exposed. The codons corresponding to Phe52 or Tyr198 in the gene for a 27 kDa protein Sj GST, were replaced with amber codons. The orthogonal synthetase tRNA pair was then used to site specifically incorporate pBpa into SjGST in *E.coli* at these sites. Upon irradiation with long wavelength ultraviolet radiation, purified SjGST was converted to a covalently linked homodimer as judged by denaturing SDS PAGE. Approximately 70% of the SjGST present was crosslinked in 5 minutes. In contrast, control experiments using either wild type SjGST or SjGST containing pBpa at residue 198, which lies outside the dimer interface, shows no detectable crosslinking in response to UV irradiation.

These results demonstrate that site-specific pBpa substitution can be used to define amino acids involved in a protein-protein interaction.

Characterization of Mutant Synthetases Individual synthetase clones in DH10B/pREP(2)/YC-JYCUA were used to inoculate 0.5 mL of LB supplemented with kanamycin and tetracycline to 30, 20 mg/L. After 20 hours growth (37° C., 300 rpm) cells were diluted $10_4$ fold in dH20 and replica spotted on two sets of GMML plates. One set of plates were supplemented with kanamycin and tetracycline at 30 and 20 micrograms/L, respectively, and chloramphenicol at concentrations ranging from 0 micrograms/L to 110 micrograms/L. The second set of plates were identical to the first, except that they were supplemented with 1 mM pBpa. After 48 h the IC50 of chloramphenicol resistance in the presence and absence of pBpa was calculated from the concentration of chloramphenicol at which half the number of colonies on the plates with no chloramphenical were visible. GFP expression in the presence and absence of pBpa was imaged using a Storm phosphoimager(Molecular dynamics). Mutant synthetase genes exhibiting the strongest amino acid dependence in both GFP signal and chloramphenicol resistance were isolated and sequenced by standard methods.

Protein Expression Plasmid PYC/SjGSTmut, which contains the mutant SjGST gene on an arabinose promoter and rmB terminator, and $mtRNA_{CUA}^{Tyr}$ on a lpp promoter and rmC terminator, and a tetracycline resistance marker was co-transformed with a pBK vector expressing p-BpaRS into DH10B *E.coli*. Cells were amplified in 10 mL of 2×-YT containing kanamycin at 30 micrograms/L and tetracycline at 25 micrograms/L before being washed in PBS and used to inoculate 1 L of liquid GMML with the appropriate antibiotics and pBpa to 1 mM. Protein expression was induced at an $O_{D600}$ of 0.6 by the addition of arabinose to 0.2% followed by 5 hours growth. Cells were harvested by centrifugation and protein was purified by virtue of a C-terminal hexa-histidine tag using Ni-NTA affinity chromatography.

Sperm whale myoglobin was expressed and purified from cells containing pBAD/JYAMB-4TAG in an analogous manner to SjGST, except that induction was constitutive with 0.002% arabinose. Samples for mass spectrometry were desalted on a NAP-10 column (Pharmacia) and purified by HPLC. To verify the incorporation of pBpa, the protein mass was ascertained by electrospray-ionization ion trap mass spectrometry.

Mutant Sj GST Cloning Mutant SjGST genes were assembled by overlapping PCR, using pGEX-3 (Pharmacia) as a template. All PCR reactions were carried out using the Expand PCR kit (Roche) according to the manufacturers instructions. The resulting genes were digested with Nco I and Kpn I restriction enzymes and cloned into predigested, dephosphorylated pBADJYC vector between the same restriction sites and in frame with a C-terminal hexa-histidine tag. All final constructs were confirmed by DNA sequencing.

Photo-activated crosslinking. Crosslinking reactions were performed in a 96 well microtitre plate (Nuncsorb) using 100 μL of 10 ng/μL SjGST (in 50 mM NaH2Po4, 300 mM NaCl, 250 mM imidazole) at 4° C. Samples were irradiated at 365 nm using a handheld UV lamp (115V, 60 Hz, 0.2 A; Spectronics, NY, USA), for 1 min or 5 min. Samples were removed from the wells and diluted with SDS loading buffer before resolution of products by SDS-PAGE on a 10-20% gradient gel. SjGST was transferred to PVDF (Biorad) and probed by western blot using goat anti-GST (Pharmacia) and a secondary mouse anti goat HRP conjugate (Sigma). Signal was developed using Super signal West (Pierce) and visualized by exposure on hyperfilm (Amersham).

Example 9

Synthesis of meta-substituted phenylalanines

In one aspect, the present invention provides meta substituted phenylalanines as shown in Formula IV:

IV

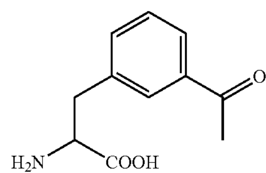

and in Formula V.:

V

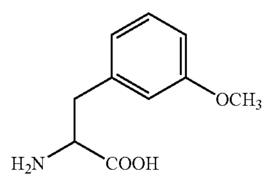

Formula IV illustrates the structure of 3-acetyl-phenylalanine and Formula V represents 3-methoxy-phenylalanine.

Meta-substituted phenylalanines are synthesized in a procedure as outlined in FIG. 14. Typically, NBS (N-bromosuccinimide) is added to a meta-substituted methylbenzene compound to give a meta-substituted benzyl bromide, which is then reacted with a malonate compound to give the meta substituted phenylalanine. Typical substituents used for the meta position include, but are not limited to, ketones, methoxy groups, alkyls, acetyls, and the like. A specific example is provided below.

NBS (N-bromosuccinimide) was recrystalized from boiling water prior to usage. NBS (1.85 g, 10.5 mmol) was added to a solution of 3-methyl acetophone (1.34 g, 10 mmol). AIBN (2', 2'-azobisiosbutyronitrile) (0.043 g, 0.25 mmol) was added to the mixture. The reaction mixture was refluxed for 4 hours. The completion of reaction was checked by TLC (8:1/hexanes: EtOAc). After aqueous workup, the organic solvent was removed and hexanes was added to give solid. The solid was filtered and washed with hexanes and EtOAc. Then the mixture was recrystallized with hexanes. The supernatant was collected and solvent was removed to give compound (1-(3-bromomethyl-phenyl)-ethanone).

Dry ethanol (50 ml) was added dropwise to pentane-washed sodium pieces (2.3 g, 0.1 mol) under argon atmosphere. After the completion of addition, stirring was required to dissolve the last pieces of sodium. A solution of diethyl acetylamido-malonate ester (21.7 g, 0.1 mol) was added over 30 minutes. 1-(3-bromoethyl-phenyl)ethanone (21.1 g, 0.1 mol) in dry ethanol was added dropwise over 90 minutes. After the mixture was refluxed overnight, ether and water was added, and the organic layer was separated. After aqueous workup, the organic layers were combined, washed with brine, dried over MgSO4 and filtered. The solvents were removed in vacuo. Hexanes-dichloromethane, 4:1, was added to the residue, and the insoluble material was filtered out and washed exhaustively with 10:1 dicholomethane-benzene to give diethyl 2-acetamido-2[3-acetyl-phenyl]-methyl]malonate. This compound was stirred with 8 M HCl in dioxane overnight. Then the mixture was taken to dryness, water was added, and it was taken to dryness again to give final compound m-acetylphenylalanine hydrochloride. HPLC was used to purify the desired compound as white solid. The total yield was 64%. 1HNMR (D2O): d 7.85-7.28 (m, 4H), 4.23 (dd, 1H), 3.2 (m, 2H), 2.7 (s, 3H). Calculated molecular weight: 243.69, obtained molecular weight: 243.07. A similar synthesis is used to produce a 3-methoxy phenylalanine. The R group on the meta position of the benzyl bromide in that case is—$OCH_3$. See, e.g., Matsoukas et al., *J. Med. Chem.*, 1995, 38, 4660-4669.

Example 10

Synthesis of 4-allyl-L-tyrosine

In another aspect, the present invention provides 4-allyl-L-tyrosine, whose structure is shown in Formula II:

II

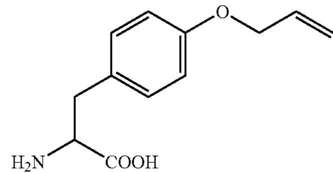

Figure 13:
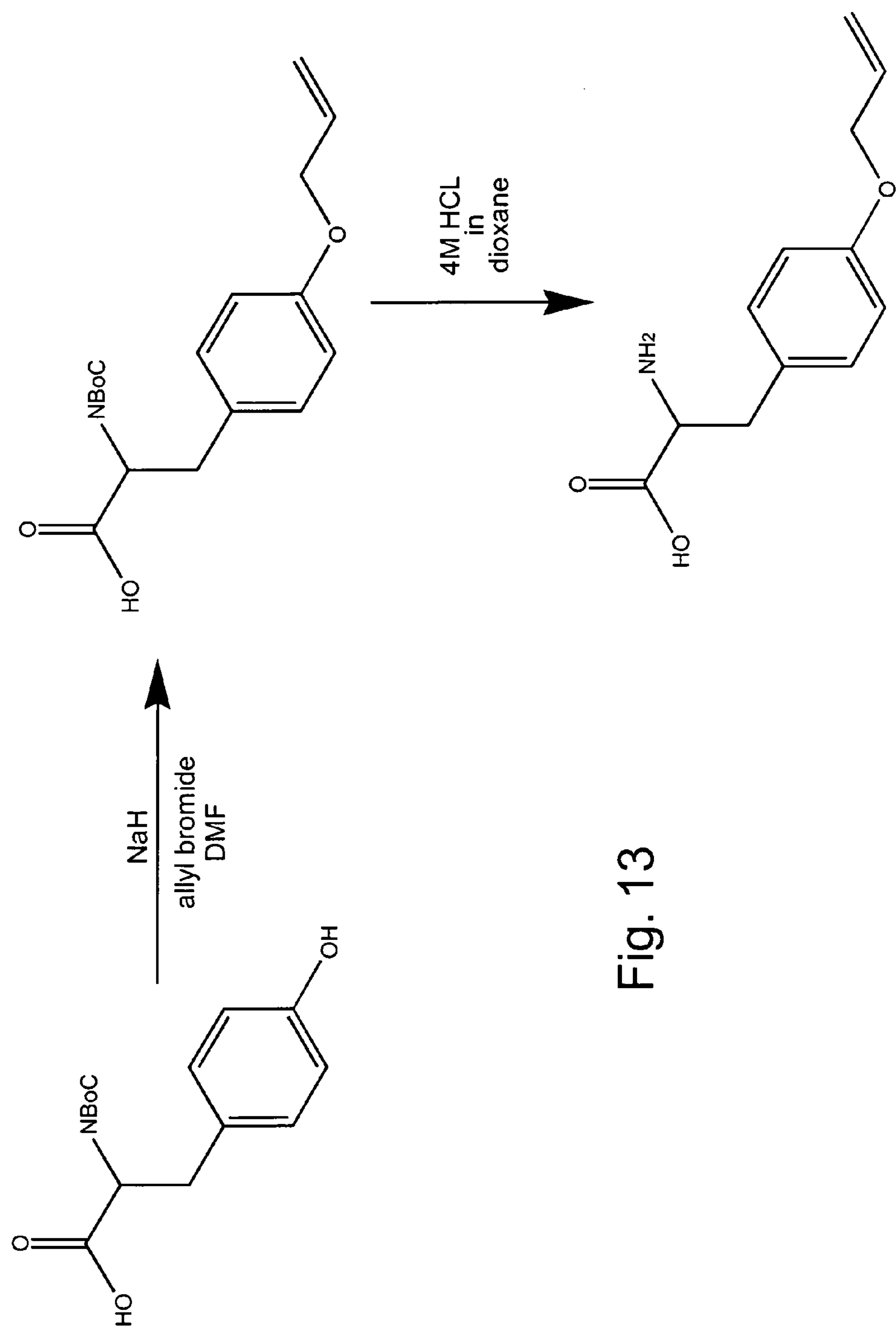
FIG. 13 illustrates a chemical scheme for the synthesis of an allyl-substituted phenylalanine.

The compound of Formula II, 4-ally-L-tyrosine, is synthesized according to the scheme set forth in FIG. 13. A protected tyrosine, e.g., an Nboc or Fmoc protected tyrosine, is reacted with allyl bromide, resulting in a protected allyl tyrosine, which is then typically deprotected to yield 4-allyl-L-tyrosine. For example, N-(tert-Butoxycarbonyl)-L-tyrosine (2.95 g, 10 mmole) was dissolved in 80 ml of DMF. The solution was chilled to 5° C. and NaH (0.63 g, 26 mmole) was added. The reaction mixture was allowed to warm up to 10° C. and stirred for additional 2 hours. After that, allyl bromide (1.33 g, 11 mmole) was added to the mixture and reaction was warmed to room temperature. The reaction mixture was stirred for 4 hours. Water was added to work up the reaction. The aqueous layer was extracted with ethyl acetate and CH2Cl2. The organic layer was dried over anhydrous MgSO4. The organic solvent was removed to give white solid. This compound was then refluxed in 4M HCl in 1.4-dioxane for 4 hours. All the solvent was evaporated to give the desired product as white solid (1.9 g, 86%). 1HNMR (CD3OD): d ppm 3.1(m, 2H), 4.1 (t, 1H), 4.5 (d, 2H), 5.3 (q, 1H), 5.9 (m, 1H), 6.9 (d, 2H), 7.1 (d, 2H). Calculated molecular weight: 221, obtained molecular weight: 222.

Example 11

Cellular Uptake Screen of Unnatural Amino Acids

Figure 29:
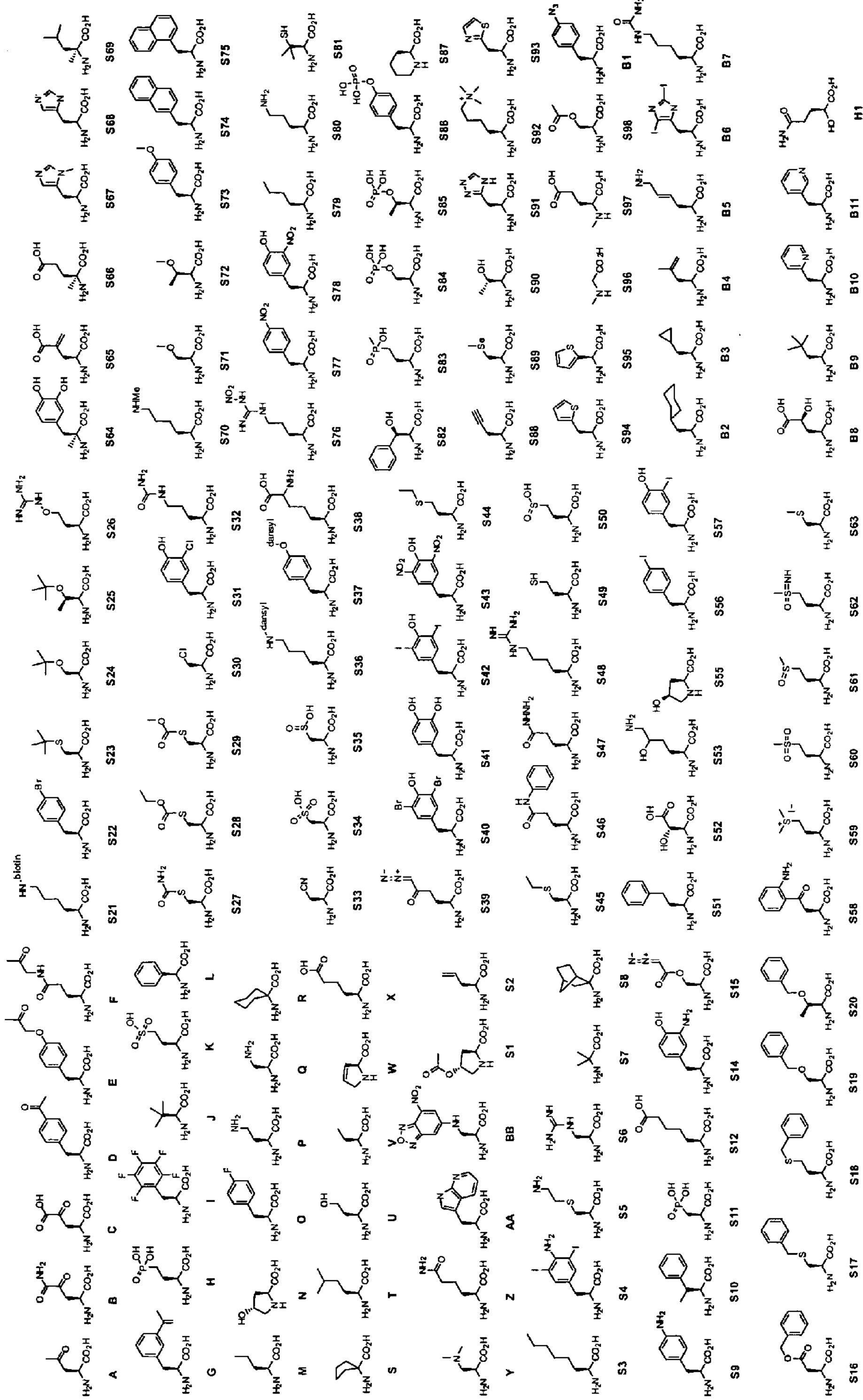
FIG. 29 illustrates a variety of unnatural amino acids, e.g., as used in a cellular uptake study.

A variety of unnatural amino acids and α-hydroxy acids of interest, obtained commercially or by short syntheses from available starting materials (I. Shin, B. Herberich, A. Varvak, T. Magliery, P. Schultz, unpublished results, were screened for cell toxicity). For example, FIG. 29 provides a library of unnatural amino acids useful for the following screen. Each amino acid was screened at 1 mM in glycerol minimal media for toxicity to cells, e.g., to DH10B harboring pBLAM-YQRS and pACYsupA38. Toxicities are sorted into five groups: (1) no toxicity, in which no significant change in doubling times occurs; (2) low toxicity, in which doubling times increase by less than about 10% (seen with the following compounds in FIG. 29: S63, S69, S74, S75, S81, S95); (3) moderate toxicity, in which doubling times increase by about 10% to about 50% (seen in the following compounds shown in FIG. 29: B, M, P, S12, S14, S22, S41, S45, S49, S52, S62, S64, S65, S71, S91, S93, B10); (4) high toxicity, in which doubling times increase by about 50% to about 100% (seen in the following compounds from FIG. 29: C, Q, V, BB, S2, S5, S50, S60, S78, S83, S89, S90); and (5) extreme toxicity, in which doubling times increase by more than about 100% (observed for the following compounds from FIG. 29: W, S15, S26, S27, S30, S31, S39, S47, S88, S94). See, e.g., Liu, D. R. & Schultz, P. G. Progress toward the evolution of an organism with an expanded genetic code. *Proceedings of the National Academy of Sciences of the United States of America* 96, 4780-4785 (1999).

The toxicity of amino acids scoring as highly or extremely toxic is typically measured as a function of their concentration to obtain IC50 values. In general, amino acids which are very close analogs of natural amino acids (e.g., Q, W, S5, S26, S27, S50, S90, S94) or which display reactive functionality (e.g., S15, S39, S47) demonstrated the highest toxicities.

To identify possible uptake pathways for toxic amino acids, toxicity assays were repeated at IC50 levels (typically 3 μM to 500 μM) in media supplemented with an excess (2 mM) of a structurally similar natural amino acid. For toxic amino acids, the presence of excess natural amino acid rescued the ability of the cells to grow in the presence of the toxin, presumably because the natural amino acid effectively outcompeted the toxin for either cellular uptake or for binding to essential enzymes. In these cases, the toxic amino acid can be assigned a possible uptake pathway and labeled a "lethal allele" whose complementation is required for cell survival. Lethal alleles identified in this manner (16 of the toxic unnatural amino acids) span ten possible amino acid uptake groups: alanine, glutamic acid, lysine, leucine, methionine, proline, glutamine, arginine, threonine, and tyrosine.

These lethal alleles are extremely useful for assaying the ability of cells to uptake nontoxic unnatural amino acids. Each nontoxic unnatural amino acid was added at 2 mM to media containing IC50 levels of each lethal allele. Complementation of the toxic allele, evidenced by the restoration of cell growth, shows that the nontoxic amino acid is taken up by the cell, possibly by the same uptake pathway as that assigned to the lethal allele. A lack of complementation is inconclusive.

Using this method, the ability of 22 glutamine and glutamic acid analogs to be taken up by DH10B was evaluated. Amino acids S27 and S47 were used as toxic glutamine alleles at 100 μM and 30 μM, respectively, while S50 was employed as a toxic glutamic acid allele at 150 μM. Results from S27 and S47 complementation were in complete agreement and identified amino acids B, Z, S6, S60, S61, and S62 (in addition to S27 and S47) as being uptaken by cells possibly via the glutamine uptake pathway. Similarly, complementation of S50 identified B, C, K, X, S60, S65, and S84 as being uptaken into DH10B, possibly via the glutamic acid transport system.

These findings indicate that the *E. coli* glutamine and glutamic acid transport pathways may tolerate significant perturbations in amino acid structure, including side chain elongation (X and Z), ketone or methylene placement at the y-position (B, C, S65), carboxamide replacement with a sulfoxide (S61), a known substrate for a bacterial glutamine transporter or hydrazide (S47), also a known glutamine transporter substrate as well as a variety of hybridization changes at the side chain terminus (S60, S62, K, S84). See, e.g., Jucovic, M. & Hartley, R. W. Protein-protein interaction: a genetic selection for compensating mutations at the bamase-barstar interface. *Proceedings of the National Academy of Sciences of the United States of America* 93, 2343-2347 (1996) and Weiner, J. H., Furlong, C. E. & Heppel, L. A. A binding protein for L-glutamine and its relation to active transport in *E. coli*. *Archives of Biochemistry and Biophysics* 142, 715-7 (1971).

Example 12

Biosynthesis of p-aminophenylalanine

To produce the unnatural amino acid p-aminophenylalanine (pAF) in vivo, genes relied on in the pathways leading to chloramphenicol and pristinamycin are optionally used. For example, in *Streptomyces Venezuelae* and *Streptomyces pristinaespiralis*, these genes produce pAF as a metabolic intermediate. See, e.g., Yanai, K. and e. al., *Streptomyces venezuelae* genes papA, papB, papC, in PCT Int. Appl. 2001, Meiji Seika Kaisha Ltd.: Japan. p. 1-83; and Blanc, V., et al., Identification and analysis of genes from Streptomyces pristinaespiralis encoding enzymes involved in the biosynthesis of the 4-dimethylamino-L-phenylalanine precursor of pristinamycin I. Molecular Microbiology, 1997. 23(2): p. 191-202.

Figure 15B:
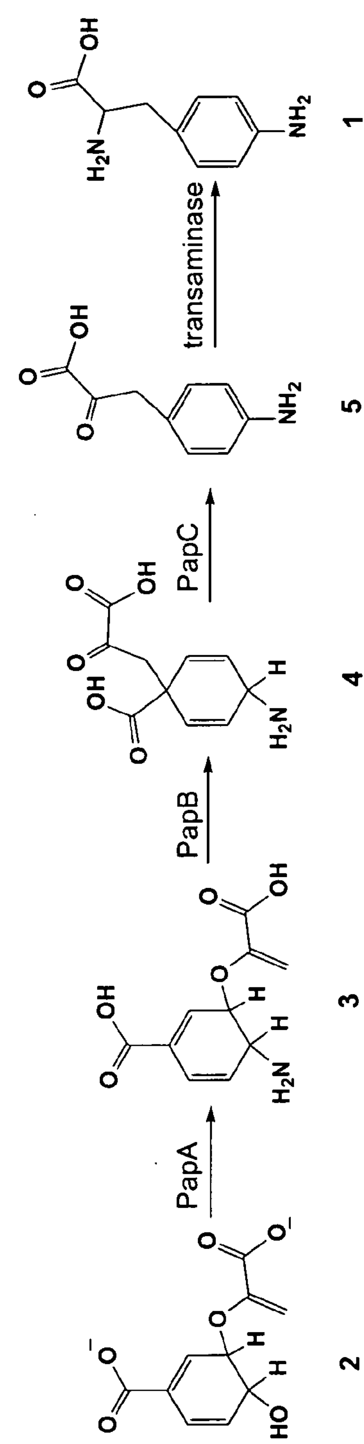
Figure 16:
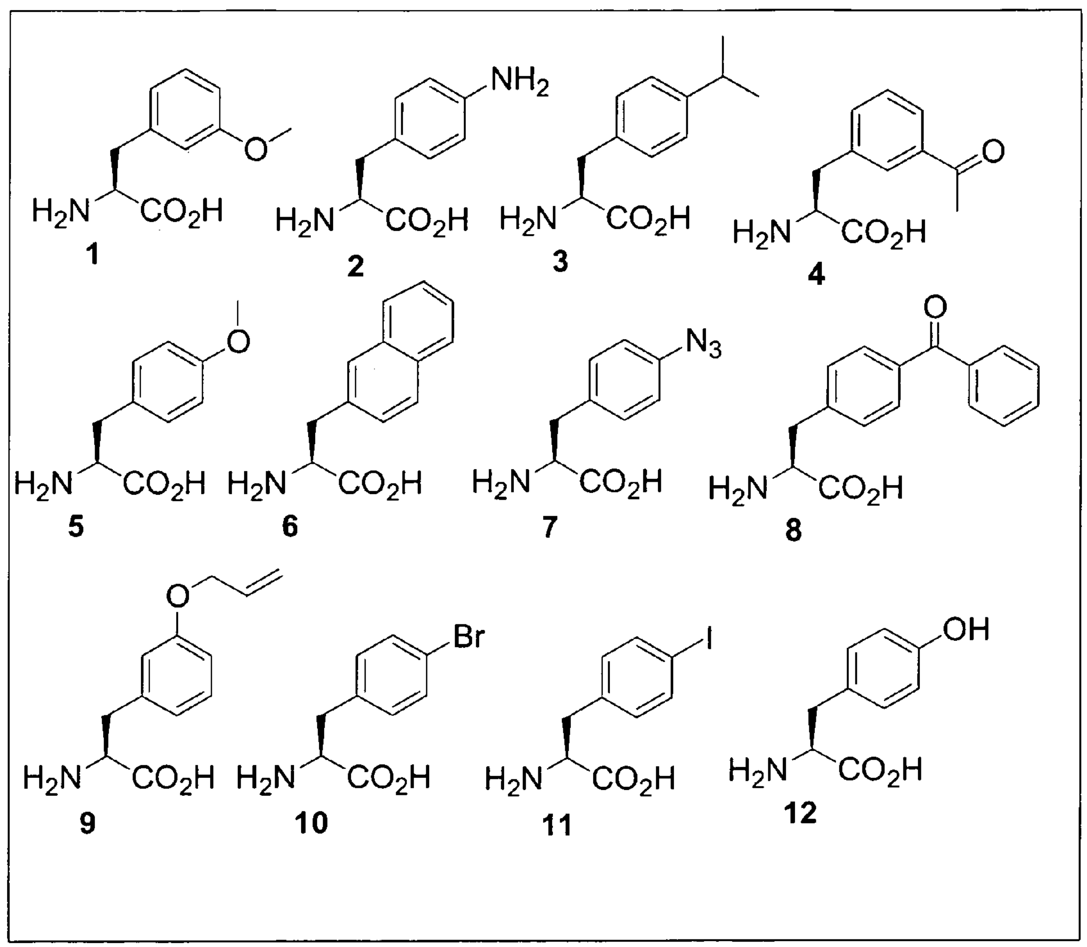
FIG. 16 illustrates a variety of unnatural amino acids.
Figure 17:
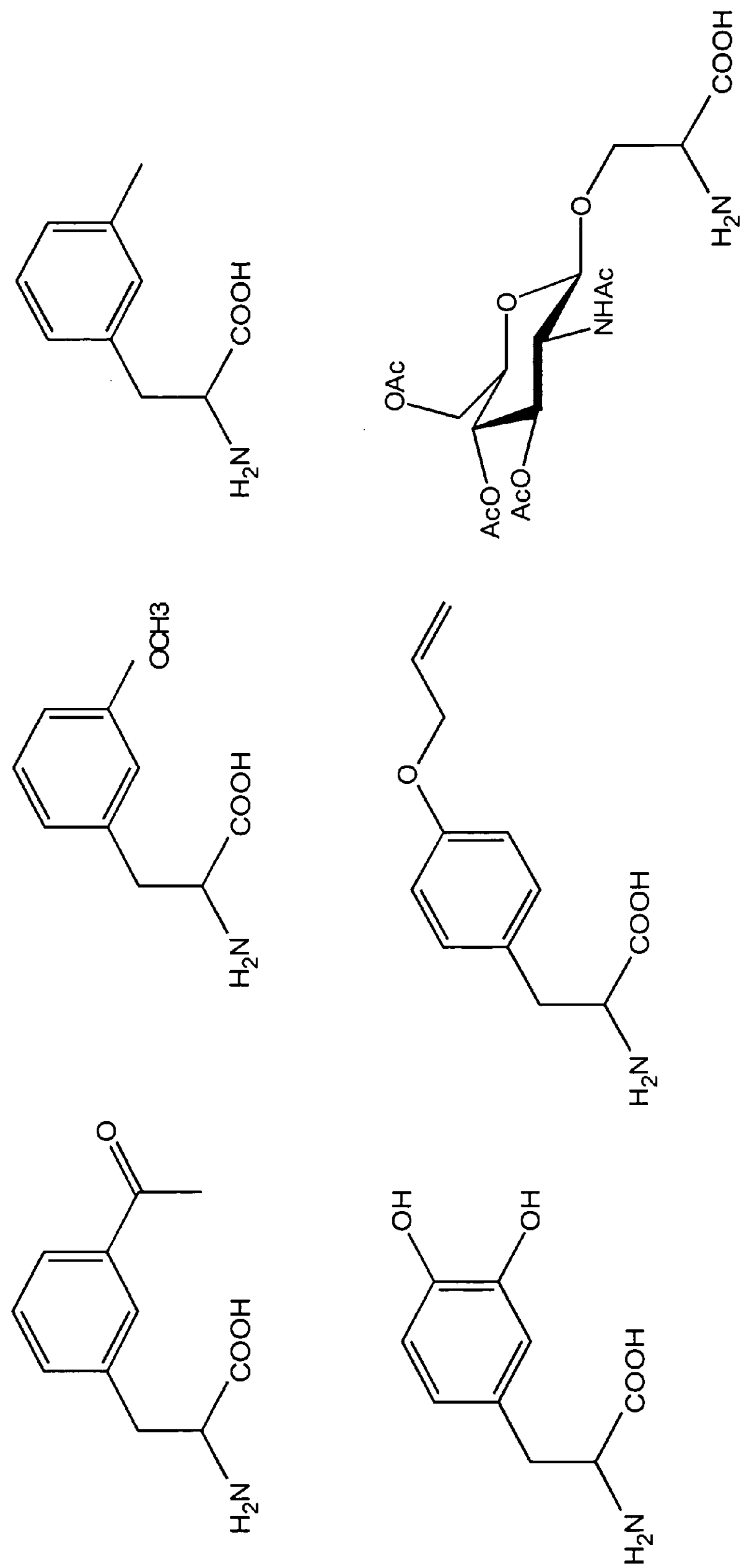
FIG. 17 illustrates a variety of unnatural amino acids.
Figure 18:
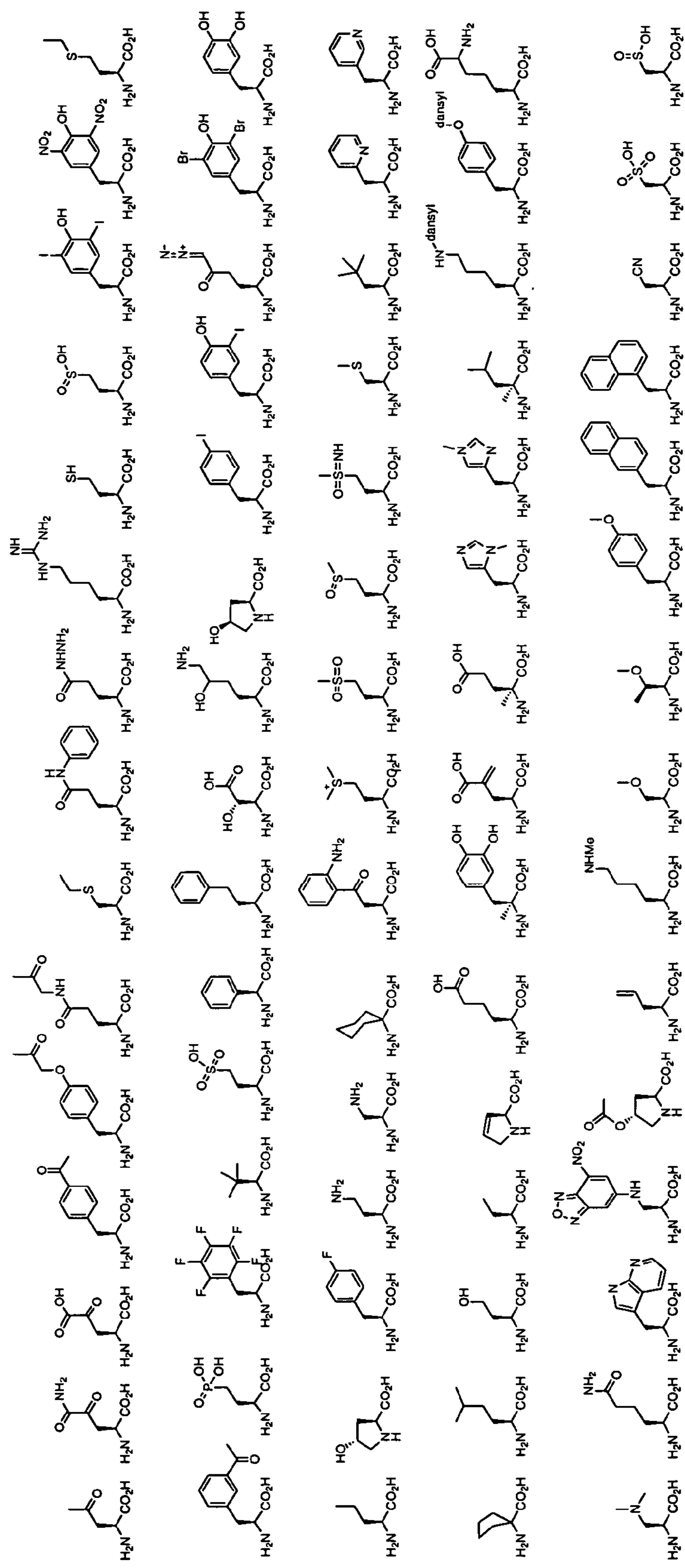
FIG. 18 illustrates a variety of unnatural amino acids.
Figure 19:
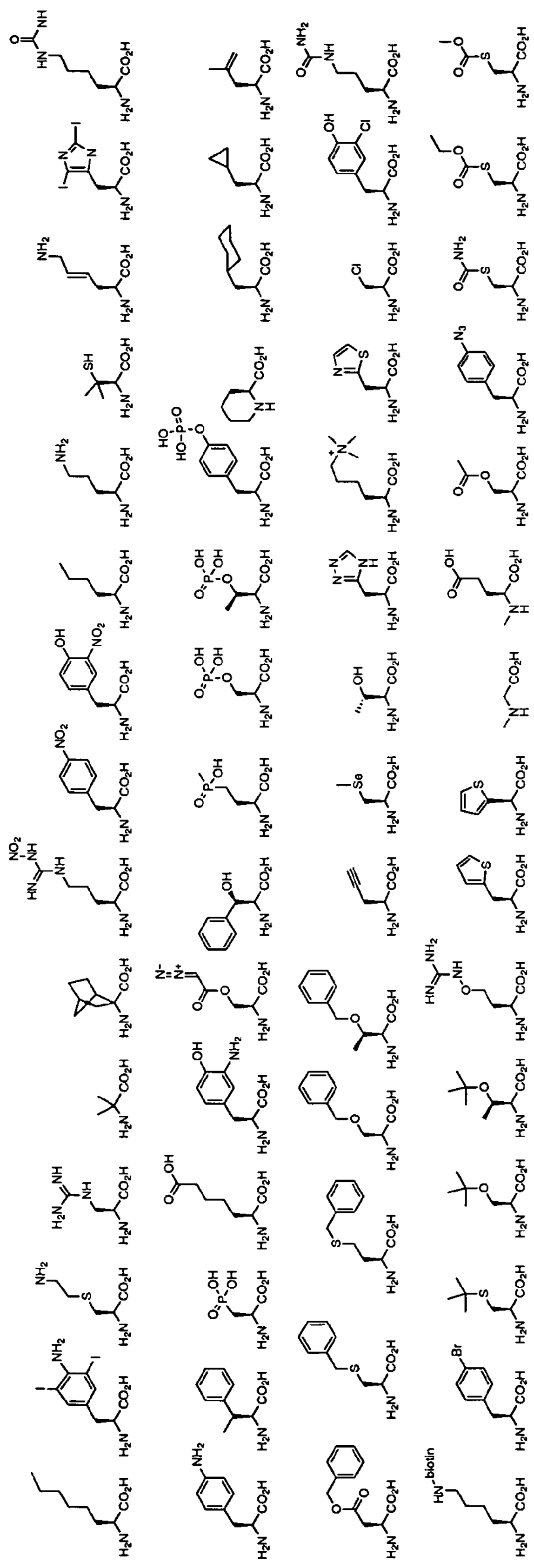
FIG. 19 illustrates additional amino acids, natural and unnatural for incorporation into proteins via in vivo suppression.

A biosynthetic pathway for pAF is shown in FIG. 15, Panel B. pAF is optionally synthesized in *E. coli* from chorismate (compound 2 In FIG. 15, Panel B), which is a biosynthetic intermediate in the synthesis of aromatic amino acids. To synthesize pAF from chorismate, a cell typically uses a chorismate synthase, a chorismate mutase, a dehydrogenase, e.g., a prephenate dehydrogense, and an amino transferase. For example, using the *S. Venezuelae* enzymes PapA, PapB, and PapC together with an *E. coli* aminotransferase, e.g., as shown in FIG. 15, Panel B, PapA, chorismate is used to produce pAF.

For example, 4-amino-4-deoxychorismate synthase converts chorismate to 4-amino-4-deoxychorismic acid (compound 3 in FIG. 15, Panel B), e.g., using ammonia (from glutamine) in a simple addition-elimination reaction. PapB and PapC, which are analogous to chorismate mutase and prephenate dehydrogenase, respectively, are used to convert 4-amino-4-deoxychorismic acid to 4-amino-4-deoxyprephenic acid (compound 4 in FIG. 15, Panel B) and then to p-aminophenyl-pyruvic acid (compound 5 in FIG. 15, panel B). A non-specific tyrosine aminotransferase, e.g., from *E. coli* is used to convert p-aminophenyl-pyruvic acid to pAF. See, e.g., *Escherichia coli* and *Salmonella*, 2nd ed, ed. F. C. Neidhardt. Vol. 1. 1996, Washington, D.C.: ASM Press. For example, tyrB, aspS, or ilvE is optionally used to produce pAF from p-aminophenyl-pyruvic acid.

FIG. 13 illustrates a plasmid for use in the biosynthesis of pAF. The plasmid depicted comprises *S. Venezuele* genes papA, papB, and papC cloned into a pSC101 derived μLASC plasmid, e.g., under control of the lac or lpp promotor. The plasmid is used to transform a cell, e.g., a bacterial cell, such that cell produces the enzymes encoded by the genes. When expressed, the enzymes catalyze one or more reactions designed to produce a desired unnatural amino acid, e.g., pAF. For example, proteins PapA, PapB and PapC convert chorismate to p-aminophenyl-pyruvic acid, while an *E. coli* aromatic aminotransferase completes the biosynthesis to afford pAF.

Typically, the synthesis of pAF from chorismate, in the present invention does not affect the concentration of other amino acids produced in the cell, e.g., other aromatic amino acids typically produced from chorismate. Typically, p-aminophenylalanine is produced in a concentration sufficient for efficient protein biosynthesis, e.g., a natural cellular amount, but not to such a degree as to affect the concentration of the other aromatic amino acids or exhaust cellular resources. Typical concentrations of pAF produced in vivo in this manner are about 10 mM to about 0.05 mM. In *S. Venezuelae* evidence suggests that the regulation of the shikimate pathway is modified to account for chorismate consumption in making a fourth aromatic amino acid. See, e.g., He, J., et al., *Microbiology*, 2001 147: p. 2817-2829. Once a bacterium is transformed with the plasmid comprising the genes used to produce enzymes used in the above pathway, and pAF as a twenty-first amino acid is generated, in vivo selections are optionally used to further optimize the production of pAF for both ribosomal protein synthesis and cell growth.

Since a pAF tRNA-synthetase pair allows the suppression of a TAG codon in a nonessential position of a protein, biosynthetic pathway effectiveness is optionally monitored and optimized by the production of that protein. Only cells that produce a concentration of pAF sufficient for protein biosynthesis are able to suppress the TAG codon. At the same time, one can select for optimal pAF production based on *E. coli* growth rates if the TAG-protein is an essential protein to cell growth. Placing the biosynthetic genes on a plasmid allows the level of pAF produced to be modified, e.g., by changing plasmid copy number and promotor strength. To determine if the addition of a pAF biosynthetic pathway affects the production of other aromatic amino acids in *E. coli*, and to quantitte pAF production, the cellular concentrations of the aromatic amino acids is optionally monitored, e.g., by extraction and LCMS analysis. See, e.g., Moss, R. E., *Methods in Enzymology*, 1995. 262: p. 497-499 and Mimura, H., S. Nagata, and T. Matsumoto, *Biosci. Biotech. Biochem*., 1994. 58(10): p. 1873-1874

Example 13

Biosynthesis of Dopa

Figure 20:
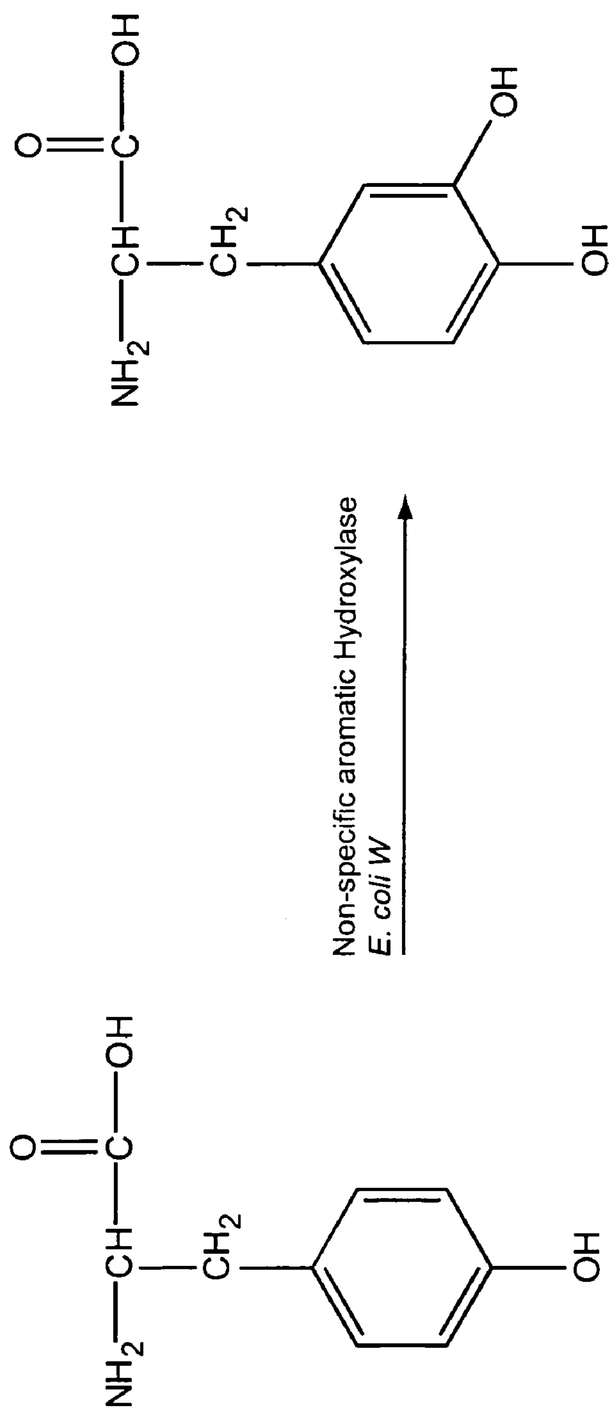
FIG. 20 provides a biosynthetic scheme for production of dopa.

To biosynthetically produce dopa in vivo, one or more genes, e.g., hpaBC, for a nonspecific aromatic hydroxylase, e.g., from *E. coli* are cloned into a low copy number vector, e.g., a pSC101 derivative, which is typically placed under control of an lpp promotor. This construct produces dopa (2) from tyrosine (1), in vivo, as shown in FIG. 20 while not being toxic to the growing cells. Similar work was done with this gene to overproduce dopa for purification purposes. See, e.g., Jang-Young Lee, Luying Xun, *Biotechnology Letters*, 1998, 20, 479-482. However, as described above, overproduction is not typically desired. In this application, a low copy plasmid is used to produce dopa in a natural cellular amount.

Example 14

Biosynthesis of O-methyl-L-tyrosine

O-methyl-L-tyrosine is optionally produced biosynthetically by plant O-methyltransferases are enzymes involved in secondary metabolism, which converts a hydroxyl group into a methoxyl group. Two such enzymes were selected: (iso)eugenol O-methyltransferase (IEMT) and caffeic acid O-methyltransferase (COMT). Both of them are from *Clarkia breweri*. IEMT methylates eugenol/isoeugenol, and COMT methylates caffeic acid. The substrates of these two enzymes are similar to tyrosine. However, both enzymes have high substrate specificity and methylation regiospecificity. Therefore, a combinatorial approach to evolve these two enzymes was adopted so that they would take tyrosine as their substrate and convert tyrosine into O-methyl-L-tyrosine. Active site residues were selected for mutation, and large mutant libraries were created. After several rounds of selection, at least about three hits have been identified.

In other embodiments, the enzymes used to produce O-methyl-L-tyrosine can also be artificially evolved, e.g., to produce a meta substituted methoxy phenylalanine as provided in Formula III.

Example 15

Biosynthesis of glycosylated amino acids

Figure 28:
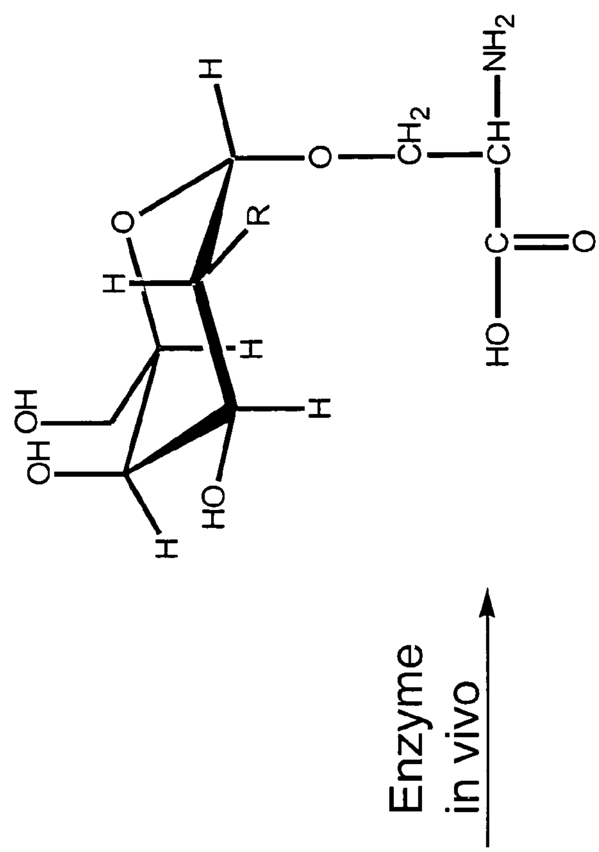
FIG. 28 illustrates a biosynthetic scheme for producing glycosylated amino acids.
Figure 28:
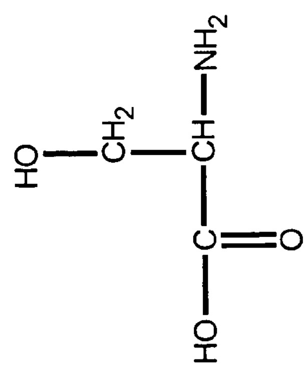

The present invention also provides biosynthetic methods for the production of glycosylated amino acids. Forming glycosylated amino acids in vivo is optionally performed in a number of ways. For example, transforming a cell with a plasmid comprising a gene for a N-acetyl-galactosaminidase, a transglycosylase, or a hydralase, e.g., serine-glycosyl hydrolase, e.g., acting in the reverse direction, provides a cell that produces a glycosylated amino acid. When combined with a translation system as provided below, the biosynthetic pathway results in a cell that produces and incorporates a glycosylated amino acid into one or more proteins within the cell. For example, see, e.g., FIG. 28, illustrating the formation of a glycosylated amino acid, wherein R is optionally an alcohol, an amine, or an N-acetyl amine. An example structure is shown by Formula IV:

IV

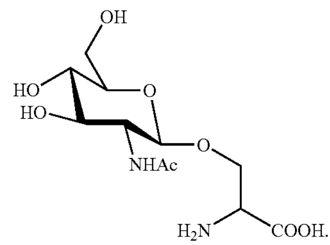

Example 16

Identification of Advantages Due to Incorporation of Unnatural Amino Acids

Given the capability presented herein of developing a completely autonomous bacterium that can biosynthesize a unnatural amino acid from basic carbon sources and incorporate this amino acid into proteins, e.g., in response to a nonsense codon in DNA, with high translational efficiency and fidelity, the question remains whether such additions actually provide an advantage to the bacterium over an organism that incorporates only the twenty natural amino acids. The present invention provides a method of determining if an expanded genetic code provides any such advantage as well as identifying the type of advantage and the unnatural amino acid to which it is due.

Since the 19th century bacteriologists have been interested in the extraordinary changes of bacterial cultures grown under various conditions. See, e.g., Summers, W. C., *J. Hist. Biol*., 1991, 24: P. 171-190. However, all forms of evolution have been studied with twenty amino acid organisms. The present invention addresses the feasibility of expanding the genetic code of *E. coli* with unnatural amino acids and provides methods of testing whether the ability to incorporate additional amino acids provides *E. coli* with an evolutionary advantage.

To determine whether the addition of novel amino acids to the genetic code can provide an evolutionary advantage to *E. coli* the evolution of a twenty-one amino acid bacteria is optionally compared to that of a twenty amino acid bacteria. The approach combines new sets of translational machinery for incorporation of unnatural amino acids into proteins with a mutagenized *E. coli* genomic library placed under selective pressures. The genetic, selection approach described above and elsewhere by Schultz and coworkers has, thus far, produced at least about eleven new aminoacyl synthetases that can incorporate novel amino acid into proteins efficiently and with high fidelity in response to the TAG codon.

Figure 21:
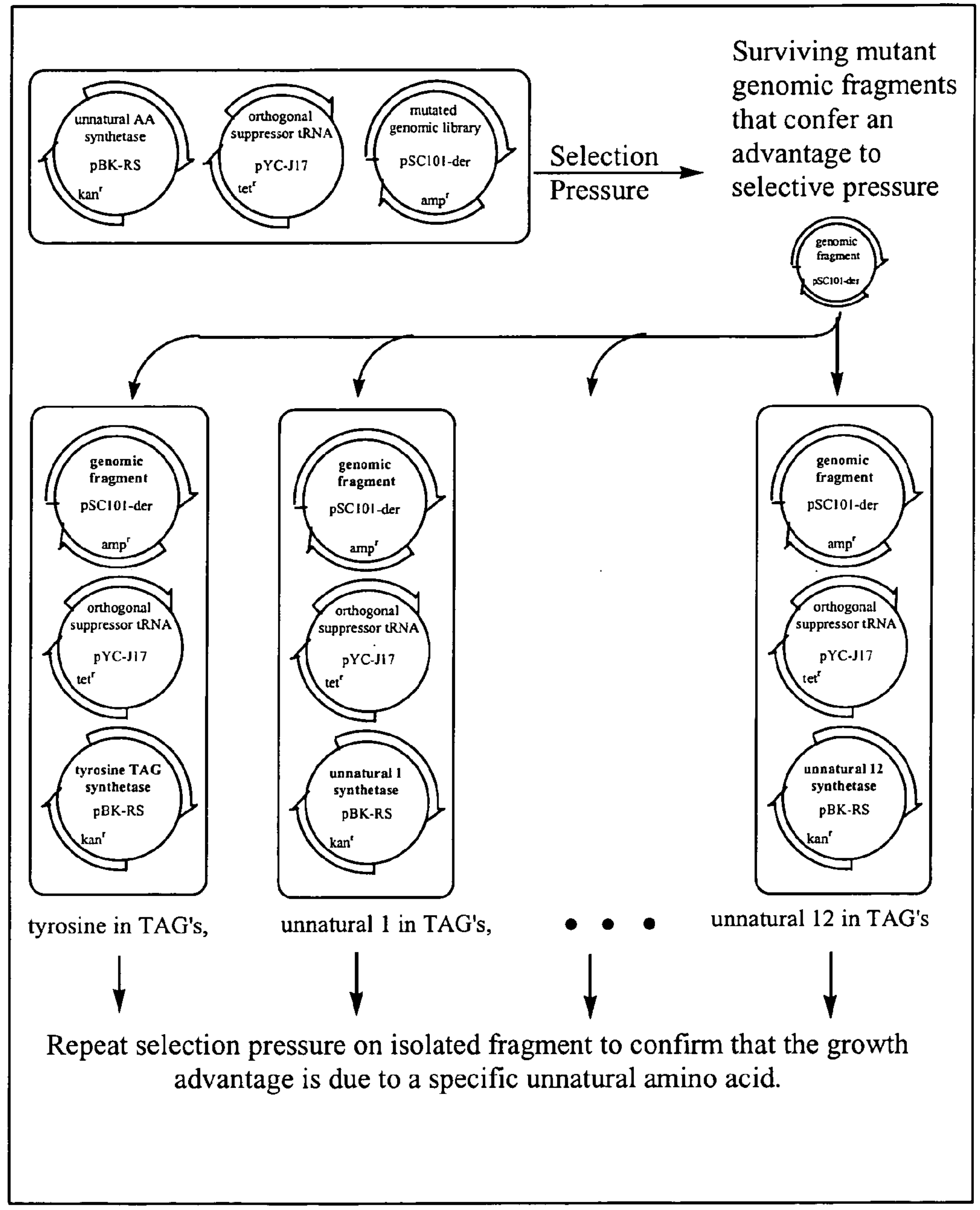
FIG. 21 illustrates a method for determining evolutionary advantages in a cell due to the ability to specifically incorporate twenty-one amino acids.
Figure 22:
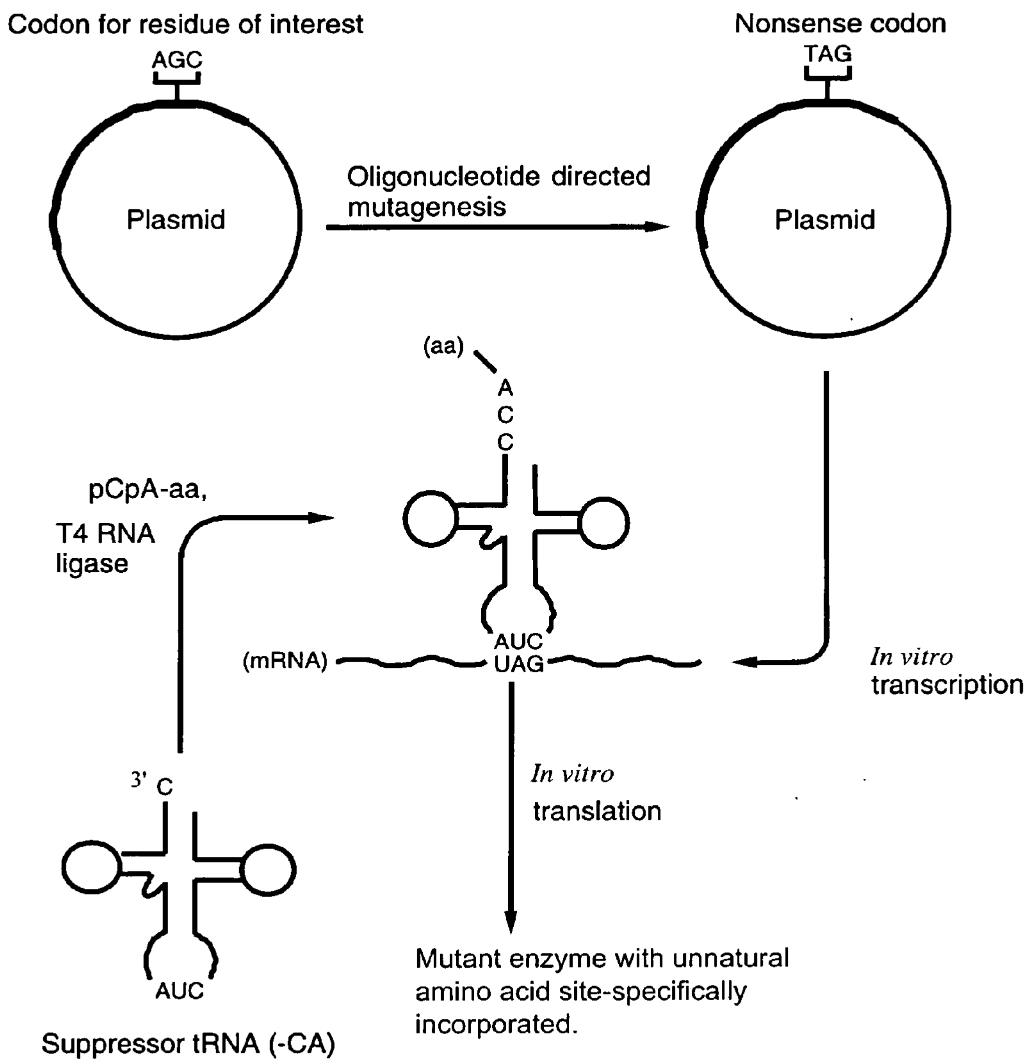
FIG. 22 illustrates a method for site-specific incorporation of unnatural amino acids.

Mutagenizing a plasmid library of the *E. coli* genome scrambles codons and randomly adds TAG nonsense codons throughout the genome. The new TAG codons can be suppressed by the incorporation of new amino acids into the expressed protein. These bacterial systems are placed under selective pressures to select for enhanced *E. coli* growth. See, e.g., FIG. 21. The selected genomic fragments from the library that confer an advantage are optionally isolated and screened for enhanced growth ability when incorporating the other unnatural amino acids and tyrosine in response to TAG codons.

A pSC101 low copy vector (approximately 5 copies/cell) is optionally used to construct a large insert (7-14 kb) *E. coli* genomic library by standard methods known to those of skill in the art. For example, a 600 member pSC101 based *E. coli* genomic library provides complete coverage of the *E. coli* genome and is also compatible with the aminoacyl synthetase, and tRNA plasmids described above. Many mutagens have been studied for there ability to incorporate TAG codons into genes. See, e.g., Miller, J. H., A short course in bacterial genetics. 1992, Plainview: Cold Spring Harbor Laboratory Press. Multiple mutagenesis methods are optionally used since each mutagen is not completely random in its formation of TAG codons. By mutagenizing the same 600 member *E. coli* genomic library with four different mutagens TAG codons are typically placed in as many sites as possible. Four optional methods include, but are not limited to, UV irradiation, a mutator strain (XL1 red), 4-nitro-quinoline-1-oxide (NQO), and ethylmethane sulfonate (EMS) to mutate the genomic library, and combine them to make one large mutated genomic libraries of >1010 members. These mutation methods all rely primarily on forming point mutation but complement each other in the mechanism of mutagenesis resulting over all in a more even distribution of TAG codons. UV irradiation and the mutator strain generate all base substitutions while NQO and EMS principally cause G:C to A:T transitions. Most of the point mutations generated form codons that code for one of the twenty natural amino acids. Since only about 12.5% of the single point mutations can form a TAG codon large highly mutagenized genomic libraries are needed. This method typically generates a least about 106 mutated copies of each gene with many new randomly placed codons. The genomic library is then typically checked for TAG codon incorporation by sequencing a subset of library members before and after mutagenesis.

To determine which genes might be improved by incorporation of one of the new amino acids any of a variety of selective pressures are optionally used for screening that target a range of cellular biology: catalytic functions, protein interactions, carbon sources, multiple response genes, and broad metabolic functions. For example, selection pressure based on quinolones is used to target topoisomerase and DNA gyrase. 5-fluorouracil is used to target DNA synthesis; omeprazole is used to target proton pump inhibitors; the use of fatty acids as a sole carbon source and acidic media are used to target a variety of genes related to utilization of carbon and response; and a reductive media is used to target the thiol-redox pathway and disulfide containing proteins. See, e.g., Bronson, J. J. and J. F. Barrett, *Curr. Med. Chemistry*, 2001 8: p. 1775-1793; Bearden, D. T. and L. H. Danziger, *Pharmacotherapy*, 2001 21(10): p. 224S-232S; Matthews, D. A., et al., *J. Mol. Biol.*, 1990. 2144(4): p. 937-948; Knox, M. R. and J. E. Harris, *Arch. Microbiol.*, 1988. 149(6): p. 557-60; McGowan, C. C., T. L. Cover, and M. J. Blaser, *Gasteroenterology*, 1994. 107(5): p. 1573-8; Clark, D. P. and J. E. Cronan, Two carbon compounds and fatty acids as carbon sources. *Escheria coli* and *Salmonella* cellular and molecular biology, ed. F. C. Neidhardt. Vol. 1. 1996, Washington D.C.: ASM press; Slonczewski, J. L. and J. W. Foster, pH-regulated genes and survival at extreme pH. *Escheria coli* and *Salmonella* cellular and molecular biology, ed. F. C. Neidhardt. Vol. 1. 1996, Washington D.C.: ASM press; and Ritz, D. and J. Beckwith, *Annu. Rev. Microbiol.*, 2001. 55: p. 21-48.

The screening of the mutated genomic library produces a set of mutated genomic fragments that confer a growth advantage under a certain selection pressure. These fragments are compared to determine if they are the same found in screens with no unnatural amino acid present by restriction mapping and sequencing. Fragments that produce a growth enhancement from an unnatural amino acid selection this fragment are optionally re-screened by comparing growth rate with each unnatural amino acid and tyrosine suppressing the TAG codon. See, e.g., FIG. 21. This re-screening of selected genomic fragments insures that the unnatural amino acid is the factor in conferring a growth advantage. For fragments that show a selective growth advantage with an unnatural amino acid being inserted into TAG codons, the gene(s) that confers an advantage is optionally isolated and identified, e.g., by digestion and subcloning. The protein can be studied to identify how the unnatural amino acid is enhancing cellular function. The enhanced protein is optionally purified and compared to a natural protein with both in vitro and in vivo studies. Standard enzyme techniques are optionally used to study protein stability, kinetics, and its interaction with other biosynthetic pathway components.

Example 17

Sequences

| SEQ ID # | Sequence | Notes | tRNA or RS |
|---|---|---|---|
| 1 | CCGGCGGTAGTTCAGCAGGGCAGAACGGCGGACTCTAAATCCGCATGGCGCTGGTTCA AATCCGGCCCGCCGGACCA | *M. jannaschii* mtRNA$_{CUA}^{Tyr}$ | tRNA |
| 2 | CCCAGGGTAG CCAAGCTCGG CCAACGGCGA CGGACTCTAA ATCCGTTCTC GTAGGAGTTC GAGGGTTCGA ATCCCTTCCC TGGGACCA | HLAD03; an optimized amber supressor tRNA | tRNA |
| 3 | GCGAGGGTAG CCAAGCTCGG CCAACGGCGA CGGACTTCCT AATCCGTTCT CGTAGGAGTT CGAGGGTTCG AATCCCTCCC CTCGCACCA | HL325A; an optimized AGGA framshift supressor tRNA | tRNA |
| 4 | ATGGACGAATTTGAAATGATAAAGAGAAACACATCTGAAATTATCAGCGAGGAAGAGT TAAGAGAGGTTTTAAAAAAAGATGAAAAATCTGCTCAGATAGGTTTTGAACCAAGTGG TAAAATACATTTAGGGCATTATCTCCAAATAAAAAAGATGATTGATTTACAAAATGCT GGATTTGATATAATTATATTGTTGGCTGATTTACACGCCTATTTAAACCAGAAAGGAG AGTTGGATGAGATTAGAAAAATAGGAGATTATAACAAAAAAGTTTTTGAAGCAATGGG GTTAAAGGCAAAATATGTTTATGGAAGTACTTTCCAGCTTGATAAGGATTATACACTG AATGTCTATAGATTGGCTTTAAAAACTACCTTAAAAACAGCAAGAAGGAGTATGGAAC TTATAGCAAGAGAGGATGAAAATCCAAAGGTTGCTGAAGTTATCTATCCAATAATGCA GGTTAATGCAATTCATTATCCTGGCGTTGATGTTGCAGTTGGAGGGATGGAGCAGAGA | mutant TyrRS (LWJ16) | RS |

-continued

| SEQ ID # | Sequence | Notes | tRNA or RS |
|---|---|---|---|
| | AAAATACACATGTTAGCAAGGGAGCTTTTACCAAAAAAGGTTGTTTGTATTCACAACC<br>CTGTCTTAACGGGTTTGGATGGAGAAGGGAAGATGAGTTCTTCAAAAGGGAATTTTAT<br>AGCTGTTGATGACTCTCCAGAAGAGATTAGGGCTAAGATAAAGAAAGCATACTGCCCA<br>GCTGGAGTTGTTGAAGGAAATCCAATAATGGAGATAGCTAAATACTTCCTTGAATATC<br>CTTTAACCATAAAAAGGCCAGAAAAATTTGGTGGAGATTTGACAGTTAGTAGCTATGA<br>GGAGTTAGAGAGTTTATTTAAAAATAAGGAATTGCATCCAATGGATTTAAAAAATGCT<br>GTAGCTGAAGAACTTATAAAGATTTTAGAGCCAATTAGAAAGAGATTATAA | | |
| 5 | ATGGACGAATTTGAAATGATAAAGAGAAACACATCTGAAATTATCAGCGAGGAAGAG<br>TTAAGAGAGGTTTTAAAAAAAGATGAAAAATCTGCTGGGATAGGTTTTGAACCAAGT<br>GGTAAAATACATTTAGGGCATTATCTCCAAATAAAAAAGATGATTGATTTACAAAAT<br>GCTGGATTTGATATAATTATATTGTTGGCTGATTTACACGCCTATTTAAACCAGAAA<br>GGAGAGTTGGATGAGATTAGAAAAATAGGAGATTATAACAAAAAAGTTTTTGAAGCA<br>ATGGGGTTAAAGGCAAAATGTGCTTATGGAAGTCCTTTCCAGCTTGATAAGGATTAT<br>ACACTGAATGTCTATAGATTGGCTTTAAAAACTACCTTAAAAAGAGCAAGAAGGAGT<br>ATGGAACTTATAGAAGAGAGGATGAAAATCCAAAGGTTGCTGAAGTTATCTATCCAA<br>TAATGCAGGTTAATGGTTATCATTATCTTGGCGTTGATGTTGCAGTTGGAGGGATGG<br>AGCAGAGAAAAATACACATGTTAGCAAGGGAGCTTTTACCAAAAAAGGTTGTTTGTA<br>TTCACAACCCTGTCTTAACGGGTTTGGATGGAGAAGGAAAGATGAGTTCTTCAAAAG<br>GGAATTTTATAGCTGTTGATGACTCTCCAGAAGAGATTAGGGCTAAGATAAAGAAAG<br>CATACTGCCCAGCTGGAGTTGTTGAAGGAAATCCAATAATGGAGATAGCTAAATACT<br>TCCTTGAATATCCTTTAACCATAAAAAGGCCAGAAAAATTTGGTGGAGATTTGACAG<br>TTAATAGCTATGAGGAGTTAGAGAGTTTATTTAAAAATAAGGAATTGCATCCAATGG<br>ATTTAAAAAATGCTGTAGCTGAAGAACTTATAAAGATTTTAGAGCCAATTAGAAAGA<br>GATTA | p-iPr-PheRS | RS |
| 6 | ATGGACGAATTTGAAATGATAAAGAGAAACACATCTGAAATTATCAGCGAGGAAGAG<br>TTAAGAGAGGTTTTAAAAAAAGATGAAAAATCTGCTCAGATAGGTTTTGAACCAAGT<br>GGTAAAATACATTTAGGGCATTATCTCCAAATAAAAAAGATGATTGATTTACAAAAT<br>GCTGGATTTGATATAATTATATTGTTGGCTGATTTACACGCCTATTTAAACCAGAAA<br>GGAGAGTTGGATGAGATTAGAAAAATAGGAGATTATAACAAAAAAGTTTTTGAAGCA<br>ATGGGGTTAAAGGCAAAATATGTTTATGGAAGTCCTTTCCAGCTTGATAAGGATTAT<br>ACACTGAATGTCTATAGATTGGCTTTAAAAACTACCTTAAAAAGAGCAAGAAGGAGT<br>ATGGAACTTATAGAAGAGAGGATGAAAATCCAAAGGTTCCTGAAGTTATCTATCCAA<br>TAATGCAGGTTAATTGTTCTCATTATTATGGCGTTGATGTTGCAGTTGGAGGGATGG<br>AGCAGAGAAAAATACACATGTTAGCAAGGGAGCTTTTACCAAAAAAGGTTGTTTGTA<br>TTCACAACCCTGTCTTAACGGGTTTGGATGGAGAAGGAAAGATGAGTTCTTCAAAAG<br>GGAATTTTATAGCTGTTGATGACTCTCCAGAAGAGATTAGGGCTAAGATAAAGAAAG<br>CATACTGCCCAGCTGGAGTTGTTGAAGGAAATCCAATAATGGAGATAGCTAAATACT<br>TCCTTGAATATCCTTTAACCATAAAAAGGCCAGAAAAATTTGGTGGAGATTTGACAG<br>TTAATAGCTATGAGGAGTTAGAGAGTTTATTTAAAAATAAGGAATTGCATCCAATGG<br>ATTTAAAAAATGCTGTAGCTGAAGAACTTATAAAGATTTTAGAGCCAATTAGAAAGA<br>GATTA | p-$NH_2$-PheRS(1) | RS |
| 7 | ATGGACGAATTTGAAATGATAAAGAGAAACACATCTGAAATTATCAGCGAGGAAGAG<br>TTAAGAGAGGTTTTAAAAAAAGATGAAAAATCTGCTACTATAGGTTTTGAACCAAGT<br>GGTAAAATACATTTAGGGCATTATCTCCAAATAAAAAAGATGATTGATTTACAAAAT<br>GCTGGATTTGATATAATTATATTGTTGGCTGATTTACACGCCTATTTAAACCAGAAA<br>GGAGAGTTGGATGAGATTAGAAAAATAGGAGATTATAACAAAAAAGTTTTTGAAGCA<br>ATGGGGTTAAAGGCAAAATATGTTTATGGAAGTACGTTCCAGCTTGATAAGGATTAT<br>ACACTGAATGTCTATAGATTGGCTTTAAAAACTACCTTAAAAAGAGCAAGAAGGAGT<br>ATGGAACTTATAGAAGAGAGGATGAAAATCCAAAGGTTGCTGAAGTTATCTATCCAA<br>TAATGCAGGTTAATCCGTTGCATTATGCTGGCGTTGATGTTGCAGTTGGAGGGATGG<br>AGCAGAGAAAAATACACATGTTAGCAAGGGAGCTTTTACCAAAAAAGGTTGTTTGTA<br>TTCACAACCCTGTCTTAACGGGTTTGGATGGAGAAGGAAAGATGAGTTCTTCAAAAG<br>GGAATTTTATAGCTGTTGATGACTCTCCAGAAGAGATTAGGGCTAAGATAAACAAAG<br>CATACTGCCCAGCTGGAGTTGTTGAAGGAAATCCAATAATGGAGATAGCTAAATACT<br>TCCTTGAATATCCTTTAACCATAAAAAGGCCAGAAAAATTTGGTGGAGATTTGACAG<br>TTAATAGCTATGAGGAGTTAGAGAGTTTATTTAAAAATAAGGAATTGCATCCAATGG<br>ATTTAAAAAATGCTGTAGCTGAAGAACTTATAAAGATTTTAGAGCCAATTAGAAAGA<br>GATTA | p-$NH_2$-PheRS(2) | RS |
| 8 | ATGGACGAATTTGAAATGATAAAGAGAAACACATCTGAAATTATCAGCGAGGAAGAG<br>TTAAGAGAGGTTTTAAAAAAAGATGAAAAATCTGCTCATATAGGTTTTGAACCAAGT<br>GGTAAAATACATTTAGGGCATTATCTCCAAATAAAAAAGATGATTGATTTACAAAAT<br>GCTGGATTTGATATAATTATATTGTTGGCTGATTTACACGCCTATTTAAACCAGAAA<br>GGAGAGTTGGATGAGATTAGAAAAATAGGAGATTATAACAAAAAAGTTTTTGAAGCA<br>ATGGGGTTAAAGGCAAAATATGTTTATGGAAGTGAGTTCCAGCTTGATAAGGATTAT<br>ACACTGAATGTCTATAGATTGGCTTTAAAAACTACCTTAAAAAGAGCAAGAAGGAGT<br>ATGGAACTTATAGAAGAGAGGATGAAAATCCAAAGGTTGCTGAAGTTATCTATCCAA<br>TAATGCAGGTTAATCGGCCGCATTATCCTGGCGTTGATGTTGCAGTTGGAGGGATGG<br>AGCAGAGAAAAATACACATGTTAGCAAGGGAGCTTTTACCAAAAAAGGTTGTTTGTA<br>TTCACAACCCTGTCTTAACGGGTTTGGATGGAGAAGGAAAGATGAGTTCTTCAAAAG<br>GGAATTTTATAGCTGTTGATGACTCTCCAGAAGAGATTAGGGCTAAGATAAAGAAAG<br>CATACTGCCCAGCTGGAGTTGTTGAAGGAAATCCAATAATGGAGATAGCTAAATACT<br>TCCTTGAATATCCTTTAACCATAAAAAGGCCAGAAAAATTTGGTGGAGATTTGACAG<br>TTAATAGCTATGAGGAGTTAGAGAGTTTATTTAAAAATAAGGAATTGCATCCAATGG<br>ATTTAAAAAATGCTGTAGCTGAAGAACTTATAAAGATTTTAGAGCCAATTAGAAAGA<br>GATTA | p-$NH_2$-PheRS(3a) | RS |

-continued

| SEQ ID # | Sequence | Notes | tRNA or RS |
|---|---|---|---|
| 9 | ATGGACGAATTTGAAATGATAAAGAGAAACACATCTGAAATTATCAGCGAGGAAGAG<br>TTAAGAGAGGTTTTAAAAAAAGATGAAAAATCTGCTTATATAGGTTTTGAACCAAGT<br>GGTAAAATACATTTAGGGCATTATCTCCAAATAAAAAAGATGATTGATTTACAAAAT<br>GCTGGATTTGATATAATTATATTGTTGGCTGATTTACACGCCTATTTAAACCAGAAA<br>GGAGAGTTGGATGAGATTAGAAAAATAGGAGATTATAACAAAAAAGTTTTTGAAGCA<br>ATGGGGTTAAAGGCAAAATATGTTTATGGAAGTCCTTTCCAGCTTGATAAGGATTAT<br>ACACTGAATGTCTATAGATTGGCTTTAAAAACTACCTTAAAAAGAGCAAGAAGGAGT<br>ATGGAACTTATAGAAGAGAGGATGAAAATCCAAAGGTTGCTGAAGTTATCTATCCAA<br>TAATGCAGGTTAATCAGAGTCATTATGATGGCGTTGATGTTGCAGTTGGAGGGATGG<br>AGCAGAGAAAAATACACATGTTAGCAAGGGAGCTTTTACCAAAAAAGGTTGTTTGTA<br>TTCACAACCCTGTCTTAACGGGTTTGGATGGAGAAGGAAAGATGAGTTCTTCAAAAG<br>GGAATTTTATAGCTGTTGATGACTCTCCAGAAGAGATTAGGGCTAAGATAAAGAAAG<br>CATACTGCCCAGCTGGAGTTGTTGAAGGAAATCCAATAATGGAGATAGCTAAATACT<br>TCCTTGAATATCCTTTAACCATAAAAAGGCCAGAAAAATTTGGTGGAGATTTGACAG<br>TTAATAGCTATGAGGAGTTAGAGAGTTTATTTAAAAATAAGGAATTGCATCCAATGG<br>ATTTAAAAAATGCTGTAGCTGAAGAACTTATAAAGATTTTAGAGCCAATTAGAAAGA<br>GATTA | p-$NH_2$-PheRS(3b) | RS |
| 10 | ATGGACGAATTTGAAATGATAAAGAGAAACACATCTGAAATTATCAGCGAGGAAGAG<br>TTAAGAGAGGTTTTAAAAAAAGATGAAAAATCTGCTTCGATAGGTTTTGAACCAAGT<br>GGTAAAATACATTTAGGGCATTATCTCCAAATAAAAAAGATGATTGATTTACAAAAT<br>GCTGGATTTGATATAATTATATTGTTGGCTGATTTACACGCCTATTTAAACCAGAAA<br>GGAGAGTTGGATGAGATTAGAAAAATAGGAGATTATAACAAAAAAGTTTTTGAAGCA<br>ATGGGGTTAAAGGCAAAATATGTTTATGGAAGTACGTTCCAGCTTGATAAGGATTAT<br>ACACTGAATGTCTATAGATTGGCTTTAAAAACTACCTTAAAAAGAGCAAGAAGGAGT<br>ATGGAACTTATAGAAGAGAGGATGAAAATCCAAAGGTTGCTGAAGTTATCTATCCAA<br>TAATGCAGGTTAATACGTATCATTATGCTGGCGTTGATGTTGCAGTTGGAGGGATGG<br>AGCAGAGAAAAATACACATGTTAGCAAGGGAGCTTTTACCAAAAAAGGTTGTTTGTA<br>TTCACAACCCTGTCTTAACGGGTTTGGATGGAGAAGGAAAGATGAGTTCTTCAAAAG<br>GGAATTTTATAGCTGTTGATGACTCTCCAGAAGAGATTAGGGCTAAGATAAAGAAAG<br>CATACTGCCCAGCTGGAGTTGTTGAAGGAAATCCAATAATGGAGATAGCTAAATACT<br>TCCTTGAATATCCTTTAACCATAAAAAGGCCAGAAAAATTTGGTGGAGATTTGACAG<br>TTAATAGCTATGAGGAGTTAGAGAGTTTATTTAAAAATAAGGAATTGCATCCAATGG<br>ATTTAAAAAATGCTGTAGCTGAAGAACTTATAAAGATTTTAGAGCCAATTAGAAAGA<br>GATTA | O-Allyl-TyrRS(1) | RS |
| 11 | ATGGACGAATTTGAAATGATAAAGAGAAACACATCTGAAATTATCAGCGAGGAAGAGT<br>TAAGAGAGGTTTTAAAAAAAGATGAAAAATCTGCTCCTATAGGTTTTGAACCAAGTGG<br>TAAAATACATTTAGGGCATTATCTCCAAATAAAAAAGATGATTGATTTACAAAATGCT<br>GGATTTGATATAATTATATTGTTGGCTGATTTACACGCCTATTTAAACCAGAAAGGAG<br>AGTTGGATGAGATTAGAAAAATAGGAGATTATAACAAAAAAGTTTTTGAAGCAATGGG<br>GTTAAAGGCAAAATATGTTTATGGAAGTATGTTCCAGCTTGATAAGGATTATACACTG<br>AATGTCTATAGATTGGCTTTAAAAACTACCTTAAAAAGAGCAAGAAGGAGTATGGAAC<br>TTATAGAAGAGAGGATGAAAATCCAAAGGTTGCTGAAGTTATCTATCCAATAATGCAG<br>GTTAATAATACGCATTATGGGGGCGTTGATGTTGCAGTTGGAGGGATGGAGCAGAGAA<br>AAATACACATGTTAGCAAGGGAGCTTTTACCAAAAAAGGTTGTTTGTATTCACAACCC<br>TGTCTTAACGGGTTTGGATGGAGAAGGAAAGATGAGTTCTTCAAAAGGGAATTTTATA<br>GCTGTTGATGACTCTCCAGAAGAGATTAGGGCTAAGATAAAGAAAGCATACTGCCCAG<br>CTGGAGTTGTTGAAGGAAATCCAATAATGGAGATAGCTAAATACTTCCTTGAATATCC<br>TTTAACCATAAAAAGGCCAGAAAAATTTGGTGGAGATTTGACAGTTAATAGCTATGAG<br>GAGTTAGAGAGTTTATTTAAAAATAAGGAATTGCATCCAATGGATTTAAAAAATGCTG<br>TAGCTGAAGAACTTATAAAGATTTTAGAGCCAATTAGAAAGAGATTA | O-Allyl-TyrRS(3) | RS |
| 12 | ATGGACGAATTTGAAATGATAAAGAGAAACACATCTGAAATTATCAGCGAGGAAGAGT<br>TAAGAGAGGTTTTAAAAAAAGATGAAAAATCTGCTACGATAGGTTTTGAACCAAGTGG<br>TAAAATACATTTAGGGCATTATCTCCAAATAAAAAAGATGATTGATTTACAAAATGCT<br>GGATTTGATATAATTATATTGTTGGCTGATTTACACGCCTATTTAAACCAGAAAGCAG<br>AGTTGGATGAGATTAGAAAAATAGGAGATTATAACAAAAAAGTTTTTGAAGCAATGGG<br>GTTAAAGGCAAAATATGTTTATGGAAGTCATTTCCAGCTTGATAAGGATTATACACTG<br>AATGTCTATAGATTGGCTTTAAAAACTACCTTAAAAAGAGCAAGAAGGAGTATGGAAC<br>TTATAGAAGAGAGGATGAAAATCCAAAGGTTGCTGAAGTTATCTATCCAATAATGCAG<br>GTTAATCAGACTCATTATGAGGGCGTTGATGTTGCAGTTGGAGGGATGGAGCAGAGAA<br>AAATACACATGTTAGCAAGGGAGCTTTTACCAAAAAAGGTTGTTTGTATTCACAACCC<br>TGTCTTAACGGGTTTGGATGGAGAAGGAAAGATGAGTTCTTCAAAAGGGAATTTTATA<br>GCTGTTGATGACTCTCCAGAAGAGATTAGGGCTAAGATAAAGAAAGCATACTGCCCAG<br>CTGGAGTTGTTGAAGGAAATCCAATAATGGAGATAGCTAAATACTTCCTTGAATATCC<br>TTTAACCATAAAAAGGCCAGAAAAATTTGGTGGAGATTTGACAGTTAATAGCTATGAG<br>GAGTTAGAGAGTTTATTTAAAAATAAGGAATTGCATCCAATGGATTTAAAAAATGCTG<br>TAGCTGAAGAACTTATAAAGATTTTAGAGCCAATTAGAAAGAGATTA | O-Allyl-TyrRS(4) | RS |
| 13 | ATGGACGAATTTGAAATGATAAAGAGAAACACATCTGAAATTATCAGCGAGGAAGAGT<br>TAAGAGAGGTTTTAAAAAAAGATGAAAAATCTGCTCATATAGGTTTTGAACCAAGTGG<br>TAAAATACATTTAGGGCATTATCTCCAAATAAAAAAGATGATTGATTTACAAAATGCT<br>GGATTTGATATAATTATATTGTTGGCTGATTTACACGCCTATTTAAACCAGAAAGGAG<br>AGTTGGATGAGATTAGAAAAATAGGAGATTATAACAAAAAAGTTTTTGAAGCAATGGG<br>GTTAAAGGCAAAATATGTTTATGGAAGTAAGTTCCAGCTTGATAAGGATTATACACTG<br>AATGTCTATAGATTGGCTTTAAAAACTACCTTAAAAAGAGCAAGAAGGAGTATGGAAC<br>TTATAGAAGAGAGGATGAAAATCCAAAGGTTGCTGAAGTTATCTATCCAATAATGCAG<br>GTTAATCCGTGTCATTATCATGGCGTTGATGTTGCAGTTGGAGGGATGGAGCAGAGAA<br>AAATACACATGTTAGCAAGGGAGCTTTTACCAAAAAAGGTTGTTTGTATTCACAACCC | p-Br-PheRS | RS |

-continued

| SEQ ID # | Sequence | Notes | tRNA or RS |
|---|---|---|---|
| | TGTCTTAACGGGTTTGGATGGAGAAGGAAAGATGAGTTCTTCAAAAGGGAATTTTATA<br>GCTGTTGATGACTCTCCAGAAGAGATTAGGGCTAAGATAAAGAAAGCATACTGCCCAG<br>CTGGAGTTGTTGAAGGAAATCCAATAATGGAGATAGCTAAATACTTCCTTGAATATCC<br>TTTAACCATAAAAAGGCCAGAAAAATTTGGTGGAGATTTGACAGTTAATAGCTATGAG<br>GAGTTAGAGAGTTTATTTAAAAATAAGGAATTGCATCCAATGGATTTAAAAAATGCTG<br>TAGCTGAAGAACTTATAAAGATTTTAGAGCCAATTAGAAAGAGATTA | | |
| 14 | ATGGACGAATTTGAAATGATAAAGAGAAACACATCTGAAATTATCAGCGAGGAAGAGT<br>TAAGAGAGGTTTTAAAAAAAGATGAAAAATCTGCTGCTATAGGTTTTGAACCAAGTGG<br>TAAAATACATTTAGGGCATTATCTCCAAATAAAAAAGATGATTGATTTACAAAATGCT<br>GGATTTGATATAATTATATTGTTGGCTGATTTACACGCCTATTTAAACCAGAAAGGAG<br>AGTTGGATGAGATTAGAAAAATAGGAGATTATAACAAAAAAGTTTTTGAAGCAATGGG<br>GTTAAAGGCAAAATATGTTTATGGAAGTCGGTTCCAGCTTGATAAGGATTATACACTG<br>AATGTCTATAGATTGGCTTTAAAAACTACCTTAAAAAGAGCAAGAAGGAGTATGGAAC<br>TTATAGAAGAGAGGATGAAAATCCAAAGGTTGCTGAAGTTATCTATCCAATAATGCAG<br>GTTAATGTGATTCATTATGATGGCGTTGATGTTGCAGTTGGAGGGATGGAGCAGAGAA<br>AAATACACATGTTAGCAAGGGAGCTTTTACCAAAAAAGGTTGTTTGTATTCACAACCC<br>TGTCTTAACGGGTTTGGATGGAGAAGGAAAGATGAGTTCTTCAAAAGGGAATTTTATA<br>GCTGTTGATGACTCTCCAGAAGAGATTAGGGCTAAGATAAAGAAAGCATACTGCCCAG<br>CTGGAGTTGTTGAAGGAAATCCAATAATGGAGATAGCTAAATACTTCCTTGAATATCC<br>TTTAACCATAAAAAGGCCAGAAAAATTTGGTGGAGATTTGACAGTTAATAGCTATGAG<br>GAGTTAGAGAGTTTATTTAAAAATAAGGAATTGCATCCAATGGATTTAAAAAATGCTG<br>TAGCTGAAGAACTTATAAAGATTTTAGAGCCAATTAGAAAGAGATTA | p-Az-PheRS(1) | RS |
| 15 | ATGGACGAATTTGAAATGATAAAGAGAAACACATCTGAAATTATCAGCGAGGAAGAGT<br>TAAGAGAGGTTTTAAAAAAAGATGAAAAATCTGCTGGGATAGGTTTTGAACCAAGTGG<br>TAAAATACATTTAGGGCATTATCTCCAAATAAAAAAGATGATTGATTTACAAAATGCT<br>GGATTTGATATAATTATATTGTTGGCTGATTTACACGCCTATTTAAACCAGAAAGGAG<br>AGTTGGATGAGATTAGAAAAATAGGAGATTATAACAAAAAAGTTTTTGAAGCAATGGG<br>GTTAAAGGCAAAATATGTTTATGGAAGTACTTTCCAGCTTGATAAGGATTATACACTG<br>AATGTCTATAGATTGGCTTTAAAAACTACCTTAAAAAGAGCAAGAAGGAGTATGGAAC<br>TTATAGAAGAGACGATGAAAATCCAAAGGTTGCTGAAGTTATCTATCCAATAATGCAG<br>GTTAATACGTATTATTATGCTGGCGTTGATGTTGCAGTTGGAGGGATGGAGCAGAGAA<br>AAATACACATGTTAGCAAGGGAGCTTTTACCAAAAAAGGTTGTTTGTATTCACAACCC<br>TGTCTTAACGGGTTTGGATGGAGAAGGAAAGATGAGTTCTTCAAAAGGGAATTTTATA<br>GCTGTTGATGACTCTCCAGAAGAGATTAGGGCTAAGATAAAGAAAGCATACTGCCCAG<br>CTGGAGTTGTTGAAGGAAATCCAATAATGGAGATAGCTAAATACTTCCTTGAATATCC<br>TTTAACCATAAAAAGGCCAGAAAAATTTGGTGGAGATTTGACAGTTAATAGCTATGAG<br>GAGTTAGAGAGTTTATTTAAAAATAAGGAATTGCATCCAATGGATTTAAAAAATGCTG<br>TAGCTGAAGAACTTATAAAGATTTTAGAGCCAATTAGAAAGAGATTA | p-Az-PheRS(3) | RS |
| 16 | ATGGACGAATTTGAAATGATAAAGAGAAACACATCTGAAATTATCAGCGAGGAAGAGT<br>TAAGAGAGGTTTTAAAAAAAGATGAAAAATCTGCTCTGATAGGTTTTGAACCAAGTGG<br>TAAAATACATTTAGGGCATTATCTCCAAATAAAAAAGATGATTGATTTACAAAATGCT<br>GGATTTGATATAATTATATTGTTGGCTGATTTACACGCCTATTTAAACCAGAAAGGAG<br>AGTTGGATGAGATTAGAAAAATAGGAGATTATAACAAAAAAGTTTTTGAAGCAATGGG<br>GTTAAAGGCAAAATATGTTTATGGAAGTCCGTTCCAGCTTGATAAGGATTATACACTG<br>AATGTCTATAGATTGGCTTTAAAAACTACCTTAAAAAGAGCAAGAAGGAGTATGGAAC<br>TTATAGAAGAGAGGATGAAAATCCAAAGGTTGCTGAAGTTATCTATCCAATAATGCAG<br>GTTAATCAGATTCATTCTAGTGGCGTTGATGTTGCAGTTGGAGGGATGGAGCAGAGAA<br>AAATACACATGTTAGCAAGGGAGCTTTTACCAAAAAAGGTTGTTTGTATTCACAACCC<br>TGTCTTAACGGGTTTGGATGGAGAAGGAAAGATGAGTTCTTCAAAAGGGAATTTTATA<br>GCTGTTGATGACTCTCCAGAAGAGATTAGGGCTAACATAAAGAAAGCATACTGCCCAG<br>CTGGAGTTGTTGAAGGAAATCCAATAATGGAGATAGCTAAATACTTCCTTGAATATCC<br>TTTAACCATAAAAAGGCCAGAAAAATTTGGTGGAGATTTGACAGTTAATAGCTATGAG<br>GAGTTAGAGAGTTTATTTAAAAATAAGGAATTGCATCCAATGGATTTAAAAAATGCTG<br>TAGCTGAAGAACTTATAAAGATTTTAGAGCCAATTAGAAAGAGATTA | p-Az-PheRS(5) | RS |
| 17 | ATGGACGAATTTGAAATGATAAAGAGAAACACATCTGAAATTATCAGCGAGGAAGAGT<br>TAAGAGAGGTTTTAAAAAAAGATGAAAAATCTGCTGACATAGGTTTTGAACCAAGTGG<br>TAAAATACATTTAGGGCATTATCTCCAAATAAAAAAGATGATTGATTTACAAAATGCT<br>GGATTTGATATAATTATATTGTTGGCTGATTTACACGCCTATTTAAACCAGAAAGGAG<br>AGTTGGATGAGATTAGAAAAATAGGAGATTATAACAAAAAAGTTTTTGAAGCAATGGG<br>GTTAAAGGCAAAATATGTTTATGGAAGTGAATTCCAGCTTGATAAGGATTATACACTG<br>AATGTCTATAGATTGGCTTTAAAAACTACCTTAAAAAGAGCAAGAAGGAGTATGGAAC<br>TTATAGCAAGAGAGGATGAAAATCCAAAGGTTGCTGAAGTTATCTATCCAATAATGCA<br>GGTTAATGGAATGCATTATCAAGGCGTTGATGTTGCAGTTGGAGGGATGGAGCAGAGA<br>AAAATACACATGTTAGCAAGGGAGCTTTTACCAAAAAAGGTTGTTTGTATTCACAACC<br>CTGTCTTAACGGGTTTGGATGGAGAAGGAAAGATGAGTTCTTCAAAAGGGAATTTTAT<br>AGCTGTTGATGACTCTCCAGAAGAGATTAGGGCTAAGATAAAGAAAGCATACTGCCCA<br>GCTGGAGTTGTTGAAGGAAATCCAATAATGGAGATAGCTAAATACTTCCTTGAATATC<br>CTTTAACCATAAAAAGGCCAGAAAAATTTGGTGGAGATTTGACAGTTAATAGCTATGA<br>GGAGTTAGAGAGTTTATTTAAAAATAAGGAATTGCATCCAATGGATTTAAAAAATGCT<br>GTAGCTGAAGAACTTATAAAGATTTTAGAGCCAATTAGAAAGAGATTATAA | Mutant synthetases to incorporate m-acyl phenylalanine into proteins (Ketone 3-4) | RS |
| 18 | ATGGACGAATTTGAAATGATAAAGAGAAACACATCTGAAATTATCAGCGAGGAAGAGT<br>TAAGAGAGGTTTTAAAAAAAGATGAAAAATCTGCTTACATAGGTTTTGAACCAAGTGG<br>TAAAATACATTTAGGGCATTATCTCCAAATAAAAAAGATGATTGATTTACAAAATGCT<br>GGATTTGATATAATTATATTGTTGGCTGATTTACACGCCTATTTAAACCAGAAAGGAG<br>AGTTGGATGAGATTAGAAAAATAGGAGATTATAACAAAAAAGTTTTTGAAGCAATGGG<br>GTTAAAGGCAAAATATGTTTATGGAAGTCTATTCCAGCTTGATAAGGATTATACACTG | Mutant synthetase to incorporate m-acyl phenylalanine into proteins (Ketone 3-7) | RS |

-continued

| SEQ ID # | Sequence | Notes | tRNA or RS |
|---|---|---|---|
| | AATGTCTATAGATTGGCTTTAAAAACTACCTTAAAAAGAGCAAGAAGGAGTATGGAAC<br>TTATAGCAAGAGAGGATGAAAATCCAAAGGTTGCTGAAGTTATCTATCCAATAATGCA<br>GGTTAATGATATTCATTATACAGGCGTTGATGTTGCAGTTGGAGGGATGGAGCAGAGA<br>AAAATACACATGTTAGCAAGGGAGCTTTTACCAAAAAAGGTTGTTTGTATTCACAACC<br>CTGTCTTAACGGGTTTGGATGGAGAAGGAAAGATGAGTTCTTCAAAAGGGAATTTTAT<br>AGCTGTTGATGACTCTCCAGAAGAGATTAGGGCTAAGATAAAGAAAGCATACTGCCCA<br>GCTGGAGTTGTTGAAGGAAATCCAATAATGGAGATAGCTAAATACTTCCTTGAATATC<br>CTTTAACCATAAAAAGGCCAGAAAAATTTGGTGGAGATTTGACAGTTAATAGCTATGA<br>GGAGTTAGAGAGTTTATTTAAAAATAAGGAATTGCATCCAATGGATTTAAAAAATGCT<br>GTAGCTGAAGAACTTATAAACATTTTAGAGCCAATTAGAAAGAGATTATAA | | |
| 19 | ATGGACGAATTTGAAATGATAAAGAGAAACACATCTGAAATTATCAGCGAGGAAGAGT<br>TAAGAGAGGTTTTAAAAAAAGATGAAAAATCTGCTCTAATAGGTTTTGAACCAAGTGG<br>TAAAATACATTTAGGGCATTATCTCCAAATAAAAAAGATGATTGATTTACAAAATGCT<br>GGATTTGATATAATTATATTGTTGACAGATTTAAACGCCTATTTAAACCAGAAAGGAG<br>AGTTGGATGAGATTAGAAAAATAGGAGATTATAACAAAAAAGTTTTTGAAGCAATGGG<br>GTTAAAGGCAAAATATGTTTATGGAAGTGAATTCCAGCTTGATAAGGATTATACACTG<br>AATGTCTATAGATTGGCTTTAAAAACTACCTTAAAAAGAGCAAGAAGGAGTATGGAAC<br>TTATAGCAAGAGAGGATGAAAATCCAAAGGTTGCTGAAGTTATCTATCCAATAATGCA<br>GGTTAATGATATTCATTATTTAGGCGTTGATGTTGCAGTTGGAGGGATGGAGCAGAGA<br>AAAATACACATGTTAGCAAGGGAGCTTTTACCAAAAAAGGTTGTTTGTATTCACAACC<br>CTGTCTTAACGGGTTTGGATGGAGAAGGAAAGATGAGTTCTTCAAAAGGGAATTTTAT<br>AGCTGTTGATGACTCTCCAGAAGAGATTAGGGCTAAGATAAAGAAAGCATACTGCCCA<br>GCTGGAGTTCTTGAAGGAAATCCAATAATGGAGATAGCTAAATACTTCCTTGAATATC<br>CTTTAACCATAAAAAGGCCAGAAAAATTTGGTGGAGATTTGACAGTTAATAGCTATGA<br>GGAGTTAGAGAGTTTATTTAAAAATAAGGAATTGCATCCAATGGATTTAAAAAATGCT<br>GTAGCTGAAGAACTTATAAAGATTTTAGAGCCAATTAGAAAGAGATTATAA | Mutant synthetase to incorporate m-acyl phenylalanine into proteins (Ketone 4-1) | RS |
| 20 | ATGGACGAATTTGAAATGATAAAGAGAAACACATCTGAAATTATCAGCGAGGAAGAGT<br>TAAGAGAGGTTTTAAAAAAAGATGAAAAATCTGCTCTAATAGGTTTTGAACCAAGTGG<br>TAAAATACATTTAGGGCATTATCTCCAAATAAAAAAGATGATTGATTTACAAAATGCT<br>GGATTTGATATAATTATATTGTTGACAGATTTAAAAGCCTATTTAAACCAGAAAGGAG<br>AGTTGGATGAGATTAGAAAAATAGGAGATTATAACAAAAAAGTTTTTGAAGCAATGGG<br>GTTAAAGGCAAAATATGTTTATGGAAGTGAATTCCAGCTTGATAAGGATTATACACTG<br>AATGTCTATAGATTGGCTTTAAAAACTACCTTAAAAAGAGCAAGAAGGAGTATGGAAC<br>TTATAGCAAGAGAGGATGAAAATCCAAAGGTTGCTGAAGTTATCTATCCAATAATGTC<br>AGTTAATGTAATTCATTATTTAGGCGTTGATGTTGTAGTTGGAGGGATGGAGCAGAGA<br>AAAATACACATGTTAGCAAGGGAGCTTTTACCAAAAAAGGTTGTTTGTATTCACAACC<br>CTGTCTTAACGGGTTTGGATGGAGAAGGAAAGATGAGTTCTTCAAAAGGGAATTTTAT<br>AGCTGTTGATGACTCTCCAGAAGAGATTAGGGCTAAGATAAAGAAAGCATACTGCCCA<br>GCTGGAGTTGTTGAAGGAAATCCAATAATGCAGATAGCTAAATACTTCCTTGAATATC<br>CTTTAACCATAAAAAGGCCAGAAAAATTTGGTGGAGATTTGACAGTTAATAGCTATGA<br>GGAGTTAGAGAGTTTATTTAAAAATAAGGAATTGCATCCAATGGATTTAAAAAATGCT<br>GTAGCTGAAGAACTTATAAAGATTTTAGAGCCAATTAGAAAGAGATTATAA | Mutant synthetase to incorporate m-acyl phenylalanine into proteins (Ketone 5-4) | RS |
| 21 | ATGGACGAATTTGAAATGATAAAGAGAAACACATCTGAAATTATCAGCGAGGAAGAGT<br>TAAGAGAGGTTTTAAAAAAAGATGAAAAATCTGCTCTAATAGGTTTTGAACCAAGTGG<br>TAAAATACATTTAGGGCATTATCTCCAAATAAAAAAGATGATTGATTTACAAAATGCT<br>GGATTTGATATAATTATATTGTTGCCAGATTTATCAGCCTATTTAAACCAGAAAGGAG<br>AGTTGGATGAGATTAGAAAAATAGGAGATTATAACAAAAAAGTTTTTGAAGCAATGGG<br>GTTAAAGGCAAAATATGTTTATGGAAGTGAATTCCAGCTTGATAAGGATTATACACTG<br>AATGTCTATAGATTGGCTTTAAAAACTACCTTAAAAAGAGCAAGAAGGAGTATGGAAC<br>TTATAGCAAGAGAGGATGAAAATCCAAAGGTTGCTGAAGTTATCTATCCAATAATGCA<br>GGTTAATGATATTCATTATTTAGGCGTTGATGTTGCAGTTGGAGGGATGGAGCAGAGA<br>AAAATACACATGTTAGCAACGGAGCTTTTACCAAAAAAGGTTGTTTGTATTCACAACC<br>CTGTCTTAACGGGTTTGGATGGAGAAGGAAAGATGAGTTCTTCAAAAGGGAATTTTAT<br>AGCTGTTGATGACTCTCCAGAAGAGATTAGGGCTAAGATAAAGAAAGCATACTGCCCA<br>GCTGGAGTTGTTGAAGGAAATCCAATAATGGAGATAGCTAAATACTTCCTTGAATATC<br>CTTTAACCATAAAAAGGCCAGAAAAATTTGGTGGAGATTTGACAGTTAATAGCTATGA<br>GGAGTTACAGAGTTTATTTAAAAATAAGGAATTGCATCCAATGGATTTAAAAAATGCT<br>GTAGCTGAAGAACTTATAAAGATTTTAGAGCCAATTAGAAAGAGATTATAA | Mutant synthetase to incorporate m-acyl phenylalanine into proteins (Ketone 6-8) | RS |
| 22 | ATGGACGAATTTGAAATGATAAAGAGAAACACATCTGAAATTATCAGCGAGGAAGAGT<br>TAAGAGAGGTTTTAAAAAAAGATGAAAAATCTGCTACAATAGGTTTTGAACCAACTGG<br>TAAAATACATTTAGGGCATTATCTCCAAATAAAAAAGATGATTGATTTACAAAATGCT<br>GGATTTGATATAATTATATTGTTGGCTGATTTACACGCCTATTTAAACCAGAAAGGAG<br>AGTTGGATGAGATTAGAAAAATAGGAGATTATAACAAAAAAGTTTTTGAAGCAATGGG<br>GTTAAAGGCAAAATATGTTTATGGAAGTGAATTCCAGCTTGATAAGGATTATACACTG<br>AATGTCTATAGATTGGCTTTAAAAACTACCTTAAAAAGAGCAAGAAGGAGTATGGAAC<br>TTATAGCAAGAGAGGATGAAAATCCAAAGGTTGCTGAAGTTATCTATCCAATAATGCA<br>GGTTAATGATATTCATTATGCAGGCGTTGATGTTGCAGTTGGAGGGATGGAGCAGAGA<br>AAAATACACATGTTAGCAAGGGAGCTTTTACCAAAAAAGGTTGTTTGTATTCACAACC<br>CTGTCTTAACGGGTTTGGATGGAGAAGGAAAGATGAGTTCTTCAAAAGGGAATTTTAT<br>AGCTGTTGATGACTCTCCAGAAGAGATTAGGGCTAAGATAAAGAAAGCATACTGCCCA<br>GCTGGAGTTGTTGAAGGAAATCCAATAATGGAGATAGCTAAATACTTCCTTGAATATC<br>CTTTAACCATAAAAAGGCCAGAAAAATTTGGTGGAGATTTGACAGTTAATAGCTATGA<br>GGAGTTAGAGAGTTTATTTAAAAATAAGGAATTGCATCCAATGCATTTAAAAAATGCT<br>GTAGCTGAAGAACTTATAAAGATTTTAGAGCCAATTAGAAAGAGATTATAA | Mutant synthetase to incorporate m-methoxy phenylalanine into proteins (OMe 1-6) | RS |

-continued

| SEQ ID # | Sequence | Notes | tRNA or RS |
|---|---|---|---|
| 23 | ATGGACGAATTTGAAATGATAAAGAGAAACACATCTGAAATTATCAGCGAGGAAGAGT<br>TAAGAGAGGTTTTAAAAAAAGATGAAAAATCTGCTACAATAGGTTTTGAACCAAGTGG<br>TAAAATACATTTAGGGCATTATCTCCAAATAAAAAAGATGATTGATTTACAAAATGCT<br>GGATTTGATATAATTATATTGTTGTCCGATTTACCAGCCTATTTAAACCAGAAAGGAG<br>AGTTGGATGAGATTAGAAAAATAGGAGATTATAACAAAAAAGTTTTTGAAGCAATGGG<br>GTTAAAGGCAAAATATGTTTATGGAAGTGAATTCCAGCTTGATAAGGATTATACACTG<br>AATGTCTATAGATTGGCTTTAAAAACTACCTTAAAAAGAGCAAGAAGGAGTATGGAAC<br>TTATAGCAAGAGAGGATGAAAATCCAAAGGTTGCTGAAGTTATCTATCCAATAATGCA<br>GGTTAATGATATTCATTATTTAGGCGTTGATGTTGCAGTTGGAGGGATGGAGCAGAGA<br>AAAATACACATGTTAGCAAGGGAGCTTTTACCAAAAAAGGTTGTTTGTATTCACAACC<br>CTGTCTTAACGGGTTTGGATGGAGAAGGAAAGATGAGTTCTTCAAAAGGGAATTTTAT<br>AGCTGTTGATCACTCTCCAGAAGAGATTAGGGCTAAGATAAAGAAAGCATACTGCCCA<br>GCTGGAGTTGTTGAAGGAAATCCAATAATGGAGATAGCTAAATACTTCCTTGAATATC<br>CTTTAACCATAAAAAGGCCAGAAAAATTTGGTGGAGATTTGACAGTTAATAGCTATGA<br>GGAGTTAGAGAGTTTATTTAAAAATAAGGAATTGCATCCAATGGATTTAAAAAATGCT<br>GTAGCTGAAGAACTTATAAAGATTTTAGAGCCAATTAGAAAGAGATTATAA | Mutant synthetases to incorporate m-methoxy phenylalanine into proteins (OMe 1-8) | RS |
| 24 | ATGGACGAATTTGAAATGATAAAGAGAAACACATCTGAAATTATCAGCGAGGAAGAGT<br>TAAGAGACGTTTTAAAAAAAGATGAAAAATCTGCTACAATAGGTTTTGAACCAAGTGG<br>TAAAATACATTTAGGGCATTATCTCCAAATAAAAAAGATGATTGATTTACAAAATGCT<br>GGATTTGATATAATTATATTGTTGGCTGATTTACACGCCTATTTAAACCAGAAAGGAG<br>AGTTGGATGAGATTAGAAAAATAGGAGATTATAACAAAAAAGTTTTTGAAGCAATGGG<br>GTTAAAGGCAAAATATGTTTATGGAAGTATGTTCCAGCTTGATAAGGATTATACACTG<br>AATGTCTATAGATTGGCTTTAAAAACTACCTTAAAAAGAGCAAGAAGGAGTATGGAAC<br>TTATAGCAAGAGAGGATGAAAATCCAAAGGTTGCTGAAGTTATCTATCCAATAATGCA<br>GGTTAATTCATCACATTATGACGGCGTTGATGTTGCAGTTGGAGGGATGGAGCAGAGA<br>AAAATACACATGTTAGCAAGGGAGCTTTTACCAAAAAAGGTTGTTTGTATTCACAACC<br>CTGTCTTAACGGGTTTGGATGGAGAAGGAAAGATGAGTTCTTCAAAAGGGAATTTTAT<br>AGCTGTTGATGACTCTCCAGAAGAGATTAGGGCTAAGATAAAGAAAGCATACTGCCCA<br>GCTGGAGTTGTTGAAGGAAATCCAATAATGGAGATAGCTAAATACTTCCTTGAATATC<br>CTTTAACCATAAAAAGGCCAGAAAAATTTGGTGGAGATTTGACAGTTAATAGCTATGA<br>GGAGTTAGAGAGTTTATTTAAAAATAAGGAATTGCATCCAATGGATTTAAAAAATGCT<br>GTAGCTGAAGAACTTATAAAGATTTTAGAGCCAATTAGAAAGAGATTATAA | Mutant synthetase to incorporate m-methoxy phenylalanine into proteins (OMe 2-7) | RS |
| 25 | ATGGACGAATTTGAAATGATAAAGAGAAACACATCTGAAATTATCAGCGAGGAAGAGT<br>TAAGAGAGGTTTTAAAAAAAGATGAAAAATCTGCTCAAATAGGTTTTGAACCAAGTGG<br>TAAAATACATTTAGGGCATTATCTCCAAATAAAAAAGATGATTGATTTACAAAATGCT<br>GGATTTGATATAATTATATTGTTGCCAGATTTACACGCCTATTTAAACCAGAAAGGAG<br>AGTTGGATGAGATTAGAAAAATAGGAGATTATAACAAAAAAGTTTTTGAAGCAATGGG<br>GTTAAAGGCAAAATATGTTTATGGAAGTGAATTCCAGCTTGATAAGGATTATACACTG<br>AATGTCTATAGATTGGCTTTAAAAACTACCTTAAAAAGAGCAAGAAGGAGTATGGAAC<br>TTATAGCAAGAGAGGATGAAAATCCAAAGGTTGCTGAAGTTATCTATCCAATAATGCA<br>GGTTAATGATATTCATTATTTAGGCGTTGATGTTGACGTTGGAGGGATGGAGCAGAGA<br>AAAATACACATGTTAGCAAGGGAGCTTTTACCAAAAAAGGTTGTTTGTATTCACAACC<br>CTGTCTTAACGGGTTTGGATGGAGAAGGAAAGATGAGTTCTTCAAAAGGGAATTTTAT<br>AGCTGTTGATGACTCTCCAGAAGAGATTAGGGCTAAGATAAAGAAAGCATACTGCCCA<br>GCTGGAGTTGTTGAAGGAAATCCAATAATGGAGATAGCTAAATACTTCCTTGAATATC<br>CTTTAACCATAAAAAGGCCAGAAAAATTTGGTGGAGATTTGACAGTTAATAGCTATGA<br>GGAGTTAGAGAGTTTATTTAAAAATAAGGAATTGCATCCAATGGATTTAAAAAATGCT<br>GTAGCTGAAGAACTTATAAAGATTTTAGAGCCAATTAGAAAGAGATTATAA | Mutant synthetase to incorporate m-methoxy phenylalanine into proteins (OMe 4-1) | RS |
| 26 | ATGGACGAATTTGAAATGATAAAGAGAAACACATCTGAAATTATCAGCGAGGAAGAGT<br>TAAGAGAGGTTTTAAAAAAAGATGAAAAATCTGCTCACATACGTTTTGAACCAAGTGG<br>TAAAATACATTTAGGGCATTATCTCCAAATAAAAAAGATGATTGATTTACAAAATGCT<br>GGATTTGATATAATTATATTGTTGGCTGATTTACACGCCTATTTAAACCAGAAAGCAG<br>AGTTGGATGAGATTAGAAAAATAGGAGATTATAACAAAAAAGTTTTTGAAGCAATGGG<br>GTTAAAGGCAAAATATGTTTATGGAAGTGCATTCCAGCTTGATAAGGATTATACACTG<br>AATGTCTATAGATTGGCTTTAAAAACTACCTTAAAAAGAGCAAGAAGGAGTATGGAAC<br>TTATAGCAAGAGAGGATGAAAATCCAAAGGTTGCTGAAGTTATCTATCCAATAATGCA<br>GGTTAATGGACACCATTATATAGGCGTTGATGTTGCAGTTGGAGGGATGGAGCAGAGA<br>AAAATACACATGTTAGCAAGGGAGCTTTTACCAAAAAAGGTTGTTTGTATTCACAACC<br>CTGTCTTAACGGGTTTGGATGGAGAAGGAAAGATGAGTTCTTCAAAAGGGAATTTTAT<br>AGCTGTTGATGACTCTCCAGAAGAGATTAGGGCTAAGATAAAGAAAGCATACTGCCCA<br>GCTGGAGTTGTTGAAGGAAATCCAATAATGGAGATAGCTAAATACTTCCTTGAATATC<br>CTTTAACCATAAAAAGGCCAGAAAAATTTGGTGGAGATTTGACAGTTAATAGCTATGA<br>GGAGTTAGAGAGTTTATTTAAAAATAAGGAATTGCATCCAATGGATTTAAAAAATGCT<br>GTAGCTGAAGAACTTATAAAGATTTTAGAGCCAATTAGAAAGAGATTATAA | Mutant synthetase to incorporate m-methoxy phenylalanine into proteins (OMe 4-8) | RS |
| 27 | ATGGACGAATTTGAAATGATAAAGAGAAACACATCTGAAATTATCAGCGAGGAAGAG<br>TTAAGAGAGGTTTTAAAAAAAGATGAAAAATCTGCTTACATAGGTTTTGAACCAAGT<br>GGTAAAATACATTTAGGGCATTATCTCCAAATAAAAAAGATGATTGATTTACAAAAT<br>GCTGGATTTGATATAATTATATTGTTGGCTGATTTACACGCCTATTTAAACCAGAAA<br>GCAGAGTTGGATGAGATTAGAAAAATAGGAGATTATAACAAAAAAGTTTTTGAAGCA<br>ATGGGGTTAAAGGCAAAATATGTTTATGGAAGTGCATTCCAGCTTGATAAGGATTAT<br>ACACTGAATGTCTATAGATTGGCTTTAAAAACTACCTTAAAAAGAGCAAGAAGGAGT<br>ATGGAACTTATAGCAAGAGAGGATGAAAATCCAAAGGTTGCTGAAGTTATCTATCCA<br>ATAATGCAGGTTAATTGCGCACATTATTTAGGCGTTGATCTTGCAGTTGGAGGGATG<br>GAGCAGAGAAAAATACACATGTTAGCAAGGGAGCTTTTACCAAAAAAGGTTGTTTGT<br>ATTCACAACCCTGTCTTAACGGGTTTGGATGGAGAAGGAAAGATGAGTTCTTCAAAA<br>GGGAATTTTATAGCTGTTGATGACTCTCCAGAAGAGATTAGGGCTAAGATAAAGAAA | Mutant synthetase to incorporate p-O-allyl tyrosine into proteins Allyl | RS |

-continued

| SEQ ID # | Sequence | Notes | tRNA or RS |
|---|---|---|---|
| | GCATACTGCCCAGCTGGAGTTGTTGAAGGAAATCCAATAATGGAGATAGCTAAATAC<br>TTCCTTGAATATCCTTTAACCATAAAAAGGCCAGAAAAATTTGGTGGAGATTTGACA<br>GTTAATAGCTATGAGGAGTTAGAGAGTTTATTTAAAAATAAGGAATTGCATCCAATG<br>GATTTAAAAAATGCTGTAGCTGAAGAACTTATAAAGATTTTAGAGCCAATTAGAAAG<br>AGATTATAA | | |
| 28 | ATGGACGAATTTGAAATGATAAAGAGAAACACATCTGAAATTATCAGCGAGGAAGAGT<br>TAAGAGAGGTTTTAAAAAAAGATGAAAAATCTGCTGGTATAGGTTTTGAACCAAGTGG<br>TAAAATACATTTAGGGCATTATCTCCAAATAAAAAAGATGATTGATTTACAAAATGCT<br>GGATTTGATATAATTATATTGTTGGCTGATTTACACGCCTATTTAAACCAGAAAGGAG<br>AGTTGGATGAGATTAGAAAAATAGGAGATTATAACAAAAAAGTTTTTGAAGCAATGGG<br>GTTAAAGGCAAAATATGTTTATGGAAGTTCCTTCCAGCTTGATAAGGATTATACACTG<br>AATGTCTATAGATTGGCTTTAAAAACTACCTTAAAAAGAGCAAGAAGGAGTATGGAAC<br>TTATAGAAGAGAGGATGAAAATCCAAAGGTTGCTGAAGTTATCTATCCAATAATGCAG<br>GTTAATACGAGTCATTATCTGGGCGTTGATGTTGCAGTTGGAGGGATGGAGCAGAGAA<br>AAATACACATCTTAGCAAGGGAGCTTTTACCAAAAAAGGTTGTTTGTATTCACAACCC<br>TGTCTTAACGGGTTTGGATGGAGAAGGAAAGATGAGTTCTTCAAAAGGGAATTTTATA<br>GCTGTTGATGACTCTCCAGAAGAGATTAGGGCTAAGATAAAGAAAGCATACTGCCCAG<br>CTGGAGTTGTTGAAGGAAATCCAATAATGGAGATAGCTAAATACTTCCTTGAATATCC<br>TTTAACCATAAAAAGGCCAGAAAAATTTGGTGGAGATTTGACAGTTAATAGCTATGAG<br>GAGTTAGAGAGTTTATTTAAAAATAAGGAATTGCATCCAATGGATTTAAAAAATGCTG<br>TAGCTGAAGAACTTATAAAGATTTTAGAGCCAATTAGAAAGAGATTA | Aminoacyl tRNA synthetase clone for the incorporation of p-benzoyl-L-phenylalanine (p-BpaRS(H6)) | RS |
| 29 | ATGGACGAATTTGAAATGATAAAGAGAAACACATCTGAAATTATCAGCGAGGAAGAGT<br>TAAGAGAGGTTTTAAAAAAAGATGAAAAATCTGCTACGATAGGTTTTGAACCAAGTGG<br>TAAAATACATTTAGGGCATTATCTCCAAATAAAAAAGATGATTGATTTACAAAATGCT<br>GGATTTGATATAATTATATTGTTGGCTGATTTACACGCCTATTTAAACCAGAAAGGAG<br>AGTTGGATGAGATTAGAAAAATAGGAGATTATAACAAAAAAGTTTTTGAAGCAATGGG<br>GTTAAAGGCAAAATATGTTTATGGAAGTAATTTCCAGCTTGATAACGATTATACACTG<br>AATGTCTATAGATTGGCTTTAAAAACTACCTTAAAAAGAGCAAGAAGGAGTATGGAAC<br>TTATAGAAGAGAGGATGAAAATCCAAAGGTTGCTGAAGTTATCTATCCAATAATGCAG<br>GTTAATCCGCTTCATTATCAGGGCGTTCATGTTGCAGTTGGAGGGATGGAGCAGAGAA<br>AAATACACATGTTAGCAAGGGAGCTTTTACCAAAAAAGGTTGTTTCTATTCACAACCC<br>TGTCTTAACGGGTTTGGATGGAGAAGGAAAGATGAGTTCTTCAAAAGGGAATTTTATA<br>GCTGTTGATGACTCTCCAGAAGAGATTAGGGCTAAGATAAAGAAAGCATACTGCCCAG<br>CTGGAGTTGTTGAAGGAAATCCAATAATGGAGATAGCTAAATACTTCCTTGAATATCC<br>TTTAACCATAAAAAGGCCAGAAAAATTTGGTGGAGATTTGACAGTTAATAGCTATGAG<br>GAGTTAGAGAGTTTATTTAAAAATAAGGAATTGCATCCAATGGATTTAAAAAATGCTG<br>TAGCTGAAGAACTTATAAAGATTTTAGAGCCAATTAGAAAGAGATTA | Aminoacyl tRNA synthetase clone for the incorporation of p-azido-phenylalanine (p-Az-PheRS(3)) | RS |
| 30 | ATGGACGAATTTGAAATGATAAAGAGAAACACATCTGAAATTATCAGCGAGGAAGAGT<br>TAAGAGAGGTTTTAAAAAAAGATGAAAAATCTGCTACGATAGGTTTTGAACCAAGTGG<br>TAAAATACATTTAGGGCATTATCTCCAAATAAAAAAGATGATTGATTTACAAAATGCT<br>GGATTTGATATAATTATATTGTTGGCTGATTTACACGCCTATTTAAACCAGAAAGGAG<br>AGTTGGATGAGATTAGAAAAATAGGAGATTATAACAAAAAAGTTTTTGAAGCAATGGG<br>GTTAAAGGCAAAATATGTTTATGGAAGTCTGTTCCAGCTTGATAAGGATTATACACTG<br>AATGTCTATAGATTGGCTTTAAAAACTACCTTAAAAAGAGCAAGAAGGAGTATGGAAC<br>TTATAGAAGAGAGGATGAAAATCCAAAGGTTGCTGAAGTTATCTATCCAATAATGCAG<br>GTTAATCCTCTTCATTATGAGGGCGTTGATGTTGCAGTTGGAGGGATGGAGCAGAGAA<br>AAATACACATGTTAGCAAGGGAGCTTTTACCAAAAAAGGTTGTTTGTATTCACAACCC<br>TGTCTTAACGGGTTTGGATGGAGAAGGAAAGATGAGTTCTTCAAAAGGGAATTTTATA<br>GCTGTTGATGACTCTCCAGAAGAGATTAGGGCTAAGATAAAGAAAGCATACTGCCCAG<br>CTGGAGTTGTTGAAGGAAATCCAATAATGGAGATAGCTAAATACTTCCTTGAATATCC<br>TTTAACCATAAAAAGGCCAGAAAAATTTGGTGGAGATTTGACAGTTAATAGCTATGAG<br>GAGTTAGAGAGTTTATTTAAAAATAAGGAATTGCATCCAATGGATTTAAAAAATGCTG<br>TAGCTGAAGAACTTATAAAGATTTTAGAGCCAATTAGAAAGAGATTA | Aminoacyl tRNA synthetase clone for the incorporation of p-azido-phenylalanine (p-Az-PheRS(6)) | RS |
| 31 | ATGGACGAATTTGAAATGATAAAGAGAAACACATCTGAAATTATCAGCGAGGAAGAGT<br>TAAGAGAGGTTTTAAAAAAAGATGAAAAATCTGCTCTTATAGGTTTTGAACCAAGTGG<br>TAAAATACATTTAGGGCATTATCTCCAAATAAAAAAGATGATTGATTTACAAAATGCT<br>GGATTTGATATAATTATATTGTTGGCTGATTTACACGCCTATTTAAACCAGAAAGGAG<br>AGTTGGATGAGATTAGAAAAATAGGAGATTATAACAAAAAAGTTTTTGAAGCAATGGG<br>GTTAAAGGCAAAATATGTTTATGGAAGTACTTTCCAGCTTGATAAGGATTATACACTG<br>AATGTCTATAGATTGGCTTTAAAAACTACCTTAAAAAGAGCAAGAAGGAGTATGGAAC<br>TTATAGAAGAGAGGATGAAAATCCAAAGGTTGCTGAAGTTATCTATCCAATAATGCAG<br>GTTAATCCGGTTCATTATCAGGGCGTTGATGTTGCAGTTGGAGCGATGGAGCAGAGAA<br>AAATACACATGTTAGCAAGGGAGCTTTTACCAAAAAAGATGGTTGTTTGTATTCACAACCC<br>TGTCTTAACGGGTTTGGATGGAGAAGGAAAGATGAGTTCTTCAAAAGGGAATTTTATA<br>GCTGTTGATGACTCTCCAGAAGAGATTAGGGCTAAGATAAAGAAAGCATACTGCCCAG<br>CTGGAGTTGTTGAAGGAAATCCAATAATGGAGATAGCTAAATACTTCCTTGAATATCC<br>TTTAACCATAAAAAGGCCAGAAAAATTTGGTGGAGATTTGACAGTTAATAGCTATGAG<br>GAGTTAGAGAGTTTATTTAAAAATAAGGAATTGCATCCAATGGATTTAAAAAATGCTG<br>TAGCTGAAGAACTTATAAAGATTTTAGAGCCAATTAGAAAGAGATTA | Aminoacyl tRNA synthetase clone for the incorporation of p-azido-phenylalanine (p-Az-PheRS(20) | RS |
| 32 | ATGGACGAATTTGAAATGATAAAGAGAAACACATCTGAAATTATCACCGAGGAAGAGT<br>TAAGAGAGGTTTTAAAAAAAGATGAAAAATCTGCTACTATAGGTTTTGAACCAAGTGG<br>TAAAATACATTTAGGGCATTATCTCCAAATAAAAAAGATGATTGATTTACAAAATGCT<br>GGATTTGATATAATTATATTGTTGGCTGATTTACACGCCTATTTAAACCAGAAAGGAG<br>AGTTGGATGAGATTAGAAAAATAGGAGATTATAACAAAAAAGTTTTTGAAGCAATGGG<br>GTTAAAGGCAAAATATGTTTATGGAAGTTCGTTCCAGCTTGATAAGGATTATACACTG<br>AATGTCTATAGATTGGCTTTAAAAACTACCTTAAAAAGAGCAAGAAGGAGTATGGAAC | Aminoacyl tRNA synthetase clone for the incorporation of p-azido-phenylalanine (p-Az-PheRS(24)) | RS |

-continued

| SEQ ID # | Sequence | Notes | tRNA or RS |
|---|---|---|---|
| | TTATAGAAGAGAGGATGAAAATCCAAAGGTTGCTGAAGTTATCTATCCAATAATGCAG | | |
| | GTTAATCCACTGCATTATCAGGGCGTTGATGTTGCAGTTGGAGGGATGGAGCAGAGAA | | |
| | AAATACACATGTTAGCAAGGGAGCTTTTACCAAAAAAGGTTGTTTGTATTCACAACCC | | |
| | TGTCTTAACGGGTTTGGATGGAGAAGGAAAGATGAGTTCTTCAAAAGGGAATTTTATA | | |
| | GCTGTTGATGACTCTCCAGAAGAGATTAGGGCTAAGATAAAGAAAGCATACTGCCCAG | | |
| | CTGGAGTTGTTGAAGGAAATCCAATAATGGAGATAGCTAAATACTTCCTTGAATATCC | | |
| | TTTAACCATAAAAAGGCCAGAAAAATTTGGTGGAGATTTGACAGTTAATAGCTATGAG | | |
| | GAGTTAGAGAGTTTATTTAAAAATAAGGAATTGCATCCAATGGATTTAAAAAATGCTG | | |
| | TAGCTGAAGAACTTATAAAGATTTTAGAGCCAATTAGAAAGAGATTA | | |
| 33 | ATGAGCGATT TCAGGATAAT TGAGGAGAAG TGGCAGAAGG CGTGGGAGAA | Archaeoglobus | RS |
| | GGACAGAATT TTTGAGTCCG ATCCTAATGA GAAGGAGAAG TTTTTTCTCA | fulgidus leucyl tRNA- | |
| | CAATTCCCTA TCCTTACCTT AATGGAAATC TTCACGCAGG TCACACGAGA | synthetase (AFLRS) | |
| | ACCTTCACAA TTGGCGATGC CTTCGCCAGA TACATGAGAA TGAAGGGCTA | | |
| | CAACGTTCTC TTTCCCCTCG GCTTTCATGT TACGGGCACC CCAATCATTG | | |
| | GCCTTGCGGA GCTCATAGCC AAGAGGGACG AGAGGACGAT AGAGGTTTAC | | |
| | ACCAAATACC ATGACGTTCC GCTGGAGGAC TTGCTTCAGC TCACAACTCC | | |
| | AGAGAAAATC GTTGAGTACT TCTCAAGGGA GGCGCTGCAG GCTTTGAAGA | | |
| | GCATAGGCTA CTCCATTGAC TGGAGGAGGG TTTTCACCAC AACCGATGAA | | |
| | GAGTATCAGA GATTCATCGA GTGGCAGTAC TGGAAGCTCA AGGAGCTTGG | | |
| | CCTGATTGTG AAGGGCACCC ACCCCGTCAG ATACTGCCCC CACGACCAGA | | |
| | ATCCTGTTGA AGACCACGAC CTTCTCGCTG GGGAGGAGGC AACTATTGTT | | |
| | GAATTTACCG TTATAAAGTT CAGGCTTGAA GATGGAGACC TCATTTTCCC | | |
| | CTGTGCAACT CTCCGTCCCG AAACCGTGTT TGGCGTCACG AACATCTGGG | | |
| | TAAAGCCGAC AACCTACGTA ATTGCCGAGG TGGATGGGGA AAAGTGGTTT | | |
| | GTGAGCAAAG AGGCTTACGA GAAGCTCACC TACACGGAGA AAAAAGTCAG | | |
| | GCTGCTGGAG GAGGTTGATG CGTCGCAGTT CTTCGGCAAG TACGTCATAG | | |
| | TCCCGCTGGT AAACAGAAAA GTGCCAATTC TGCCTGCAGA GTTTGTTGAC | | |
| | ACCGACAACG CAACAGGAGT TGTGATGAGC GTTCCCGCAC ACGCTCCTTT | | |
| | TGACCTGGCT GCCATTGAGG ACTTGAAGAG AGACGAGGAA ACGCTGGCGA | | |
| | AGTACGGAAT TGACAAAAGC GTTGTAGAGA GCATAAAGCC AATAGTTCTG | | |
| | ATTAAGACGG ACATTGAAGG TGTTCCTGCT GAGAAGCTAA TAAGAGAGCT | | |
| | TGGAGTGAAG AGCCAGAAGG ACAAGGAGCT GCTGGATAAG GCAACCAAGA | | |
| | CCCTCTACAA GAAGGAGTAC CACACGGGAA TCATGCTGGA CAACACGATG | | |
| | AACTATGCTG GAATGAAAGT TTCTGAGGCG AAGGAGAGAG TTCATGAGGA | | |
| | TTTGGTTAAG CTTGGCTTGG GGGATGTTTT CTACGACTTC AGCGAGAAGC | | |
| | CCGTAATCTG CAGGTGCGGA ACGAAGTGCG TTGTTAAGGT TGTTAGGGAC | | |
| | CAGTGGTTCC TGAACTACTC CAACAGAGAG TGGAAGGAGA AGGTTCTGAA | | |
| | TCACCTTGAA AAGATGCGAA TCATCCCCGA CTACTACAAG GAGGAGTTCA | | |
| | GGAACAAGAT TGAGTGGCTC AGGGACAAGG CTTGTGCCAG AAGGAAGGGG | | |
| | CTTGGAACGA GAATTCCGTG GGATAAGGAG TGGCTCATCG AGAGCCTTTC | | |
| | AGACTCAACA ATCTACATGG CCTACTACAT CCTTGCCAAG TACATCAACG | | |
| | CAGGATTGCT CAAGGCCGAG AACATGACTC CCGAGTTCCT CGACTACGTG | | |
| | CTGCTGGGCA AAGGTGAGGT TGGGAAAGTT GCGGAAGCTT CAAAACTCAG | | |
| | CGTGGAGTTA ATCCAGCAGA TCAGGGACGA CTTCGAGTAC TGGTATCCCG | | |
| | TTGACCTAAG AAGCAGTGGC AAGGACTTGG TTGCAAACCA CCTGCTCTTC | | |
| | TACCTCTTCC ACCACGTCGC CATTTTCCCG CCAGATAAGT GGCCGAGGGC | | |
| | AATTGCCGTA AACGGATACG TCAGCCTTGA GGGCAAGAAG ATGAGCAAGA | | |
| | GCAAAGGGCC CTTGCTAACG ATGAAGAGGG CGGTGCAGCA GTATGGTGCG | | |
| | GATGTGACGA GGCTCTACAT CCTCCACGCT GCAGAGTACG ACAGCGATGC | | |
| | GGACTGGAAG AGCAGAGAGG TTGAAGGGCT TGCAAACCAC CTCAGGAGGT | | |
| | TCTACAACCT CGTGAAGGAG AACTACCTGA AAGAGGTGGG AGAGCTAACA | | |
| | ACCCTCGACC GCTGGCTTGT GAGCAGGATG CAGAGGGCAA TAAAGGAAGT | | |
| | GAGGGAGGCT ATGGACAACC TGCAGACGAG GAGGGCCGTG AATGCCGCCT | | |
| | TCTTCGAGCT CATGAACGAC GTGAGATGGT ATCTGAGGAG AGGAGGTGAG | | |
| | AACCTCGCTA TAATACTGGA CGACTGGATC AAGCTCCTCG CCCCCTTTGC | | |
| | TCCGCACATT TGCGAGGAGC TGTGGCACTT GAAGCATGAC AGCTACGTCA | | |
| | GCCTCGAAAG CTACCCAGAA TACGACGAAA CCAGGGTTGA CGAGGAGGCG | | |
| | GAGAGAATTG AGGAATACCT CCGAAACCTT GTTGAGGACA TTCAGGAAAT | | |
| | CAAGAAGTTT GTTAGCGATC CGAAGGAGGT TTACATTGCT CCCGCCGAAG | | |
| | ACTGGAAGGT TAAGGCAGCA AAGGTCGTTG CTGAAAGCGG GGATGTTGGG | | |
| | GAGGCGATGA AGCAGCTTAT GCAGGACGAG GAGCTTAGGA AGCTCGGCAA | | |
| | AGAAGTGTCA AATTTCGTCA AGAAGATTTT CAAAGACAGA AAGAAGCTGA | | |
| | TGCTAGTTAA GGAGTGGGAA GTTCTGCAGC AGAACCTGAA ATTTATTGAG | | |
| | AATGAGACCG GACTCAAGGT TATTCTTGAT ACTCAGAGAG TTCCTGAGGA | | |
| | GAAGAGGAGG CAGGCAGTTC CGGGCAAGCC CGCGATTTAT GTTGCTTAA | | |
| 34 | GTGGATATTG AAAGAAAATG GCGTGATAGA TGGAGAGATG CTGGCATATT | Methanobacterium | RS |
| | TCAGGCTGAC CCTGATGACA GAGAAAAGAT ATTCCTCACA GTCGCTTACC | thermoautotrophicum | |
| | CCTACCCCAG TGGTGCGATG CACATAGGAC ACGGGAGGAC CTACACTGTC | leucyl tRNA- | |
| | CCTGATGTCT ATGCACGGTT CAAGAGGATG CAGGGCTACA ACGTCCTGTT | synthetase (MtLRS) | |
| | TCCCATGGCC TGGCATGTCA CAGGGGCCCC TGTCATAGGG ATAGCGCGGA | | |
| | GGATTCAGAG GAAGGATCCC TGGACCCTCA AAATCTACAG GGAGGTCCAC | | |
| | AGGGTCCCCG AGGATGAGCT TGAACGTTTC AGTGACCCTG AGTACATAGT | | |
| | TGAATACTTC AGCAGGGAAT ACCGGTCTGT TATGGAGGAT ATGGGCTACT | | |
| | CCATCGACTG GAGGCGTGAA TTCAAAACCA CGGATCCCAC CTACAGCAGG | | |
| | TTCATACAGT GGCAGATAAG GAAGCTGAGG GACCTTGGCC TCGTAAGGAA | | |
| | GGGCGCCCAT CCTGTTAAGT ACTGCCCTGA ATGTGAAAAC CCTGTGGGTG | | |

-continued

| SEQ ID # | Sequence | Notes | tRNA or RS |
|---|---|---|---|
| | ACCATGACCT CCTTGAGGGT GAGGGGGTTG CCATAAACCA GCTCACACTC<br>CTCAAATTCA AACTTGGAGA CTCATACCTG GTCGCAGCCA CCTTCAGGCC<br>CGAGACAATC TATGGGGCCA CCAACCTCTG GCTGAACCCT GATGAGGATT<br>ATGTGAGGGT TGAAACAGGT GGTGAGGAGT GGATAATAAG CAGGGCTGCC<br>GTGGATAATC TTTCACACCA GAAACTGGAC CTCAAGGTTT CCGGTGACGT<br>CAACCCCGGG GACCTGATAG GGATGTGCGT GGAGAATCCT GTGACGGGCC<br>AGGAACACCC CATACTCCCG GCTTCCTTCG TTGACCCTGA ATATGCCACA<br>GGTGTTGTGT TCTCTGTCCC TGCACATGCC CCTGCAGACT TCATAGCCCT<br>TGAGGACCTC AGGACAGACC ATGAACTCCT TGAAAGGTAC GGTCTTGAGG<br>ATGTGGTTGC TGATATTGAG CCCGTGAATG TCATAGCAGT GGATGGCTAC<br>GGTGAGTTCC CGGCGGCCGA GGTTATAGAG AAATTTGGTG TCAGAAACCA<br>GGAGGACCCC CGCCTTGAGG ATGCCACCGG GGAGCTATAC AAGATCGAGC<br>ATGCGAGGGG TGTTATGAGC AGCCACATCC CTGTCTATGG TGGTATGAAG<br>GTCTCTGAGG CCCGTGAGGT CATCGCTGAT GAACTGAAGG ACCAGGGCCT<br>TGCAGATGAG ATGTATGAAT TCGCTGAGCG ACCTGTTATA TGCCGCTGCG<br>GTGGCAGGTG CGTTGTGAGG GTCATGGAGG ACCAGTGGTT CATGAAGTAC<br>TCTGATGACG CCTGGAAGGA CCTCGCCCAC AGGTGCCTCG ATGGCATGAA<br>GATAATACCC GAGGAGGTCC GGGCCAACTT TGAATACTAC ATCGACTGGC<br>TCAATGACTG GGCATGTTCA AGGAGGATAG GCCTTGGAAC AAGGCTGCCC<br>TGGGATGAGA GGTGGATCAT CGAACCCCTC ACAGACTCAA CAATCTACAT<br>GGCATATTAC ACCATCGCAC ACCGCCTCAG GGAGATGGAT GCCGGGGAGA<br>TGGACGATGA GTTCTTTGAT GCCATATTCC TAGATGATTC AGGAACCTTT<br>GAGGATCTCA GGGAGGAATT CCGGTACTGG TACCCCCTTG ACTGGAGGCT<br>CTCTGCAAAG GACCTCATAG GCAATCACCT GACATTCCAT ATATTCCACC<br>ACTCAGCCAT ATTCCCTGAG TCAGGGTGGC CCCGGGGGGC TGTGGTCTTT<br>GGTATGGGCC TTCTTGAGGG CAACAAGATG TCATCCTCCA AGGGCAACGT<br>CATACTCCTG AGGGATGCCA TCGAGAAGCA CGGTGCAGAC GTGGTGCGGC<br>TCTTCCTCAT GTCCTCAGCA GAGCCATGGC AGGACTTTGA CTGGAGGGAG<br>AGTGAGGTCA TCGGGACCCG CAGGAGGATT GAATGGTTCA GGGAATTCGG<br>AGAGAGGGTC TCAGGTATCC TGGATGGTAG GCCAGTCCTC AGTGAGGTTA<br>CTCCAGCTGA ACCTGAAAGC TTCATTGGAA GGTGGATGAT GGGTCAGCTG<br>AACCAGAGGA TACGTGAAGC CACAAGGGCC CTTGAATCAT TCCAGACAAG<br>AAAGGCAGTT CAGGAGGCAC TCTATCTCCT TAAAAAGGAT GTTGACCACT<br>ACCTTAAGCG TGTTGAGGGT AGAGTTGATG ATGAGGTTAA ATCTGTCCTT<br>GCAAACGTTC TGCACGCCTG GATAAGGCTC ATGGCTCCAT TCATACCCTA<br>CACTGCTGAG GAGATGTGGG AGAGGTATGG TGGTGAGGGT TTTGTAGCAG<br>AAGCTCCATG GCCTGACTTC TCAGATGATG CAGAGAGCAG GGATGTGCAG<br>GTTGCAGAGG AGATGGTCCA GAATACCGTT AGAGACATTC AGGAAATCAT<br>GAAGATCCTT GGATCCACCC CGGAGAGGGT CCACATATAC ACCTCACCAA<br>AATGGAAATG GGATGTGCTA AGGGTCGCAG CAGAGGTAGG AAAACTAGAT<br>ATGGGCTCCA TAATGGGAAG GGTTTCAGCT GAGGGCATCC ATGATAACAT<br>GAAGGAGGTT GCTGAATTTG TAAGGAGGAT CATCAGGGAC CTTGGTAAAT<br>CAGAGGTTAC GGTGATAGAC GAGTACAGCG TACTCATGGA TGCATCTGAT<br>TACATTGAAT CAGAGGTTGG AGCCAGGGTT GTGATACACA GCAAACCAGA<br>CTATGACCCT GAAAACAAGG CTGTGAATGC CGTTCCCCTG AAGCCAGCCA<br>TATACCTTGA ATGA | | |
| 35 | MDEFEMIKRNTSEIISEEELREVLKKDEKSAQIGFEPSGKIHLGHYLQIKKMIDLQNA<br>GFDIIILLADLHAYLNQKGELDEIRKIGDYNKKVFEANGLKAKYVYGSTFQLDKDYTL<br>NVYRLALKTTLKRARRSMELIAREDENPKVAEVIYPIMQVNAIHYPGVDVAVGGMEQR<br>KIHMLARELLPKKVVCIHNPVLTGLDGEGKMSSSKGNFIAVDDSPEEIRAKIKKAYCP<br>AGVVEGNPIMEIAKYFLEYPLTIKRPEKFGGDLTVSSYEELESLFKNKELHPMDLKNA<br>VAEELIKILEPIRKRL | mutant TyrRS (LWJ16) | RS |
| 36 | MDEFEMIKRNTSEIISEEELREVLKKDEKSALIGFEPSGKIHLGHYLQIKKMIDLQNA<br>GFDIIILLADLHAYLNQKGELDEIRKIGDYNKKVFEANGLKAKYVYGSEFQLDKDYTL<br>NVYRLALKTTLKRARRSMELIAREDENPKVAEVIYPIMQVNAIHYPGVDVAVGGMEQR<br>KIHMLARELLPKKVVCIHNPVLTGLDGEGKMSSSKGNFIAVDDSPEEIRAKIKKAYCP<br>AGVVEGNPIMEIAKYFLEYPLTI | TyrRS (SS12) | RS |
| 37 | MDEFEMIKRNTSEIISEEELREVLKKDEKSAGIGFEPSGKIHLGHYLQIKKMIDLQN<br>AGFDIIILLADLHAYLNQKGELDEIRKIGDYNKKVFEANGLKAKCAYGSPFQLDKDY<br>TLNVYRLALKTTLKRARRSMELIAREDENPKVAEVIYPIMQVNGYHYLGVDVAVGGM<br>EQRKIHMLARELLPKKVVCIHNPVLTGLDGEGKMSSSKGNFIAVDDSPEEIRAKIKK<br>AYCPAGVVEGNPIMEIAKYFLEYPLTIKRPEKFGGDLTVNSYEELESLFKNKELHPM<br>DLKNAVAEELIKILEPIRKRL | p-iPr-PheRS | RS |
| 38 | MDEFEMIKRNTSEIISEEELREVLKKDEKSAQIGFEPSGKIHLGHYLQIKKMIDLQN<br>AGFDIIILLADLHAYLNQKGELDEIRKIGDYNKKVFEAMGLKAKYVYGSPFQLDKDY<br>TLNVYRLALKTTLKRARRSMELIAREDENPKVAEVIYPIMQVNGYHYLGVDVAVGGM<br>EQRKIHMLARELLPKKVVCIHNPVLTGLDGEGKMSSSKGNFIAVDDSPEEIRAKIKK<br>AYCPAGVVEGNPIMEIAKYFLEYPLTIKRPEKFGGDLTVNSYEELESLFKNKELHPM<br>DLKNAVAEELIKILEPIRKRL | p-$NH_2$-PheRS(1) | RS |
| 39 | MDEFEMIKRNTSEIISEEELREVLKKDEKSATIGFEPSGKIHLGHYLQIKKMIDLQNA<br>GFDIIILLADLHAYLMQKGELDEIRKIGDYNKKVFEAMGLKAKYVYGSTPQLDKDYTL<br>NVYRLALKTTLKRARRSMELIAREDENPKVAEVIYPIMQVNPLHYAGVDVAVGOMEQR<br>KIHMLARELLPKKVVCIHNPVLTGLDGEGKMSSSKGNFIAVDDSPEEIRAKIKKAYCP<br>AGVVEGNPIMEIAKYFLEYPLTIKRPEKFGGDLTVNSYEELESLFKNKELHPMDLKNA<br>VAEELIKILEPIRKRL | p-$NH_2$-PheRS(2) | RS |

-continued

| SEQ ID # | Sequence | Notes | tRNA or RS |
|---|---|---|---|
| 40 | MDEFEMIKRNTSEIISEEELREVLKKDEKSAHIGFEPSGKIHLGHYLQIKKMIDLQN<br>AGFDIIILLADLHAYLNQKGELDEIRKIGDYNKKVFEANGLKAKYVYGSEFQLDKDY<br>TLNVYRLALKTTLKRARRSMELIAREDENPKVAEVIYPIMQVNRPHYLGVDVAVGGM<br>EQRKIHMLARELLPKKVVCIHNPVLTGLDGEGKMSSSKGNFIAVDDSPEEIRAKIKK<br>AYCPAGVVEGNPIMEIAKYFLEYPLTIKRPEKFGGDLTVNSYEELESLFKNKELHPM<br>DLKNAVAEELIKILEPIRKRL | p-NH$_2$-PheRS(3a) | RS |
| 41 | MDEFEMIKRNTSEIISEEELREVLKKDEKSAQIGFEPSGKIELGEYLQIKKMIDLQN<br>AGFDIIILLADLHAYLNQKGELDEIRKIGDYNKKVFEAMGLKAKYVYGSPFQLDKDY<br>TLNVYRLALKTTLKRARRSMELIAREDENPKVAEVIYPIMQVNQSHYDOVDVAVGGM<br>EQRKIHMLARELLPKKVVCIHNPVLTGLDGEGKMSSSKGNFIAVDDSPEEIRAKIEK<br>AYCPAGVVEGNPIMEIAKYFLEYPLTIKRPEKFGGDLTVNSYEELESLFKNKELHPM<br>DLKNAVAEELIKILEPIRKRL | p-NH$_2$-PheRS(3b) | RS |
| 42 | MDEFEMIKRNTSEIISEEELREVLKKDEKSASIGFEPSGKIHLGHYLQIKKNIDLQN<br>AGFDIIILLADLHAYLNQKGELDEIRKIGDYNKKVFEAMGLKAKYVYGSTFQLDKDY<br>TLNVYRLALKTTLKRARRSMELIAREDENPKVAEVIYPIMQVNTYHYAGVDVAVGGM<br>EQRKIHMLARELLPKKVVCIHNPVLTGLDGEGKMSSSKGNFIAVDDSPEEIRAKIKK<br>AYCPAGVVEGMPIMEIAKYFLEYPLTIKRPEKFGGDLTVNSYEELESLFKNKELHPM<br>DLKNAVAEELIKILEPIRKRL | O-Allyl-TyrRS(1) | RS |
| 43 | MDEFEMIKRNTSEIISEEELREVLKKDEKSAPIGFEPSGKIHLGHYLQIKKMIDLQN<br>AGFDIIILLADLRAYLNQKGELDEIRKIGDYMKKVFEAMGLKAKYVYGSMFQLDKDY<br>TLMVYRLALKTTLKRARRSMELIAREDENPKVAEVIYPIMQVNNTHYGGVDVAVGGM<br>EQRKIHMLARELLPKKVVCIHMPVLTGLDGEGKMSSSKGNFIAVDDSPEEIRAKIKK<br>AYCPAGVVEGNPIMEIAKYFLEYPLTIKRPEKFGGDLTVMSYEELESLFKNKELHPM<br>DLKNAVAEELIKILEPIRKRL | O-Allyl-TyrRS(3) | RS |
| 44 | MDEFEMIKRNTSEIISEEELREVLKKDEKSATIGFEPSGKIMLGHYLQIKKMIDLQN<br>AGFDIIILLADLHAYLNQKGELDEIRKIGDYNKKVFEAMGLKAKYVYCSHFQLDKDY<br>TLNVYRLALKTTLKRARRSMELIAREDENPKVAEVIYPIMQVNQTHYEGVDVAVGGM<br>EQRKIHMLARELLPKKVVCIHNPVLTGLDGEGKMSSSKGNFIAVDDSPEEIRAKIKK<br>AYCPAGVVEGNPIMEIAKYFLEYPLTIKRPEKFGGDLTVNSYEELESLFKNKELHPM<br>DLKNAVAEELIKILEPIRKRL | O-Allyl-TyrRS(4) | RS |
| 45 | MDEFEMIKRNTSEIISEEELREVLKKDEKSAHIGFEPSGKIHLGHYLQIKKMIDLQN<br>AGFDIIILLADLHAYLNQKGELDEIRKIGDYNKKVFEAMGLKAKYVYGSKFQLDKDY<br>TLNVYRLALKTTLKRARRSMELIAREDENPKVAEVIYPIMQVNPCEYHGVDVAVGGM<br>EQRKIHMLARELLPKKVVCIHNPVLTGLDGEGKNSSSKGNFIAVDDSPEEIRAKIKK<br>AYCPAGVVEGNPIMEIAKYFLEYPLTIKRPEKFGGDLTVNSYEELESLFKNKELHPM<br>DLKNAVAEELIKILEPIRKRL | p-Br-PheRS | RS |
| 46 | MDEFEMIKRNTSEIISEEELREVLKKDEKSAAIGFEPSGKIMLGHYLQIKKMIDLQN<br>AGFDIIILLADLHAYLNQKGELDEIRKIGDYNKKVFEAMGLKAKYVYGSRFQLDKDY<br>TLNVYRLALKTTLKRARRSMELIAREDEMPKVAEVIYPIMQVNVYHYDGVDVAVGGM<br>EQRKIHMLARELLPKKVVCIHNPVLTGLDGEGKMSSSKGNFIAVDDSPEEIRAKIKK<br>AYCPAGVVEGNPIMEIAKYFLEYPLTIKRPEKFGGDLTVNSYEELESLFKNKELHPM<br>DLKNAVAEELIKILEPIRKRL | p-Az-PheRS(1) | RS |
| 47 | MDEFEMIKRNTSEIISEEELREVLKKDEKSAGIGFEPSGKIHLGHYLQIKKMIDLQN<br>AGFDIIILLADLHAYLNQKGELDEIRKIGDYNKKVFEAMGLKAKYVYGSTFQLDKDY<br>TLNVYRLALKTTLKRARRSMELIAREDENPKVAEVIYPIMQVNTYYYLGVDVAVGGM<br>EQRKIHMLARELLPKKVVCIHNPVLTGLDGEGKMSSSKGNFIAVDDSPEEIRAKIKK<br>AYCPAGVVEGNPIMEIAKYFLEYPLTIKRPEKFGGDLTVNSYEELESLFKNKELHPM<br>DLKNAVAEELIKILEPIRKRL | p-Az-PheRS(3) | RS |
| 48 | MDEFEMIKRNTSEIISEEELREVLKKDEKSALIGFEPSGKIHLGHYLQIKKMIDLQNA<br>GFDIIILLADLHAYLNQKGELDEIRKIGDYNKKVFEANGLKAKYVYGSPFQLDKDYTL<br>NVYRLALKTTLKRARRSMELIAREDENPKVAEVIYPIMQVNQIHSSGVDVAVGGMEQR<br>KIHMLARELLPKKVVCIHNPVLTGLDGEGKMSSSKGNFIAVDDSPEEIRAKIKKAYCP<br>AGVVEGNPIMEIAKYFLEYPLTIKRPEKFGGDLTVMSYEELESLFKNKELHPMDLKNA<br>VAEELIKILEPIRKRL | p-Az-PheRS(5) | RS |
| 49 | MDEFEMIKRNTSEIISEEELREVLKKDEKSADIGFEPSGKIHLGHYLQIKKMIDLQNA<br>GFDIIILLADLHAYLNQKGELDEIRKIGDYNKKVFEANGLKAKYVYGSEFQLDKDYTL<br>NVYRLALKTTLKRARRSMELIAREDEMPKVAEVIYPIMQVNGMHYQGVDVAVGGMEQR<br>KIHMLARELLPKKVVCIHNPVLTGLDGEGKMSSSKGMFIAVDDSPEEIRAKIKKAYCP<br>AGVVEGMPIMEIAKYFLEYPLTIKPEKFGGDLTVNSYEELESLFKNKELHPMDLKNA<br>VAEELIKILEPIRKRL# | Mutant synthetase to incorporate m-acyl phenylalanine into proteins (Ketone 3-4) | RS |
| 50 | MDEFEMIKRNTSEIISEEELREVLKKDEKSAYIGFEPSGKIHLGHYLQIKKMIDLQNA<br>GFDIIILLADLHAYLNQKGELDEIRKIGDYNKKVFEANGLKAKYVYGSEFQLDKDYTL<br>NVYRLALKTTLKRARRSMELIAREDENPKVAEVIYPIMQVNDIHYTGVDVAVGGMEQR<br>KIHMLARELLPKKVVCIHNPVLTGLDGEGKMSSSKGNFIAVDDSPEEIRAKIKKAYCP<br>AGVVEGNPIMEIAKYFLEYPLTIKRPEKFGGDLTVNSYEELESLFKNKELHPMDLKNA<br>VAEELIKILEPIRKRL# | Mutant synthetase to incorporate m-acyl phenylalanine into proteins (Ketone 3-7) | RS |
| 51 | MDEFEMIKRNTSEIISEEELREVLKKDEKSALIGFEPSGKIHLGHYLQIKKMIDLQNA<br>GFDIIILLADLHAYLNQKGELDEIRKIGDYNKKVFEANGLKAKYVYGSEFQLDKDYTL<br>NVYRLALKTTLKRARRSMELIAREDENPKVAEVIYPIMQVNDIHYLGVDVAVGGMEQR<br>KIHMLARELLPKKVVCIHNPVLTGLDGEGKMSSSKGNFIAVDDSPEEIRAKIKKAYCP<br>AGVVEGNVIMEIAKYFLEYPLTIKRPEKFGGDLTVNSYEELESLFKNKELHPMDLKNA<br>VAEELIKILEPIRKRL# | Mutant synthetase to incorporate m-acyl phenylalanine into proteins (Ketone 4-1) | RS |
| 52 | MDEFEMIKRNTSEIISEEELREVLKKDEKSALIGFEPSGKIHLGHYLQIKKMIDLQNA<br>GFDIIILLTDLKAYLNQKGELDEIRKIGDYNKKVFEANGLKAKYVYGSEFQLDKDYTL<br>NVYRLALKTTLKRARRSMELIAREDENPKVAEVIYPIMSVNVIHYLGVDVVVGGMEQR<br>KIHMLARELLPKKVVCIHNPVLTGLDGEGKMSSSKGNFIAVDDSPEEIRAKIKKAYCP | Mutant synthetase to incorporate m-acyl phenylalanine into proteins (Ketone 5-4) | RS |

-continued

| SEQ ID # | Sequence | Notes | tRNA or RS |
|---|---|---|---|
| | AGVVEGNPIMEIAKYFLEYPLTIKRPEKFGGDLTVNSYEELESLFKNKELHPMDLKNA<br>VAEELIKILEPIRKRL# | | |
| 53 | MDEFEMIKRNTSEIISEEELREVLKKDEKSALIGFEPSGKIHLGHYLQIKKMIDLQNA<br>GFDIIILLPDLSAYLNQKGELDEIRKIGDYNKKVFEAMGLKAKYVYGSEFQLDKDYTL<br>NVYRLALKTTLKRARRSMELIAREDENPKVAEVIYPIMQVNDIHYLGVDVAVGGMEQR<br>KIHMLARELLPKKVVCIHNPVLTGLDGEGKMSSSKGNFIAVDDSPEEIRAKIKKAYCP<br>AGVVEGNPIMEIAKYFLEYPLTIKRPEKFGGDLTVNSYEELESLFKNKELHPMDLKNA<br>VAEELIKILEPIRKRL# | Mutant synthetase to incorporate m-acyl phenylalanine into proteins (Ketone 6-8) | RS |
| 54 | MDEFEMIKRNTSEIISEEELREVLKKDEKSATIGFEPSGKIHLGHYLOIKICNIDLQNA<br>GFDIIILLADLHAYLNQKGELDEIRKIGDYNKKVFEAMGLKAKYVYGSEFQLDKDYTL<br>NVYRLALKTTLKRARRSMELIAREDENPKVAEVIYPIMQVNDIHYAGVDVAVGGMEQR<br>KIHMLARELLPKKVVCIHNPVLTGLDGEGKMSSSKGNFIAVDDSPEEIRAKIKKAYCP<br>AGVVEGNPIMEIAKYFLEYPLTIKRPEKFGGDLTVNSYEELESLFKNKELHPMDLKNA<br>VAEELIKILEPIRKRL# | Mutant synthetase to incorporate m-methoxy phenylalanine into proteins (OMe 1-6) | RS |
| 55 | MDEFEMIKRNTSEIISEEELREVLKKDEKSATIGFEPSGKIHLGHYLQIKKMIDLQNA<br>GFDIIILLSDLPAYLNQKGELDEIRKIGDYNKKVFEANGLKAKYVYGSEFQLDKDYTL<br>NVYRLALKTTLKRARRSMELIAREOENPKVAEVIYPIMQVNDIHYLGVDVAVGGMEQR<br>KIHMLARELLPKKVVCIHNPVLTGLDGEGKMSSSKGNFIAVDDSPEEIRAKIKKAYCP<br>AGVVEGNPIMEIAKYFLEYPLTIKRPEKFGGDLTVNSYEELESLFKNKELHPMDLKNA<br>VAEELIKILEPIRKRL# | Mutant synthetase to incorporate m-methoxy phenylalanine into proteins (OMe 1-8) | RS |
| 56 | MDEFEMIKRNTSEIISEEELREVLKKDEKSATIGFEPSGKIHLGHYLQIKKMIDLQNA<br>GFDIIILLADLHAYLNQKGELDEIRKIGDYNKKVFEAMGLKAKYVYGSMFQLDKDYTL<br>NVYRLALKTTLKRARRSMELIAREDENPKVAEVIYPIMQVNSSHYDGVDVAVGGMEQR<br>KIHMLARELLPKKVVCIHNPVLTGLDGEGKMSSSKGNFIAVDOSPEEIRAKIKKAYCP<br>AGVVEGNPIMEIAKYFLEYPLTIKRPEKFGGDLTVNSYEELESLFKNKELHPMDLKNA<br>VAEELIKILEPIRKRL# | Mutant synthetase to incorporate m-methoxy phenylalanine into proteins (OMe 2-7) | RS |
| 57 | MDEFEMIKRNTSEIISEEELREVLKKDEKSAQIGFEPSGKIHLGNYLQIKKNIDLQNA<br>GFDIIILLPDLHAYLNQKGELDEIRKIGDYNKKVFEANGLKAKYVYGSEFQLDKDYTL<br>NVYRLALKTTLKRARRSMELIAREDENPKVAEVIYPIMQVNDIHYLGVDVDVGGMEQR<br>KIHMLARELLPKKVVCIHNPVLTGLDGEGKMSSSKGNFIAVDDSPEEIRAKIKKAYCP<br>AGVVEGNPIMEIAKYFLEYPLTIKRPEKFGGDLTVNSYEELESLFKNKELHPMDLKNA<br>VAEELIKILEPIRKRL# | Mutant synthetase to incorporate m-methoxy phenylalanine into proteins OMe4-1 | RS |
| 58 | MDEFEMIKRNTSEIISEEELREVLKKDEKSAHIGFEPSGKIHLGHYLQIKKNIDLQNA<br>GFDIIILLADLHAYLNQKGELDEIRKIGDYNKKVFEANGLKAKYVYGSAFQLDKDYTL<br>NVYRLALKTTLKRARRSMELIAREOENPKVAEVIYPIMQVNGHHYIGVDVAVGGMEQR<br>KIHMLARELLPKKVVCIHNPVLTGLDGECKMSSSKGNFIAVDDSPEEIRAKIKKAYCP<br>AGVVEGNPIMEIAKYFLEYPLTIKRPEKFGGDLTVNSYEELESLFKWKELHPMDLKNA<br>VAEELIKILEPIRKRL# | Mutant synthetase to incorporate m-methoxy phenylalanine into proteins OMe4-8 | RS |
| 59 | MDEFEMIKRNTSEIISEEELREVLKKDEKSAYIGFEPSGKIHLGHYLQIKKNIDLQNA<br>GFDIIILLADLHAYLNQKGELOEIRKIGDYNKKVFEANGLKAKYVYGSAFQLDKDYTL<br>NVYRLALKTTLKRARRSMELIAREDENPKVAEVIYPIMQVNCAHYLGVDVAVGGMEOR<br>KIHMLARELLPKKVVCIHNPVLTGLDGEGKMSSSKGNFIAVDDSPEEIRAKIKKAYCP<br>AGVVEGNPIMEIAKYFLEYPLTIKRPEKFGGDLTVNSYEELESLFKNKELHPMDLKNA<br>VAEELIKILEPIRKRL# | Mutant synthetase to incorporate p-O-allyl tyrosine into proteins Allyl | RS |
| 60 | MDEFEMIKRNTSEIISEEELREVLKKDEKSAGIGFEPSGKIHLGHYLQIKKNIDLQN<br>AGFDIIILLADLHAYLNQKCELDEIRKIGDYNKKVFEANGLKAKYVYGSSFQLDKDY<br>TLNVYRLALKTTLKRARRSMELIAREDENPKVAEVIYPIMQVNTSHYLGVDVAVGCM<br>EQRKIHMLARELLPKKVVCIHNPVLTGLDGEGKMSSSKGNFIAVDDSPEEIRAKIKK<br>AYCPAGVVEGNPIMEIAKYFLEYPLTIKRPEKFGGDLTVNSYEELESLFKNKELHPM<br>DLKNAVAEELIKILEPIRKRL | Aminoacyl tRNA synthetase for the incorporation of p-benzoyl-L-phenylalanine p-BpaRS(H6) | RS |
| 61 | MDEFEMIKRNTSEIISEEELREVLKKDEKSAGIGFEPSGKIHLGHYLQIKKNIDLQN<br>AGFDIIILLADLHAYLNQKGELDEIRKIGDYNKKVFEANGLKAKYVYGSNFQLDKDY<br>TLNVYRLALKTTLKRARRSMELIAREDENPKVAEVIYPIMQVNPLHYQGVDVAVGGM<br>EQRKIHMLARELLPKKVVCIHNPVLTGLDGEGKMSSSKGNFIAVDDSPEEIRAKIKK<br>AYCPAGVVEGNPIMEIAKYFLEYPLTIKRPEKFGGDLTVNSYEELESLFKNKELHPM<br>DLKNAVAEELIKILEPIRKRL | Aminoacyl tRNA synthetase for the incorporation of p-azido-phenylalanine p-Az-PheRS(3) | RS |
| 62 | MDEFEMIKRNTSEIISEEELREVLKKDEKSAGIGFEPSGKIHLGHYLQIKKNIDLQN<br>AGFDIIILLADLHAYLNQKGELDEIRKIGDYNKKVFEANGLKAKYVYGSSFQLDKDY<br>TLNVYRLALKTTLKRARRSMELIAREDENPKVAEVIYPIMQVNPLHYQGVDVAVGGM<br>EQRKIHMLARELLPKKVVCIHNPVLTGLDGEGKMSSSKGNFIAVDDSPEEIRAKIKK<br>AYCPAGVVEGNPIMEIAKYFLEYPLTIKRPEKFGGDLTVNSYEELESLFKNKELHPM<br>DLKNAVAEELIKILEPIRKRL | Aminoacyl tRNA synthetase for the incorporation of p-azido-phenylalanine p-Az-PheRS(6) | RS |
| 63 | MDEFEMIKRNTSEIISEEELREVLKKDEKSALIGFEPSGKIHLGHYLQIKKMIDLQN<br>AGFDIIILLADLHAYLNQKGELDEIRKIGDYNKKVFEANGLKAKYVYGSTFQLDKDY<br>TLNVYRLALKTTLKRARRSMELIAREDENPKVAEVIYPIMQVNPVHYQGVDVAVGGM<br>EQRKIHMLARELLPKKVVCIHNPVLTGLDGEGKMSSSKGNFIAVDDSPEEIRAKIKK<br>AYCPAGVVEGNPIMEIAKYFLEYPLTIKRPEKFGGDLTVNSYEELESLFKNKELHPM<br>DLKNAVAEELIKILEPIRKRL | Aminoacyl tRNA synthetase for the incorporation of p-azido-phenylalanine p-Az-PheRS(20) | RS |
| 64 | MDEFEMIKRNTSEIISEEELREVLKKDEKSATIGFEPSGKIHLGHYLQIKKNIDLQNA<br>GFDIIILLADLHAYLNQKGELDEIRKIGDYNKKVFEANGLKAKYVYGSSFQLDKDYTL<br>NVYRLALKTTLKRARRSMELIAREDENPKVAEVIYPIMQVNPSHYQGVDVAVGGMEQR<br>KIHMLARELLPKKVVCIHNPVLTGLDGEGKMSSSKGNFIAVDDSPEEIRAKIKKAYCP<br>AGVVEGNPIMEIAKYFLEYPLTIKRPEKFCGDLTVNSYEELESLFKNKELHPMDLKNA<br>VAEELIKILEPIRKRL | Aminoacyl tRNA synthetase for the incorporation of p-azido-phenylalanine p-Az-PheRS(24) | RS |

-continued

| SEQ ID # | Sequence | Notes | tRNA or RS |
|---|---|---|---|
| 65 | MSDFRIIEEK WQKAWEKDRI FESDPNEKEK FFLTIPYPYL NGNLHAGHTR<br>TFTIGDAFAR YMRNKGYNVL FPLGFHVTGT PIIGLAELIA KRDERTIEVY<br>TKYHDVPLED LLQLTTPEKI VEYFSREALQ ALKSIGYSID WRRVFIEWQY<br>EYQRFIEWQY WKLKELGLIV KGTHPVRYCP HDQNPVEDHD LLAGEEATIV<br>EFTVIKFRLE DGDLIFPCAT LRPETVFGVT NIWVKPTTYV IAEVDGEKWF<br>VSKEAYEKLT YTEKKVRLLE EVDASQFFGK YVIVPLVNRK VPILPAEFVD<br>TDNATGVVMS VPAMAPFDLA AIEDLKRDEE TLAKYGIDKS VVESIKPIVL<br>IKTDIEGVPA EKLIRELGVK SQKDKELLDK ATKTLYKKEY HTGIMLDNTM<br>NYAGMKVSEA KERVHEDLVK LGLGDVFYEF SEKPVICRCG TKCVVKVVRD<br>QWFLNYSNRE WKEKVLNHLE KMRIIPDYYK EEFRNKIEWL RDKACARRKG<br>LGTRIPWDKE WLIESLSDST IYMAYYILAK YINAGLLKAE NMTPEFLDYV<br>LLGKGEVGKV AEASKLSVEL IQQIRDDFEY WYPVDLRSSG KDLVANHLLF<br>YLFHHVAIFP PDKWPRAIAV NGYVSLEGKK HSKSKGPLLT MKRAVQQYGA<br>DVTRLYILNA AEYDSDADWK SREVEGLANH LRRFYNLVKE NYLKEVOELT<br>TLDRWLVSRN QRAIKEVREA MDNLQTRRAV NAAFFELMND VRWYLRRGGE<br>NLAIILDDWI KLLAPFAPHI CEELWHLKHD SYVSLESYPE YDETRVOEEA<br>ERIEEYLRNL VEDIQEIKKF VSDAKEVYIA PAEDWKVKAA KVVAESGDVG<br>EANKQLMQDE ELRKLGKEVS NFVKKIFKDR KKLMLVKEWE VLQQNLKFIE<br>NETGLKVILD TQRVPEEKRR QAVPGKPAIY VA* | Archaeoglobus fulgidus leucyl trna-synthetase (AFLRS) | RS |
| 66 | VDIERKWRDR WRDAGIFQAD PDDREKIFLT VAYPYPSGAM NIGHGRTYTV<br>PDVYARFKRN QGYNVLFPMA WHVTGAPVIG IARRIQRKDP WTLKIYREVH<br>RVPEDELERF SDPEYIVEYF SREYRSVMED MGYSIDWRRE FKTTDPTYSR<br>FIQWQIRKLR DLGLVRKGAH PVKYCPECEN PVGDNDLLEG EGVAINQLTL<br>LKFKLGDSYL VAATFRPETI YGATNLWLNP DEDYVRVETG GEEWIISRAA<br>VDNLSHQKLD LKVSGDVNPG DLIGMCVENP VTGQEHPILP ASFVDPEYAT<br>GVVFSVPAHA PADFIALEDL RTDHELLERY GLEDVVADIE PVNVIAVDGY<br>GEFPAAEVIE KFGVRNQEDP RLEDATGELY KIEHARGVNS SHIPVYGGMK<br>VSEAREVIAD ELKDQGLADE MYEFAERPVI CRCGGRCVVR VMEDQWFMKY<br>SDDAWKDLAH RCLDGMKIIP EEVRANFEYY IDWLNDWACS RRIGLGTRLP<br>WDERWIIEPL TDSTIYMAYY TIAHRLREMD AGEMDDEFFD AIFLDDSGTF<br>EDLREEFRYW YPLDWRLSAK DLIGNHLTFH IFEHSAIFPE SGWPRGAVVF<br>GMGLLEGNKM SSSKGNVILL RDAIEKHGAD VVRLFLMSSA EPWQDFDWRE<br>SEVIGTRRRI EWFREFGERV SGILDGRPVL SEVTPAEPES FIGRWMMGQL<br>NQRIREATRA LESFQTRKAV QEALYLLKKD VDHYLKRVEG RVDDEVKSVL<br>ANVLHAWIRL MAPFIPYTAE EMWERYGGEG FVAEAPWPDF SDDAESRDVQ<br>VAEEMVQNTV RDIQEIMKIL GSTPERVHIY TSPKWKWDVL RVAAEVGKLD<br>MGSIMGRVSA EGIHDNMKEV AEFVRRIIRD LGKSEVTVID EYSVLMDASD<br>YIESEVGARV VIHSKPDYDP ENKAVNAVPL KPAIYLE* | Methanobacterium thermoautotrophicum leucyl trna-synthetase (MtLRS) | RS |
| 67 | GAATTCACAC ACAGGAAACA GCTATGCGCA CGCTTCTGAT CGACAACTAC<br>GCCCCCCGTC GTGCCCAACG ACGCCGACTG GTCGCGGCTG CCCCTCGAGG<br>ACTTCGACGC GATCGTCGTG TCCCCGGGCC CCGGCAGCCC CGACCGGGAA<br>CGGGACTTCG GGATCAGCCG CCGGGCGATC ACCGACAGCG GCCTGCCCGT<br>CCTCGGCGTC TGCCTCGGCC ACCAGGGCAT CGCCCAGCTC TCGGCGGAAC<br>CCATGCACGG CCGGGTCTCC GAGGTGCGGC ACACCGGCGA GGACGTCTTC<br>CGGGGCCTCC CCTCGCCGTT CACCGCCGTG CGCTACCACT CCCTGGCCGC<br>CACCGACCTC CCCGACGAGC TCGAACCCCT CGCCTGGAGC GACGACGGCG<br>TCGTCATGGG CCTGCGGCAC CGCGAGAAGC CGCTGATGGG CGTCCAGTTC<br>CCACCGGAGT CCATCGGCAG CGACTTCGGC CGGGAGATCA TGGCCAACTT<br>CCGCGACCTC GCCCTCGCCC ACCACCGGGC ACGTCGCGAC GCGGCCGACT<br>GGGGCTACGA ACTCCACGTG CGCCGCGTCG ACGTGCTGCC GGACGCCCAA<br>GAGGTACGCC GCGCTGCCTG CCCGGCCGAG GGCGCCACGT TCTGGCTGGA<br>CAGCAGCTCC GTCCTCGAAG GCGCCTCGCC GTTCTCCTTC CTCGGCGACG<br>ACCGCGGCCC GCTCGCCGAG TACCTCACCT ACCGCGTCGC CGACGGCGTC<br>GTCTCCGTCC GCGGCTCCGA CGGCACCACG ACCCGGGACG CGGCGACCCT<br>CTTCAGCTAC CTGGAGGAGC AGCTCGAACC GCCGGCGGGT CCCGTCGCCC<br>CCGACCTGCC CTTCGAGTTC AACCTCGGCT ACGTCGGCTA CCTCGGCTAC<br>GAGCTGAAGG CGGAGACCAC CGGCGACCCC GCACTACCGG CCCCGCACCC<br>CGACGCCGCG TTCCTCTTCG CCGACCGCGC CATCGCCCTC GACCACCAGG<br>AAGGCTGCTG CTACCTCCTG GCCCTCGACC GCCGGGGCCA CGACGACGGC<br>GCCCGCGCCT GGCTGCGGGA GACGGCCGAG ACCCTCACCG GCCTGGCCGT<br>CCGCGTCCGG CCGAGGCCGA CCCCCGCCAT GGTCTTCGGG GTCCCCGAGG<br>CGGCGGCCGG CTTCGGCCCC CTGGCTCGCG CACGCCACGA CAAGGACGCC<br>TCGGCGCTCC GCAACGGCGA GTCGTACGAG ATCTGCCTGA CCAACATGGT<br>CACCGCGCCG ACCGAGGCGA CGGCCCTGCC GCTCTACTCC GCGCTGCGCC<br>GCATCAGCCC CGTCCCGTCT GGCGCCCTGC TCGAGTTCCC CGAGCTGTCG<br>GTGCTCAGCG CCTCGCCCGA GCGGTTCCTC ACGATCGGCG CCGACGGCGG<br>CGTCGAGTCC AAGCCCATCA AGGGGACCCG CCCCCGGGGC GCACCGGCGC<br>AGGAGGACGA GCGGCTCCGC GCCGACCTGG CCGGCCGGGA GAAGGACCGG<br>GCCGAGAACC TGATGATCGT CGACCTGGTC CGCAACGACC TCAACAGCGT<br>CTGCGCGATC GGCTCCGTCC ACGTGCCCCG GCTCTTCGAG GTGGGAGACC<br>TCGCGCCCGT GCACCAGCTG GTGTCGACCA TCCGGGGACG GCTGCGGCCC<br>GGCACCAGCA CCGCCGCCTG CGTACGCGCC GCCTTCCCCG GCGGCTCCAT<br>GACCGGCGCG CCCAAGAAGC GACCCATGGA GATCATCGAC CGCCTGGAGG<br>AAGGCCCCCG GGGCGTCTTA CCCGGGGCGC TCGGATGGTT CGCCCTCAGC<br>GGCGCCGCCG ACCTCAGCAT CGTCATCCGC ACCATCGTGC TGGCCGACGG<br>CCGGGCCGAG TTCGGCGTCG GCGGGGCGAT CGTGTCCCTC TCCGACCAGG | (plasc-papabc) | Plasmid |

-continued

| SEQ ID # | Sequence | Notes | tRNA or RS |
|---|---|---|---|
| | AGGAGGAGTT CAGGCAGACC GTGGTCAAGG CCCGCGCCAT GGTCACCGCC | | |
| | CTCGACGGCA GCGCAGTGGC GGGCGCACGA TGACACCAAC AAGGACCATA | | |
| | GCATATGACC GAGCAGAACG AGCTGCAGGT TGCGGCTGCG CGCGGAGCTC | | |
| | GACGCCCTCG ACGGGACGCT TCTGGACACG GTGCGGCGCC GCATCGACCT | | |
| | CGGTGTCCGC ATCGCGCGGT ACAAGTCCCG GCACGGCGTC CCGATGATGC | | |
| | AGCCCGGCCG GGTCAGCCTG GTCAAGGACA GGGCCGCCCG CTACGCCGCC | | |
| | GACCACGGCC TCGACGAATC GTTCCTGGTG AACCTCTACG ACGTGATCAT | | |
| | CACGGAGATG TGCCGCGTCG AGGACCTGGT GATGAGCCCG TCATGTACTA | | |
| | AGGAGGTTGT ATGAGTGGCT TCCCCCGGAG CGTCGTCGTC GGCGGCAGCG | | |
| | GAGCGGTGGG CGGCATGTTC GCCGGGCTGC TGCGGGAGGC GGGCAGCCGC | | |
| | ACGCTCGTCG TCGACCTCGT ACCGCCGCCG GGACGGCCGG ACGCCTGCCT | | |
| | GGTGGGCGAC GTCACCGCGC CGGGGCCCGA GCTCGCGGCC GCCCTCCGGG | | |
| | ACGCGGACCT CGTCCTGCTC GCCGTACACG AGGACGTGGC CCTCAAGGCC | | |
| | GTGGCGCCCG TGACCCGGCT CATGCGACCG GGCGCGCTGC TCGCCGACAC | | |
| | CCTGTCCGTC CGGACGGGCA TGGCCGCGGA GCTCGCGGCC CACGCCCCCG | | |
| | GCGTCCAGCA CGTGGGCCTC AACCCGATGT TCGCCCCCGC CGCCGGCATG | | |
| | ACCGGCCGGC CCGTGGCCGC CGTGGTCACC AGGGACGGGC CGGGCGTCAC | | |
| | GGCCCTGCTG CGGCTCGTCG AGGGCGGCGG CGGCAGGCCC GTACGGCTCA | | |
| | CGGCGGAGGA GCACGACCGG ACGACGGCGG CGACCCAGGC CCTGACGCAC | | |
| | GCCGTGATCC TCTCCTTCGG GCTCGCCCTC GCCCGCCTCG GCGTCGACGT | | |
| | CCGGGCCCTG GCGGCGACGG CACCGCCGCC CCACCAGGTG CTGCTCGCCC | | |
| | TCCTGGCCCG TGTGCTCGGC GGCAGCCCCG AGGTGTACGG GGACATCCAG | | |
| | CGGTCCAACC CCCGGGCCGC GTCCGCGCGC CGGGCGCTCG CCGAGGCCCT | | |
| | GCGCTCCTTC GCCGCGCTGA TCGGCGACGA CCCGGACCGC GCCGAGGACC | | |
| | CGGACCGCGC CGACGACCCC GACCGCACCG ACAACCCCGG CCATCCCGGG | | |
| | GGATGCGACG GCGCCGGGAA CCTCGACGGC GTCTTCGAGG AACTCCGCCG | | |
| | GCTCATGGGA CCGGAGCTCG CGGCGGGCCA GGACCACTGC CAGGAGCTGT | | |
| | TCCGCACCCT CCACCGCACC GACGACGAAG GCGAGAAGGA CCGATGAATT | | |
| | TAGGTGACAC TATAGGGATC CTCTACGCCG GACGCATCGT GGCCGGCATC | | |
| | ACCGGCGCCA CAGGTGCGGT TGCTGGCGCC TATATCGCCG ACATCACCGA | | |
| | TGGGGAAGAT CGGGCTCGCC ACTTCGGGCT CATGAGCGCT TGTTTCGGCG | | |
| | TGGGTATGGT GGCAGGCCCC CTGGCCGGGG GACTGTTGGG CGCCATCTCC | | |
| | TTGCATGCAC CATTCCTTGC GGCGGCGGTG CTCAACGGCC TCAACCTACT | | |
| | ACTGGGCTGC TTCCTAATGC AGGAGTCGCA TAAGGGAGAG CGTCGACCGA | | |
| | TGCCCTTGAG AGCCTTCAAC CCAGTCAGCT CCTTCCGGTG GGCGCGGGGC | | |
| | ATGACTATCG TCGCCGCACT TATGACTGTC TTCTTTATCA TGCAACTCGT | | |
| | AGGACAGGTG CCGGCAGCGC TCTGGGTCAT TTTCGGCGAG GACCGCTTTC | | |
| | GCTGGAGCGC GACGATGATC GGCCTGTCGC TTGCGGTATT CGGAATCTTG | | |
| | CACGCCCTCG CTCAAGCCTT CGTCACTGGT CCCGCCACCA AACGTTTCGG | | |
| | CGAGAAGCAG GCCATTATCG CCGGCATGGC GGCCGACGCG CTGGGCTACG | | |
| | TCTTGCTGGC GTTCGCGACG CGAGGCTGGA TGGCCTTCCC CATTATGATT | | |
| | CTTCTCGCTT CCGGCGGCAT CGGGATGCCC GCGTTGCAGG CCATGCTGTC | | |
| | CAGGCAGGTA GATGACGACC ATCAGGGACA GCTTCAAGGA TCGCTCGCGG | | |
| | CTCTTACCAG CCTAACTTCG ATCACTGGAC CGCTGATCGT CACGGCGATT | | |
| | TATGCCGCCT CGGCGAGCAC ATGGAACGGG TTGGCATGGA TTGTAGGCGC | | |
| | CGCCCTATAC CTTGTCTGCC TCCCCGCGTT GCGTCGCGGT GCATGGAGCC | | |
| | GGGCCACCTC GACCTGAATG GAAGCCGGCG GCACCTCGCT AACGGATTCA | | |
| | CCACTCCAAG AATTGGAGCC AATCAATTCT TGCGGAGAAC TGTGAATGCG | | |
| | CAAACCAACC CTTGGCAGAA CATATCCATC GCGTCCGCCA TCTCCAGCAG | | |
| | CCGCACGCGG CGCATCTCGG GCAGCGTTGG GTCCTGGCCA CCGGTGCGCA | | |
| | TGATCGTGCT CCTGTCGTTG AGGACCCGGC TAGGCTCGCG GGGTTGCCTT | | |
| | ACTGGTTAGC AGAATGAATC ACCGATACGC GAGCGAACGT GAAGCGACTG | | |
| | CTGCTGCAAA ACGTCTGCGA CCTGAGCAAC AACATGAATG GTCTTCGGTT | | |
| | TCCGTGTTTC GTAAAGTCTG GAAACGCGGA AGTCCCCTAC GTGCTGCTGA | | |
| | AGTTGCCCGC AACAGAGAGT GGAACCAACC GGTGATACCA CGATACTATG | | |
| | ACTGAGAGTC AACGCCATGA GCGGCCTCAT TTCTTATTCT GAGTTACAAC | | |
| | AGTCCGCACC GCTGCCGGTA GCTACTTGAC TATCCGGCTG CACTAGCCCT | | |
| | GCGTCAGATG GCTCTGATCC AAGGCAAACT GCCAAAATAT CTGCTGGCAC | | |
| | CGGAAGTCAG CGCCCTGCAC CATTATGTTC CGGATCTGCA TCGCAGGATG | | |
| | CTGCTGGCTA CCCTGTGGAA CACCTACATC TGTATTAACG AAGCGCTGGC | | |
| | ATTGACCCTG AGTGATTTTT CTCTGGTGCC GCCCTATCCC TTTGTGCAGC | | |
| | TTGCCACGCT CAAAGGGGTT TGAGGTCCAA CCGTACGAAA ACGTACGGTA | | |
| | AGAGGAAAAT TATCGTCTGA AAAATCGATT AGTAGACAAG AAAGTCCGTT | | |
| | AAGTGCCAAT TTTCGATTAA AAAGACACCG TTTTGATGGC GTTTTCCAAT | | |
| | GTACATTATG TTTCGATATA TCAGACAGTT ACTTCACTAA CGTACGTTTT | | |
| | CGTTCTATTG GCCTTCAGAC CCCATATCCT TAATGTCCTT TATTTCCTGG | | |
| | GGTTATCAGA TCCCCCCGAC ACGTTTAATT AATGCTTTCT CCGCCGGAGA | | |
| | TCGACGCACA GGCTTCTGTG TCTATGATGT TATTTCTTAA TAATCATCCA | | |
| | GGTATTCTCT TTATCACCAT ACGTAGTGCG AGTGTCCACC TTAACGCAGG | | |
| | GCTTTCCGTC ACAGCGCGAT ATGTCAGCCA GCGGGGCTTT CTTTTGCCAG | | |
| | ACCGCTTCCA TCCTCTGCAT TTCAGCAATC TGGCTATACC CGTCATTCAT | | |
| | AAACCACGTA AATGCCGTCA CGCAGGAAGC CAGGACGAAG AATATCGTCA | | |
| | GTACAAGATA AATCGCGGAT TTCCACGTAT AGCGTGACAT CTCACGACGC | | |
| | ATTTCATGGA TCATCGCTTT CGCCGTATCG GCAGCCTGAT TCAGCGCTTC | | |
| | TGTCGCCGGT TTCTGCTGTG CTAATCCGGC TTGTTTCAGT TCTTTCTCAA | | |
| | CCTGAGTGAG CGCGGAACTC ACCGATTTCC TGACGGTGTC AGTCATATTA | | |

-continued

| SEQ ID # | Sequence | Notes | tRNA or RS |
|---|---|---|---|
| | CCGGACGCGC TGTCCAGCTC ACGAATGACC CTGCTCAGCG TTTCACTTTG | | |
| | CTGCTGTAAT TGTGATGAGG CGGCCTGAAA CTGTTCTGTC AGAGAAGTAA | | |
| | CACGCTTTTC CAGCGCCTGA TGATGCCCGA TAAGGGCGGC AATTTGTTTA | | |
| | ATTTCGTCGC TCATACAAAA TCCTGCCTAT CGTGAGAATG ACCAGCCTTT | | |
| | ATCCGGCTTC TGTCGTATCT GTTCGGCGAG TCGCTGTCGT TCTTTCTCCT | | |
| | GCTGACGCTG TTTTTCCGCC AGACGTTCGC GCTCTCTCTG CCTTTCCATC | | |
| | TCCTGATGTA TCCCCTGGAA CTCCGCCATC GCATCGTTAA CAAGGGACTG | | |
| | AAGATCGATT TCTTCCTGTA TATCCTTCAT GGCATCACTG ACCAGTGCGT | | |
| | TCAGCTTGTC AGGCTCTTTT TCAAAATCAA ACGTTCTGCC GGAATGGGAT | | |
| | TCCTGCTCAG GCTCTGACTT CAGCTCCTGT TTTAGCGTCA GAGTATCCCT | | |
| | CTCGCTGAGG GCTTCCCGTA ACGAGGTAGT CACGTCAATT ACGCTGTCAC | | |
| | GTTCATCACG GGACTGCTGC ACCTGCCTTT CAGCCTCCCT GCGCTCAAGA | | |
| | ATGGCCTGTA GCTGCTCAGT ATCGAATCGC TGAACCTGAC CCGCGCCCAG | | |
| | ATGCCGCTCA GGCTCACGGT CAATGCCCTG CGCCTTCAGG GAACGGGAAT | | |
| | CAACCCGGTC AGCGTGCTGA TACCGTTCAA GGTGCTTATT CTGGAGGTCA | | |
| | GCCCAGCGTC TCCCTCTGGG CAACAAGGTA TTCTTTGCGT TCGGTCGGTG | | |
| | TTTCCCCGAA ACGTGCCTTT TTTGCGCCAC CGCGTCCGGC TCTTTGGTGT | | |
| | TAGCCCGTTT AAAATACTGC TCAGGGTCAC GGTCAATACC GTCATTAATG | | |
| | CGTTCAGAGA ACATGATATG GGCGTGGGGC TGCTCGCCAC CGGCTATCGC | | |
| | TGCTTTCGGA TTATGGATAG CGAACTGATA GGCATGGCGG TCGCCAATTT | | |
| | CCTGTTGGAC AAAATCGCGG ACAAGCTCAA GACGTTGTTC GGGTTTTAAC | | |
| | TCACGCGGCA GGGCAATCTC GATTTCACGG TAGGTACAGC CGTTGGCACG | | |
| | TTCAGACGTG TCAGCGGCTT TCCAGAACTC GGACGGTTTA TGCGCTGCCC | | |
| | ACGCCGGCAT ATTGCCGGAC TCCTTGTGCT CAAGGTCGGA GTCTTTTTCA | | |
| | CGGGCATACT TTCCCTCACG CGCAATATAA TCGGCATGAG GAGAGGCACT | | |
| | GCCTTTTCCG CCGGTTTTTA CGCTGAGATG ATAGGATGCC ATCGTGTTTT | | |
| | ATCCCGCTGA AGGGCGCACG TTTCTGAACG AAGTGAAGAA AGTCTAAGTG | | |
| | CGCCCTGATA AATAAAAGAG TTATCAGGGA TTGTAGTGGG ATTTGACCTC | | |
| | CTCTGCCATC ATGAGCGTAA TCATTCCGTT AGCATTCAGG AGGTAAACAG | | |
| | CATGAATAAA AGCGAAAAAA CAGGAACAAT GGGCAGCAGA AAGAGTGCAG | | |
| | TATATTCGCG GCTTAAAGTC GCCGAATGAG CAACAGAAAC TTATGCTGAT | | |
| | ACTGACGGAT AAAGCAGATA AAACAGCACA GGATATCAAA ACGCTGTCCC | | |
| | TGCTGATGAA GGCTGAACAG GCAGCAGAGA AAGCGCAGGA ACCCAGAGCG | | |
| | AAAGTCATGA ACCTGATACA GGCAGAAAAG CGAGCCGAAG CCAGAGCCGC | | |
| | CCGTAAAGCC CGTGACCATG CTCTGTACCA GTCTGCCGGA TTGCTTATCC | | |
| | TGGCGGGTCT GGTTGACAGT AAGACGGGTA AGCCTGTTGA TGATACCGCT | | |
| | GCCTTACTGG GTGCATTAGC CAGTCTGAAT GACCTGTCAC GGGATAATCC | | |
| | GAAGTGGTCA GACTGGAAAA TCAGAGGGCA GGAACTGCTG AACAGCAAAA | | |
| | AGTCAGATAG CACCACATAG CAGACCCGCC ATAAAACGCC CTGAGAAGCC | | |
| | CGTGACGGGC TTTTCTTGTA TTATGGGTAG TTTCCTTGCA TGAATCCATA | | |
| | AAAGGCGCCT GTAGTGCCAT TTACCCCCAT TCACTGCCAG AGCCGTGAGC | | |
| | GCAGCGAACT GAATGTCACG AAAAAGACAG CGACTCAGGT GCCTGATGGT | | |
| | CGGAGACAAA AGGAATATTC AGCGATTTGC CCGAGCTTGC GAGGGTGCTA | | |
| | CTTAAGCCTT TAGGGTTTTA AGGTCTGTTT TGTAGAGGAG CAAACAGCGT | | |
| | TTGCGACATC CTTTTGTAAT ACTGCGGAAC TGACTAAAGT AGTGAGTTAT | | |
| | ACACAGGGCT GGGATCTATT CTTTTTATCT TTTTTTATTC TTTCTTTATT | | |
| | CTATAAATTA TAACCACTTG AATATAAACA AAAAAAACAC ACAAAGGTCT | | |
| | AGCGGAATTT ACAGAGGGTC TAGCAGAATT TACAAGTTTT CCAGCAAAGG | | |
| | TCTAGCAGAA TTTACAGATA CCCACAACTC AAAGGAAAAG GACTAGTAAT | | |
| | TATCATTGAC TAGCCCATCT CAATTGGTAT AGTGATTAAA ATCACCTAGA | | |
| | CCAATTGAGA TGTATGTCTG AATTAGTTGT TTTCAAAGCA AATGAACTAG | | |
| | CGATTAGTCG CTATGACTTA ACGGAGCATG AAACCAAGCT AATTTTATGC | | |
| | TGTGTGGCAC TACTCAACCC CACGATTGAA AACCCTACAA GGAAAGAACG | | |
| | GACGGTATCG TTCACTTATA ACCAATACGC TCAGATGATG AACATCAGTA | | |
| | GGGAAAATGC TTATGGTGTA TTAGCTAAAG CAACCAGAGA GCTGATGACG | | |
| | AGAACTGTGG AAATCAGGAA TCCTTTGGTT AAAGGCTTTG AGATTTTCCA | | |
| | GTGGACAAAC TATGCCAAGT TCTCAAGCGA AAAATTAGAA TTAGTTTTTA | | |
| | GTGAAGAGAT ATTGCCTTAT CTTTTCCAGT TAAAAAAATT CATAAAATAT | | |
| | AATCTGGAAC ATGTTAAGTC TTTTGAAAAC AAATACTCTA TGAGGATTTA | | |
| | TGAGTGGTTA TTAAAAGAAC TAACACAAAA GAAAACTCAC AAGGCAAATA | | |
| | TAGAGATTAG CCTTGATGAA TTTAAGTTCA TGTTAATGCT TGAAAATAAC | | |
| | TACCATGAGT TTAAAAGGCT TAACCAATGG GTTTTGAAAC CAATAAGTAA | | |
| | AGATTTAAAC ACTTACAGCA ATATGAAATT GGTGGTTGAT AAGCGAGGCC | | |
| | GCCCGACTGA TACGTTGATT TTCCAAGTTG AACTAGATAG ACAAATGGAT | | |
| | CTCGTAACCG AACTTGAGAA CAACCAGATA AAAATGAATG GTGACAAAAT | | |
| | ACCAACAACC ATTACATCAG ATTCCTACCT ACGTAACGGA CTAAGAAAAA | | |
| | CACTACACGA TGCTTTAACT GCAAAAATTC AGCTCACCAG TTTTGAGGCA | | |
| | AAATTTTTGA GTGACATGCA AAGTAAGCAT GATCTCAATG GTTCGTTCTC | | |
| | ATGGCTCACG CAAAAACAAC GAACCACACT AGAGAACATA CTGGCTAAAT | | |
| | ACGGAAGGAT CTGAGGTTCT TATGGCTCTT GTATCTATCA GTGAAGCATC | | |
| | AAGACTAACA AACAAAAGTA GAACAACTGT TCACCGTTAG ATATCAAAGG | | |
| | GAAAACTGTC CATATGCACA GATGAAAACG GTGTAAAAAA GATAGATACA | | |
| | TCAGAGCTTT TACGAGTTTT TGGTGCATTT AAAGCTGTTC ACCATGAACA | | |
| | GATCGACAAT GTAACAGATG AACAGCATGT AACACCTAAT AGAACAGGTG | | |
| | AAACCAGTAA AACAAAGCAA CTAGAACATG AAATTGAACA CCTGAGACAA | | |
| | CTTGTTACAG CTCAACAGTC ACACATAGAC AGCCTGAAAC AGGCGATGCT | | |

-continued

| SEQ ID # | Sequence | Notes | tRNA or RS |
|---|---|---|---|
| | GCTTATCGAA TCAAAGCTGC CGACAACACG GGAGCCAGTG ACGCCTCCCG | | |
| | TGGGGAAAAA ATCATGGCAA TTCTGGAAGA AATAGCGCTT TCAGCCGGCA | | |
| | AACCTGAAGC CGGATCTGCG ATTCTGATAA CAAACTAGCA ACACCAGAAC | | |
| | AGCCCGTTTG CGGGCAGCAA AACCCGTACT TTTGGACGTT CCGGCGGTTT | | |
| | TTTGTGGCGA GTGGTGTTCG GGCGGTGCGC GCAAGATCCA TTATGTTAAA | | |
| | CGGGCGAGTT TACATCTCAA AACCGCCCGC TTAACACCAT CAGAAATCCT | | |
| | CAGCGCGATT TTAAGCACCA ACCCCCCCCC GTAACACCCA AATCCATACT | | |
| | GAAAGTGGCT TTGTTGAATA AATCGAACTT TTGCTGAGTT GAAGGATCAG | | |
| | ATCACGCATC CTCCCGACAA CACAGACCAT TCCGTGGCAA AGCAAAAGTT | | |
| | CAGAATCACC AACTGGTCCA CCTACAACAA AGCTCTCATC AACCGTGGCT | | |
| | CCCTCACTTT CTGGCTGGAT GATGAGGCGA TTCAGGCCTG GTATGAGTCG | | |
| | GCAACACCTT CATCACGAGG AAGGCCCCAG CGCTATTCTG ATCTCGCCAT | | |
| | CACCACCGTT CTGGTGATTA AACGCGTATT CCGGCTGACC CTGCGGGCTG | | |
| | CGCAGGGTTT TATTGATTCC ATTTTTGCCC TGATGAACGT TCCGTTGCGC | | |
| | TGCCCGGATT ACACCAGTGT CAGTAAGCGG GCAAAGTCGG TTAATGTCAG | | |
| | TTTCAAAACG TCCACCCGGG GTGAAATCGC ACACCTGGTG ATTGATTCCA | | |
| | CCGGGCTGAA GGTCTTTGGT GAAGGCGAAT GGAAAGTCAG AAAGCACGGC | | |
| | AAAGAGCGCC GTCGTATCTG GCGAAAGTTG CATCTTGCTG TTGACAGCAA | | |
| | CACACATGAA GTTGTCTCTG CAGACCTGTC GCTGAATAAC GTCACGGACT | | |
| | CAGAAGCCTT CCCGGGCCTT ATCCGGCAGA CTCACAGAAA AATCAGGGCA | | |
| | GCCGCGGCAG ACGGGGCTTA CGATACCCGG CTCTGTCACG ATGAACTGCG | | |
| | CCGCAAAAAA ATCACCGCGC TTATTCCTCC CCGAAAAGGT GCGGGTTACT | | |
| | GGCCCGGTGA ATATGCAGAC CGTAACCGTG CAGTGGCTAA TCAGCGAATG | | |
| | ACCGGGAGTA ATGCGCGGTG GAAATGGACA ACAGATTACA ACCGTCGCTC | | |
| | GATAGCGGAA ACGGCGATGT ACCGGGTAAA ACAGCTGTTC GGGGGTTCAC | | |
| | TGACGCTGCG TGACTACGAT GGTCAGGTTG CGGAGGCTAT GGCCCTGGTA | | |
| | CGAGCGCTGA ACAAAATGAC GAAAGCAGGT ATGCCTGAAA GCGTGCGTAT | | |
| | TGCCTGAAAA CACAACCCGC TACGGGGGAG ACTTACCCGA AATCTGATTT | | |
| | ATTCAACAAA GCCGGGTGTG GTGAACTACA AAGCAGACCC GTTGAGGTTA | | |
| | TCAGTTCGAT GCACAATCAG CAGCGCATAA AATATGCACA AGAACAGGAG | | |
| | CACCCTTCGC ATTAAGCTGT GGTGGTAACA AGTAGTGCCG GGCTACCATC | | |
| | AGCGAGCATG ATGCGCTCCC ACAGCATTCG CCTTGGCAGT ATGGAAGTTC | | |
| | CTCGCTCCAG TTCGGGCCGG TATCCACCTC GAGAGGTGGC ACTTTTCGGG | | |
| | GAAATGTGCG CGGAACCCCT ATTTGTTTAT TTTTCTAAAT ACATTCAAAT | | |
| | ATGTATCCGC TCATGAGACA ATAACCCTGA TAAATGCTTC AATAATATTG | | |
| | AAAAAGGAAG AGTATGAGTA TTCAACATTT CCGTGTCGCC CTTATTCCCT | | |
| | TTTTTGCGGC ATTTTGCCTT CCTGTTTTTG CTCACCCAGA AACGCTGGTG | | |
| | AAAGTAAAAG ATGCTGAAGA TCAGTTGGGT GCACGAGTGG GTTACATCGA | | |
| | ACTGGATCTC AACAGCGGTA AGATCCTTGA GAGTTTTCGC CCCGAAGAAC | | |
| | GTTTTCCAAT GATGAGCACT TTTAAAGTTC TGCTATGTGG CGCGGTATTA | | |
| | TCCCGTGTTG ACGCCGGGCA AGAGCAACTC GGTCGCCGCA TACACTATTC | | |
| | TCAGAATGAC TTGGTTGAGT ACTCACCAGT CACAGAAAAG CATCTTACGG | | |
| | ATGGCATGAC AGTAAGAGAA TTATGCAGTG CTGCCATAAC CATGAGTGAT | | |
| | AACACTGCGG CCAACTTACT TCTGACAACG ATCGGAGGAC CGAAGGAGCT | | |
| | AACCGCTTTT TTGCACAACA TGGGGGATCA TGTAACTCGC CTTGATCGTT | | |
| | GGGAACCGGA GCTGAATGAA GCCATACCAA ACGACGAGCG TGACACCACG | | |
| | ATGCCTGCAG CAATGGCAAC AACGTTGCGC AAACTATTAA CTGGCGAACT | | |
| | ACTTACTCTA GCTTCCCGGC AACAATTAAT AGACTGGATG GAGGCGGATA | | |
| | AAGTTGCAGG ACCACTTCTG CGCTCGGCCC TTCCGGCTGG CTGGTTTATT | | |
| | GCTGATAAAT CTGGAGCCGG TGAGCGTGGG TCTCGCGGTA TCATTGCAGC | | |
| | ACTGGGGCCA GATGGTAAGC CCTCCCGTAT CGTAGTTATC TACACGACGG | | |
| | GGAGTCAGGC AACTATGGAT GAACGAAATA GACAGATCGC TGAGATAGGT | | |
| | GCCTCACTGA TTAAGCATTG GTAACCCGGG ACCAAGTTTA CTCATATATA | | |
| | CGGACAGCGG TGCGGACTGT TGTAACTCAG AATAAGAAAT GAGGCCGCTC | | |
| | ATGGCGTTCT GTTGCCCGTC TCACTGGTGA AAAGAAAAAC AACCCTGGCG | | |
| | CCGCTTCTTT GAGCGAACGA TCAAAAATAA GTGGCGCCCC ATCAAAAAAA | | |
| | TATTCTCAAC ATAAAAAACT TTGTGTAATA CTTGTAACGC T | | |
| 68 | ATGCGCACGC TTCTGATCGA CAACTACGAC TCGTTCACCC AGAACCTGTT | three genes (papABC) | Plasmid |
| | CCAGTACATC GGCGAGGCCA CCGGGCAGCC CCCCGTCGTG CCCAACGACG | | |
| | CCGACTGGTC GCGGCTGCCC CTCGAGGACT TCGACGCGAT CGTCGTGTCC | | |
| | CCGGGCCCCG GCAGCCCCGA CCGGGAACGG GACTTCGGGA TCAGCCGCCG | | |
| | GGCGATCACC GACAGCGGCC TGCCCGTCCT CGGCGTCTGC CTCGGCCACC | | |
| | AGGGCATCGC CCAGCTCTCG GCGGAACCCA TGCACGGCCG GGTCTCCGAG | | |
| | GTGCGGCACA CCGGCGAGGA CGTCTTCCGG GGCCTCCCCT CGCCGTTCAC | | |
| | CGCCGTGCGC TACCACTCCC TGGCCGCCAC CGACCTCCCC GACGAGCTCG | | |
| | AACCCCTCGC CTGGAGCGAC GACGGCGTCG TCATGGGCCT GCGGCACCGC | | |
| | GAGAAGCCGC TGATGGGCGT CCAGTTCCCA CCGGAGTCCA TCGGCAGCGA | | |
| | CTTCGGCCGG GAGATCATGG CCAACTTCCG CGACCTCGCC CTCGCCCACC | | |
| | ACCGGGCACG TCGCGACGCG GCCGACTGGG GCTACGAACT CCACGTGCGC | | |
| | CGCGTCGACG TGCTGCCGGA CGCCGAAGAG GTACGCCGCG CTGCCTGCCC | | |
| | GGCCGAGGGC GCCACGTTCT GGCTGGACAG CAGCTCCGTC CTCGAAGGCG | | |
| | CCTCGCCGTT CTCCTTCCTC GGCGACGACC GCGGCCCGCT CGCCGAGTAC | | |
| | CTCACCTACC GCGTCGCCGA CGGCGTCGTC TCCGTCCGCG GCTCCGACGG | | |
| | CACCACGACC CGGGACGCGG CGACCCTCTT CAGCTACCTG GAGGAGCAGC | | |
| | TCGAACCGCC GGCGGGTCCC GTCGCCCCCG ACCTGCCCTT CGAGTTCAAC | | |
| | CTCGGCTACG TCGGCTACCT CGGCTACGAG CTGAAGGCGG AGACCACCGG | | |

-continued

| SEQ ID # | Sequence | Notes | tRNA or RS |
|---|---|---|---|
| | CGACCCCGCA GTACCGGCCC CGCACCCCGA CGCCGCGTTC CTCTTCGCCG<br>ACCGCGCCAT CGCCCTCGAC CACCAGGAAG GCTGCTGCTA CCTGCTGGCC<br>CTCGACCGCC GGGGCCACGA CGACGGCGCC CGCGCCTGGC TGCGGGAGAC<br>GGCCGAGACC CTCACCGGCC TGGCCGTCCG CGTCCGGCCG AGGCCGACCC<br>CCGCCATGGT CTTCGGGGTC CCCGAGGCGG CGGCCGGCTT CGGCCCCCTG<br>GCTCGCGCAC GCCACGACAA GGACGCCTCG GCGCTCCGCA ACGGCGAGTC<br>GTACGAGATC TGCCTGACCA ACATGGTCAC CGCGCCGACC GAGGCGACGG<br>CCCTGCCGCT CTACTCCGCG CTGCGCCGCA TCAGCCCCGT CCCGTCTGGC<br>GCCCTGCTCG AGTTCCCCGA GCTGTCGGTG CTCAGCGCCT CGCCCGAGCG<br>GTTCCTCACG ATCGGCGCCG ACGGCGGCGT CGAGTCCAAG CCCATCAAGG<br>GGACCCGCCC CCGGGGCGCA CCGGCGGAGG AGGACGAGCG GCTCCGCGCC<br>GACCTGGCCG GCCGGGAGAA GGACCGGGCC GAGAACCTGA TGATCGTCGA<br>CCTGGTCCGC AACGACCTCA ACAGCGTCTG CGCGATCGGC TCCGTCCACG<br>TGCCCCGGCT CTTCGAGGTG GGAGACCTCG CGCCCGTGCA CCAGCTGGTG<br>TCGACCATCC GGGGACGGCT GCGGCCCGGC ACCAGCACCG CCGCCTGCGT<br>ACGCGCCGCC TTCCCCGGCG GCTCCATGAC CGGCGCGCCC AAGAAGCGAC<br>CCATGGAGAT CATCGACCGC CTGGAGGAAG GCCCCCGGGG CGTCTTACCC<br>GGGGCGCTCG GATGGTTCGC CCTCAGCGGC GCCGCCGACC TCAGCATCGT<br>CATCCGCACC ATCGTGCTGG CCGACGGCCG GGCCGAGTTC GGCGTCGGCG<br>GGGCGATCGT GTCCCTCTCC GACCAGGAGG AGGAGTTCAG GCAGACCGTG<br>GTCAAGGCCC GCGCCATGGT CACCGCCCTC GACGGCAGCG CAGTGGCGGG<br>CGCCCGATGA GCGGCTTCCC CCGGAGCGTC GTCGTCGGCG GCAGCGGAGC<br>GGTGGGCGGC ATGTTCGCCG GGCTGCTGCG GGAGGCGGGC AGCCGCACGC<br>TCGTCGTCGA CCTCGTACCG CCGCCGGGAC GGCCGGACGC CTGCCTGGTG<br>GGCGACGTCA CCGCGCCGGG GCCCGAGCTC GCGGCCGCCC TCCGGGACGC<br>GGACCTCGTC CTGCTCGCCG TACACGAGGA CGTGGCCCTC AAGGCCGTGG<br>CGCCCGTGAC CCGGCTCATG CGACCGGGCG CGCTGCTCGC CGACACCCTG<br>TCCGTCCGGA CGGGCATGGC CGCGGAGCTC GCGGCCCACG CCCCCGGCGT<br>CCAGCACGTG GGCCTCAACC CGATGTTCGC CCCCGCCGCC GGCATGACCG<br>GCCGGCCCGT GGCCGCCGTG GTCACCAGGG ACGGGCCGGG CGTCACGGCC<br>CTGCTGCGGC TCGTCGAGGG CGGCGGCGGC AGGCCCGTAC GGCTCACGGC<br>GGAGGAGCAC GACCGGACGA CGGCGGCGAC CCAGGCCCTG ACGCACGCCG<br>TGATCCTCTC CTTCGGGCTC GCCCTCGCCC GCCTCGGCGT CGACGTCCGG<br>GCCCTGGCGG CGACGGCACC GCCGCCCCAC CAGGTGCTGC TCGCCCTCCT<br>GGCCCGTGTG CTCGGCGGCA GCCCCGAGGT GTACGGGGAC ATCCAGCGGT<br>CCAACCCCCG GGCGGCGTCC GCGCGCCGGG CGCTCGCCGA GGCCCTGCGC<br>TCCTTCGCCG CGCTGATCGG CGACGACCCG GACCGCGCCG AGGACCCGGA<br>CCGCGCCGAC GACCCCGACC GCACCGACAA CCCCGGCCAT CCCGGGGGAT<br>GCGACGGCGC CGGGAACCTC GACGGCGTCT TCGAGGAACT CCGCCGGCTC<br>ATGGGACCGG AGCTCGCGGC GGGCCAGGAC CACTGCCAGG AGCTGTTCCG<br>CACCCTCCAC CGCACCGACG ACGAAGGCGA GAAGGACCGA TGACCGAGCA<br>GAACGAGCTG CAGGTTGCGG CTGCGCGCGG AGCTCGACGC CCTCGACGGG<br>ACGCTTCTGG ACACGGTGCG GCGCCGCATC GACCTCGGTG TCCGCATCGC<br>GCGGTACAAG TCCCGGCACG GCGTCCCGAT GATGCAGCCC GGCCGGGTCA<br>GCCTGGTCAA GGACAGGGCC GCCCGCTACG CCGCCGACCA CGGCCTCGAC<br>GAATCGTTCC TGGTGAACCT CTACGACGTG ATCATCACGG AGATGTGCCG<br>CGTCGAGGAC CTGGTGATGA GCCGGGAGAG CCTGACGGCC GAGGACCGGC<br>GGTGA | | |

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. An isolated or cultured eukaryotic cell comprising:

(a.) an orthogonal tRNA synthetase that aminoacylates endogenous tRNAs of the cell with a reduced efficiency as compared to aminoacylation of the endogenous tRNAs by endogenous tRNA synthetases of the cell; and, (b.) an orthogonal tRNA that is aminoacylated by the endogenous tRNA synthetases with reduced efficiency as compared to aminoacylation of the endogenous tRNAs by the endogenous tRNA synthetases;

wherein said orthogonal tRNA synthetase preferentially aminoacylates said orthogonal tRNA, as compared to the endogenous tRNAs, with an unnatural amino acid in said cell, and wherein the orthogonal tRNA synthetase preferentially aminoacylates said orthogonal tRNA with the unnatural amino acid, as compared to a natural amino acid, the orthogonal tRNA synthetase having a lower $K_m$ for the unnatural amino acid than for the natural amino acid, and wherein said orthogonal tRNA recognizes a selector codon of an mRNA in said cell.

2. The eukaryotic cell of claim 1, wherein the cell is a yeast cell.

3. The eukaryotic cell of claim 1, wherein the orthogonal tRNA synthetase and the orthogonal tRNA are derived from a prokaryotic tRNA synthetase and a prokaryotic tRNA.

4. The eukaryotic cell of claim 1, wherein the cell is in a cell culture.

* * * * *

UNITED STATES PATENT AND TRADEMARK OFFICE

CERTIFICATE OF CORRECTION

PATENT NO. : 7,368,275 B2
APPLICATION NO. : 11/254161
DATED : May 6, 2008
INVENTOR(S) : Schultz et al.

It is certified that error appears in the above-identified patent and that said Letters Patent is hereby corrected as shown below:

In the Specification

Column 1, at Line 15, the paragraph STATEMENT REGARDING FEDERALLY SPONSORED RESEARCH AND DEVELOPMENT should be changed to:
-- STATEMENT OF GOVERNMENT LICENSE RIGHTS
This invention was made with government support under grant numbers GM062159 awarded by The National Institutes of Health, DE-FG03-00FR45812 and DE-AC03-76SF00098 awarded by The Department of Energy, and N00014-98-F-0402 awarded by The Office of Naval Research. The government has certain rights in the invention. --

Signed and Sealed this
Twenty-fifth Day of August, 2020

Andrei Iancu
*Director of the United States Patent and Trademark Office*

SEQUENCE LISTING

<160> NUMBER OF SEQ ID NOS: 79

<210> SEQ ID NO 1
<211> LENGTH: 77
<212> TYPE: DNA
<213> ORGANISM: Methanococcus jannaschii

<400> SEQUENCE: 1

```
ccggcggtag ttcagcaggg cagaacggcg gactctaaat ccgcatggcg ctggttcaaa     60

tccggcccgc cggacca                                                    77


<210> SEQ ID NO 2
<211> LENGTH: 88
<212> TYPE: DNA
<213> ORGANISM: Halobacterium sp. NRC-1

<400> SEQUENCE: 2

cccagggtag ccaagctcgg ccaacggcga cggactctaa atccgttctc gtaggagttc     60

gagggttcga atcccttccc tgggacca                                        88


<210> SEQ ID NO 3
<211> LENGTH: 89
<212> TYPE: DNA
<213> ORGANISM: Halobacterium sp. NRC-1

<400> SEQUENCE: 3

gcgagggtag ccaagctcgg ccaacggcga cggacttcct aatccgttct cgtaggagtt     60

cgagggttcg aatccctccc ctcgcacca                                       89


<210> SEQ ID NO 4
<211> LENGTH: 921
<212> TYPE: DNA
<213> ORGANISM: Methanococcus jannaschii

<400> SEQUENCE: 4

atggacgaat ttgaaatgat aaagagaaac acatctgaaa ttatcagcga ggaagagtta     60

agagaggttt taaaaaaaga tgaaaaatct gctcagatag gttttgaacc aagtggtaaa    120

atacatttag ggcattatct ccaaataaaa aagatgattg atttacaaaa tgctggattt    180

gatataatta tattgttggc tgatttacac gcctatttaa accagaaagg agagttggat    240

gagattagaa aaataggaga ttataacaaa aaagtttttg aagcaatggg gttaaaggca    300

aaatatgttt atggaagtac tttccagctt gataaggatt atacactgaa tgtctataga    360

ttggctttaa aaactacctt aaaaagagca agaaggagta tggaacttat agcaagagag    420

gatgaaaatc caaaggttgc tgaagttatc tatccaataa tgcaggttaa tgcaattcat    480

tatcctggcg ttgatgttgc agttggaggg atggagcaga gaaaaataca catgttagca    540

agggagcttt taccaaaaaa ggttgtttgt attcacaacc ctgtcttaac gggtttggat    600

ggagaaggga agatgagttc ttcaaaaggg aattttatag ctgttgatga ctctccagaa    660

gagattaggg ctaagataaa gaaagcatac tgcccagctg gagttgttga aggaaatcca    720

ataatggaga tagctaaata cttccttgaa tatcctttaa ccataaaaag gccagaaaaa    780

tttggtggag atttgacagt tagtagctat gaggagttag agagtttatt taaaaataag    840

gaattgcatc caatggattt aaaaaatgct gtagctgaag aacttataaa gattttagag    900

ccaattagaa agagattata a                                              921


<210> SEQ ID NO 5
<211> LENGTH: 917
<212> TYPE: DNA
<213> ORGANISM: Methanococcus jannaschii

<400> SEQUENCE: 5

atggacgaat ttgaaatgat aaagagaaac acatctgaaa ttatcagcga ggaagagtta     60

agagaggttt taaaaaaaga tgaaaaatct gctgggatag gttttgaacc aagtggtaaa    120
```

```
atacatttag ggcattatct ccaaataaaa aagatgattg atttacaaaa tgctggattt    180

gatataatta tattgttggc tgatttacac gcctatttaa accagaaagg agagttggat    240

gagattagaa aaataggaga ttataacaaa aaagtttttg aagcaatggg gttaaaggca    300

aaatgtgctt atggaagtcc tttccagctt gataaggatt atacactgaa tgtctataga    360

ttggctttaa aaactacctt aaaaagagca agaaggagta tggaacttat agaagagagg    420

atgaaaatcc aaaggttgct gaagttatct atccaataat gcaggttaat ggttatcatt    480

atcttggcgt tgatgttgca gttggaggga tggagcagag aaaaatacac atgttagcaa    540

gggagctttt accaaaaaag gttgtttgta ttcacaaccc tgtcttaacg ggtttggatg    600

gagaaggaaa gatgagttct tcaaaaggga attttatagc tgttgatgac tctccagaag    660

agattagggc taagataaag aaagcatact gcccagctgg agttgttgaa ggaaatccaa    720

taatggagat agctaaatac ttccttgaat atcctttaac cataaaaagg ccagaaaaat    780

ttggtggaga tttgacagtt aatagctatg aggagttaga gagtttattt aaaaataagg    840

aattgcatcc aatggattta aaaaatgctg tagctgaaga acttataaag attttagagc    900

caattagaaa gagatta                                                   917
```

```
<210> SEQ ID NO 6
<211> LENGTH: 917
<212> TYPE: DNA
<213> ORGANISM: Methanococcus jannaschii

<400> SEQUENCE: 6

atggacgaat ttgaaatgat aaagagaaac acatctgaaa ttatcagcga ggaagagtta     60

agagaggttt taaaaaaaga tgaaaaatct gctcagatag gttttgaacc aagtggtaaa    120

atacatttag ggcattatct ccaaataaaa aagatgattg atttacaaaa tgctggattt    180

gatataatta tattgttggc tgatttacac gcctatttaa accagaaagg agagttggat    240

gagattagaa aaataggaga ttataacaaa aaagtttttg aagcaatggg gttaaaggca    300

aaatatgttt atggaagtcc tttccagctt gataaggatt atacactgaa tgtctataga    360

ttggctttaa aaactacctt aaaaagagca agaaggagta tggaacttat agaagagagg    420

atgaaaatcc aaaggttgct gaagttatct atccaataat gcaggttaat tgttctcatt    480

attatggcgt tgatgttgca gttggaggga tggagcagag aaaaatacac atgttagcaa    540

gggagctttt accaaaaaag gttgtttgta ttcacaaccc tgtcttaacg ggtttggatg    600

gagaaggaaa gatgagttct tcaaaaggga attttatagc tgttgatgac tctccagaag    660

agattagggc taagataaag aaagcatact gcccagctgg agttgttgaa ggaaatccaa    720

taatggagat agctaaatac ttccttgaat atcctttaac cataaaaagg ccagaaaaat    780

ttggtggaga tttgacagtt aatagctatg aggagttaga gagtttattt aaaaataagg    840

aattgcatcc aatggattta aaaaatgctg tagctgaaga acttataaag attttagagc    900

caattagaaa gagatta                                                   917
```

```
<210> SEQ ID NO 7
<211> LENGTH: 917
<212> TYPE: DNA
<213> ORGANISM: Methanococcus jannaschii

<400> SEQUENCE: 7

atggacgaat ttgaaatgat aaagagaaac acatctgaaa ttatcagcga ggaagagtta     60
```

-continued

```
agagaggttt taaaaaaaga tgaaaaatct gctactatag gttttgaacc aagtggtaaa    120

atacatttag ggcattatct ccaaataaaa aagatgattg atttacaaaa tgctggattt    180

gatataatta tattgttggc tgatttacac gcctatttaa accagaaagg agagttggat    240

gagattagaa aaataggaga ttataacaaa aaagtttttg aagcaatggg gttaaaggca    300

aaatatgttt atggaagtac gttccagctt gataaggatt atacactgaa tgtctataga    360

ttggctttaa aaactacctt aaaaagagca agaaggagta tggaacttat agaagagagg    420

atgaaaatcc aaaggttgct gaagttatct atccaataat gcaggttaat ccgttgcatt    480

atgctggcgt tgatgttgca gttggaggga tggagcagag aaaaatacac atgttagcaa    540

gggagctttt accaaaaaag gttgtttgta ttcacaaccc tgtcttaacg ggtttggatg    600

gagaaggaaa gatgagttct tcaaaaggga attttatagc tgttgatgac tctccagaag    660

agattagggc taagataaag aaagcatact gcccagctgg agttgttgaa ggaaatccaa    720

taatggagat agctaaatac ttccttgaat atcctttaac cataaaaagg ccagaaaaat    780

ttggtggaga tttgacagtt aatagctatg aggagttaga gagtttattt aaaaataagg    840

aattgcatcc aatggattta aaaaatgctg tagctgaaga acttataaag attttagagc    900

caattagaaa gagatta                                                    917
```

<210> SEQ ID NO 8
<211> LENGTH: 917
<212> TYPE: DNA
<213> ORGANISM: Methanococcus jannaschii

<400> SEQUENCE: 8

```
atggacgaat ttgaaatgat aaagagaaac acatctgaaa ttatcagcga ggaagagtta     60

agagaggttt taaaaaaaga tgaaaaatct gctcatatag gttttgaacc aagtggtaaa    120

atacatttag ggcattatct ccaaataaaa aagatgattg atttacaaaa tgctggattt    180

gatataatta tattgttggc tgatttacac gcctatttaa accagaaagg agagttggat    240

gagattagaa aaataggaga ttataacaaa aaagtttttg aagcaatggg gttaaaggca    300

aaatatgttt atggaagtga gttccagctt gataaggatt atacactgaa tgtctataga    360

ttggctttaa aaactacctt aaaaagagca agaaggagta tggaacttat agaagagagg    420

atgaaaatcc aaaggttgct gaagttatct atccaataat gcaggttaat cggccgcatt    480

atcctggcgt tgatgttgca gttggaggga tggagcagag aaaaatacac atgttagcaa    540

gggagctttt accaaaaaag gttgtttgta ttcacaaccc tgtcttaacg ggtttggatg    600

gagaaggaaa gatgagttct tcaaaaggga attttatagc tgttgatgac tctccagaag    660

agattagggc taagataaag aaagcatact gcccagctgg agttgttgaa ggaaatccaa    720

taatggagat agctaaatac ttccttgaat atcctttaac cataaaaagg ccagaaaaat    780

ttggtggaga tttgacagtt aatagctatg aggagttaga gagtttattt aaaaataagg    840

aattgcatcc aatggattta aaaaatgctg tagctgaaga acttataaag attttagagc    900

caattagaaa gagatta                                                    917
```

<210> SEQ ID NO 9
<211> LENGTH: 917
<212> TYPE: DNA
<213> ORGANISM: Methanococcus jannaschii

<400> SEQUENCE: 9

```
atggacgaat ttgaaatgat aaagagaaac acatctgaaa ttatcagcga ggaagagtta     60
```

-continued agagaggttt taaaaaaaga tgaaaaatct gcttatatag gttttgaacc aagtggtaaa 120
atacatttag ggcattatct ccaaataaaa aagatgattg atttacaaaa tgctggattt 180
gatataatta tattgttggc tgatttacac gcctatttaa accagaaagg agagttggat 240
gagattagaa aaataggaga ttataacaaa aaagtttttg aagcaatggg gttaaaggca 300
aaatatgttt atggaagtcc tttccagctt gataaggatt atacactgaa tgtctataga 360
ttggctttaa aaactacctt aaaaagagca agaaggagta tggaacttat agaagagagg 420
atgaaaatcc aaaggttgct gaagttatct atccaataat gcaggttaat cagagtcatt 480
atgatggcgt tgatgttgca gttggaggga tggagcagag aaaaatacac atgttagcaa 540
gggagctttt accaaaaaag gttgtttgta ttcacaaccc tgtcttaacg ggtttggatg 600
gagaaggaaa gatgagttct tcaaaaggga attttatagc tgttgatgac tctccagaag 660
agattagggc taagataaag aaagcatact gcccagctgg agttgttgaa ggaaatccaa 720
taatggagat agctaaatac ttccttgaat atcctttaac cataaaaagg ccagaaaaat 780
ttggtggaga tttgacagtt aatagctatg aggagttaga gagtttattt aaaaataagg 840
aattgcatcc aatggattta aaaaatgctg tagctgaaga acttataaag attttagagc 900
caattagaaa gagatta 917

<210> SEQ ID NO 10
<211> LENGTH: 917
<212> TYPE: DNA
<213> ORGANISM: Methanococcus jannaschii

<400> SEQUENCE: 10
atggacgaat ttgaaatgat aaagagaaac acatctgaaa ttatcagcga ggaagagtta 60
agagaggttt taaaaaaaga tgaaaaatct gcttcgatag gttttgaacc aagtggtaaa 120
atacatttag ggcattatct ccaaataaaa aagatgattg atttacaaaa tgctggattt 180
gatataatta tattgttggc tgatttacac gcctatttaa accagaaagg agagttggat 240
gagattagaa aaataggaga ttataacaaa aaagtttttg aagcaatggg gttaaaggca 300
aaatatgttt atggaagtac gttccagctt gataaggatt atacactgaa tgtctataga 360
ttggctttaa aaactacctt aaaaagagca agaaggagta tggaacttat agaagagagg 420
atgaaaatcc aaaggttgct gaagttatct atccaataat gcaggttaat acgtatcatt 480
atgctggcgt tgatgttgca gttggaggga tggagcagag aaaaatacac atgttagcaa 540
gggagctttt accaaaaaag gttgtttgta ttcacaaccc tgtcttaacg ggtttggatg 600
gagaaggaaa gatgagttct tcaaaaggga attttatagc tgttgatgac tctccagaag 660
agattagggc taagataaag aaagcatact gcccagctgg agttgttgaa ggaaatccaa 720
taatggagat agctaaatac ttccttgaat atcctttaac cataaaaagg ccagaaaaat 780
ttggtggaga tttgacagtt aatagctatg aggagttaga gagtttattt aaaaataagg 840
aattgcatcc aatggattta aaaaatgctg tagctgaaga acttataaag attttagagc 900
caattagaaa gagatta 917

<210> SEQ ID NO 11
<211> LENGTH: 917
<212> TYPE: DNA
<213> ORGANISM: Methanococcus jannaschii

<400> SEQUENCE: 11

-continued

```
atggacgaat ttgaaatgat aaagagaaac acatctgaaa ttatcagcga ggaagagtta    60

agagaggttt taaaaaaaga tgaaaaatct gctcctatag gttttgaacc aagtggtaaa   120

atacatttag ggcattatct ccaaataaaa aagatgattg atttacaaaa tgctggattt   180

gatataatta tattgttggc tgatttacac gcctatttaa accagaaagg agagttggat   240

gagattagaa aaataggaga ttataacaaa aaagtttttg aagcaatggg gttaaaggca   300

aaatatgttt atggaagtat gttccagctt gataaggatt atacactgaa tgtctataga   360

ttggctttaa aaactacctt aaaaagagca agaaggagta tggaacttat agaagagagg   420

atgaaaatcc aaaggttgct gaagttatct atccaataat gcaggttaat aatacgcatt   480

atgggggcgt tgatgttgca gttggaggga tggagcagag aaaaatacac atgttagcaa   540

gggagctttt accaaaaaag gttgtttgta ttcacaaccc tgtcttaacg ggtttggatg   600

gagaaggaaa gatgagttct tcaaaaggga attttatagc tgttgatgac tctccagaag   660

agattagggc taagataaag aaagcatact gcccagctgg agttgttgaa ggaaatccaa   720

taatggagat agctaaatac ttccttgaat atcctttaac cataaaaagg ccagaaaaat   780

ttggtggaga tttgacagtt aatagctatg aggagttaga gagtttattt aaaaataagg   840

aattgcatcc aatggattta aaaaatgctg tagctgaaga acttataaag attttagagc   900

caattagaaa gagatta                                                  917
```

<210> SEQ ID NO 12
<211> LENGTH: 917
<212> TYPE: DNA
<213> ORGANISM: Methanococcus jannaschii

<400> SEQUENCE: 12

```
atggacgaat ttgaaatgat aaagagaaac acatctgaaa ttatcagcga ggaagagtta    60

agagaggttt taaaaaaaga tgaaaaatct gctacgatag gttttgaacc aagtggtaaa   120

atacatttag ggcattatct ccaaataaaa aagatgattg atttacaaaa tgctggattt   180

gatataatta tattgttggc tgatttacac gcctatttaa accagaaagg agagttggat   240

gagattagaa aaataggaga ttataacaaa aaagtttttg aagcaatggg gttaaaggca   300

aaatatgttt atggaagtca tttccagctt gataaggatt atacactgaa tgtctataga   360

ttggctttaa aaactacctt aaaaagagca agaaggagta tggaacttat agaagagagg   420

atgaaaatcc aaaggttgct gaagttatct atccaataat gcaggttaat cagactcatt   480

atgagggcgt tgatgttgca gttggaggga tggagcagag aaaaatacac atgttagcaa   540

gggagctttt accaaaaaag gttgtttgta ttcacaaccc tgtcttaacg ggtttggatg   600

gagaaggaaa gatgagttct tcaaaaggga attttatagc tgttgatgac tctccagaag   660

agattagggc taagataaag aaagcatact gcccagctgg agttgttgaa ggaaatccaa   720

taatggagat agctaaatac ttccttgaat atcctttaac cataaaaagg ccagaaaaat   780

ttggtggaga tttgacagtt aatagctatg aggagttaga gagtttattt aaaaataagg   840

aattgcatcc aatggattta aaaaatgctg tagctgaaga acttataaag attttagagc   900

caattagaaa gagatta                                                  917
```

<210> SEQ ID NO 13
<211> LENGTH: 917
<212> TYPE: DNA
<213> ORGANISM: Methanococcus jannaschii

<400> SEQUENCE: 13

```
atggacgaat ttgaaatgat aaagagaaac acatctgaaa ttatcagcga ggaagagtta     60

agagaggttt taaaaaaaga tgaaaaatct gctcatatag gttttgaacc aagtggtaaa    120

atacatttag ggcattatct ccaaataaaa aagatgattg atttacaaaa tgctggattt    180

gatataatta tattgttggc tgatttacac gcctatttaa accagaaagg agagttggat    240

gagattagaa aaataggaga ttataacaaa aaagtttttg aagcaatggg gttaaaggca    300

aaatatgttt atggaagtaa gttccagctt gataaggatt atacactgaa tgtctataga    360

ttggctttaa aaactacctt aaaaaagagca agaaggagta tggaacttat agaagagagg    420

atgaaaatcc aaaggttgct gaagttatct atccaataat gcaggttaat ccgtgtcatt    480

atcatggcgt tgatgttgca gttggaggga tggagcagag aaaaatacac atgttagcaa    540

gggagctttt accaaaaaag gttgtttgta ttcacaaccc tgtcttaacg ggtttggatg    600

gagaaggaaa gatgagttct tcaaaaggga attttatagc tgttgatgac tctccagaag    660

agattagggc taagataaag aaagcatact gcccagctgg agttgttgaa ggaaatccaa    720

taatggagat agctaaatac ttccttgaat atcctttaac cataaaaagg ccagaaaaat    780

ttggtggaga tttgacagtt aatagctatg aggagttaga gagtttattt aaaaataagg    840

aattgcatcc aatggattta aaaaatgctg tagctgaaga acttataaag attttagagc    900

caattagaaa gagatta                                                   917
```

<210> SEQ ID NO 14
<211> LENGTH: 917
<212> TYPE: DNA
<213> ORGANISM: Methanococcus jannaschii

<400> SEQUENCE: 14

```
atggacgaat ttgaaatgat aaagagaaac acatctgaaa ttatcagcga ggaagagtta     60

agagaggttt taaaaaaaga tgaaaaatct gctgctatag gttttgaacc aagtggtaaa    120

atacatttag ggcattatct ccaaataaaa aagatgattg atttacaaaa tgctggattt    180

gatataatta tattgttggc tgatttacac gcctatttaa accagaaagg agagttggat    240

gagattagaa aaataggaga ttataacaaa aaagtttttg aagcaatggg gttaaaggca    300

aaatatgttt atggaagtcg gttccagctt gataaggatt atacactgaa tgtctataga    360

ttggctttaa aaactacctt aaaaaagagca agaaggagta tggaacttat agaagagagg    420

atgaaaatcc aaaggttgct gaagttatct atccaataat gcaggttaat gtgattcatt    480

atgatggcgt tgatgttgca gttggaggga tggagcagag aaaaatacac atgttagcaa    540

gggagctttt accaaaaaag gttgtttgta ttcacaaccc tgtcttaacg ggtttggatg    600

gagaaggaaa gatgagttct tcaaaaggga attttatagc tgttgatgac tctccagaag    660

agattagggc taagataaag aaagcatact gcccagctgg agttgttgaa ggaaatccaa    720

taatggagat agctaaatac ttccttgaat atcctttaac cataaaaagg ccagaaaaat    780

ttggtggaga tttgacagtt aatagctatg aggagttaga gagtttattt aaaaataagg    840

aattgcatcc aatggattta aaaaatgctg tagctgaaga acttataaag attttagagc    900

caattagaaa gagatta                                                   917
```

<210> SEQ ID NO 15
<211> LENGTH: 917
<212> TYPE: DNA
<213> ORGANISM: Methanococcus jannaschii

<400> SEQUENCE: 15

```
atggacgaat ttgaaatgat aaagagaaac acatctgaaa ttatcagcga ggaagagtta    60

agagaggttt taaaaaaaga tgaaaaatct gctgggatag gttttgaacc aagtggtaaa   120

atacatttag ggcattatct ccaaataaaa aagatgattg atttacaaaa tgctggattt   180

gatataatta tattgttggc tgatttacac gcctatttaa accagaaagg agagttggat   240

gagattagaa aaataggaga ttataacaaa aaagtttttg aagcaatggg gttaaaggca   300

aaatatgttt atggaagtac tttccagctt gataaggatt atacactgaa tgtctataga   360

ttggctttaa aaactacctt aaaaagagca agaaggagta tggaacttat agaagagagg   420

atgaaaatcc aaaggttgct gaagttatct atccaataat gcaggttaat acgtattatt   480

atgctggcgt tgatgttgca gttggaggga tggagcagag aaaaatacac atgttagcaa   540

gggagctttt accaaaaaag gttgtttgta ttcacaaccc tgtcttaacg ggtttggatg   600

gagaaggaaa gatgagttct tcaaaaggga attttatagc tgttgatgac tctccagaag   660

agattagggc taagataaag aaagcatact gcccagctgg agttgttgaa ggaaatccaa   720

taatggagat agctaaatac ttccttgaat atcctttaac cataaaaagg ccagaaaaat   780

ttggtggaga tttgacagtt aatagctatg aggagttaga gagtttattt aaaaataagg   840

aattgcatcc aatggattta aaaaatgctg tagctgaaga acttataaag attttagagc   900

caattagaaa gagatta                                                  917
```

<210> SEQ ID NO 16
<211> LENGTH: 917
<212> TYPE: DNA
<213> ORGANISM: Methanococcus jannaschii

<400> SEQUENCE: 16

```
atggacgaat ttgaaatgat aaagagaaac acatctgaaa ttatcagcga ggaagagtta    60

agagaggttt taaaaaaaga tgaaaaatct gctctgatag gttttgaacc aagtggtaaa   120

atacatttag ggcattatct ccaaataaaa aagatgattg atttacaaaa tgctggattt   180

gatataatta tattgttggc tgatttacac gcctatttaa accagaaagg agagttggat   240

gagattagaa aaataggaga ttataacaaa aaagtttttg aagcaatggg gttaaaggca   300

aaatatgttt atggaagtcc gttccagctt gataaggatt atacactgaa tgtctataga   360

ttggctttaa aaactacctt aaaaagagca agaaggagta tggaacttat agaagagagg   420

atgaaaatcc aaaggttgct gaagttatct atccaataat gcaggttaat cagattcatt   480

ctagtggcgt tgatgttgca gttggaggga tggagcagag aaaaatacac atgttagcaa   540

gggagctttt accaaaaaag gttgtttgta ttcacaaccc tgtcttaacg ggtttggatg   600

gagaaggaaa gatgagttct tcaaaaggga attttatagc tgttgatgac tctccagaag   660

agattagggc taagataaag aaagcatact gcccagctgg agttgttgaa ggaaatccaa   720

taatggagat agctaaatac ttccttgaat atcctttaac cataaaaagg ccagaaaaat   780

ttggtggaga tttgacagtt aatagctatg aggagttaga gagtttattt aaaaataagg   840

aattgcatcc aatggattta aaaaatgctg tagctgaaga acttataaag attttagagc   900

caattagaaa gagatta                                                  917
```

<210> SEQ ID NO 17
<211> LENGTH: 921
<212> TYPE: DNA
<213> ORGANISM: Methanococcus jannaschii

<400> SEQUENCE: 17

```
atggacgaat ttgaaatgat aaagagaaac acatctgaaa ttatcagcga ggaagagtta     60
agagaggttt taaaaaaaga tgaaaaatct gctgacatag gttttgaacc aagtggtaaa    120
atacatttag ggcattatct ccaaataaaa aagatgattg atttacaaaa tgctggattt    180
gatataatta tattgttggc tgatttacac gcctatttaa accagaaagg agagttggat    240
gagattagaa aaataggaga ttataacaaa aaagtttttg aagcaatggg gttaaaggca    300
aaatatgttt atggaagtga attccagctt gataaggatt atacactgaa tgtctataga    360
ttggctttaa aaactacctt aaaaagagca agaaggagta tggaacttat agcaagagag    420
gatgaaaatc caaaggttgc tgaagttatc tatccaataa tgcaggttaa tggaatgcat    480
tatcaaggcg ttgatgttgc agttggaggg atggagcaga gaaaaataca catgttagca    540
agggagcttt taccaaaaaa ggttgtttgt attcacaacc ctgtcttaac gggtttggat    600
ggagaaggaa agatgagttc ttcaaaaggg aattttatag ctgttgatga ctctccagaa    660
gagattaggg ctaagataaa gaaagcatac tgcccagctg gagttgttga aggaaatcca    720
ataatggaga tagctaaata cttccttgaa tatcctttaa ccataaaaag gccagaaaaa    780
tttggtggag atttgacagt taatagctat gaggagttag agagtttatt taaaaataag    840
gaattgcatc caatggattt aaaaaatgct gtagctgaag aacttataaa gattttagag    900
ccaattagaa agagattata a                                              921
```

<210> SEQ ID NO 18
<211> LENGTH: 921
<212> TYPE: DNA
<213> ORGANISM: Methanococcus jannaschii

<400> SEQUENCE: 18

```
atggacgaat ttgaaatgat aaagagaaac acatctgaaa ttatcagcga ggaagagtta     60
agagaggttt taaaaaaaga tgaaaaatct gcttacatag gttttgaacc aagtggtaaa    120
atacatttag ggcattatct ccaaataaaa aagatgattg atttacaaaa tgctggattt    180
gatataatta tattgttggc tgatttacac gcctatttaa accagaaagg agagttggat    240
gagattagaa aaataggaga ttataacaaa aaagtttttg aagcaatggg gttaaaggca    300
aaatatgttt atggaagtct attccagctt gataaggatt atacactgaa tgtctataga    360
ttggctttaa aaactacctt aaaaagagca agaaggagta tggaacttat agcaagagag    420
gatgaaaatc caaaggttgc tgaagttatc tatccaataa tgcaggttaa tgatattcat    480
tatacaggcg ttgatgttgc agttggaggg atggagcaga gaaaaataca catgttagca    540
agggagcttt taccaaaaaa ggttgtttgt attcacaacc ctgtcttaac gggtttggat    600
ggagaaggaa agatgagttc ttcaaaaggg aattttatag ctgttgatga ctctccagaa    660
gagattaggg ctaagataaa gaaagcatac tgcccagctg gagttgttga aggaaatcca    720
ataatggaga tagctaaata cttccttgaa tatcctttaa ccataaaaag gccagaaaaa    780
tttggtggag atttgacagt taatagctat gaggagttag agagtttatt taaaaataag    840
gaattgcatc caatggattt aaaaaatgct gtagctgaag aacttataaa gattttagag    900
ccaattagaa agagattata a                                              921
```

<210> SEQ ID NO 19
<211> LENGTH: 921
<212> TYPE: DNA

-continued

<213> ORGANISM: Methanococcus jannaschii

<400> SEQUENCE: 19

```
atggacgaat ttgaaatgat aaagagaaac acatctgaaa ttatcagcga ggaagagtta     60
agagaggttt taaaaaaaga tgaaaaatct gctctaatag gttttgaacc aagtggtaaa    120
atacatttag ggcattatct ccaaataaaa aagatgattg atttacaaaa tgctggattt    180
gatataatta tattgttgac agatttaaac gcctatttaa accagaaagg agagttggat    240
gagattagaa aaataggaga ttataacaaa aaagtttttg aagcaatggg gttaaaggca    300
aaatatgttt atggaagtga attccagctt gataaggatt atacactgaa tgtctataga    360
ttggctttaa aaactacctt aaaaagagca agaaggagta tggaacttat agcaagagag    420
gatgaaaatc caaaggttgc tgaagttatc tatccaataa tgcaggttaa tgatattcat    480
tatttaggcg ttgatgttgc agttggaggg atggagcaga gaaaaataca catgttagca    540
agggagcttt taccaaaaaa ggttgtttgt attcacaacc ctgtcttaac gggtttggat    600
ggagaaggaa agatgagttc ttcaaaaggg aattttatag ctgttgatga ctctccagaa    660
gagattaggg ctaagataaa gaaagcatac tgcccagctg gagttgttga aggaaatcca    720
ataatggaga tagctaaata cttccttgaa tatcctttaa ccataaaaag gccagaaaaa    780
tttggtggag atttgacagt taatagctat gaggagttag agagtttatt taaaaataag    840
gaattgcatc caatggattt aaaaaatgct gtagctgaag aacttataaa gattttagag    900
ccaattagaa agagattata a                                              921
```

<210> SEQ ID NO 20
<211> LENGTH: 921
<212> TYPE: DNA
<213> ORGANISM: Methanococcus jannaschii

<400> SEQUENCE: 20

```
atggacgaat ttgaaatgat aaagagaaac acatctgaaa ttatcagcga ggaagagtta     60
agagaggttt taaaaaaaga tgaaaaatct gctctaatag gttttgaacc aagtggtaaa    120
atacatttag ggcattatct ccaaataaaa aagatgattg atttacaaaa tgctggattt    180
gatataatta tattgttgac agatttaaaa gcctatttaa accagaaagg agagttggat    240
gagattagaa aaataggaga ttataacaaa aaagtttttg aagcaatggg gttaaaggca    300
aaatatgttt atggaagtga attccagctt gataaggatt atacactgaa tgtctataga    360
ttggctttaa aaactacctt aaaaagagca agaaggagta tggaacttat agcaagagag    420
gatgaaaatc caaaggttgc tgaagttatc tatccaataa tgtcagttaa tgtaattcat    480
tatttaggcg ttgatgttgt agttggaggg atggagcaga gaaaaataca catgttagca    540
agggagcttt taccaaaaaa ggttgtttgt attcacaacc ctgtcttaac gggtttggat    600
ggagaaggaa agatgagttc ttcaaaaggg aattttatag ctgttgatga ctctccagaa    660
gagattaggg ctaagataaa gaaagcatac tgcccagctg gagttgttga aggaaatcca    720
ataatggaga tagctaaata cttccttgaa tatcctttaa ccataaaaag gccagaaaaa    780
tttggtggag atttgacagt taatagctat gaggagttag agagtttatt taaaaataag    840
gaattgcatc caatggattt aaaaaatgct gtagctgaag aacttataaa gattttagag    900
ccaattagaa agagattata a                                              921
```

<210> SEQ ID NO 21
<211> LENGTH: 921

-continued

<212> TYPE: DNA
<213> ORGANISM: Methanococcus jannaschii

<400> SEQUENCE: 21

```
atggacgaat ttgaaatgat aaagagaaac acatctgaaa ttatcagcga ggaagagtta     60
agagaggttt taaaaaaaga tgaaaaatct gctctaatag gttttgaacc aagtggtaaa    120
atacatttag ggcattatct ccaaataaaa aagatgattg atttacaaaa tgctggattt    180
gatataatta tattgttgcc agatttatca gcctatttaa accagaaagg agagttggat    240
gagattagaa aaataggaga ttataacaaa aaagtttttg aagcaatggg gttaaaggca    300
aaatatgttt atggaagtga attccagctt gataaggatt atacactgaa tgtctataga    360
ttggctttaa aaactacctt aaaaagagca agaaggagta tggaacttat agcaagagag    420
gatgaaaatc caaaggttgc tgaagttatc tatccaataa tgcaggttaa tgatattcat    480
tatttaggcg ttgatgttgc agttggaggg atggagcaga gaaaaataca catgttagca    540
agggagcttt taccaaaaaa ggttgtttgt attcacaacc ctgtcttaac gggtttggat    600
ggagaaggaa agatgagttc ttcaaaaggg aattttatag ctgttgatga ctctccagaa    660
gagattaggg ctaagataaa gaaagcatac tgcccagctg gagttgttga aggaaatcca    720
ataatggaga tagctaaata cttccttgaa tatcctttaa ccataaaaag gccagaaaaa    780
tttggtggag atttgacagt taatagctat gaggagttag agagtttatt taaaaataag    840
gaattgcatc caatggattt aaaaaatgct gtagctgaag aacttataaa gattttagag    900
ccaattagaa agagattata a                                              921
```

<210> SEQ ID NO 22
<211> LENGTH: 921
<212> TYPE: DNA
<213> ORGANISM: Methanococcus jannaschii

<400> SEQUENCE: 22

```
atggacgaat ttgaaatgat aaagagaaac acatctgaaa ttatcagcga ggaagagtta     60
agagaggttt taaaaaaaga tgaaaaatct gctacaatag gttttgaacc aagtggtaaa    120
atacatttag ggcattatct ccaaataaaa aagatgattg atttacaaaa tgctggattt    180
gatataatta tattgttggc tgatttacac gcctatttaa accagaaagg agagttggat    240
gagattagaa aaataggaga ttataacaaa aaagtttttg aagcaatggg gttaaaggca    300
aaatatgttt atggaagtga attccagctt gataaggatt atacactgaa tgtctataga    360
ttggctttaa aaactacctt aaaaagagca agaaggagta tggaacttat agcaagagag    420
gatgaaaatc caaaggttgc tgaagttatc tatccaataa tgcaggttaa tgatattcat    480
tatgcaggcg ttgatgttgc agttggaggg atggagcaga gaaaaataca catgttagca    540
agggagcttt taccaaaaaa ggttgtttgt attcacaacc ctgtcttaac gggtttggat    600
ggagaaggaa agatgagttc ttcaaaaggg aattttatag ctgttgatga ctctccagaa    660
gagattaggg ctaagataaa gaaagcatac tgcccagctg gagttgttga aggaaatcca    720
ataatggaga tagctaaata cttccttgaa tatcctttaa ccataaaaag gccagaaaaa    780
tttggtggag atttgacagt taatagctat gaggagttag agagtttatt taaaaataag    840
gaattgcatc caatggattt aaaaaatgct gtagctgaag aacttataaa gattttagag    900
ccaattagaa agagattata a                                              921
```

<210> SEQ ID NO 23

<211> LENGTH: 921
<212> TYPE: DNA
<213> ORGANISM: Methanococcus jannaschii

<400> SEQUENCE: 23

```
atggacgaat ttgaaatgat aaagagaaac acatctgaaa ttatcagcga ggaagagtta     60
agagaggttt taaaaaaaga tgaaaaatct gctacaatag gttttgaacc aagtggtaaa    120
atacatttag ggcattatct ccaaataaaa aagatgattg atttacaaaa tgctggattt    180
gatataatta tattgttgtc cgatttacca gcctatttaa accagaaagg agagttggat    240
gagattagaa aaataggaga ttataacaaa aaagtttttg aagcaatggg gttaaaggca    300
aaatatgttt atggaagtga attccagctt gataaggatt atacactgaa tgtctataga    360
ttggctttaa aaactacctt aaaaagagca agaaggagta tggaacttat agcaagagag    420
gatgaaaatc caaaggttgc tgaagttatc tatccaataa tgcaggttaa tgatattcat    480
tatttaggcg ttgatgttgc agttggaggg atggagcaga gaaaaataca catgttagca    540
agggagcttt taccaaaaaa ggttgtttgt attcacaacc ctgtcttaac gggtttggat    600
ggagaaggaa agatgagttc ttcaaaaggg aattttatag ctgttgatga ctctccagaa    660
gagattaggg ctaagataaa gaaagcatac tgcccagctg gagttgttga aggaaatcca    720
ataatggaga tagctaaata cttccttgaa tatcctttaa ccataaaaag gccagaaaaa    780
tttggtggag atttgacagt taatagctat gaggagttag agagtttatt taaaaataag    840
gaattgcatc caatggattt aaaaaatgct gtagctgaag aacttataaa gattttagag    900
ccaattagaa agagattata a                                               921
```

<210> SEQ ID NO 24
<211> LENGTH: 921
<212> TYPE: DNA
<213> ORGANISM: Methanococcus jannaschii

<400> SEQUENCE: 24

```
atggacgaat ttgaaatgat aaagagaaac acatctgaaa ttatcagcga ggaagagtta     60
agagaggttt taaaaaaaga tgaaaaatct gctacaatag gttttgaacc aagtggtaaa    120
atacatttag ggcattatct ccaaataaaa aagatgattg atttacaaaa tgctggattt    180
gatataatta tattgttggc tgatttacac gcctatttaa accagaaagg agagttggat    240
gagattagaa aaataggaga ttataacaaa aaagtttttg aagcaatggg gttaaaggca    300
aaatatgttt atggaagtat gttccagctt gataaggatt atacactgaa tgtctataga    360
ttggctttaa aaactacctt aaaaagagca agaaggagta tggaacttat agcaagagag    420
gatgaaaatc caaaggttgc tgaagttatc tatccaataa tgcaggttaa ttcatcacat    480
tatgacggcg ttgatgttgc agttggaggg atggagcaga gaaaaataca catgttagca    540
agggagcttt taccaaaaaa ggttgtttgt attcacaacc ctgtcttaac gggtttggat    600
ggagaaggaa agatgagttc ttcaaaaggg aattttatag ctgttgatga ctctccagaa    660
gagattaggg ctaagataaa gaaagcatac tgcccagctg gagttgttga aggaaatcca    720
ataatggaga tagctaaata cttccttgaa tatcctttaa ccataaaaag gccagaaaaa    780
tttggtggag atttgacagt taatagctat gaggagttag agagtttatt taaaaataag    840
gaattgcatc caatggattt aaaaaatgct gtagctgaag aacttataaa gattttagag    900
ccaattagaa agagattata a                                               921
```

<210> SEQ ID NO 25
<211> LENGTH: 921
<212> TYPE: DNA
<213> ORGANISM: Methanococcus jannaschii

<400> SEQUENCE: 25
atggacgaat ttgaaatgat aaagagaaac acatctgaaa ttatcagcga ggaagagtta 60
agagaggttt taaaaaaaga tgaaaaatct gctcaaatag gttttgaacc aagtggtaaa 120
atacatttag ggcattatct ccaaataaaa aagatgattg atttacaaaa tgctggattt 180
gatataatta tattgttgcc agatttacac gcctatttaa accagaaagg agagttggat 240
gagattagaa aaataggaga ttataacaaa aaagtttttg aagcaatggg gttaaaggca 300
aaatatgttt atggaagtga attccagctt gataaggatt atacactgaa tgtctataga 360
ttggctttaa aaactacctt aaaaagagca agaaggagta tggaacttat agcaagagag 420
gatgaaaatc caaaggttgc tgaagttatc tatccaataa tgcaggttaa tgatattcat 480
tatttaggcg ttgatgttga cgttggaggg atggagcaga gaaaaataca catgttagca 540
agggagcttt taccaaaaaa ggttgtttgt attcacaacc ctgtcttaac gggtttggat 600
ggagaaggaa agatgagttc ttcaaaaggg aattttatag ctgttgatga ctctccagaa 660
gagattaggg ctaagataaa gaaagcatac tgcccagctg gagttgttga aggaaatcca 720
ataatggaga tagctaaata cttccttgaa tatcctttaa ccataaaaag gccagaaaaa 780
tttggtggag atttgacagt taatagctat gaggagttag agagtttatt taaaaataag 840
gaattgcatc caatggattt aaaaaatgct gtagctgaag aacttataaa gattttagag 900
ccaattagaa agagattata a 921

<210> SEQ ID NO 26
<211> LENGTH: 921
<212> TYPE: DNA
<213> ORGANISM: Methanococcus jannaschii

<400> SEQUENCE: 26
atggacgaat ttgaaatgat aaagagaaac acatctgaaa ttatcagcga ggaagagtta 60
agagaggttt taaaaaaaga tgaaaaatct gctcacatag gttttgaacc aagtggtaaa 120
atacatttag ggcattatct ccaaataaaa aagatgattg atttacaaaa tgctggattt 180
gatataatta tattgttggc tgatttacac gcctatttaa accagaaagg agagttggat 240
gagattagaa aaataggaga ttataacaaa aaagtttttg aagcaatggg gttaaaggca 300
aaatatgttt atggaagtgc attccagctt gataaggatt atacactgaa tgtctataga 360
ttggctttaa aaactacctt aaaaagagca agaaggagta tggaacttat agcaagagag 420
gatgaaaatc caaaggttgc tgaagttatc tatccaataa tgcaggttaa tggacaccat 480
tatataggcg ttgatgttgc agttggaggg atggagcaga gaaaaataca catgttagca 540
agggagcttt taccaaaaaa ggttgtttgt attcacaacc ctgtcttaac gggtttggat 600
ggagaaggaa agatgagttc ttcaaaaggg aattttatag ctgttgatga ctctccagaa 660
gagattaggg ctaagataaa gaaagcatac tgcccagctg gagttgttga aggaaatcca 720
ataatggaga tagctaaata cttccttgaa tatcctttaa ccataaaaag gccagaaaaa 780
tttggtggag atttgacagt taatagctat gaggagttag agagtttatt taaaaataag 840
gaattgcatc caatggattt aaaaaatgct gtagctgaag aacttataaa gattttagag 900
ccaattagaa agagattata a 921

<210> SEQ ID NO 27
<211> LENGTH: 921
<212> TYPE: DNA
<213> ORGANISM: Methanococcus jannaschii

<400> SEQUENCE: 27

```
atggacgaat ttgaaatgat aaagagaaac acatctgaaa ttatcagcga ggaagagtta     60
agagaggttt taaaaaaaga tgaaaaatct gcttacatag gttttgaacc aagtggtaaa    120
atacatttag ggcattatct ccaaataaaa aagatgattg atttacaaaa tgctggattt    180
gatataatta tattgttggc tgatttacac gcctatttaa accagaaagg agagttggat    240
gagattagaa aaataggaga ttataacaaa aaagtttttg aagcaatggg gttaaaggca    300
aaatatgttt atggaagtgc attccagctt gataaggatt atacactgaa tgtctataga    360
ttggctttaa aaactacctt aaaaagagca agaaggagta tggaacttat agcaagagag    420
gatgaaaatc caaaggttgc tgaagttatc tatccaataa tgcaggttaa ttgcgcacat    480
tatttaggcg ttgatgttgc agttggaggg atggagcaga gaaaaataca catgttagca    540
agggagcttt taccaaaaaa ggttgtttgt attcacaacc ctgtcttaac gggtttggat    600
ggagaaggaa agatgagttc ttcaaaaggg aattttatag ctgttgatga ctctccagaa    660
gagattaggg ctaagataaa gaaagcatac tgcccagctg gagttgttga aggaaatcca    720
ataatggaga tagctaaata cttccttgaa tatcctttaa ccataaaaag gccagaaaaa    780
tttggtggag atttgacagt taatagctat gaggagttag agagtttatt taaaaataag    840
gaattgcatc caatggattt aaaaaatgct gtagctgaag aacttataaa gattttagag    900
ccaattagaa agagattata a                                              921
```

<210> SEQ ID NO 28
<211> LENGTH: 917
<212> TYPE: DNA
<213> ORGANISM: Methanococcus jannaschii

<400> SEQUENCE: 28

```
atggacgaat ttgaaatgat aaagagaaac acatctgaaa ttatcagcga ggaagagtta     60
agagaggttt taaaaaaaga tgaaaaatct gctggtatag gttttgaacc aagtggtaaa    120
atacatttag ggcattatct ccaaataaaa aagatgattg atttacaaaa tgctggattt    180
gatataatta tattgttggc tgatttacac gcctatttaa accagaaagg agagttggat    240
gagattagaa aaataggaga ttataacaaa aaagtttttg aagcaatggg gttaaaggca    300
aaatatgttt atggaagttc cttccagctt gataaggatt atacactgaa tgtctataga    360
ttggctttaa aaactacctt aaaaagagca agaaggagta tggaacttat agaagagagg    420
atgaaaatcc aaaggttgct gaagttatct atccaataat gcaggttaat acgagtcatt    480
atctgggcgt tgatgttgca gttggaggga tggagcagag aaaaatacac atgttagcaa    540
gggagctttt accaaaaaag gttgtttgta ttcacaaccc tgtcttaacg ggtttggatg    600
gagaaggaaa gatgagttct tcaaaaggga attttatagc tgttgatgac tctccagaag    660
agattagggc taagataaag aaagcatact gcccagctgg agttgttgaa ggaaatccaa    720
taatggagat agctaaatac ttccttgaat atcctttaac cataaaaagg ccagaaaaat    780
ttggtggaga tttgacagtt aatagctatg aggagttaga gagtttattt aaaaataagg    840
aattgcatcc aatggattta aaaaatgctg tagctgaaga acttataaag attttagagc    900
caattagaaa gagatta                                                   917
```

<210> SEQ ID NO 29
<211> LENGTH: 917
<212> TYPE: DNA
<213> ORGANISM: Methanococcus jannaschii

<400> SEQUENCE: 29

```
atggacgaat ttgaaatgat aaagagaaac acatctgaaa ttatcagcga ggaagagtta     60
agagaggttt taaaaaaaga tgaaaaatct gctacgatag gttttgaacc aagtggtaaa    120
atacatttag ggcattatct ccaaataaaa aagatgattg atttacaaaa tgctggattt    180
gatataatta tattgttggc tgatttacac gcctatttaa accagaaagg agagttggat    240
gagattagaa aaataggaga ttataacaaa aaagtttttg aagcaatggg gttaaaggca    300
aaatatgttt atggaagtaa tttccagctt gataaggatt atacactgaa tgtctataga    360
ttggctttaa aaactacctt aaaaagagca agaaggagta tggaacttat agaagagagg    420
atgaaaatcc aaaggttgct gaagttatct atccaataat gcaggttaat ccgcttcatt    480
atcagggcgt tgatgttgca gttggaggga tggagcagag aaaaatacac atgttagcaa    540
gggagctttt accaaaaaag gttgtttgta ttcacaaccc tgtcttaacg ggtttggatg    600
gagaaggaaa gatgagttct tcaaaaggga attttatagc tgttgatgac tctccagaag    660
agattagggc taagataaag aaagcatact gcccagctgg agttgttgaa ggaaatccaa    720
taatggagat agctaaatac ttccttgaat atcctttaac cataaaaagg ccagaaaaat    780
ttggtggaga tttgacagtt aatagctatg aggagttaga gagtttattt aaaaataagg    840
aattgcatcc aatggattta aaaaatgctg tagctgaaga acttataaag attttagagc    900
caattagaaa gagatta                                                   917
```

<210> SEQ ID NO 30
<211> LENGTH: 917
<212> TYPE: DNA
<213> ORGANISM: Methanococcus jannaschii

<400> SEQUENCE: 30

```
atggacgaat ttgaaatgat aaagagaaac acatctgaaa ttatcagcga ggaagagtta     60
agagaggttt taaaaaaaga tgaaaaatct gctacgatag gttttgaacc aagtggtaaa    120
atacatttag ggcattatct ccaaataaaa aagatgattg atttacaaaa tgctggattt    180
gatataatta tattgttggc tgatttacac gcctatttaa accagaaagg agagttggat    240
gagattagaa aaataggaga ttataacaaa aaagtttttg aagcaatggg gttaaaggca    300
aaatatgttt atggaagtct gttccagctt gataaggatt atacactgaa tgtctataga    360
ttggctttaa aaactacctt aaaaagagca agaaggagta tggaacttat agaagagagg    420
atgaaaatcc aaaggttgct gaagttatct atccaataat gcaggttaat cctcttcatt    480
atgagggcgt tgatgttgca gttggaggga tggagcagag aaaaatacac atgttagcaa    540
gggagctttt accaaaaaag gttgtttgta ttcacaaccc tgtcttaacg ggtttggatg    600
gagaaggaaa gatgagttct tcaaaaggga attttatagc tgttgatgac tctccagaag    660
agattagggc taagataaag aaagcatact gcccagctgg agttgttgaa ggaaatccaa    720
taatggagat agctaaatac ttccttgaat atcctttaac cataaaaagg ccagaaaaat    780
ttggtggaga tttgacagtt aatagctatg aggagttaga gagtttattt aaaaataagg    840
aattgcatcc aatggattta aaaaatgctg tagctgaaga acttataaag attttagagc    900
```

caattagaaa gagatta 917

<210> SEQ ID NO 31
<211> LENGTH: 917
<212> TYPE: DNA
<213> ORGANISM: Methanococcus jannaschii

<400> SEQUENCE: 31
atggacgaat ttgaaatgat aaagagaaac acatctgaaa ttatcagcga ggaagagtta 60
agagaggttt taaaaaaaga tgaaaaatct gctcttatag gttttgaacc aagtggtaaa 120
atacatttag ggcattatct ccaaataaaa aagatgattg atttacaaaa tgctggattt 180
gatataatta tattgttggc tgatttacac gcctatttaa accagaaagg agagttggat 240
gagattagaa aaataggaga ttataacaaa aaagtttttg aagcaatggg gttaaaggca 300
aaatatgttt atggaagtac tttccagctt gataaggatt atacactgaa tgtctataga 360
ttggctttaa aaactacctt aaaaagagca agaaggagta tggaacttat agaagagagg 420
atgaaaatcc aaaggttgct gaagttatct atccaataat gcaggttaat ccggttcatt 480
atcagggcgt tgatgttgca gttggaggga tggagcagag aaaaatacac atgttagcaa 540
gggagctttt accaaaaaag gttgtttgta ttcacaaccc tgtcttaacg ggtttggatg 600
gagaaggaaa gatgagttct tcaaaaggga attttatagc tgttgatgac tctccagaag 660
agattagggc taagataaag aaagcatact gcccagctgg agttgttgaa ggaaatccaa 720
taatggagat agctaaatac ttccttgaat atcctttaac cataaaaagg ccagaaaaat 780
ttggtggaga tttgacagtt aatagctatg aggagttaga gagtttattt aaaaataagg 840
aattgcatcc aatggattta aaaaatgctg tagctgaaga acttataaag attttagagc 900
caattagaaa gagatta 917

<210> SEQ ID NO 32
<211> LENGTH: 917
<212> TYPE: DNA
<213> ORGANISM: Methanococcus jannaschii

<400> SEQUENCE: 32
atggacgaat ttgaaatgat aaagagaaac acatctgaaa ttatcagcga ggaagagtta 60
agagaggttt taaaaaaaga tgaaaaatct gctactatag gttttgaacc aagtggtaaa 120
atacatttag ggcattatct ccaaataaaa aagatgattg atttacaaaa tgctggattt 180
gatataatta tattgttggc tgatttacac gcctatttaa accagaaagg agagttggat 240
gagattagaa aaataggaga ttataacaaa aaagtttttg aagcaatggg gttaaaggca 300
aaatatgttt atggaagttc gttccagctt gataaggatt atacactgaa tgtctataga 360
ttggctttaa aaactacctt aaaaagagca agaaggagta tggaacttat agaagagagg 420
atgaaaatcc aaaggttgct gaagttatct atccaataat gcaggttaat ccactgcatt 480
atcagggcgt tgatgttgca gttggaggga tggagcagag aaaaatacac atgttagcaa 540
gggagctttt accaaaaaag gttgtttgta ttcacaaccc tgtcttaacg ggtttggatg 600
gagaaggaaa gatgagttct tcaaaaggga attttatagc tgttgatgac tctccagaag 660
agattagggc taagataaag aaagcatact gcccagctgg agttgttgaa ggaaatccaa 720
taatggagat agctaaatac ttccttgaat atcctttaac cataaaaagg ccagaaaaat 780
ttggtggaga tttgacagtt aatagctatg aggagttaga gagtttattt aaaaataagg 840
aattgcatcc aatggattta aaaaatgctg tagctgaaga acttataaag attttagagc 900

-continued

```
caattagaaa gagatta                                                   917

<210> SEQ ID NO 33
<211> LENGTH: 2799
<212> TYPE: DNA
<213> ORGANISM: Archaeoglobus fulgidus

<400> SEQUENCE: 33

atgagcgatt tcaggataat tgaggagaag tggcagaagg cgtgggagaa ggacagaatt     60

tttgagtccg atcctaatga gaaggagaag ttttttctca caattcccta tccttacctt    120

aatggaaatc ttcacgcagg tcacacgaga accttcacaa ttggcgatgc cttcgccaga    180

tacatgagaa tgaagggcta caacgttctc tttcccctcg gctttcatgt tacgggcacc    240

ccaatcattg gccttgcgga gctcatagcc aagagggacg agaggacgat agaggtttac    300

accaaatacc atgacgttcc gctggaggac ttgcttcagc tcacaactcc agagaaaatc    360

gttgagtact tctcaaggga ggcgctgcag gctttgaaga gcataggcta ctccattgac    420

tggaggaggg ttttcaccac aaccgatgaa gagtatcaga gattcatcga gtggcagtac    480

tggaagctca aggagcttgg cctgattgtg aagggcaccc accccgtcag atactgcccc    540

cacgaccaga atcctgttga agaccacgac cttctcgctg gggaggaggc aactattgtt    600

gaatttaccg ttataaagtt caggcttgaa gatggagacc tcattttccc ctgtgcaact    660

ctccgtcccg aaaccgtgtt tggcgtcacg aacatctggg taaagccgac aacctacgta    720

attgccgagg tggatgggga aaagtggttt gtgagcaaag aggcttacga gaagctcacc    780

tacacggaga aaaaagtcag gctgctggag gaggttgatg cgtcgcagtt cttcggcaag    840

tacgtcatag tcccgctggt aaacagaaaa gtgccaattc tgcctgcaga gtttgttgac    900

accgacaacg caacaggagt tgtgatgagc gttcccgcac acgctccttt tgacctggct    960

gccattgagg acttgaagag agacgaggaa acgctggcga agtacggaat tgacaaaagc   1020

gttgtagaga gcataaagcc aatagttctg attaagacgg acattgaagg tgttcctgct   1080

gagaagctaa taagagagct tggagtgaag agccagaagg acaaggagct gctggataag   1140

gcaaccaaga ccctctacaa gaaggagtac cacacgggaa tcatgctgga caacacgatg   1200

aactatgctg gaatgaaagt ttctgaggcg aaggagagag ttcatgagga tttggttaag   1260

cttggcttgg gggatgtttt ctacgagttc agcgagaagc ccgtaatctg caggtgcgga   1320

acgaagtgcg ttgttaaggt tgttagggac cagtggttcc tgaactactc caacagagag   1380

tggaaggaga aggttctgaa tcaccttgaa aagatgcgaa tcatccccga ctactacaag   1440

gaggagttca ggaacaagat tgagtggctc agggacaagg cttgtgccag aaggaagggg   1500

cttggaacga gaattccgtg ggataaggag tggctcatcg agagcctttc agactcaaca   1560

atctacatgg cctactacat ccttgccaag tacatcaacg caggattgct caaggccgag   1620

aacatgactc ccgagttcct cgactacgtg ctgctgggca aaggtgaggt tgggaaagtt   1680

gcggaagctt caaaactcag cgtggagtta atccagcaga tcagggacga cttcgagtac   1740

tggtatcccg ttgacctaag aagcagtggc aaggacttgg ttgcaaacca cctgctcttc   1800

tacctcttcc accacgtcgc cattttcccg ccagataagt ggccgagggc aattgccgta   1860

aacggatacg tcagccttga gggcaagaag atgagcaaga gcaaagggcc cttgctaacg   1920

atgaagaggg cggtgcagca gtatggtgcg gatgtgacga ggctctacat cctccacgct   1980

gcagagtacg acagcgatgc ggactggaag agcagagagg ttgaagggct tgcaaaccac   2040
```

```
ctcaggaggt tctacaacct cgtgaaggag aactacctga aagaggtggg agagctaaca   2100

accctcgacc gctggcttgt gagcaggatg cagagggcaa taaaggaagt gagggaggct   2160

atggacaacc tgcagacgag gagggccgtg aatgccgcct tcttcgagct catgaacgac   2220

gtgagatggt atctgaggag aggaggtgag aacctcgcta taatactgga cgactggatc   2280

aagctcctcg ccccctttgc tccgcacatt tgcgaggagc tgtggcactt gaagcatgac   2340

agctacgtca gcctcgaaag ctacccagaa tacgacgaaa ccagggttga cgaggaggcg   2400

gagagaattg aggaatacct ccgaaacctt gttgaggaca ttcaggaaat caagaagttt   2460

gttagcgatg cgaaggaggt ttacattgct cccgccgaag actggaaggt taaggcagca   2520

aaggtcgttg ctgaaagcgg ggatgttggg gaggcgatga agcagcttat gcaggacgag   2580

gagcttagga agctcggcaa agaagtgtca aatttcgtca agaagatttt caaagacaga   2640

aagaagctga tgctagttaa ggagtgggaa gttctgcagc agaacctgaa atttattgag   2700

aatgagaccg gactgaaggt tattcttgat actcagagag ttcctgagga gaagaggagg   2760

caggcagttc cgggcaagcc cgcgatttat gttgcttaa                          2799
```

<210> SEQ ID NO 34
<211> LENGTH: 2814
<212> TYPE: DNA
<213> ORGANISM: Methanobacterium thermoautotrophicum

<400> SEQUENCE: 34

```
gtggatattg aaagaaaatg gcgtgataga tggagagatg ctggcatatt tcaggctgac     60

cctgatgaca gagaaaagat attcctcaca gtcgcttacc cctaccccag tggtgcgatg    120

cacataggac acgggaggac ctacactgtc cctgatgtct atgcacggtt caagaggatg    180

cagggctaca acgtcctgtt tcccatggcc tggcatgtca caggggcccc tgtcataggg    240

atagcgcgga ggattcagag gaaggatccc tggaccctca aaatctacag ggaggtccac    300

agggtccccg aggatgagct tgaacgtttc agtgaccctg agtacatagt tgaatacttc    360

agcagggaat accggtctgt tatggaggat atgggctact ccatcgactg gaggcgtgaa    420

ttcaaaacca cggatcccac ctacagcagg ttcatacagt ggcagataag gaagctgagg    480

gaccttggcc tcgtaaggaa gggcgcccat cctgttaagt actgccctga atgtgaaaac    540

cctgtgggtg accatgacct ccttgagggt gagggggttg ccataaacca gctcacactc    600

ctcaaattca aacttggaga ctcataccctg gtcgcagcca ccttcaggcc cgagacaatc    660

tatggggcca ccaacctctg gctgaaccct gatgaggatt atgtgagggt tgaaacaggt    720

ggtgaggagt ggataataag cagggctgcc gtggataatc tttcacacca gaaactggac    780

ctcaaggttt ccggtgacgt caaccccggg gacctgatag ggatgtgcgt ggagaatcct    840

gtgacgggcc aggaacaccc catactcccg gcttccttcg ttgaccctga atatgccaca    900

ggtgttgtgt tctctgtccc tgcacatgcc cctgcagact tcatagccct tgaggacctc    960

aggacagacc atgaactcct tgaaaggtac ggtcttgagg atgtggttgc tgatattgag   1020

cccgtgaatg tcatagcagt ggatggctac ggtgagttcc cggcggccga ggttatagag   1080

aaatttggtg tcagaaacca ggaggacccc cgccttgagg atgccaccgg ggagctatac   1140

aagatcgagc atgcgagggg tgttatgagc agccacatcc ctgtctatgg tggtatgaag   1200

gtctctgagg cccgtgaggt catcgctgat gaactgaagg accagggcct tgcagatgag   1260

atgtatgaat tcgctgagcg acctgttata tgccgctgcg gtggcaggtg cgttgtgagg   1320

gtcatggagg accagtggtt catgaagtac tctgatgacg cctggaagga cctcgcccac   1380
```

-continued

```
aggtgcctcg atggcatgaa gataataccc gaggaggtcc gggccaactt tgaatactac   1440
atcgactggc tcaatgactg ggcatgttca aggaggatag gccttggaac aaggctgccc   1500
tgggatgaga ggtggatcat cgaacccctc acagactcaa caatctacat ggcatattac   1560
accatcgcac accgcctcag ggagatggat gccggggaga tggacgatga gttctttgat   1620
gccatattcc tagatgattc aggaaccttt gaggatctca gggaggaatt ccggtactgg   1680
tacccccttg actggaggct ctctgcaaag gacctcatag gcaatcacct gacattccat   1740
atattccacc actcagccat attccctgag tcagggtggc ccccggggggc tgtggtcttt   1800
ggtatgggcc ttcttgaggg caacaagatg tcatcctcca agggcaacgt catactcctg   1860
agggatgcca tcgagaagca cggtgcagac gtggtgcggc tcttcctcat gtcctcagca   1920
gagccatggc aggactttga ctggagggag agtgaggtca tcgggacccg caggaggatt   1980
gaatggttca gggaattcgg agagagggtc tcaggtatcc tggatggtag gccagtcctc   2040
agtgaggtta ctccagctga acctgaaagc ttcattggaa ggtggatgat gggtcagctg   2100
aaccagagga tacgtgaagc cacaagggcc cttgaatcat tccagacaag aaaggcagtt   2160
caggaggcac tctatctcct taaaaaggat gttgaccact accttaagcg tgttgagggt   2220
agagttgatg atgaggttaa atctgtcctt gcaaacgttc tgcacgcctg gataaggctc   2280
atggctccat tcatacccta cactgctgag gagatgtggg agaggtatgg tggtgagggt   2340
tttgtagcag aagctccatg gcctgacttc tcagatgatg cagagagcag ggatgtgcag   2400
gttgcagagg agatggtcca gaataccgtt agagacattc aggaaatcat gaagatcctt   2460
ggatccaccc cggagagggt ccacatatac acctcaccaa aatggaaatg ggatgtgcta   2520
agggtcgcag cagaggtagg aaaactagat atgggctcca taatgggaag ggtttcagct   2580
gagggcatcc atgataacat gaaggaggtt gctgaatttg taaggaggat catcagggac   2640
cttggtaaat cagaggttac ggtgatagac gagtacagcg tactcatgga tgcatctgat   2700
tacattgaat cagaggttgg agccagggtt gtgatacaca gcaaaccaga ctatgaccct   2760
gaaaacaagg ctgtgaatgc cgttcccctg aagccagcca tataccttga atga         2814
```

<210> SEQ ID NO 35
<211> LENGTH: 306
<212> TYPE: PRT
<213> ORGANISM: Methanococcus jannaschii

<400> SEQUENCE: 35

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gln
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Thr Phe Gln Leu Asp Lys
            100                 105                 110

Asp Tyr Thr Leu Asn Val Tyr Arg Leu Ala Leu Lys Thr Thr Leu Lys
```

```
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Ala Ile His
145                 150                 155                 160

Tyr Pro Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Ser Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305


<210> SEQ ID NO 36
<211> LENGTH: 255
<212> TYPE: PRT
<213> ORGANISM: Methanococcus jannaschii

<400> SEQUENCE: 36

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Pro Ala His
145                 150                 155                 160

Tyr Gln Gly Val Asp Val Val Val Gly Gly Met Glu Gln Arg Lys Ile
                165                 170                 175
```

-continued

```
His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile
                245                 250                 255


<210> SEQ ID NO 37
<211> LENGTH: 306
<212> TYPE: PRT
<213> ORGANISM: Methanococcus jannaschii

<400> SEQUENCE: 37

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gly
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Cys Ala Tyr Gly Ser Pro Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gly Tyr His
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300
```

```
Arg Leu
305


<210> SEQ ID NO 38
<211> LENGTH: 306
<212> TYPE: PRT
<213> ORGANISM: Methanococcus jannaschii

<400> SEQUENCE: 38

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gln
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Pro Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Cys Ser His
145                 150                 155                 160

Tyr Tyr Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305


<210> SEQ ID NO 39
<211> LENGTH: 306
<212> TYPE: PRT
<213> ORGANISM: Methanococcus jannaschii

<400> SEQUENCE: 39
```

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Thr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Thr Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Pro Leu His
145                 150                 155                 160

Tyr Ala Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305
```

<210> SEQ ID NO 40
<211> LENGTH: 306
<212> TYPE: PRT
<213> ORGANISM: Methanococcus jannaschii

<400> SEQUENCE: 40

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala His
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
```

-continued

```
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Arg Pro His
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305


<210> SEQ ID NO 41
<211> LENGTH: 306
<212> TYPE: PRT
<213> ORGANISM: Methanococcus jannaschii

<400> SEQUENCE: 41

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gln
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Pro Phe Gln Leu Asp Lys
            100                 105                 110
```

-continued

```
Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gln Ser His
145                 150                 155                 160

Tyr Asp Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305


<210> SEQ ID NO 42
<211> LENGTH: 306
<212> TYPE: PRT
<213> ORGANISM: Methanococcus jannaschii

<400> SEQUENCE: 42

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ser
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Thr Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Thr Tyr His
145                 150                 155                 160

Tyr Ala Gly Val Asp Val Ala Val Gly Gly Met Glu Gln Arg Lys Ile
                165                 170                 175
```

```
His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305


<210> SEQ ID NO 43
<211> LENGTH: 306
<212> TYPE: PRT
<213> ORGANISM: Methanococcus jannaschii

<400> SEQUENCE: 43

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Pro
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Met Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Asn Thr His
145                 150                 155                 160

Tyr Gly Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
```

-continued

```
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305


<210> SEQ ID NO 44
<211> LENGTH: 306
<212> TYPE: PRT
<213> ORGANISM: Methanococcus jannaschii

<400> SEQUENCE: 44

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Thr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser His Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gln Thr His
145                 150                 155                 160

Tyr Glu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285
```

```
Asn Ala Val Ala Glu Glu Leu Ile Lys Ile Leu Glu Pro Ile Arg Lys
    290                 295                 300

Arg Leu
305


<210> SEQ ID NO 45
<211> LENGTH: 306
<212> TYPE: PRT
<213> ORGANISM: Methanococcus jannaschii

<400> SEQUENCE: 45

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala His
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Lys Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Pro Cys His
145                 150                 155                 160

Tyr His Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305


<210> SEQ ID NO 46
<211> LENGTH: 306
<212> TYPE: PRT
<213> ORGANISM: Methanococcus jannaschii
```

<400> SEQUENCE: 46

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Arg Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Val Tyr His
145                 150                 155                 160

Tyr Asp Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305
```

<210> SEQ ID NO 47
<211> LENGTH: 306
<212> TYPE: PRT
<213> ORGANISM: Methanococcus jannaschii

<400> SEQUENCE: 47

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gly
            20                  25                  30

Ile Gly Phe Glu Pro Ser Gly Lys Ile His Leu Gly His Tyr Leu Gln
        35                  40                  45
```

```
Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Thr Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Thr Tyr Tyr
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305


<210> SEQ ID NO 48
<211> LENGTH: 306
<212> TYPE: PRT
<213> ORGANISM: Methanococcus jannaschii

<400> SEQUENCE: 48

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Pro Phe Gln Leu Asp Lys
```

-continued

```
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gln Ile His
145                 150                 155                 160

Ser Ser Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305


<210> SEQ ID NO 49
<211> LENGTH: 306
<212> TYPE: PRT
<213> ORGANISM: Methanococcus jannaschii

<400> SEQUENCE: 49

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Asp
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gly Met His
145                 150                 155                 160
```

-continued

```
Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305


<210> SEQ ID NO 50
<211> LENGTH: 306
<212> TYPE: PRT
<213> ORGANISM: Methanococcus jannaschii

<400> SEQUENCE: 50

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Tyr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Leu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Asp Ile His
145                 150                 155                 160

Tyr Thr Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220
```

```
Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305


<210> SEQ ID NO 51
<211> LENGTH: 306
<212> TYPE: PRT
<213> ORGANISM: Methanococcus jannaschii

<400> SEQUENCE: 51

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Thr Asp Leu Asn Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Asp Ile His
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
```

```
        275                 280                 285

Asn Ala Val Ala Glu Glu Leu Ile Lys Ile Leu Glu Pro Ile Arg Lys
    290                 295                 300

Arg Leu
305


<210> SEQ ID NO 52
<211> LENGTH: 306
<212> TYPE: PRT
<213> ORGANISM: Methanococcus jannaschii

<400> SEQUENCE: 52

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Thr Asp Leu Lys Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Ser Val Asn Val Ile His
145                 150                 155                 160

Tyr Leu Gly Val Asp Val Val Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305


<210> SEQ ID NO 53
<211> LENGTH: 306
```

-continued

<212> TYPE: PRT
<213> ORGANISM: Methanococcus jannaschii

<400> SEQUENCE: 53

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Pro Asp Leu Ser Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Asp Ile His
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305
```

<210> SEQ ID NO 54
<211> LENGTH: 306
<212> TYPE: PRT
<213> ORGANISM: Methanococcus jannaschii

<400> SEQUENCE: 54

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Thr
            20                  25                  30
```

-continued

```
Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Asp Ile His
145                 150                 155                 160

Tyr Ala Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305


<210> SEQ ID NO 55
<211> LENGTH: 306
<212> TYPE: PRT
<213> ORGANISM: Methanococcus jannaschii

<400> SEQUENCE: 55

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Thr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ser Asp Leu Pro Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95
```

```
Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Asp Ile His
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305


<210> SEQ ID NO 56
<211> LENGTH: 306
<212> TYPE: PRT
<213> ORGANISM: Methanococcus jannaschii

<400> SEQUENCE: 56

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Thr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Met Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Ser Ser His
```

-continued

```
145                 150                 155                 160

Tyr Asp Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305


<210> SEQ ID NO 57
<211> LENGTH: 306
<212> TYPE: PRT
<213> ORGANISM: Methanococcus jannaschii

<400> SEQUENCE: 57

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gln
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Pro Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Asp Ile His
145                 150                 155                 160

Tyr Leu Gly Val Asp Val Asp Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205
```

-continued

```
Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305


<210> SEQ ID NO 58
<211> LENGTH: 306
<212> TYPE: PRT
<213> ORGANISM: Methanococcus jannaschii

<400> SEQUENCE: 58

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala His
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Ala Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gly His His
145                 150                 155                 160

Tyr Ile Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270
```

```
Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305
```

<210> SEQ ID NO 59
<211> LENGTH: 306
<212> TYPE: PRT
<213> ORGANISM: Methanococcus jannaschii

<400> SEQUENCE: 59

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Tyr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Ala Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Cys Ala His
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305
```

-continued

<210> SEQ ID NO 60
<211> LENGTH: 306
<212> TYPE: PRT
<213> ORGANISM: Methanococcus jannaschii

<400> SEQUENCE: 60

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gly
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Ser Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Thr Ser His
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305
```

<210> SEQ ID NO 61
<211> LENGTH: 306
<212> TYPE: PRT
<213> ORGANISM: Methanococcus jannaschii

<400> SEQUENCE: 61

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Thr
```

```
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Asn Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Pro Leu His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305


<210> SEQ ID NO 62
<211> LENGTH: 306
<212> TYPE: PRT
<213> ORGANISM: Methanococcus jannaschii

<400> SEQUENCE: 62

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Thr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80
```

-continued

```
Glu Ile Arg Lys Ile Gly Asp Tyr Asn Lys Lys Val Phe Glu Ala Met
                85                  90                  95

Gly Leu Lys Ala Lys Tyr Val Tyr Gly Ser Ser Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Pro Leu His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305
```

<210> SEQ ID NO 63
<211> LENGTH: 306
<212> TYPE: PRT
<213> ORGANISM: Methanococcus jannaschii

<400> SEQUENCE: 63

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Thr Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140
```

```
Lys Val Ala Glu Val Ile Tyr Pro Ile Met Gln Val Asn Pro Val His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305


<210> SEQ ID NO 64
<211> LENGTH: 306
<212> TYPE: PRT
<213> ORGANISM: Methanococcus jannaschii

<400> SEQUENCE: 64

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Thr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Ser Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Pro Ser His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
```

-continued

```
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305


<210> SEQ ID NO 65
<211> LENGTH: 932
<212> TYPE: PRT
<213> ORGANISM: Archaeoglobus fulgidus

<400> SEQUENCE: 65

Met Ser Asp Phe Arg Ile Ile Glu Glu Lys Trp Gln Lys Ala Trp Glu
1               5                   10                  15

Lys Asp Arg Ile Phe Glu Ser Asp Pro Asn Glu Lys Glu Lys Phe Phe
            20                  25                  30

Leu Thr Ile Pro Tyr Pro Tyr Leu Asn Gly Asn Leu His Ala Gly His
        35                  40                  45

Thr Arg Thr Phe Thr Ile Gly Asp Ala Phe Ala Arg Tyr Met Arg Met
    50                  55                  60

Lys Gly Tyr Asn Val Leu Phe Pro Leu Gly Phe His Val Thr Gly Thr
65                  70                  75                  80

Pro Ile Ile Gly Leu Ala Glu Leu Ile Ala Lys Arg Asp Glu Arg Thr
                85                  90                  95

Ile Glu Val Tyr Thr Lys Tyr His Asp Val Pro Leu Glu Asp Leu Leu
            100                 105                 110

Gln Leu Thr Thr Pro Glu Lys Ile Val Glu Tyr Phe Ser Arg Glu Ala
        115                 120                 125

Leu Gln Ala Leu Lys Ser Ile Gly Tyr Ser Ile Asp Trp Arg Arg Val
    130                 135                 140

Phe Thr Thr Thr Asp Glu Glu Tyr Gln Arg Phe Ile Glu Trp Gln Tyr
145                 150                 155                 160

Trp Lys Leu Lys Glu Leu Gly Leu Ile Val Lys Gly Thr His Pro Val
                165                 170                 175

Arg Tyr Cys Pro His Asp Gln Asn Pro Val Glu Asp His Asp Leu Leu
            180                 185                 190

Ala Gly Glu Glu Ala Thr Ile Val Glu Phe Thr Val Ile Lys Phe Arg
        195                 200                 205

Leu Glu Asp Gly Asp Leu Ile Phe Pro Cys Ala Thr Leu Arg Pro Glu
    210                 215                 220

Thr Val Phe Gly Val Thr Asn Ile Trp Val Lys Pro Thr Thr Tyr Val
225                 230                 235                 240

Ile Ala Glu Val Asp Gly Glu Lys Trp Phe Val Ser Lys Glu Ala Tyr
                245                 250                 255
```

-continued

```
Glu Lys Leu Thr Tyr Thr Glu Lys Lys Val Arg Leu Leu Glu Glu Val
            260                 265                 270

Asp Ala Ser Gln Phe Phe Gly Lys Tyr Val Ile Val Pro Leu Val Asn
        275                 280                 285

Arg Lys Val Pro Ile Leu Pro Ala Glu Phe Val Asp Thr Asp Asn Ala
    290                 295                 300

Thr Gly Val Val Met Ser Val Pro Ala His Ala Pro Phe Asp Leu Ala
305                 310                 315                 320

Ala Ile Glu Asp Leu Lys Arg Asp Glu Glu Thr Leu Ala Lys Tyr Gly
                325                 330                 335

Ile Asp Lys Ser Val Val Glu Ser Ile Lys Pro Ile Val Leu Ile Lys
            340                 345                 350

Thr Asp Ile Glu Gly Val Pro Ala Glu Lys Leu Ile Arg Glu Leu Gly
        355                 360                 365

Val Lys Ser Gln Lys Asp Lys Glu Leu Leu Asp Lys Ala Thr Lys Thr
    370                 375                 380

Leu Tyr Lys Lys Glu Tyr His Thr Gly Ile Met Leu Asp Asn Thr Met
385                 390                 395                 400

Asn Tyr Ala Gly Met Lys Val Ser Glu Ala Lys Glu Arg Val His Glu
                405                 410                 415

Asp Leu Val Lys Leu Gly Leu Gly Asp Val Phe Tyr Glu Phe Ser Glu
            420                 425                 430

Lys Pro Val Ile Cys Arg Cys Gly Thr Lys Cys Val Val Lys Val Val
        435                 440                 445

Arg Asp Gln Trp Phe Leu Asn Tyr Ser Asn Arg Glu Trp Lys Glu Lys
    450                 455                 460

Val Leu Asn His Leu Glu Lys Met Arg Ile Ile Pro Asp Tyr Tyr Lys
465                 470                 475                 480

Glu Glu Phe Arg Asn Lys Ile Glu Trp Leu Arg Asp Lys Ala Cys Ala
                485                 490                 495

Arg Arg Lys Gly Leu Gly Thr Arg Ile Pro Trp Asp Lys Glu Trp Leu
            500                 505                 510

Ile Glu Ser Leu Ser Asp Ser Thr Ile Tyr Met Ala Tyr Tyr Ile Leu
        515                 520                 525

Ala Lys Tyr Ile Asn Ala Gly Leu Leu Lys Ala Glu Asn Met Thr Pro
    530                 535                 540

Glu Phe Leu Asp Tyr Val Leu Leu Gly Lys Gly Glu Val Gly Lys Val
545                 550                 555                 560

Ala Glu Ala Ser Lys Leu Ser Val Glu Leu Ile Gln Gln Ile Arg Asp
                565                 570                 575

Asp Phe Glu Tyr Trp Tyr Pro Val Asp Leu Arg Ser Ser Gly Lys Asp
            580                 585                 590

Leu Val Ala Asn His Leu Leu Phe Tyr Leu Phe His His Val Ala Ile
        595                 600                 605

Phe Pro Pro Asp Lys Trp Pro Arg Ala Ile Ala Val Asn Gly Tyr Val
    610                 615                 620

Ser Leu Glu Gly Lys Lys Met Ser Lys Ser Lys Gly Pro Leu Leu Thr
625                 630                 635                 640

Met Lys Arg Ala Val Gln Gln Tyr Gly Ala Asp Val Thr Arg Leu Tyr
                645                 650                 655

Ile Leu His Ala Ala Glu Tyr Asp Ser Asp Ala Asp Trp Lys Ser Arg
            660                 665                 670

Glu Val Glu Gly Leu Ala Asn His Leu Arg Arg Phe Tyr Asn Leu Val
```

```
        675                 680                 685

Lys Glu Asn Tyr Leu Lys Glu Val Gly Glu Leu Thr Thr Leu Asp Arg
    690                 695                 700

Trp Leu Val Ser Arg Met Gln Arg Ala Ile Lys Glu Val Arg Glu Ala
705                 710                 715                 720

Met Asp Asn Leu Gln Thr Arg Arg Ala Val Asn Ala Ala Phe Phe Glu
            725                 730                 735

Leu Met Asn Asp Val Arg Trp Tyr Leu Arg Arg Gly Gly Glu Asn Leu
            740                 745                 750

Ala Ile Ile Leu Asp Asp Trp Ile Lys Leu Leu Ala Pro Phe Ala Pro
        755                 760                 765

His Ile Cys Glu Glu Leu Trp His Leu Lys His Asp Ser Tyr Val Ser
    770                 775                 780

Leu Glu Ser Tyr Pro Glu Tyr Asp Glu Thr Arg Val Asp Glu Glu Ala
785                 790                 795                 800

Glu Arg Ile Glu Glu Tyr Leu Arg Asn Leu Val Glu Asp Ile Gln Glu
            805                 810                 815

Ile Lys Lys Phe Val Ser Asp Ala Lys Glu Val Tyr Ile Ala Pro Ala
            820                 825                 830

Glu Asp Trp Lys Val Lys Ala Ala Lys Val Val Ala Glu Ser Gly Asp
        835                 840                 845

Val Gly Glu Ala Met Lys Gln Leu Met Gln Asp Glu Glu Leu Arg Lys
    850                 855                 860

Leu Gly Lys Glu Val Ser Asn Phe Val Lys Lys Ile Phe Lys Asp Arg
865                 870                 875                 880

Lys Lys Leu Met Leu Val Lys Glu Trp Glu Val Leu Gln Gln Asn Leu
            885                 890                 895

Lys Phe Ile Glu Asn Glu Thr Gly Leu Lys Val Ile Leu Asp Thr Gln
            900                 905                 910

Arg Val Pro Glu Glu Lys Arg Arg Gln Ala Val Pro Gly Lys Pro Ala
        915                 920                 925

Ile Tyr Val Ala
    930


<210> SEQ ID NO 66
<211> LENGTH: 937
<212> TYPE: PRT
<213> ORGANISM: Methanobacterium thermoautotrophicum

<400> SEQUENCE: 66

Val Asp Ile Glu Arg Lys Trp Arg Asp Arg Trp Arg Asp Ala Gly Ile
1               5                   10                  15

Phe Gln Ala Asp Pro Asp Asp Arg Glu Lys Ile Phe Leu Thr Val Ala
            20                  25                  30

Tyr Pro Tyr Pro Ser Gly Ala Met His Ile Gly His Gly Arg Thr Tyr
        35                  40                  45

Thr Val Pro Asp Val Tyr Ala Arg Phe Lys Arg Met Gln Gly Tyr Asn
    50                  55                  60

Val Leu Phe Pro Met Ala Trp His Val Thr Gly Ala Pro Val Ile Gly
65                  70                  75                  80

Ile Ala Arg Arg Ile Gln Arg Lys Asp Pro Trp Thr Leu Lys Ile Tyr
            85                  90                  95

Arg Glu Val His Arg Val Pro Glu Asp Glu Leu Glu Arg Phe Ser Asp
            100                 105                 110
```

-continued

```
Pro Glu Tyr Ile Val Glu Tyr Phe Ser Arg Glu Tyr Arg Ser Val Met
        115                 120                 125

Glu Asp Met Gly Tyr Ser Ile Asp Trp Arg Arg Glu Phe Lys Thr Thr
    130                 135                 140

Asp Pro Thr Tyr Ser Arg Phe Ile Gln Trp Gln Ile Arg Lys Leu Arg
145                 150                 155                 160

Asp Leu Gly Leu Val Arg Lys Gly Ala His Pro Val Lys Tyr Cys Pro
                165                 170                 175

Glu Cys Glu Asn Pro Val Gly Asp His Asp Leu Leu Glu Gly Glu Gly
            180                 185                 190

Val Ala Ile Asn Gln Leu Thr Leu Leu Lys Phe Lys Leu Gly Asp Ser
        195                 200                 205

Tyr Leu Val Ala Ala Thr Phe Arg Pro Glu Thr Ile Tyr Gly Ala Thr
    210                 215                 220

Asn Leu Trp Leu Asn Pro Asp Glu Asp Tyr Val Arg Val Glu Thr Gly
225                 230                 235                 240

Gly Glu Glu Trp Ile Ile Ser Arg Ala Ala Val Asp Asn Leu Ser His
                245                 250                 255

Gln Lys Leu Asp Leu Lys Val Ser Gly Asp Val Asn Pro Gly Asp Leu
            260                 265                 270

Ile Gly Met Cys Val Glu Asn Pro Val Thr Gly Gln Glu His Pro Ile
        275                 280                 285

Leu Pro Ala Ser Phe Val Asp Pro Glu Tyr Ala Thr Gly Val Val Phe
    290                 295                 300

Ser Val Pro Ala His Ala Pro Ala Asp Phe Ile Ala Leu Glu Asp Leu
305                 310                 315                 320

Arg Thr Asp His Glu Leu Leu Glu Arg Tyr Gly Leu Glu Asp Val Val
                325                 330                 335

Ala Asp Ile Glu Pro Val Asn Val Ile Ala Val Asp Gly Tyr Gly Glu
            340                 345                 350

Phe Pro Ala Ala Glu Val Ile Glu Lys Phe Gly Val Arg Asn Gln Glu
        355                 360                 365

Asp Pro Arg Leu Glu Asp Ala Thr Gly Glu Leu Tyr Lys Ile Glu His
    370                 375                 380

Ala Arg Gly Val Met Ser Ser His Ile Pro Val Tyr Gly Gly Met Lys
385                 390                 395                 400

Val Ser Glu Ala Arg Glu Val Ile Ala Asp Glu Leu Lys Asp Gln Gly
                405                 410                 415

Leu Ala Asp Glu Met Tyr Glu Phe Ala Glu Arg Pro Val Ile Cys Arg
            420                 425                 430

Cys Gly Gly Arg Cys Val Val Arg Val Met Glu Asp Gln Trp Phe Met
        435                 440                 445

Lys Tyr Ser Asp Asp Ala Trp Lys Asp Leu Ala His Arg Cys Leu Asp
    450                 455                 460

Gly Met Lys Ile Ile Pro Glu Glu Val Arg Ala Asn Phe Glu Tyr Tyr
465                 470                 475                 480

Ile Asp Trp Leu Asn Asp Trp Ala Cys Ser Arg Arg Ile Gly Leu Gly
                485                 490                 495

Thr Arg Leu Pro Trp Asp Glu Arg Trp Ile Ile Glu Pro Leu Thr Asp
            500                 505                 510

Ser Thr Ile Tyr Met Ala Tyr Tyr Thr Ile Ala His Arg Leu Arg Glu
        515                 520                 525

Met Asp Ala Gly Glu Met Asp Asp Glu Phe Phe Asp Ala Ile Phe Leu
```

```
    530                 535                 540

Asp Asp Ser Gly Thr Phe Glu Asp Leu Arg Glu Glu Phe Arg Tyr Trp
545                 550                 555                 560

Tyr Pro Leu Asp Trp Arg Leu Ser Ala Lys Asp Leu Ile Gly Asn His
                565                 570                 575

Leu Thr Phe His Ile Phe His His Ser Ala Ile Phe Pro Glu Ser Gly
            580                 585                 590

Trp Pro Arg Gly Ala Val Val Phe Gly Met Gly Leu Leu Glu Gly Asn
        595                 600                 605

Lys Met Ser Ser Ser Lys Gly Asn Val Ile Leu Leu Arg Asp Ala Ile
    610                 615                 620

Glu Lys His Gly Ala Asp Val Val Arg Leu Phe Leu Met Ser Ser Ala
625                 630                 635                 640

Glu Pro Trp Gln Asp Phe Asp Trp Arg Glu Ser Glu Val Ile Gly Thr
                645                 650                 655

Arg Arg Arg Ile Glu Trp Phe Arg Glu Phe Gly Glu Arg Val Ser Gly
            660                 665                 670

Ile Leu Asp Gly Arg Pro Val Leu Ser Glu Val Thr Pro Ala Glu Pro
        675                 680                 685

Glu Ser Phe Ile Gly Arg Trp Met Met Gly Gln Leu Asn Gln Arg Ile
    690                 695                 700

Arg Glu Ala Thr Arg Ala Leu Glu Ser Phe Gln Thr Arg Lys Ala Val
705                 710                 715                 720

Gln Glu Ala Leu Tyr Leu Leu Lys Lys Asp Val Asp His Tyr Leu Lys
                725                 730                 735

Arg Val Glu Gly Arg Val Asp Asp Glu Val Lys Ser Val Leu Ala Asn
            740                 745                 750

Val Leu His Ala Trp Ile Arg Leu Met Ala Pro Phe Ile Pro Tyr Thr
        755                 760                 765

Ala Glu Glu Met Trp Glu Arg Tyr Gly Gly Glu Gly Phe Val Ala Glu
    770                 775                 780

Ala Pro Trp Pro Asp Phe Ser Asp Asp Ala Glu Ser Arg Asp Val Gln
785                 790                 795                 800

Val Ala Glu Glu Met Val Gln Asn Thr Val Arg Asp Ile Gln Glu Ile
                805                 810                 815

Met Lys Ile Leu Gly Ser Thr Pro Glu Arg Val His Ile Tyr Thr Ser
            820                 825                 830

Pro Lys Trp Lys Trp Asp Val Leu Arg Val Ala Ala Glu Val Gly Lys
        835                 840                 845

Leu Asp Met Gly Ser Ile Met Gly Arg Val Ser Ala Glu Gly Ile His
    850                 855                 860

Asp Asn Met Lys Glu Val Ala Glu Phe Val Arg Arg Ile Ile Arg Asp
865                 870                 875                 880

Leu Gly Lys Ser Glu Val Thr Val Ile Asp Glu Tyr Ser Val Leu Met
                885                 890                 895

Asp Ala Ser Asp Tyr Ile Glu Ser Glu Val Gly Ala Arg Val Val Ile
            900                 905                 910

His Ser Lys Pro Asp Tyr Asp Pro Glu Asn Lys Ala Val Asn Ala Val
        915                 920                 925

Pro Leu Lys Pro Ala Ile Tyr Leu Glu
    930                 935

<210> SEQ ID NO 67
```

<211> LENGTH: 12391
<212> TYPE: DNA
<213> ORGANISM: Plasmid pSC101, Streptomycese venezuelae papABC

<400> SEQUENCE: 67
gaattcacac acaggaaaca gctatgcgca cgcttctgat cgacaactac gactcgttca 60
cccagaacct gttccagtac atcggcgagg ccaccgggca gccccccgtc gtgcccaacg 120
acgccgactg gtcgcggctg cccctcgagg acttcgacgc gatcgtcgtg tccccgggcc 180
ccggcagccc cgaccgggaa cgggacttcg ggatcagccg ccgggcgatc accgacagcg 240
gcctgcccgt cctcggcgtc tgcctcggcc accagggcat cgcccagctc tcggcggaac 300
ccatgcacgg ccgggtctcc gaggtgcggc acaccggcga ggacgtcttc cggggcctcc 360
cctcgccgtt caccgccgtg cgctaccact ccctggccgc caccgacctc cccgacgagc 420
tcgaacccct cgcctggagc gacgacggcg tcgtcatggg cctgcggcac cgcgagaagc 480
cgctgatggg cgtccagttc ccaccggagt ccatcggcag cgacttcggc cgggagatca 540
tggccaactt ccgcgacctc gccctcgccc accaccgggc acgtcgcgac gcggccgact 600
ggggctacga actccacgtg cgccgcgtcg acgtgctgcc ggacgccgaa gaggtacgcc 660
gcgctgcctg cccggccgag ggcgccacgt tctggctgga cagcagctcc gtcctcgaag 720
gcgcctcgcc gttctccttc ctcggcgacg accgcggccc gctcgccgag tacctcacct 780
accgcgtcgc cgacggcgtc gtctccgtcc gcggctccga cggcaccacg acccgggacg 840
cggcgaccct cttcagctac ctggaggagc agctcgaacc gccggcgggt cccgtcgccc 900
ccgacctgcc cttcgagttc aacctcggct acgtcggcta cctcggctac gagctgaagg 960
cggagaccac cggcgacccc gcagtaccgg ccccgcaccc cgacgccgcg ttcctcttcg 1020
ccgaccgcgc catcgccctc gaccaccagg aaggctgctg ctacctgctg gccctcgacc 1080
gccggggcca cgacgacggc gcccgcgcct ggctgcggga gacggccgag accctcaccg 1140
gcctggccgt ccgcgtccgg ccgaggccga cccccgccat ggtcttcggg gtccccgagg 1200
cggcggccgg cttcggcccc ctggctcgcg cacgccacga caaggacgcc tcggcgctcc 1260
gcaacggcga gtcgtacgag atctgcctga ccaacatggt caccgcgccg accgaggcga 1320
cggccctgcc gctctactcc gcgctgcgcc gcatcagccc cgtcccgtct ggcgccctgc 1380
tcgagttccc cgagctgtcg gtgctcagcg cctcgcccga gcggttcctc acgatcggcg 1440
ccgacggcgg cgtcgagtcc aagcccatca aggggacccg cccccggggc gcaccggcgg 1500
aggaggacga gcggctccgc gccgacctgg ccggccggga gaaggaccgg gccgagaacc 1560
tgatgatcgt cgacctggtc cgcaacgacc tcaacagcgt ctgcgcgatc ggctccgtcc 1620
acgtgccccg gctcttcgag gtgggagacc tcgcgcccgt gcaccagctg gtgtcgacca 1680
tccggggacg gctgcggccc ggcaccagca ccgccgcctg cgtacgcgcc gccttccccg 1740
gcggctccat gaccggcgcg cccaagaagc gacccatgga gatcatcgac cgcctggagg 1800
aaggcccccg gggcgtctta cccggggcgc tcggatggtt cgccctcagc ggcgccgccg 1860
acctcagcat cgtcatccgc accatcgtgc tggccgacgg ccgggccgag ttcggcgtcg 1920
gcggggcgat cgtgtccctc tccgaccagg aggaggagtt caggcagacc gtggtcaagg 1980
cccgcgccat ggtcaccgcc ctcgacggca gcgcagtggc gggcgcacga tgacaccaac 2040
aaggaccata gcatatgacc gagcagaacg agctgcaggt tgcggctgcg cgcggagctc 2100
gacgccctcg acgggacgct tctggacacg gtgcggcgcc gcatcgacct cggtgtccgc 2160
atcgcgcggt acaagtcccg gcacggcgtc ccgatgatgc agcccggccg ggtcagcctg 2220

```
gtcaaggaca gggccgcccg ctacgccgcc gaccacggcc tcgacgaatc gttcctggtg   2280
aacctctacg acgtgatcat cacggagatg tgccgcgtcg aggacctggt gatgagcccg   2340
tcatgtacta aggaggttgt atgagtggct tcccccggag cgtcgtcgtc ggcggcagcg   2400
gagcggtggg cggcatgttc gccgggctgc tgcgggaggc gggcagccgc acgctcgtcg   2460
tcgacctcgt accgccgccg ggacggccgg acgcctgcct ggtgggcgac gtcaccgcgc   2520
cggggcccga gctcgcggcc gccctccggg acgcggacct cgtcctgctc gccgtacacg   2580
aggacgtggc cctcaaggcc gtggcgcccg tgacccggct catgcgaccg ggcgcgctgc   2640
tcgccgacac cctgtccgtc cggacgggca tggccgcgga gctcgcggcc cacgcccccg   2700
gcgtccagca cgtgggcctc aacccgatgt tcgcccccgc cgccggcatg accggccggc   2760
ccgtggccgc cgtggtcacc agggacgggc cgggcgtcac ggccctgctg cggctcgtcg   2820
agggcggcgg cggcaggccc gtacggctca cggcggagga gcacgaccgg acgacggcgg   2880
cgacccaggc cctgacgcac gccgtgatcc tctccttcgg gctcgccctc gcccgcctcg   2940
gcgtcgacgt ccgggccctg gcggcgacgg caccgccgcc ccaccaggtg ctgctcgccc   3000
tcctggcccg tgtgctcggc ggcagccccg aggtgtacgg ggacatccag cggtccaacc   3060
cccgggcggc gtccgcgcgc cgggcgctcg ccgaggccct gcgctccttc gccgcgctga   3120
tcggcgacga cccggaccgc gccgaggacc cggaccgcgc cgacgacccc gaccgcaccg   3180
acaaccccgg ccatcccggg ggatgcgacg gcgccgggaa cctcgacggc gtcttcgagg   3240
aactccgccg gctcatggga ccggagctcg cggcgggcca ggaccactgc caggagctgt   3300
tccgcaccct ccaccgcacc gacgacgaag gcgagaagga ccgatgaatt taggtgacac   3360
tatagggatc ctctacgccg gacgcatcgt ggccggcatc accggcgcca caggtgcggt   3420
tgctggcgcc tatatcgccg acatcaccga tggggaagat cgggctcgcc acttcgggct   3480
catgagcgct tgtttcggcg tgggtatggt ggcaggcccc gtggccgggg gactgttggg   3540
cgccatctcc ttgcatgcac cattccttgc ggcggcggtg ctcaacggcc tcaacctact   3600
actgggctgc ttcctaatgc aggagtcgca taagggagag cgtcgaccga tgcccttgag   3660
agccttcaac ccagtcagct ccttccggtg ggcgcggggc atgactatcg tcgccgcact   3720
tatgactgtc ttctttatca tgcaactcgt aggacaggtg ccggcagcgc tctgggtcat   3780
tttcggcgag gaccgctttc gctggagcgc gacgatgatc ggcctgtcgc ttgcggtatt   3840
cggaatcttg cacgccctcg ctcaagcctt cgtcactggt cccgccacca aacgtttcgg   3900
cgagaagcag gccattatcg ccggcatggc ggccgacgcg ctgggctacg tcttgctggc   3960
gttcgcgacg cgaggctgga tggccttccc cattatgatt cttctcgctt ccggcggcat   4020
cgggatgccc gcgttgcagg ccatgctgtc caggcaggta gatgacgacc atcagggaca   4080
gcttcaagga tcgctcgcgg ctcttaccag cctaacttcg atcactggac cgctgatcgt   4140
cacggcgatt tatgccgcct cggcgagcac atggaacggg ttggcatgga ttgtaggcgc   4200
cgccctatac cttgtctgcc tccccgcgtt gcgtcgcggt gcatggagcc gggccacctc   4260
gacctgaatg gaagccggcg gcacctcgct aacggattca ccactccaag aattggagcc   4320
aatcaattct tgcggagaac tgtgaatgcg caaaccaacc cttggcagaa catatccatc   4380
gcgtccgcca tctccagcag ccgcacgcgg cgcatctcgg gcagcgttgg gtcctggcca   4440
cgggtgcgca tgatcgtgct cctgtcgttg aggacccggc taggctggcg gggttgcctt   4500
actggttagc agaatgaatc accgatacgc gagcgaacgt gaagcgactg ctgctgcaaa   4560
```

-continued

```
acgtctgcga cctgagcaac aacatgaatg gtcttcggtt tccgtgtttc gtaaagtctg   4620
gaaacgcgga agtcccctac gtgctgctga agttgcccgc aacagagagt ggaaccaacc   4680
ggtgatacca cgatactatg actgagagtc aacgccatga gcggcctcat ttcttattct   4740
gagttacaac agtccgcacc gctgccggta gctacttgac tatccggctg cactagccct   4800
gcgtcagatg gctctgatcc aaggcaaact gccaaaatat ctgctggcac cggaagtcag   4860
cgccctgcac cattatgttc cggatctgca tcgcaggatg ctgctggcta ccctgtggaa   4920
cacctacatc tgtattaacg aagcgctggc attgaccctg agtgattttt ctctggtgcc   4980
gccctatccc tttgtgcagc ttgccacgct caaaggggtt tgaggtccaa ccgtacgaaa   5040
acgtacggta agaggaaaat tatcgtctga aaaatcgatt agtagacaag aaagtccgtt   5100
aagtgccaat tttcgattaa aaagacaccg ttttgatggc gttttccaat gtacattatg   5160
tttcgatata tcagacagtt acttcactaa cgtacgtttt cgttctattg gccttcagac   5220
cccatatcct taatgtcctt tatttgctgg ggttatcaga tccccccgac acgtttaatt   5280
aatgctttct ccgccggaga tcgacgcaca ggcttctgtg tctatgatgt tatttcttaa   5340
taatcatcca ggtattctct ttatcaccat acgtagtgcg agtgtccacc ttaacgcagg   5400
gctttccgtc acagcgcgat atgtcagcca gcggggcttt cttttgccag accgcttcca   5460
tcctctgcat ttcagcaatc tggctatacc cgtcattcat aaaccacgta aatgccgtca   5520
cgcaggaagc caggacgaag aatatcgtca gtacaagata aatcgcggat ttccacgtat   5580
agcgtgacat ctcacgacgc atttcatgga tcatcgcttt cgccgtatcg gcagcctgat   5640
tcagcgcttc tgtcgccggt ttctgctgtg ctaatccggc ttgtttcagt tctttctcaa   5700
cctgagtgag cgcggaactc accgatttcc tgacggtgtc agtcatatta ccggacgcgc   5760
tgtccagctc acgaatgacc ctgctcagcg tttcactttg ctgctgtaat tgtgatgagg   5820
cggcctgaaa ctgttctgtc agagaagtaa cacgcttttc cagcgcctga tgatgcccga   5880
taagggcggc aatttgttta atttcgtcgc tcatacaaaa tcctgcctat cgtgagaatg   5940
accagccttt atccggcttc tgtcgtatct gttcggcgag tcgctgtcgt tctttctcct   6000
gctgacgctg tttttccgcc agacgttcgc gctctctctg cctttccatc tcctgatgta   6060
tcccctggaa ctccgccatc gcatcgttaa caagggactg aagatcgatt tcttcctgta   6120
tatccttcat ggcatcactg accagtgcgt tcagcttgtc aggctctttt tcaaaatcaa   6180
acgttctgcc ggaatgggat tcctgctcag gctctgactt cagctcctgt tttagcgtca   6240
gagtatccct ctcgctgagg gcttcccgta acgaggtagt cacgtcaatt acgctgtcac   6300
gttcatcacg ggactgctgc acctgccttt cagcctccct gcgctcaaga atggcctgta   6360
gctgctcagt atcgaatcgc tgaacctgac ccgcgcccag atgccgctca ggctcacggt   6420
caatgccctg cgccttcagg gaacgggaat caacccggtc agcgtgctga taccgttcaa   6480
ggtgcttatt ctggaggtca gcccagcgtc tccctctggg caacaaggta ttctttgcgt   6540
tcggtcggtg tttccccgaa acgtgccttt tttgcgccac cgcgtccggc tctttggtgt   6600
tagcccgttt aaaatactgc tcagggtcac ggtgaatacc gtcattaatg cgttcagaga   6660
acatgatatg ggcgtggggc tgctcgccac cggctatcgc tgctttcgga ttatggatag   6720
cgaactgata ggcatggcgg tcgccaattt cctgttggac aaaatcgcgg acaagctcaa   6780
gacgttgttc gggttttaac tcacgcggca gggcaatctc gatttcacgg taggtacagc   6840
cgttggcacg ttcagacgtg tcagcggctt tccagaactc ggacggttta tgcgctgccc   6900
acgccggcat attgccggac tccttgtgct caaggtcgga gtctttttca cgggcatact   6960
```

-continued

```
ttccctcacg cgcaatataa tcggcatgag gagaggcact gccttttccg ccggttttta   7020
cgctgagatg ataggatgcc atcgtgtttt atcccgctga agggcgcacg tttctgaacg   7080
aagtgaagaa agtctaagtg cgccctgata aataaaagag ttatcaggga ttgtagtggg   7140
atttgacctc ctctgccatc atgagcgtaa tcattccgtt agcattcagg aggtaaacag   7200
catgaataaa agcgaaaaaa caggaacaat gggcagcaga aagagtgcag tatattcgcg   7260
gcttaaagtc gccgaatgag caacagaaac ttatgctgat actgacggat aaagcagata   7320
aaacagcaca ggatatcaaa acgctgtccc tgctgatgaa ggctgaacag gcagcagaga   7380
aagcgcagga agccagagcg aaagtcatga acctgataca ggcagaaaag cgagccgaag   7440
ccagagccgc ccgtaaagcc cgtgaccatg ctctgtacca gtctgccgga ttgcttatcc   7500
tggcgggtct ggttgacagt aagacgggta agcctgttga tgataccgct gccttactgg   7560
gtgcattagc cagtctgaat gacctgtcac gggataatcc gaagtggtca gactggaaaa   7620
tcagagggca ggaactgctg aacagcaaaa agtcagatag caccacatag cagacccgcc   7680
ataaaacgcc ctgagaagcc cgtgacgggc ttttcttgta ttatgggtag tttccttgca   7740
tgaatccata aaaggcgcct gtagtgccat ttacccccat tcactgccag agccgtgagc   7800
gcagcgaact gaatgtcacg aaaaagacag cgactcaggt gcctgatggt cggagacaaa   7860
aggaatattc agcgatttgc ccgagcttgc gagggtgcta cttaagcctt tagggtttta   7920
aggtctgttt tgtagaggag caaacagcgt ttgcgacatc cttttgtaat actgcggaac   7980
tgactaaagt agtgagttat acacagggct gggatctatt ctttttatct ttttttattc   8040
tttctttatt ctataaatta taaccacttg aatataaaca aaaaaaacac acaaaggtct   8100
agcggaattt acagagggtc tagcagaatt tacaagtttt ccagcaaagg tctagcagaa   8160
tttacagata cccacaactc aaaggaaaag gactagtaat tatcattgac tagcccatct   8220
caattggtat agtgattaaa atcacctaga ccaattgaga tgtatgtctg aattagttgt   8280
tttcaaagca aatgaactag cgattagtcg ctatgactta acggagcatg aaaccaagct   8340
aattttatgc tgtgtggcac tactcaaccc cacgattgaa aaccctacaa ggaaagaacg   8400
gacggtatcg ttcacttata accaatacgc tcagatgatg aacatcagta gggaaaatgc   8460
ttatggtgta ttagctaaag caaccagaga gctgatgacg agaactgtgg aaatcaggaa   8520
tcctttggtt aaaggctttg agattttcca gtggacaaac tatgccaagt tctcaagcga   8580
aaaattagaa ttagttttta gtgaagagat attgccttat cttttccagt taaaaaaatt   8640
cataaaatat aatctggaac atgttaagtc ttttgaaaac aaatactcta tgaggattta   8700
tgagtggtta ttaaaagaac taacacaaaa gaaaactcac aaggcaaata tagagattag   8760
ccttgatgaa tttaagttca tgttaatgct tgaaaataac taccatgagt ttaaaaggct   8820
taaccaatgg gttttgaaac caataagtaa agatttaaac acttacagca atatgaaatt   8880
ggtggttgat aagcgaggcc gcccgactga tacgttgatt ttccaagttg aactagatag   8940
acaaatggat ctcgtaaccg aacttgagaa caaccagata aaaatgaatg gtgacaaaat   9000
accaacaacc attacatcag attcctacct acgtaacgga ctaagaaaaa cactacacga   9060
tgctttaact gcaaaaattc agctcaccag ttttgaggca aaatttttga gtgacatgca   9120
aagtaagcat gatctcaatg gttcgttctc atggctcacg caaaaacaac gaaccacact   9180
agagaacata ctggctaaat acggaaggat ctgaggttct tatggctctt gtatctatca   9240
gtgaagcatc aagactaaca aacaaaagta gaacaactgt tcaccgttag atatcaaagg   9300
```

-continued

```
gaaaactgtc catatgcaca gatgaaaacg gtgtaaaaaa gatagataca tcagagcttt   9360
tacgagtttt tggtgcattt aaagctgttc accatgaaca gatcgacaat gtaacagatg   9420
aacagcatgt aacacctaat agaacaggtg aaaccagtaa aacaaagcaa ctagaacatg   9480
aaattgaaca cctgagacaa cttgttacag ctcaacagtc acacatagac agcctgaaac   9540
aggcgatgct gcttatcgaa tcaaagctgc cgacaacacg ggagccagtg acgcctcccg   9600
tggggaaaaa atcatggcaa ttctggaaga aatagcgctt tcagccggca aacctgaagc   9660
cggatctgcg attctgataa caaactagca acaccagaac agcccgtttg cgggcagcaa   9720
aacccgtact tttggacgtt ccggcggttt tttgtggcga gtggtgttcg ggcggtgcgc   9780
gcaagatcca ttatgttaaa cgggcgagtt tacatctcaa aaccgcccgc ttaacaccat   9840
cagaaatcct cagcgcgatt ttaagcacca acccccccc gtaacaccca aatccatact   9900
gaaagtggct ttgttgaata aatcgaactt ttgctgagtt gaaggatcag atcacgcatc   9960
ctcccgacaa cacagaccat tccgtggcaa agcaaaagtt cagaatcacc aactggtcca  10020
cctacaacaa agctctcatc aaccgtggct ccctcacttt ctggctggat gatgaggcga  10080
ttcaggcctg gtatgagtcg gcaacacctt catcacgagg aaggccccag cgctattctg  10140
atctcgccat caccaccgtt ctggtgatta aacgcgtatt ccggctgacc ctgcgggctg  10200
cgcagggttt tattgattcc atttttgccc tgatgaacgt tccgttgcgc tgcccggatt  10260
acaccagtgt cagtaagcgg gcaaagtcgg ttaatgtcag tttcaaaacg tccacccggg  10320
gtgaaatcgc acacctggtg attgattcca ccgggctgaa ggtctttggt gaaggcgaat  10380
ggaaagtcag aaagcacggc aaagagcgcc gtcgtatctg gcgaaagttg catcttgctg  10440
ttgacagcaa cacacatgaa gttgtctgtg cagacctgtc gctgaataac gtcacggact  10500
cagaagcctt cccgggcctt atccggcaga ctcacagaaa aatcagggca gccgcggcag  10560
acggggctta cgatacccgg ctctgtcacg atgaactgcg ccgcaaaaaa atcagcgcgc  10620
ttattcctcc ccgaaaaggt gcgggttact ggcccggtga atatgcagac cgtaaccgtg  10680
cagtggctaa tcagcgaatg accgggagta atgcgcggtg gaaatggaca acagattaca  10740
accgtcgctc gatagcggaa acggcgatgt accgggtaaa acagctgttc gggggttcac  10800
tgacgctgcg tgactacgat ggtcaggttg cggaggctat ggccctggta cgagcgctga  10860
acaaaatgac gaaagcaggt atgcctgaaa gcgtgcgtat tgcctgaaaa cacaacccgc  10920
tacgggggag acttacccga aatctgattt attcaacaaa gccgggtgtg gtgaactaca  10980
aagcagaccc gttgaggtta tcagttcgat gcacaatcag cagcgcataa aatatgcaca  11040
agaacaggag caccccttcgc attaagctgt ggtggtaaca agtagtgccg ggctaccatc  11100
agcgagcatg atgcgctccc acagcattcg ccttggcagt atggaagttc ctcgctccag  11160
ttcgggccgg tatccacctc gagaggtggc acttttcggg gaaatgtgcg cggaacccct  11220
atttgtttat ttttctaaat acattcaaat atgtatccgc tcatgagaca ataaccctga  11280
taaatgcttc aataatattg aaaaaggaag agtatgagta ttcaacattt ccgtgtcgcc  11340
cttattccct tttttgcggc attttgcctt cctgtttttg ctcacccaga aacgctggtg  11400
aaagtaaaag atgctgaaga tcagttgggt gcacgagtgg gttacatcga actggatctc  11460
aacagcggta agatccttga gagttttcgc cccgaagaac gttttccaat gatgagcact  11520
tttaaagttc tgctatgtgg cgcggtatta tcccgtgttg acgccgggca agagcaactc  11580
ggtcgccgca tacactattc tcagaatgac ttggttgagt actcaccagt cacagaaaag  11640
catcttacgg atggcatgac agtaagagaa ttatgcagtg ctgccataac catgagtgat  11700
```

```
aacactgcgg ccaacttact tctgacaacg atcggaggac cgaaggagct aaccgctttt  11760

ttgcacaaca tgggggatca tgtaactcgc cttgatcgtt gggaaccgga gctgaatgaa  11820

gccataccaa acgacgagcg tgacaccacg atgcctgcag caatggcaac aacgttgcgc  11880

aaactattaa ctggcgaact acttactcta gcttcccggc aacaattaat agactggatg  11940

gaggcggata aagttgcagg accacttctg cgctcggccc ttccggctgg ctggtttatt  12000

gctgataaat ctggagccgg tgagcgtggg tctcgcggta tcattgcagc actggggcca  12060

gatggtaagc cctcccgtat cgtagttatc tacacgacgg ggagtcaggc aactatggat  12120

gaacgaaata gacagatcgc tgagataggt gcctcactga ttaagcattg gtaacccggg  12180

accaagttta ctcatatata cggacagcgg tgcggactgt tgtaactcag aataagaaat  12240

gaggccgctc atggcgttct gttgcccgtc tcactggtga aaagaaaaac aaccctggcg  12300

ccgcttcttt gagcgaacga tcaaaaataa gtggcgcccc atcaaaaaaa tattctcaac  12360

ataaaaaact ttgtgtaata cttgtaacgc t                                 12391
```

```
<210> SEQ ID NO 68
<211> LENGTH: 3305
<212> TYPE: DNA
<213> ORGANISM: Streptomyces venezuelae

<400> SEQUENCE: 68

atgcgcacgc ttctgatcga caactacgac tcgttcaccc agaacctgtt ccagtacatc     60

ggcgaggcca ccgggcagcc ccccgtcgtg cccaacgacg ccgactggtc gcggctgccc    120

ctcgaggact tcgacgcgat cgtcgtgtcc ccgggccccg gcagccccga ccgggaacgg    180

gacttcggga tcagccgccg ggcgatcacc gacagcggcc tgcccgtcct cggcgtctgc    240

ctcggccacc agggcatcgc ccagctctcg gcggaaccca tgcacggccg ggtctccgag    300

gtgcggcaca ccggcgagga cgtcttccgg ggcctcccct cgccgttcac cgccgtgcgc    360

taccactccc tggccgccac cgacctcccc gacgagctcg aacccctcgc ctggagcgac    420

gacggcgtcg tcatgggcct gcggcaccgc gagaagccgc tgatgggcgt ccagttccca    480

ccggagtcca tcggcagcga cttcggccgg gagatcatgg ccaacttccg cgacctcgcc    540

ctcgcccacc accgggcacg tcgcgacgcg gccgactggg gctacgaact ccacgtgcgc    600

cgcgtcgacg tgctgccgga cgccgaagag gtacgccgcg ctgcctgccc ggccgagggc    660

gccacgttct ggctggacag cagctccgtc ctcgaaggcg cctcgccgtt ctccttcctc    720

ggcgacgacc gcggcccgct cgccgagtac ctcacctacc gcgtcgccga cggcgtcgtc    780

tccgtccgcg gctccgacgg caccacgacc cgggacgcgg cgaccctctt cagctacctg    840

gaggagcagc tcgaaccgcc ggcgggtccc gtcgcccccg acctgccctt cgagttcaac    900

ctcggctacg tcggctacct cggctacgag ctgaaggcgg agaccaccgg cgaccccgca    960

gtaccggccc cgcaccccga cgccgcgttc ctcttcgccg accgcgccat cgccctcgac   1020

caccaggaag gctgctgcta cctgctggcc ctcgaccgcc ggggccacga cgacggcgcc   1080

cgcgcctggc tgcgggagac ggccgagacc ctcaccggcc tggccgtccg cgtccggccg   1140

aggccgaccc ccgccatggt cttcggggtc cccgaggcgg cggccggctt cggccccctg   1200

gctcgcgcac gccacgacaa ggacgcctcg gcgctccgca acggcgagtc gtacgagatc   1260

tgcctgacca acatggtcac cgcgccgacc gaggcgacgg ccctgccgct ctactccgcg   1320

ctgcgccgca tcagccccgt cccgtctggc gccctgctcg agttccccga gctgtcggtg   1380
```

-continued

```
ctcagcgcct cgcccgagcg gttcctcacg atcggcgccg acggcggcgt cgagtccaag   1440

cccatcaagg ggacccgccc ccggggcgca ccggcggagg aggacgagcg gctccgcgcc   1500

gacctggccg gccgggagaa ggaccgggcc gagaacctga tgatcgtcga cctggtccgc   1560

aacgacctca acagcgtctg cgcgatcggc tccgtccacg tgccccggct cttcgaggtg   1620

ggagacctcg cgcccgtgca ccagctggtg tcgaccatcc ggggacggct gcggcccggc   1680

accagcaccg ccgcctgcgt acgcgccgcc ttccccggcg gctccatgac cggcgcgccc   1740

aagaagcgac ccatggagat catcgaccgc ctggaggaag gcccccgggg cgtcttaccc   1800

ggggcgctcg gatggttcgc cctcagcggc gccgccgacc tcagcatcgt catccgcacc   1860

atcgtgctgg ccgacggccg ggccgagttc ggcgtcggcg gggcgatcgt gtccctctcc   1920

gaccaggagg aggagttcag gcagaccgtg gtcaaggccc gcgccatggt caccgccctc   1980

gacggcagcg cagtggcggg cgcccgatga gcggcttccc ccggagcgtc gtcgtcggcg   2040

gcagcggagc ggtgggcggc atgttcgccg ggctgctgcg ggaggcgggc agccgcacgc   2100

tcgtcgtcga cctcgtaccg ccgccgggac ggccggacgc ctgcctggtg ggcgacgtca   2160

ccgcgccggg gcccgagctc gcggccgccc tccgggacgc ggacctcgtc ctgctcgccg   2220

tacacgagga cgtggccctc aaggccgtgg cgcccgtgac ccggctcatg cgaccgggcg   2280

cgctgctcgc cgacaccctg tccgtccgga cgggcatggc cgcggagctc gcggcccacg   2340

cccccggcgt ccagcacgtg ggcctcaacc cgatgttcgc ccccgccgcc ggcatgaccg   2400

gccggcccgt ggccgccgtg gtcaccaggg acgggccggg cgtcacggcc ctgctgcggc   2460

tcgtcgaggg cggcggcggc aggcccgtac ggctcacggc ggaggagcac gaccggacga   2520

cggcggcgac ccaggccctg acgcacgccg tgatcctctc cttcgggctc gccctcgccc   2580

gcctcggcgt cgacgtccgg gccctggcgg cgacggcacc gccgccccac caggtgctgc   2640

tcgccctcct ggcccgtgtg ctcggcggca gccccgaggt gtacggggac atccagcggt   2700

ccaacccccg ggcggcgtcc gcgcgccggg cgctcgccga ggccctgcgc tccttcgccg   2760

cgctgatcgg cgacgacccg gaccgcgccg aggacccgga ccgcgccgac gaccccgacc   2820

gcaccgacaa ccccggccat cccgggggat gcgacggcgc cgggaacctc gacggcgtct   2880

tcgaggaact ccgccggctc atgggaccgg agctcgcggc gggccaggac cactgccagg   2940

agctgttccg caccctccac cgcaccgacg acgaaggcga gaaggaccga tgaccgagca   3000

gaacgagctg caggttgcgg ctgcgcgcgg agctcgacgc cctcgacggg acgcttctgg   3060

acacggtgcg gcgccgcatc gacctcggtg tccgcatcgc gcggtacaag tcccggcacg   3120

gcgtcccgat gatgcagccc ggccgggtca gcctggtcaa ggacagggcc gcccgctacg   3180

ccgccgacca cggcctcgac gaatcgttcc tggtgaacct ctacgacgtg atcatcacgg   3240

agatgtgccg cgtcgaggac ctggtgatga gccgggagag cctgacggcc gaggaccggc   3300

ggtga                                                               3305
```

<210> SEQ ID NO 69
<211> LENGTH: 28
<212> TYPE: DNA
<213> ORGANISM: Artificial Sequence
<220> FEATURE:
<223> OTHER INFORMATION: synthetic oligonucleotide used as PCR primer

<400> SEQUENCE: 69

```
ggaattccat atggacgaat ttgaaatg                                      28
```

<210> SEQ ID NO 70
<211> LENGTH: 69
<212> TYPE: DNA
<213> ORGANISM: Artificial Sequence
<220> FEATURE:
<223> OTHER INFORMATION: synthetic oligonucleotide used as PCR primer
<220> FEATURE:
<221> NAME/KEY: misc_feature
<222> LOCATION: (30)..(31)
<223> OTHER INFORMATION: N=A+T+G+C

<400> SEQUENCE: 70
gtattttacc acttggttca aaacctatmn nagcagattt ttcatctttt tttcatcttt     60
ttttaaaac     69

<210> SEQ ID NO 71
<211> LENGTH: 27
<212> TYPE: DNA
<213> ORGANISM: Artificial Sequence
<220> FEATURE:
<223> OTHER INFORMATION: synthetic oligonucleotide used as PCR primer

<400> SEQUENCE: 71
taggttttga accaagtggt aaaatac     27

<210> SEQ ID NO 72
<211> LENGTH: 62
<212> TYPE: DNA
<213> ORGANISM: Artificial Sequence
<220> FEATURE:
<223> OTHER INFORMATION: synthetic oligonucleotide used as PCR primer
<220> FEATURE:
<221> NAME/KEY: misc_feature
<222> LOCATION: (33)..(34)
<223> OTHER INFORMATION: N=A+T+G+C

<400> SEQUENCE: 72
cattcagtgt ataatcctta tcaagctgga amnnacttcc ataaacatat tttgccttta     60
ac     62

<210> SEQ ID NO 73
<211> LENGTH: 30
<212> TYPE: DNA
<213> ORGANISM: Artificial Sequence
<220> FEATURE:
<223> OTHER INFORMATION: synthetic oligonucleotide used as PCR primer

<400> SEQUENCE: 73
tccagcttga taaggattat acactgaatg     30

<210> SEQ ID NO 74
<211> LENGTH: 69
<212> TYPE: DNA
<213> ORGANISM: Artificial Sequence
<220> FEATURE:
<223> OTHER INFORMATION: synthetic oligonucleotide used as PCR primer
<220> FEATURE:
<221> NAME/KEY: misc_feature
<222> LOCATION: (29)..(30)
<223> OTHER INFORMATION: N=A+T+G+C
<220> FEATURE:
<221> NAME/KEY: misc_feature
<222> LOCATION: (38)..(39)
<223> OTHER INFORMATION: N=A+T+G+C
<220> FEATURE:
<221> NAME/KEY: misc_feature
<222> LOCATION: (41)..(42)
<223> OTHER INFORMATION: N=A+T+G+C

<400> SEQUENCE: 74
catccctcca actgcaacat caacgccmnn ataatgmnnm nnattaacct gcattattgg 60
atagataac 69

<210> SEQ ID NO 75
<211> LENGTH: 26
<212> TYPE: DNA
<213> ORGANISM: Artificial Sequence
<220> FEATURE:
<223> OTHER INFORMATION: synthetic oligonucleotide used as PCR primer

<400> SEQUENCE: 75
gcgttgatgt tgcagttgga gggatg 26

<210> SEQ ID NO 76
<211> LENGTH: 33
<212> TYPE: DNA
<213> ORGANISM: Artificial Sequence
<220> FEATURE:
<223> OTHER INFORMATION: synthetic oligonucleotide used as PCR primer

<400> SEQUENCE: 76
aaactgcagt tataatctct ttctaattgg ctc 33

<210> SEQ ID NO 77
<211> LENGTH: 12
<212> TYPE: PRT
<213> ORGANISM: Escherichia coli
<220> FEATURE:
<221> NAME/KEY: MISC_FEATURE
<222> LOCATION: (3)..(3)
<223> OTHER INFORMATION: O-methyl-L-tyrosine

<400> SEQUENCE: 77

Met Ile Xaa Met Ile Ala Ala Leu Ala Val Asp Arg
1 5 10

<210> SEQ ID NO 78
<211> LENGTH: 16
<212> TYPE: PRT
<213> ORGANISM: Mus musculus
<220> FEATURE:
<221> NAME/KEY: MISC_FEATURE
<222> LOCATION: (5)..(5)
<223> OTHER INFORMATION: L-3-(2-naphthyl)-alanine

<400> SEQUENCE: 78

Leu Leu Pro Glu Xaa Thr Gly Val Leu Ser Glu Val Gln Glu Glu Lys
1 5 10 15

<210> SEQ ID NO 79
<211> LENGTH: 7
<212> TYPE: PRT
<213> ORGANISM: Artificial Sequence
<220> FEATURE:
<223> OTHER INFORMATION: leader sequence used for construction of T7 RNA
polymerase variants

<400> SEQUENCE: 79

Met Thr Met Ile Thr Val His
1 5